United States Patent
Khanna et al.

(10) Patent No.: US 11,208,397 B2
(45) Date of Patent: *Dec. 28, 2021

(54) SMALL MOLECULE ANTAGONISTS OF SUMO RELATED MODIFICATION OF CRMP2 AND USES THEREOF

(71) Applicant: Arizona Board of Regents on Behalf of the University of Arizona, Tucson, AZ (US)

(72) Inventors: May Khanna, Tucson, AZ (US); Rajesh Khanna, Tucson, AZ (US); Vijay Gokhale, Tucson, AZ (US); Reena Chawla, Tucson, AZ (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/483,644

(22) PCT Filed: Feb. 2, 2018

(86) PCT No.: PCT/US2018/016687
§ 371 (c)(1),
(2) Date: Aug. 5, 2019

(87) PCT Pub. No.: WO2018/144900
PCT Pub. Date: Aug. 9, 2018

(65) Prior Publication Data
US 2020/0277271 A1 Sep. 3, 2020

Related U.S. Application Data

(60) Provisional application No. 62/454,475, filed on Feb. 3, 2017, provisional application No. 62/506,298, filed on May 15, 2017.

(51) Int. Cl.
| | | |
|---|---|---|
| *C07D 401/04* | (2006.01) | |
| *C07D 401/14* | (2006.01) | |
| *C07D 405/14* | (2006.01) | |
| *A61P 25/04* | (2006.01) | |
| *A61K 31/4184* | (2006.01) | |

(52) U.S. Cl.
CPC ......... *C07D 401/04* (2013.01); *C07D 401/14* (2013.01); *C07D 405/14* (2013.01)

(58) Field of Classification Search
CPC .. C07D 401/04; C07D 401/14; C07D 405/14; C07D 235/08; A61P 25/04; A61K 31/4184
See application file for complete search history.

(56) References Cited

U.S. PATENT DOCUMENTS

| | | |
|---|---|---|
| 2015/0133500 A1 | 5/2015 | Tafesse |
| 2015/0361032 A1 | 12/2015 | Pajouhesh |

FOREIGN PATENT DOCUMENTS

| | | | |
|---|---|---|---|
| WO | WO-2009102155 A2 * | 8/2009 | ............ C07C 67/31 |
| WO | 2015/134920 | 9/2015 | |
| WO | 2016/117647 | 7/2016 | |
| WO | 2017/062804 | 4/2017 | |

OTHER PUBLICATIONS

CAS Registry Nos. 1420816-71-2, 1368621-60-1, 1368488-37-2, 933704-38-2, 1390430-30-4, 1389137-38-5, 1147323-08-7, 836691-52-2, and 836691-50-0 entered into database Feb. 14, 2013, Apr. 15, 2012, Apr. 15, 2012, Apr. 30, 2007, Aug. 13, 2012, Aug. 12, 2012, May 19, 2009, Feb. 24, 2005, Feb. 24, 2005, Chemical Abstracts Service2020.*

Wang, X. J., "Synthesis, biological evaluation and SAR studies of benzimidazole derivatives as H1-antihistamine agents." Chinese Chemical Letters 23.6 (2012): 707-710.*

Qing Li et al.: "Discovery of Novel 2-(piperidin4-yl)-1H-benzo[d]imidazole Derivatives as Potential Anti-Inflammatory Agents" Chemical Biology & Drug Design, vol. 86, No. 4, Mar. 16, 2015, pp. 509-516.

Supplementary EP Search Report, EP Patent Application No. 18748594.1, dated Nov. 6, 2020, 3 pages.

International Search Report & Written Opinion, Int'l Application No. PCT/US2018/016687, dated May 4, 2018, 13 pages.

\* cited by examiner

*Primary Examiner* — John M Mauro
(74) *Attorney, Agent, or Firm* — Casimir Jones, S.C.; Robert A. Goetz

(57) ABSTRACT

This invention is in the field of medicinal chemistry. In particular, the invention relates to a new class of small-molecules having a piperidinyl-benzoimidazole structure which function as antagonists of small ubiquitin like modifier (SUMO) related modification (SUMOylation) of collapsin response mediator protein 2 (CRMP2), and their use as therapeutics for the treatment of voltage gated sodium channel 1.7 (Nav1.7) related itch, anosmia, migraine event, and/or pain (e.g., neuropathic pain).

13 Claims, 26 Drawing Sheets

Specification includes a Sequence Listing.

Compound AZ145

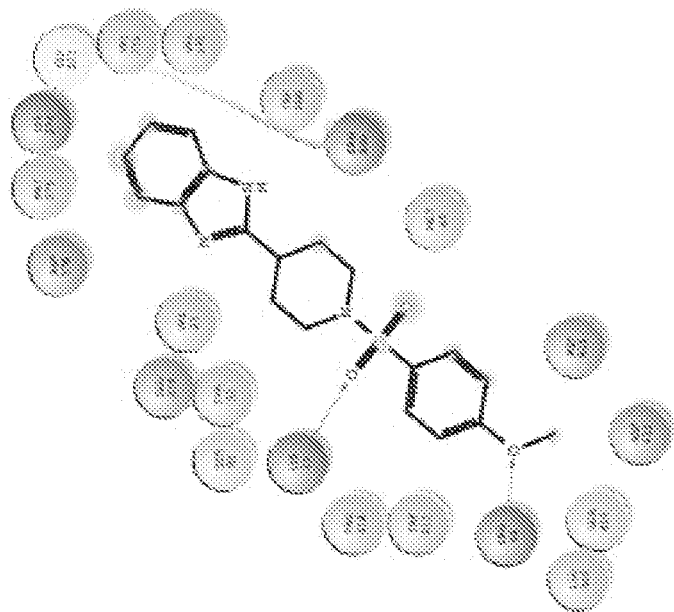
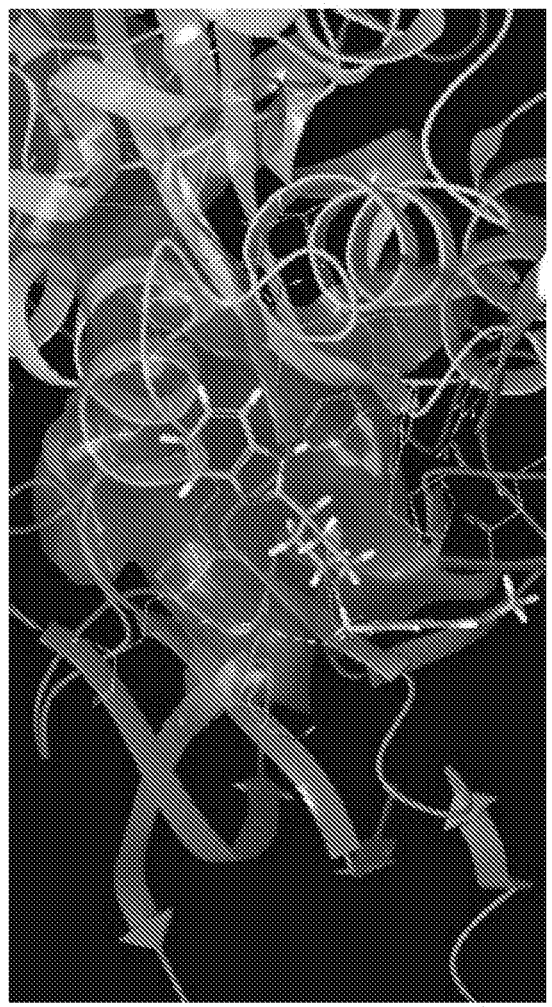
FIG. 6

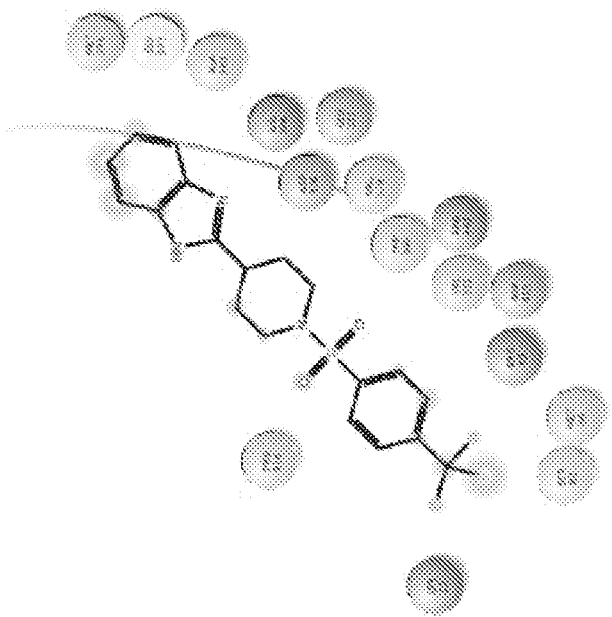
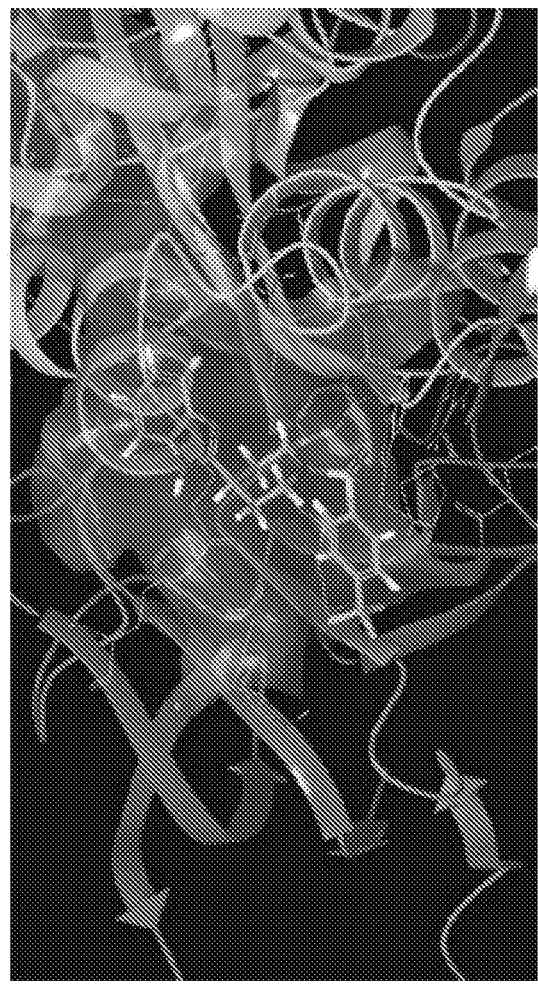
FIG. 9

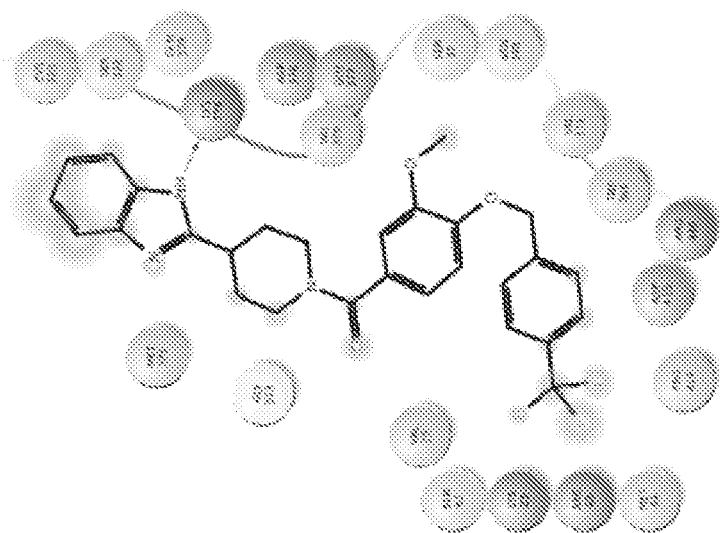
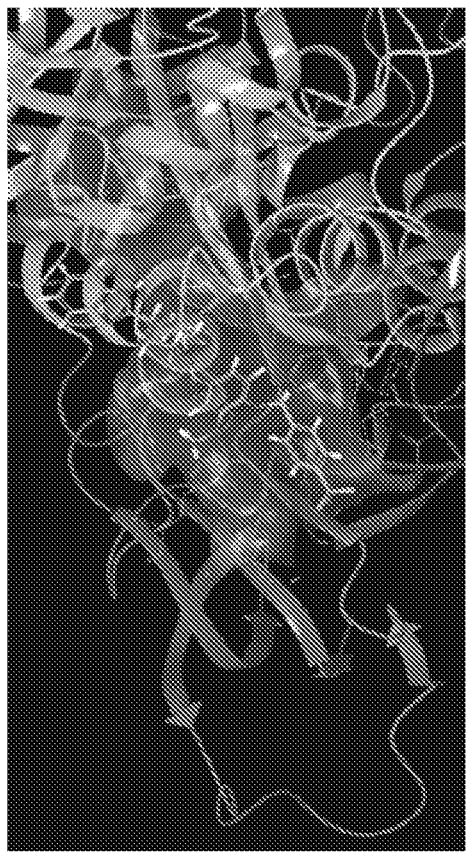
FIG. 12

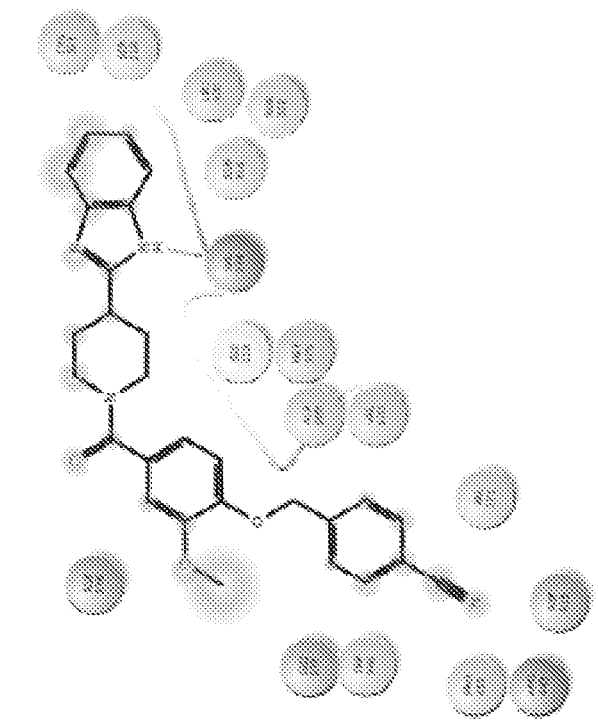
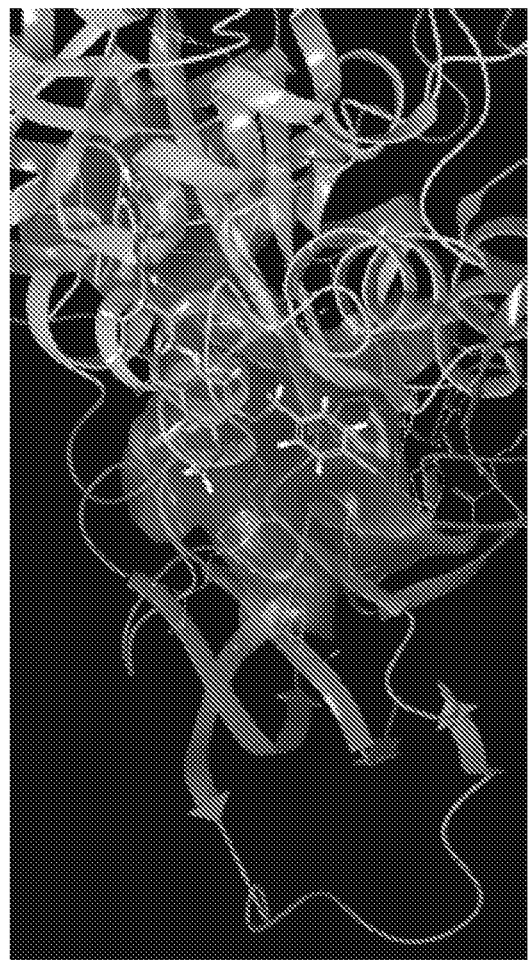
FIG. 13

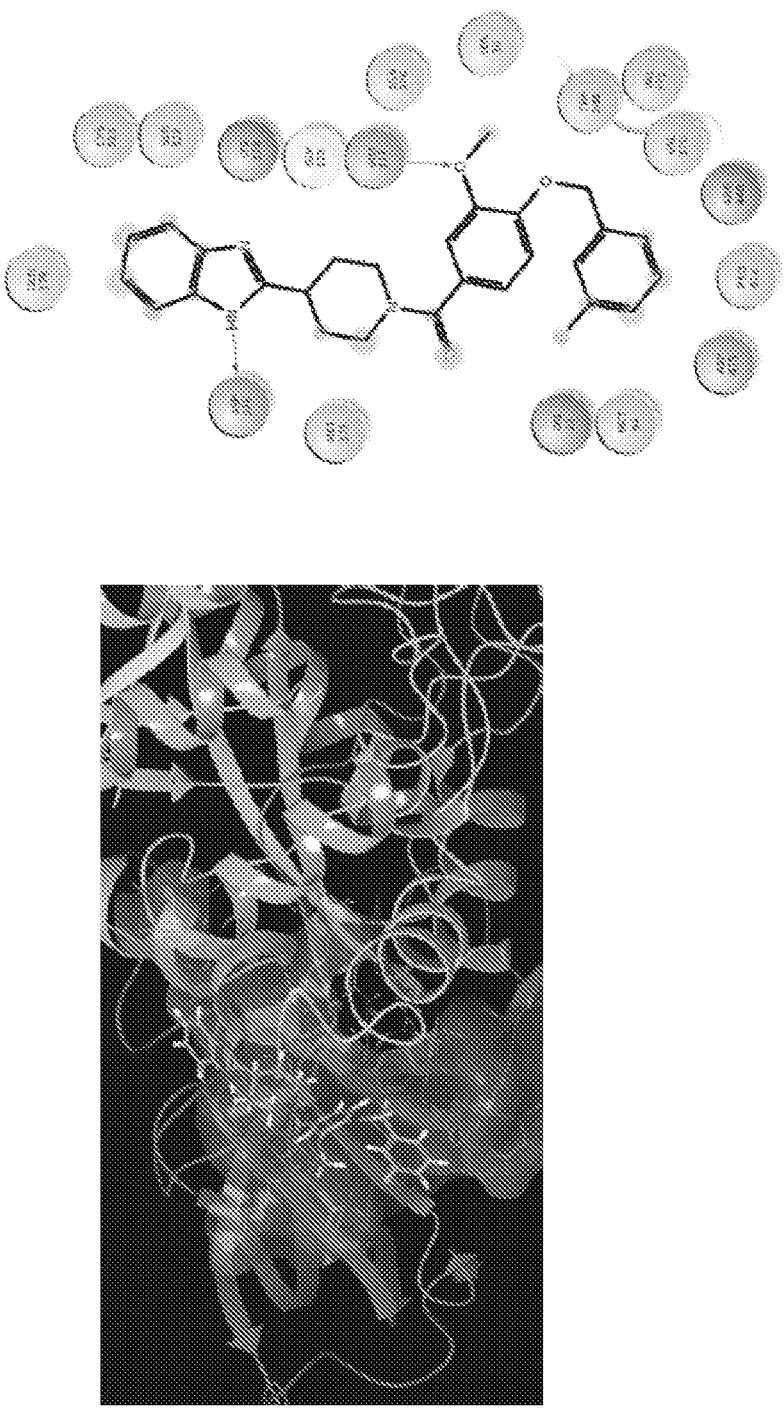
FIG. 14  Compound AZ177

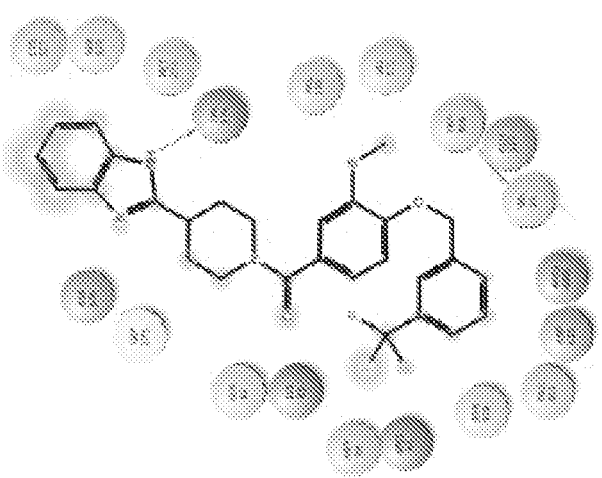
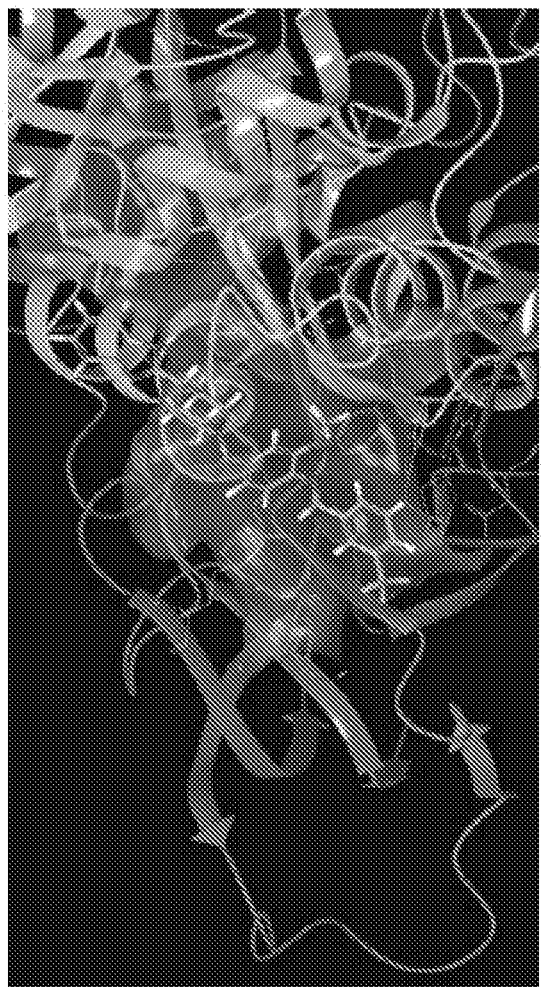
FIG. 15  AZ178

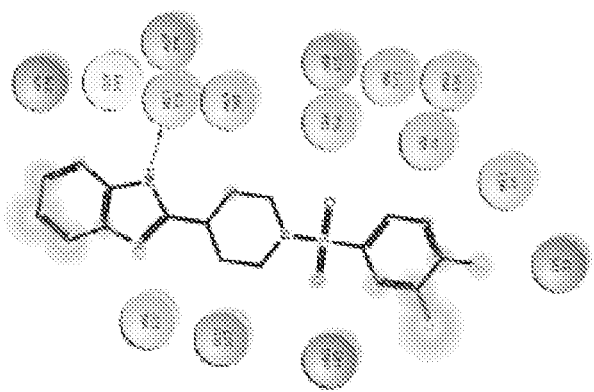
FIG. 16

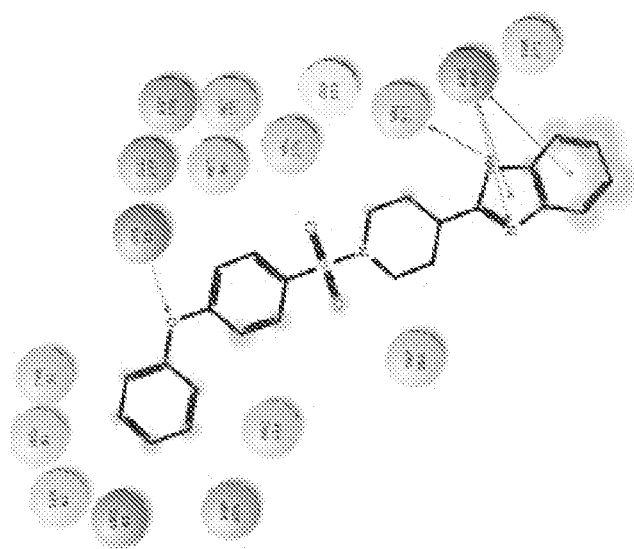
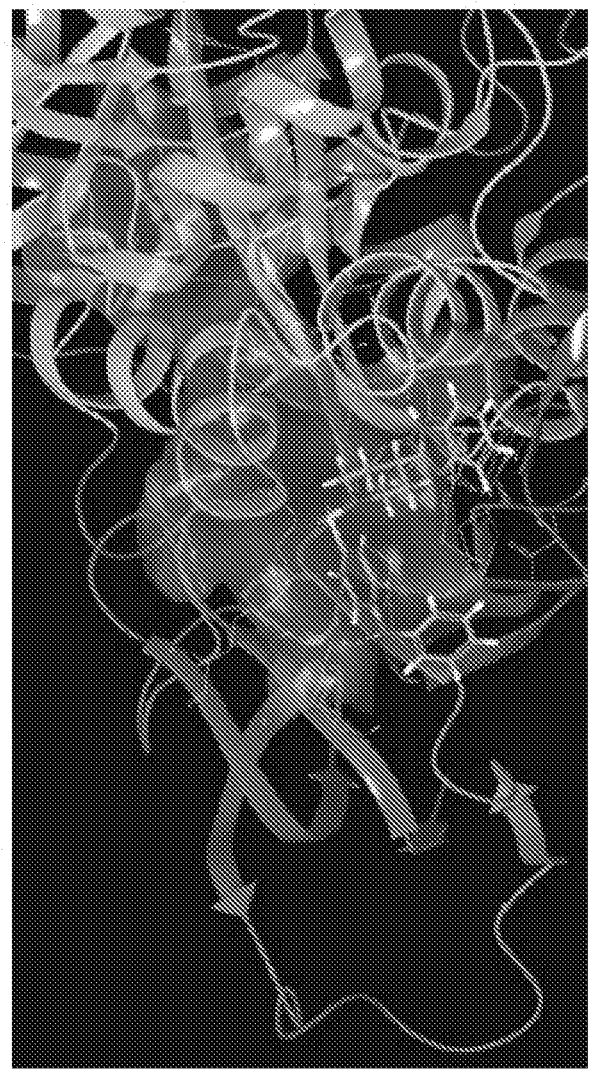
FIG. 17

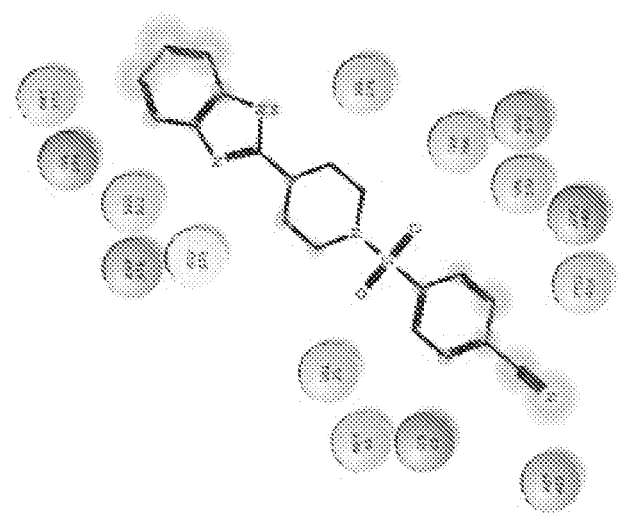
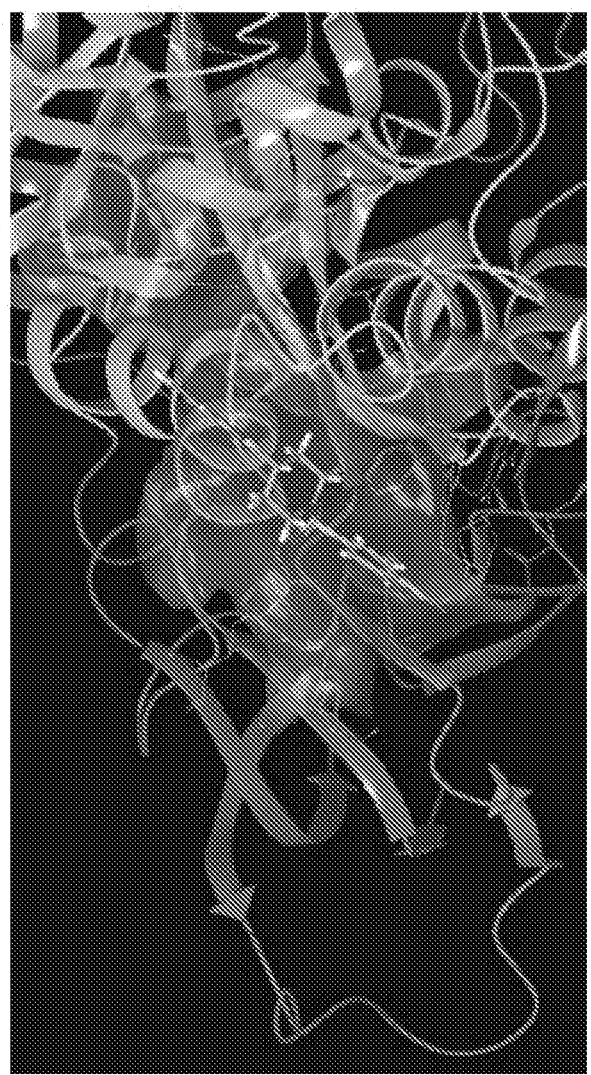
FIG. 18.

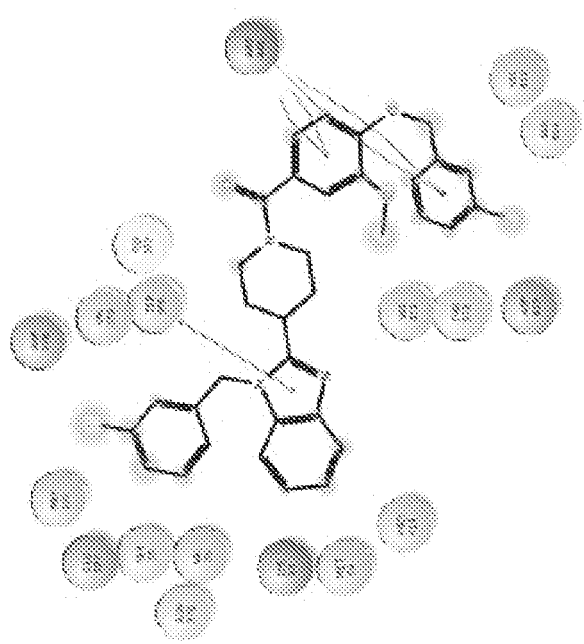
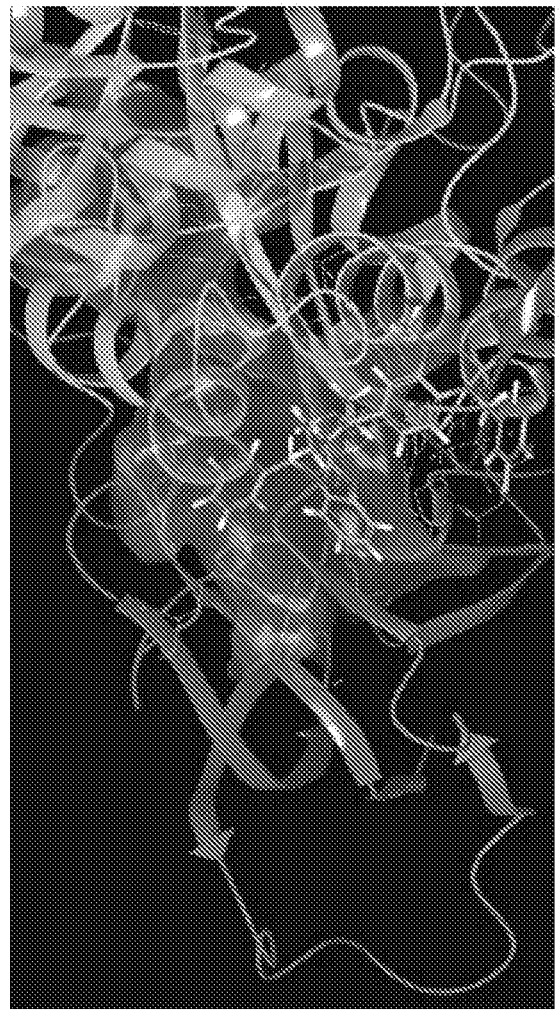
FIG. 19

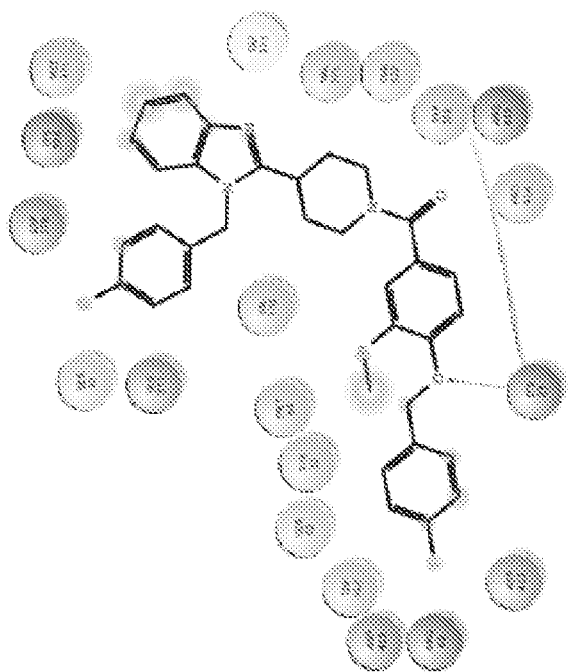
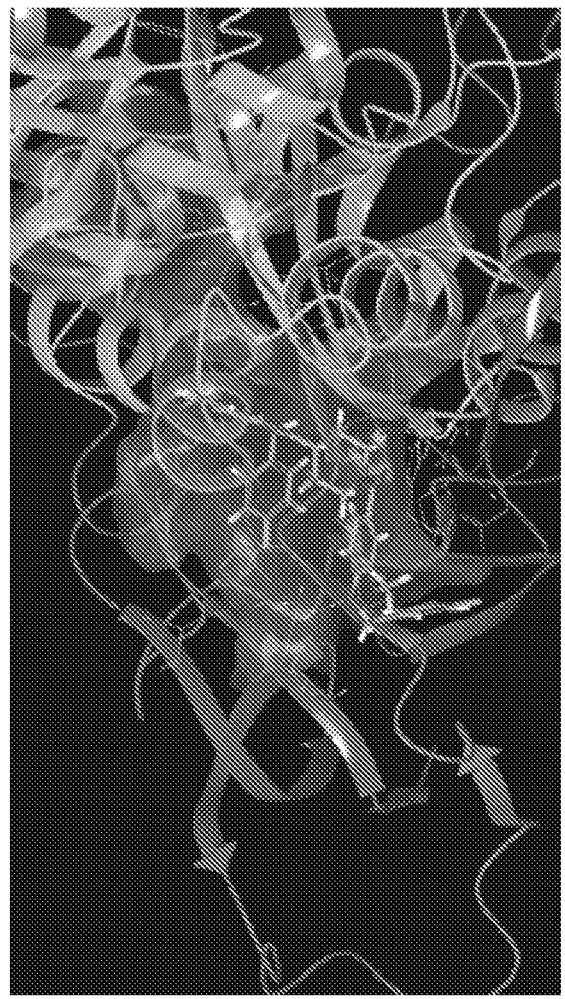
FIG. 20

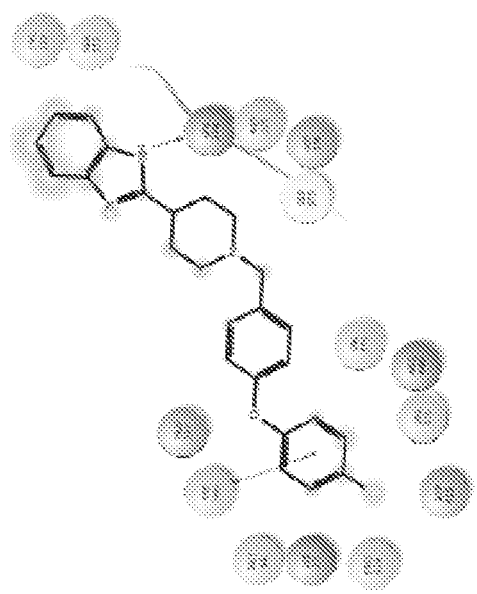
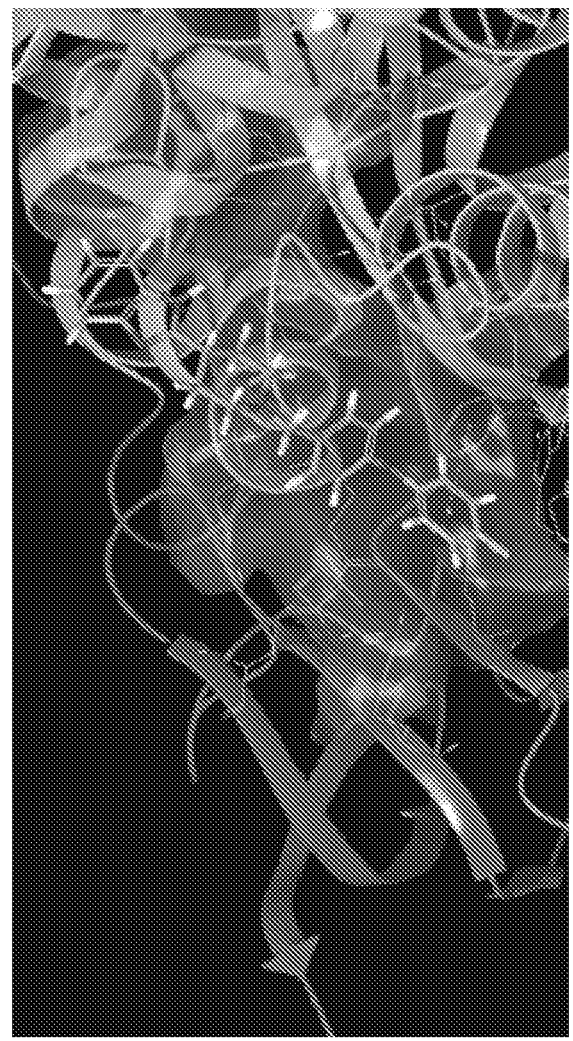
FIG. 24  AZ206

SEQUENCE LISTING

```
<160> NUMBER OF SEQ ID NOS: 1

<210> SEQ ID NO 1
<211> LENGTH: 572
<212> TYPE: PRT
<213> ORGANISM: murine

<400> SEQUENCE: 1

Met Ser Tyr Gln Gly Lys Lys Asn Ile Pro Arg Ile Thr Ser Asp Arg
1               5                   10                  15

Leu Leu Ile Lys Gly Gly Lys Ile Val Asn Asp Asp Gln Ser Phe Tyr
            20                  25                  30

Ala Asp Ile Tyr Met Glu Asp Gly Leu Ile Lys Gln Ile Gly Glu Asn
        35                  40                  45

Leu Ile Val Pro Gly Gly Val Lys Thr Ile Glu Ala His Ser Arg Met
    50                  55                  60

Val Ile Pro Gly Gly Ile Asp Val His Thr Arg Phe Gln Met Pro Asp
```

```
                65                  70                  75                  80
            Gln Gly Met Thr Ser Ala Asp Asp Phe Phe Gln Gly Thr Lys Ala Ala
                                85                  90                  95

Leu Ala Gly Gly Thr Thr Met Ile Ile Asp His Val Val Pro Glu Pro
                               100                 105                 110

Gly Thr Ser Leu Leu Ala Ala Phe Asp Gln Trp Arg Glu Trp Ala Asp
                               115                 120                 125

Ser Lys Ser Cys Cys Asp Tyr Ser Leu His Val Asp Ile Thr Glu Trp
                130                 135                 140

His Lys Gly Ile Gln Glu Glu Met Glu Ala Leu Val Lys Asp His Gly
            145                 150                 155                 160

Val Asn Ser Phe Leu Val Tyr Met Ala Phe Lys Asp Arg Phe Gln Leu
                               165                 170                 175

Thr Asp Ser Gln Ile Tyr Glu Val Leu Ser Val Ile Arg Asp Ile Gly
                               180                 185                 190

Ala Ile Ala Gln Val His Ala Glu Asn Gly Asp Ile Ile Ala Glu Glu
                               195                 200                 205

Gln Gln Arg Ile Leu Asp Leu Gly Ile Thr Gly Pro Glu Gly His Val
                               210                 215                 220

Leu Ser Arg Pro Glu Glu Val Glu Ala Glu Ala Val Asn Arg Ser Ile
            225                 230                 235                 240

Thr Ile Ala Asn Gln Thr Asn Cys Pro Leu Tyr Val Thr Lys Val Met
                               245                 250                 255

Ser Lys Ser Ala Ala Glu Val Ile Ala Gln Ala Arg Lys Lys Gly Thr
                               260                 265                 270

Val Val Tyr Gly Glu Pro Ile Thr Ala Ser Leu Gly Thr Asp Gly Ser
                               275                 280                 285

His Tyr Trp Ser Lys Asn Trp Ala Lys Ala Ala Phe Val Thr Ser
                               290                 295                 300

Pro Pro Leu Ser Pro Asp Pro Thr Thr Pro Asp Phe Leu Asn Ser Leu
            305                 310                 315                 320

Leu Ser Cys Gly Asp Leu Gln Val Thr Gly Ser Ala His Cys Thr Phe
                               325                 330                 335

Asn Thr Ala Gln Lys Ala Val Gly Lys Asp Asn Phe Thr Leu Ile Pro
                               340                 345                 350

Glu Gly Thr Asn Gly Thr Glu Glu Arg Met Ser Val Ile Trp Asp Lys
                               355                 360                 365

Ala Val Val Thr Gly Lys Met Asp Glu Asn Gln Phe Val Ala Val Thr
                               370                 375                 380

Ser Thr Asn Ala Ala Lys Val Phe Asn Leu Tyr Pro Arg Lys Gly Arg
            385                 390                 395                 400

Ile Ser Val Gly Ser Asp Ala Asp Leu Val Ile Trp Asp Pro Asp Ser
                               405                 410                 415

Val Lys Thr Ile Ser Ala Lys Thr His Asn Ser Ala Leu Glu Tyr Asn
                               420                 425                 430

Ile Phe Glu Gly Met Glu Cys Arg Gly Ser Pro Leu Val Val Ile Ser
                               435                 440                 445

Gln Gly Lys Ile Val Leu Glu Asp Gly Thr Leu His Val Thr Glu Gly
                               450                 455                 460

Ser Gly Arg Tyr Ile Pro Arg Lys Pro Phe Pro Asp Phe Val Tyr Lys
            465                 470                 475                 480

Arg Ile Lys Ala Arg Ser Arg Leu Ala Glu Leu Arg Gly Val Pro Arg
                               485                 490                 495
```

```
Gly Leu Tyr Asp Gly Pro Val Cys Glu Val Ser Val Thr Pro Lys Thr
            500             505             510

Val Thr Pro Ala Ser Ser Ala Lys Thr Ser Pro Ala Lys Gln Gln Ala
            515             520             525

Pro Pro Val Arg Asn Leu His Gln Ser Gly Phe Ser Leu Ser Gly Ala
        530             535             540

Gln Ile Asp Asp Asn Ile Pro Arg Arg Thr Thr Gln Arg Ile Val Ala
545             550             555                     560

Pro Pro Gly Gly Arg Ala Asn Ile Thr Ser Leu Gly
                565             570
```

SMALL MOLECULE ANTAGONISTS OF SUMO RELATED MODIFICATION OF CRMP2 AND USES THEREOF

CROSS REFERENCE TO RELATED APPLICATION

This application is a Section 371 U.S. national stage entry of International Patent Application No. PCT/US2018/016687, International Filing Date Feb. 2, 2018 which claims priority to and the benefit of U.S. Provisional Application No. 62/454,475, filed Feb. 3, 2017 and U.S. Provisional Application No. 62/506,298, filed May 15, 2017, which are hereby incorporated by reference in their entireties.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 6,000 byte ASCII (Text) file named "35085-253_ST25.txt." created on Mar. 11, 2020.

FIELD OF THE INVENTION

This invention is in the field of medicinal chemistry. In particular, the invention relates to a new class of small-molecules having a piperidinyl-benzoimidazole structure which function as antagonists of small ubiquitin like modifier (SUMO) related modification (SUMOylation) of collapsin response mediator protein 2 (CRMP2), and their use as therapeutics for the treatment of voltage gated sodium channel 1.7 (Nav1.7) related itch, anosmia, migraine event, and/or pain (e.g., neuropathic pain).

INTRODUCTION

The voltage-gated Nav1.7 sodium channel is preferentially expressed in the peripheral nervous system within ganglia associated with nociceptive pain, including dorsal root ganglia (DRG), trigeminal and sympathetic ganglia (see, e.g., Dib-Hajj S D, Yang Y, Black J A, & Waxman S G (2013) Nature reviews Neuroscience 14: 49-62), and olfactory epithelia (see, e.g., Ahn H S, et al., (2011) Molecular pain 7: 32). There, Nav1.7 modulates the voltage activation threshold required to fire action potentials in response to stimuli (see, e.g., Estacion M, et al. (2011) Molecular pain 7: 92; Momin A, & Wood J N (2008) Curr Opin Neurobiol 18: 383-388).

Mutations in SCN9A, the gene encoding Nav1.7, produce distinct human pain syndromes (see, e.g., Bennett D L, & Woods C G (2014) Lancet neurology 13: 587-599; Dib-Hajj S D, et al., (2008) AdvGenet 63:85-110: 85-110; Jarecki B W, et al., (2008) JPhysiol 586: 4137-4153; Waxman S G (2007) Neurology 69: 505-507). Several mouse studies have also demonstrated the importance of Nav1.7 in pain sensation. Consistent with human findings, Nav1.7 conditional knockout mice, which lack functional Nav1.7 in the Nav1.8 positive population of sensory neurons, display marked insensitivity to pain and anosmia but are otherwise phenotypically normal (see, e.g., Minett M S, et al., (2012) Nature communications 3: 791; Weiss J, et al. (2011) Nature 472: 186-190). These mice show no defects in mechanical sensitivity and supraspinal thermal sensitivity. In addition, Nav1.7 knockout mice do not develop formalin-induced inflammatory pain or complete Freund's adjuvant (CFA)-induced thermal hyperalgesia. Deletion of Nav1.7 in all sensory neurons leads to an additional loss of noxious thermosensation. Responses to neuropathic pain are unaffected when SCN9A is deleted in all sensory neurons (see, e.g., Minett M S, et al., (2012) Nature communications 3: 791).

Such studies indicate the importance of Nav1.7 in pain sensation and highlight it as an ideal drug target for pain therapies.

SUMMARY

Nav1.7 selective compounds (see, e.g., Chowdhury S, et al., (2011) Bioorganic & medicinal chemistry letters 21: 3676-3681; London C, et al., (2008) Bioorganic & medicinal chemistry letters 18: 1696-1701; Williams B S, et al., (2007) Biochemistry 46: 14693-14703), peptide toxins (see, e.g., Yang S, et al., (2013) PNAS 110: 17534-17539), and neutralizing antibodies (see, e.g., Lee J H, et al., (2014) Cell 157: 1393-1404) cause only temporary partial analgesia, and some Nav1.7 gain-of-function mutation patients respond to pan-sodium channel blockers (see, e.g., Choi J S, et al., (2009) ExpNeurol 216: 383-389; Fischer T Z, et al., (2009) AnnNeurol 65: 733-741). A precision medicine approach has been demonstrated, using genomics and molecular modeling, to treat pain in a handful of humans with gain-of-function mutations in Nav1.7 (see, e.g., Cao L, et al., (2016) Science translational medicine 8: 335ra356; Geha P, et al., (2016) JAMA Neurol 73: 659-667). Recently developed compounds (e.g., PF-0485624 (see, e.g., McCormack K, et al., (2013) PNAS 110: E2724-2732)) ((e.g., GX-674, which demonstrated equipotent inhibition of Nav1.7 and Nav1.2, and only 4-fold less potency against Nav1.6 (see, e.g., Ahuja S, et al., (2015) Science 350: aac5464)) have not progressed to clinic. Thus, despite significant investment into Nav1.7 drug development programs, there has been only marginal success.

It has recently been shown that surface expression and current density of Nav1.7 was controlled by SUMOylation of the cytosolic axonal CRMP2 (see, e.g., Dustrude et al., (2013) J Biol Chem 288(34):24316-24331; Dustrude, et al., (2016) PNAS 113, E8443-E8452). Moreover, it has recently been shown that the SUMO protein modifies CRMP2 via the SUMO E2-conjugating enzyme Ubc9 in vivo (see, e.g., Ju, et al., Channels 7:3, 153-159, 2013). CRMP2 regulates multiple processes in neurons and was initially discovered to regulate mechanisms of neuronal polarity (see, e.g., Fukata, et al., (2002) Nat Cell Biol 4(8):583-591; Yoshimura et al., (2010) Cell 120(1):137-149). CRMP2 phosphorylation by cyclin-dependent kinase 5 (Cdk5) (see, e.g., Cole, et al., (2006) J Biol Chem 281(24):16591-16598), glycogen synthase kinase 30 (see, e.g., Yoshimura et al., (2010) Cell 120(1): 137-149), Rho-associated protein kinase (see, e.g., Arimura et al., (2000) J Biol Chem 275(31):23973-23980), or the Src-family kinases Fyn (see, e.g., Uchida, et al., (2009) J Biol Chem 284(40):27393-27401) and Yes (see, e.g., Varrin-Doyer M, et al. (2009) J Biol Chem 284(19): 13265-13276) drives its diverse cellular functions, including neurite outgrowth, endocytosis, and ion-channel trafficking (see, e.g., Dustrude (2013) J Biol Chem 288(34):24316-24331; Brittain J M, et al (2011) Nat Med 17(7):822-829; Moutal A, et al., (2015) Front Cell Neurosci 8:471; Brustovetsky T, et al., (2014) J Biol Chem 289(11):7470-7482). Studies of CRMP2 trafficking functions have revealed that CRMP2 facilitates endocytosis of L1-cell adhesion molecule by interacting with the endocytic protein Numb (see, e.g., Nishimura T, et al. (2003) Nat Cell Biol 5(9):819-826)

that recruits epidermal growth factor receptor pathway substrate 15 (Eps15), an initiator of clathrin-mediated endocytosis (see, e.g., Santolini E, et al. (2000) Numb is an endocytic protein. J Cell Biol 151(6):1345-1352).

Gln379, Pro414, Asp415, Ser416, Val417, and Arg440. The wild-type CRMP2 amino acid sequence (murine; accession number 008553; www.ncbi.nlm.nih.gov/protein/008553.2) is as follows (SEQ ID NO: 1):

```
  1 msyqgkknip ritsdrllik ggkivnddqs fyadiymedg likqigenli vpggvktiea
 61 hsrmvipggi dvhtrfqmpd qgmtsaddff qgtkaalagg ttmiidhvvp epgtsllaaf
121 dqwrewadsk sccdyslhvd itewhkgiqe emealvkdhg vnsflvymaf kdrfqltdsq
181 iyevlsvird igaiaqvhae ngdiiaeeqq rildlgitgp eghvlsrpee veaeavnrsi
241 tianqtncpl yvtkvmsksa aeviaqarkk gtvvygepit aslgtdgshy wsknwakaaa
301 fvtspplspd pttpdflnsl lscgdlqvtg sahctfntaq kavgkdnftl ipegtngtee
361 rmsviwdkav vtgkmdenqf vavtstnaak vfnlyprkgr isvgsdadlv iwdpdsvkti
421 sakthnsale ynifegmecr gsplvvisqg kivledgtlh vtegsgryip rkpfpdfvyk
481 rikarsrlae lrgvprglyd gpvcevsvtp ktvtpassak tspakqqapp vrnlhqsgfs
541 lsgaqiddni prrttqriva ppggranits lg
```

Experiments conducted during the course of developing embodiments for the present invention identified small molecule compounds having a piperidinyl-benzoimidazole structure which function as inhibitors of Nav1.7 activity through antagonizing SUMO related post-translational modification (SUMOylation) of CRMP2, which is required for Nav1.7 regulation. Such compounds were further determined to be capable of indirect regulation of Nav1.7 through antagonizing SUMOylation of CRMP2, and as such, determined to be capable of hindering (e.g., preventing, diminishing, attenuating) pain associated with increased Nav1.7 activity.

Experiments conducted during the course of developing embodiments for the present invention further determined that such compounds having a piperidinyl-benzoimidazole structure are capable of upregulating endogenous opioids within a mammalian subject. Indeed, such experiments demonstrated that administration of such compounds resulted in upregulation of mRNA levels of the endogenous opioid—proenkephalin—simultaneous with inhibition of SUMOylation of CRMP2.

Experiments conducted during the course of developing embodiments for the present invention further identified a binding pocket within CRMP2 specific for E2 ubiquitin-conjugating enzyme Ubc9 (see, Example III). Specifically, such experiments demonstrated the ability of specific small molecule compounds described herein (e.g., AZ145, AZ159, AZ160, AZ161, AZ162, AZ168, AZ170, AZ172, AZ173, AZ177, AZ178, AZ190, AZ192, AZ193, AZ194, AZ195, AZ198, AZ203, AZ205, and AZ206 (see, FIGS. 5-24)) to bind with CRMP2 through this CRMP2 binding pocket. Such results further indicated that such binding with CRMP2 through the identified CRMP2 binding pocket will inhibit binding between Ubc9 and CRMP2, thereby inhibiting downstream activity dependent upon binding between Ubc9 and CRMP2 (e.g., CRMP2 SUMOylation, Nav1.7 protein expression and activity, pain related to Nav1.7 protein expression and activity). As shown in such FIGS. 5-24, the following amino acids within wild type CRMP2 (see wild type sequence below) were shown to be associated with the CRMP2 binding pocket: Lys23, Val25, Ser30, Tyr32, Met64, Ser319, Ser322, Trp366, Val370, Val371, Gly373, Lys374, Met375, Asp376, Glu377, Glu377, The present invention contemplates that exposure of animals (e.g., humans) suffering from itch or pain related to Nav1.7 activity (e.g., neuropathic pain) to therapeutically effective amounts of the small molecules of the present invention (e.g., small molecules having a piperidinyl-benzoimidazole structure configured to inhibit SUMOylation of CRMP2) will inhibit or alleviate such pain and/or increase susceptibility to the pain-relieving effects of other types of therapy. In some embodiments, such compounds are able to inhibit or alleviate such pain and/or increase susceptibility to the pain-relieving effects of other types of therapy through docking within a CRMP2 binding pocket characterized by one or more of the following CRMP2 amino acid residues (Lys23, Val25, Ser30, Tyr32, Met64, Ser319, Ser322, Trp366, Val370, Val371, Gly373, Lys374, Met375, Asp376, Glu377, Glu377, Gln379, Pro414, Asp415, Ser416, Val417, and Arg440) thereby preventing binding between CRMP2 and Ubc9, which thereby prevents SUMOylation of CRMP2.

The present invention contemplates that such antagonists of SUMO related post-translational modification (SUMOylation) of CRMP2 (thereby indirectly regulating Nav1.7 activity) satisfy an unmet need for the treatment (e.g., inhibition and/or alleviation) of itch, pain related to Nav1.7 activity (e.g., neuropathic pain), anosmia, and/or a migraine event either when administered as monotherapy to inhibit or alleviate such pain, or when administered in a temporal relationship with additional agent(s), such as other pain relieving agents, to inhibit or alleviate such pain.

Moreover, the present invention contemplates that such antagonists of SUMO related post-translational modification (SUMOylation) of CRMP2 (thereby indirectly regulating Nav1.7 activity) satisfy an unmet need for inducing endogenous opioid expression and/or activity in a subject when administered as monotherapy, or when administered in a temporal relationship with additional agent(s), such as pain relieving agents, to inhibit or alleviate pain.

Certain piperidinyl-benzoimidazole compounds of the present invention may exist as stereoisomers including optical isomers. The invention includes all stereoisomers, both as pure individual stereoisomer preparations and enriched preparations of each, and both the racemic mixtures of such stereoisomers as well as the individual diastereomers and enantiomers that may be separated according to methods that are well known to those of skill in the art.

In a particular embodiment, the present invention provides small molecule compounds having a piperidinyl-benzoimidazole structure encompassed within Formula I:

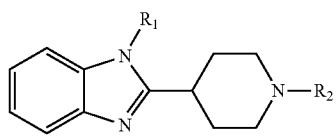

or Formula II:

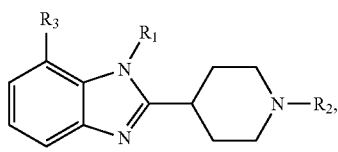

including pharmaceutically acceptable salts, solvates, and/or prodrugs thereof.

Formulas I and II are not limited to a particular chemical moiety for R1, R2 and R3. In some embodiments, the particular chemical moiety for R1, R2 and R3 independently include any chemical moiety that permits the resulting compound to prevent engagement between SUMO and CRMP2. In some embodiments, the particular chemical moiety for R1, R2 and R3 independently include any chemical moiety that permits the resulting compound to prevent SUMOylation of CRMP2. In some embodiments, the particular chemical moiety for R1, R2 and R3 independently include any chemical moiety that permits the resulting compound to indirectly inhibit Nav1.7 related activity. In some embodiments, the particular chemical moiety for R1, R2 and R3 independently include any chemical moiety that permits the resulting compound to inhibit or alleviate itch and/or pain related to Nav1.7 activity (e.g., neuropathic pain). In some embodiments, the particular chemical moiety for R1, R2 and R3 independently include any chemical moiety that permits the resulting compound to inhibit Navy 1.7 related activity through preventing SUMOylation of CRMP2, and as such, inhibit or alleviate itch and/or pain related to Nav1.7 activity (e.g., neuropathic pain). In some embodiments, the particular chemical moiety for R1, R2 and R3 independently include any chemical moiety that permits the resulting compound to induce endogenous opioid (e.g., proenkephalin) expression and/or activity. In some embodiments, the particular chemical moiety for R1, R2 and R3 independently include any chemical moiety that permits the resulting compound to bind and/or dock within a CRMP2 binding pocket characterized by one or more of the following CRMP2 amino acid residues: Lys23, Val25, Ser30, Tyr32, Met64, Ser319, Ser322, Trp366, Val370, Val371, Gly373, Lys374, Met375, Asp376, Glu377, Glu377, Gln379, Pro414, Asp415, Ser416, Val417, and Arg440. In some embodiments, the particular chemical moiety for R1, R2 and R3 independently include any chemical moiety that permits the resulting compound to inhibit binding and/or docking of Ubc9 within a CRMP2 binding pocket characterized by one or more of the following CRMP2 amino acid residues: Lys23, Val25, Ser30, Tyr32, Met64, Ser319, Ser322, Trp366, Val370, Val371, Gly373, Lys374, Met375, Asp376, Glu377, Glu377, Gln379, Pro414, Asp415, Ser416, Val417, and Arg440.

Such compounds are not limited to a particular chemical moiety for R1. In some embodiments, R1 is Hydrogen,

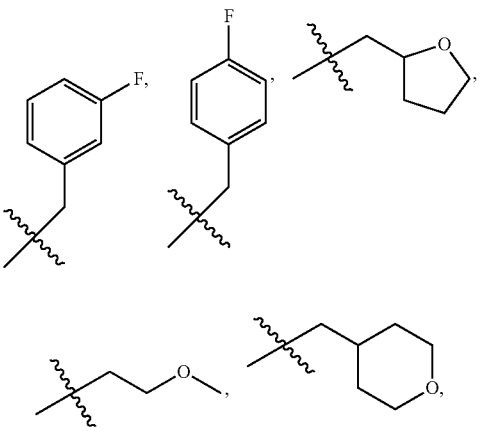

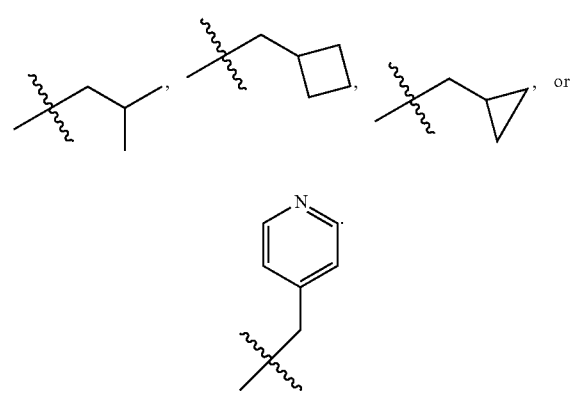

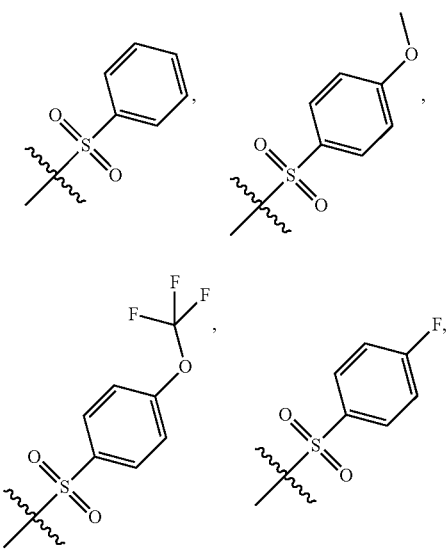

Such compounds are not limited to a particular chemical moiety for R2. In some embodiments, R2 is Hydrogen,

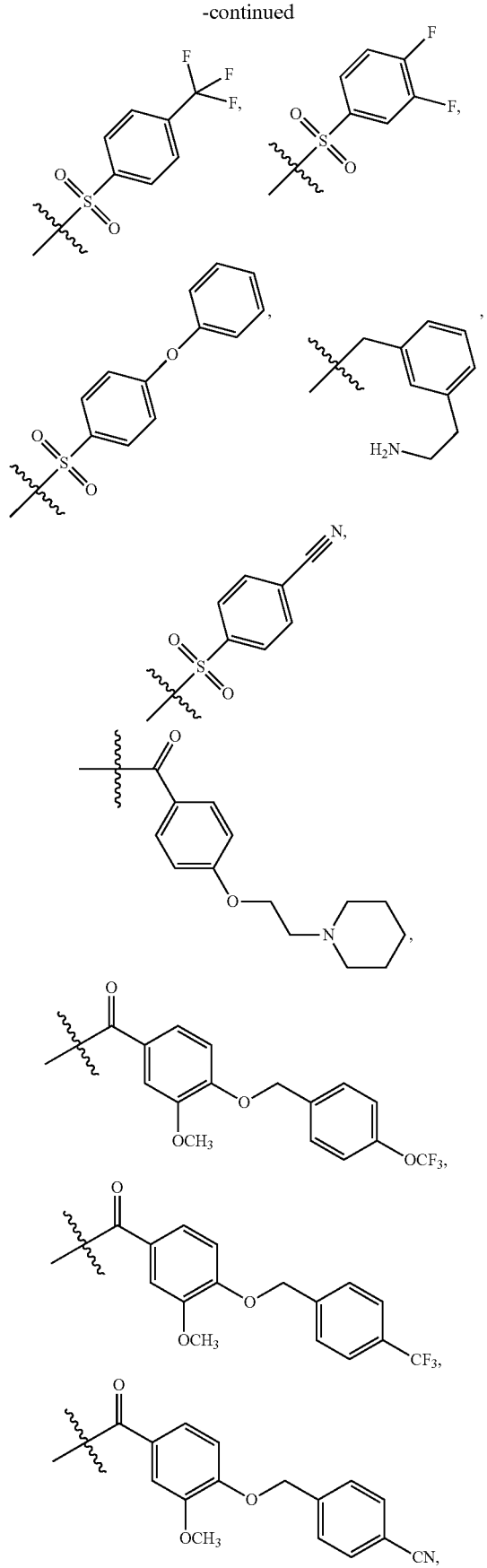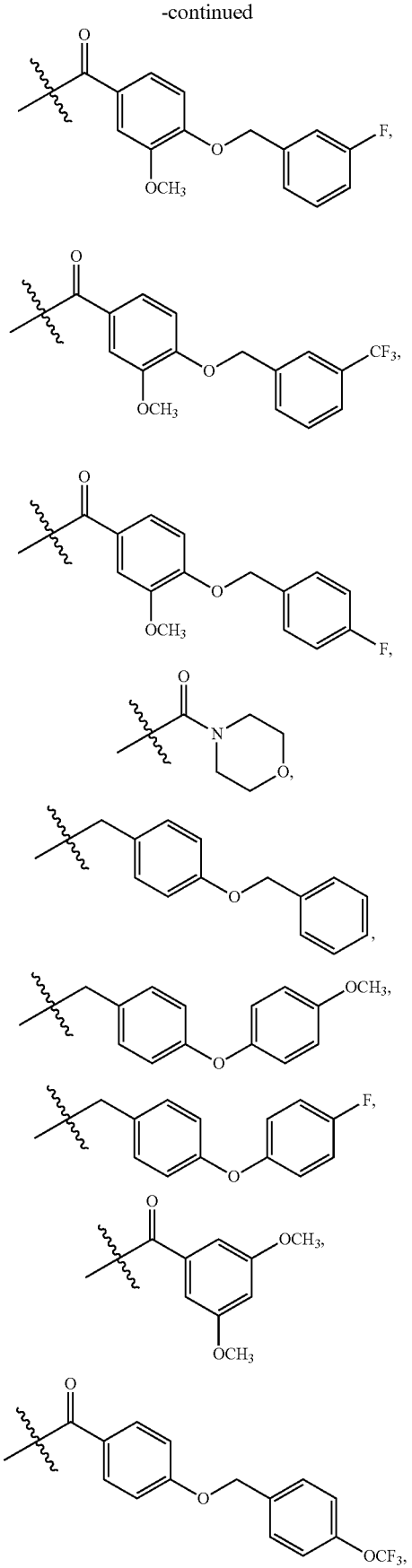

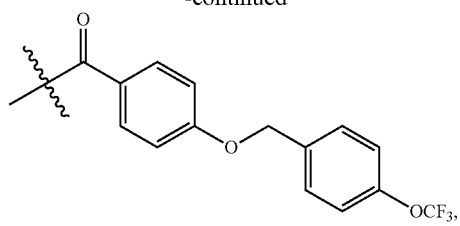
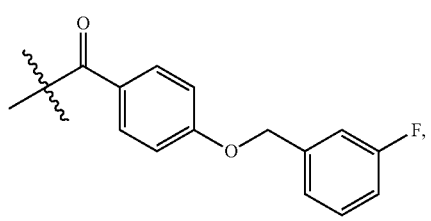
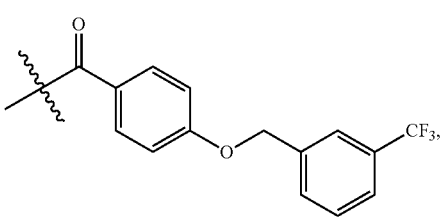
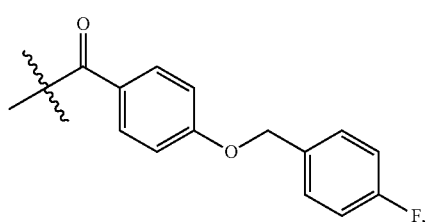
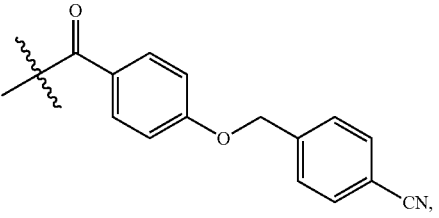
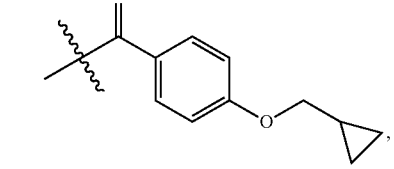
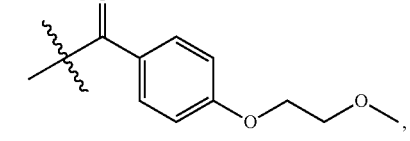
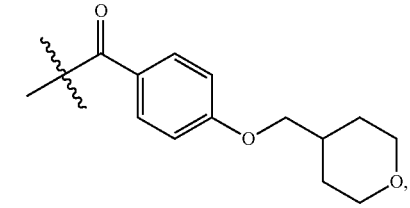
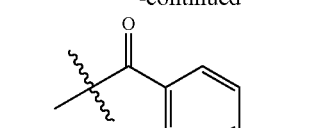
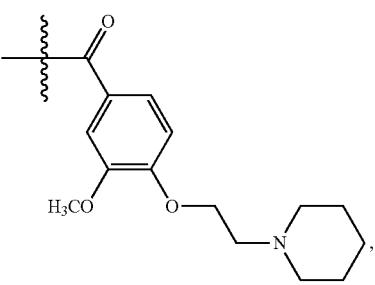
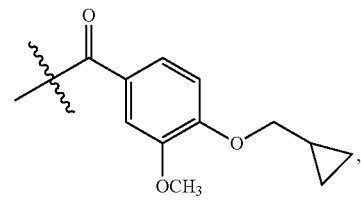
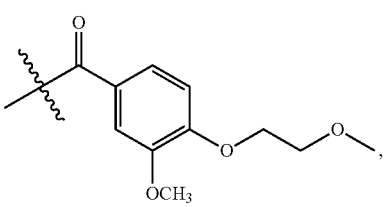
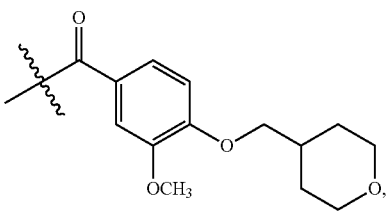
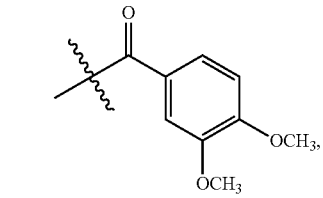
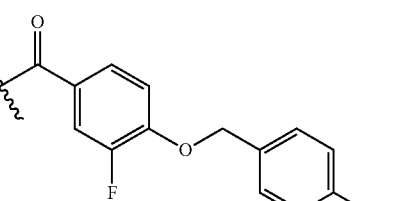
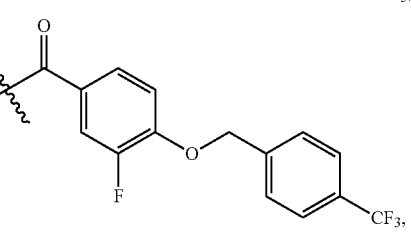

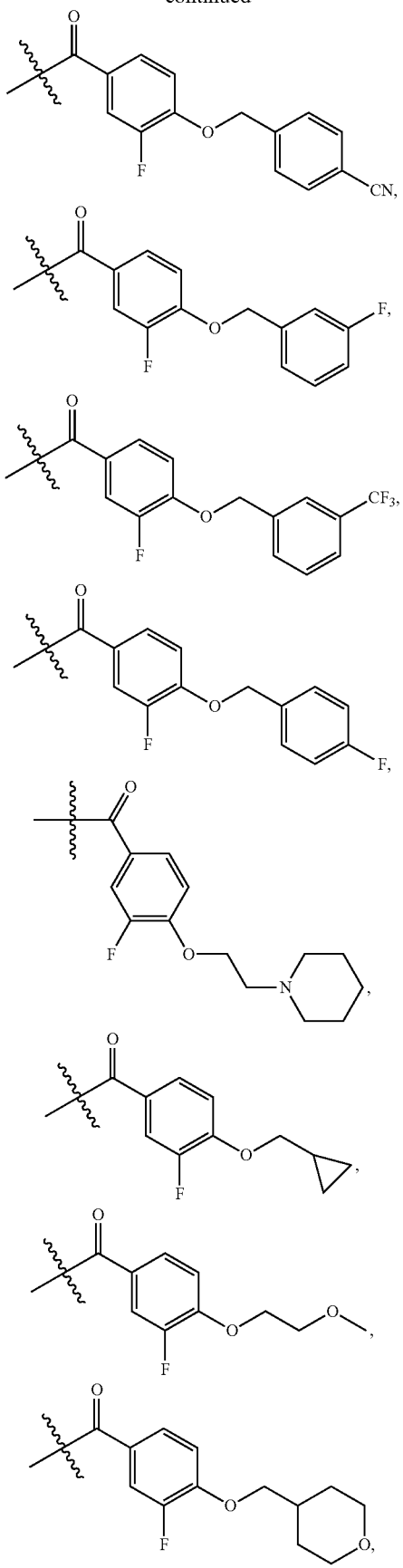

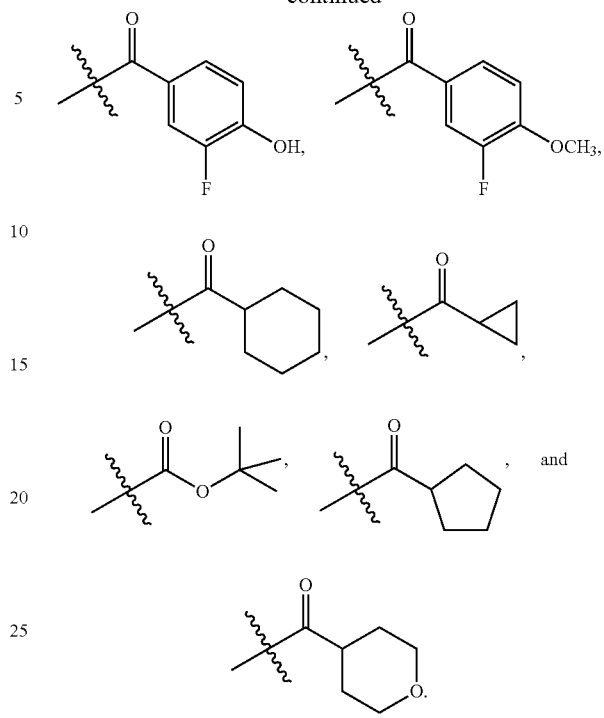

Such compounds are not limited to a particular chemical moiety for R3. In some embodiments, R3 is Hydrogen or CH3.

In some embodiments, the following compounds are contemplated for Formulas I and II:

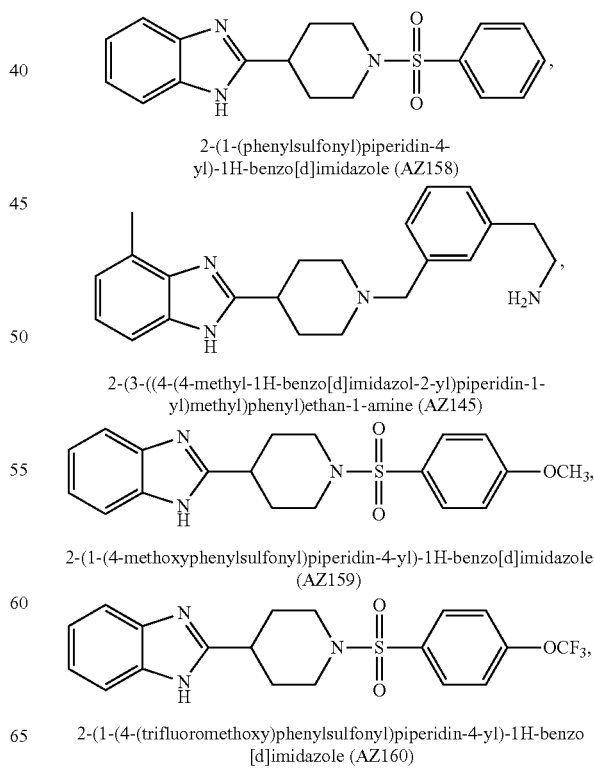

2-(1-(phenylsulfonyl)piperidin-4-yl)-1H-benzo[d]imidazole (AZ158)

2-(3-((4-(4-methyl-1H-benzo[d]imidazol-2-yl)piperidin-1-yl)methyl)phenyl)ethan-1-amine (AZ145)

2-(1-(4-methoxyphenylsulfonyl)piperidin-4-yl)-1H-benzo[d]imidazole (AZ159)

2-(1-(4-(trifluoromethoxy)phenylsulfonyl)piperidin-4-yl)-1H-benzo[d]imidazole (AZ160)

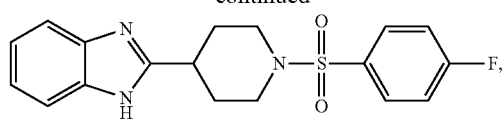

2-(1-(4-fluorophenylsulfonyl)piperidin-4-yl)-1H-benzo[d]imidazole (AZ161)

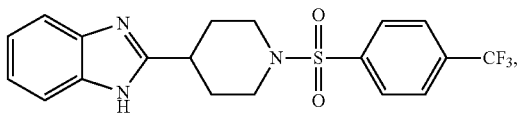

2-(1-(4-(trifluoromethyl)phenylsulfonyl)piperidin-4-yl)-1H-benzo[d]imidazole (AZ162)

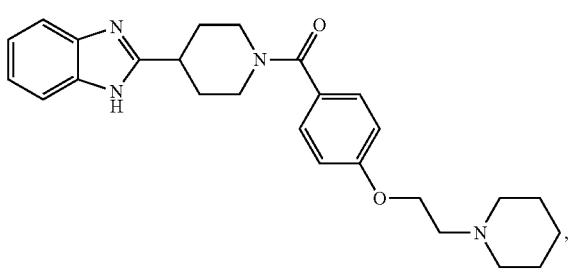

(4-(1H-benzo[d]imidazol-2-yl)piperidin-1-yl)(4-(2-(piperidin-1-yl)ethoxy)phenyl)methanone (AZ168)

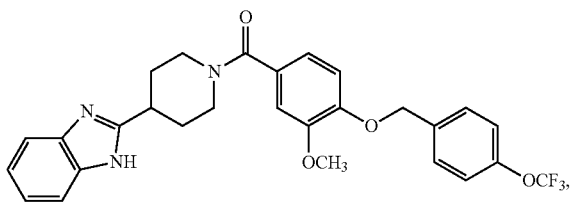

(4-(1H-benzo[d]imidazol-2-yl)piperidin-1-yl)(3-methoxy-4-(4-(trifluoromethoxy)benzyloxy)phenyl)methanone (AZ170)

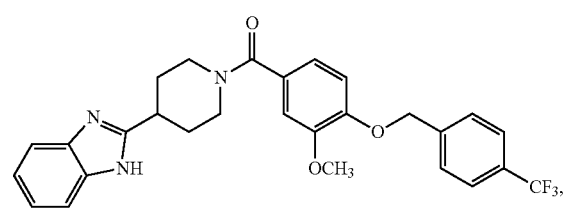

(4-(1H-benzo[d]imidazol-2-yl)piperidin-1-yl)(3-methoxy-4-(4-(trifluoromethoxy)benzyloxy)phenyl)methanone (AZ172)

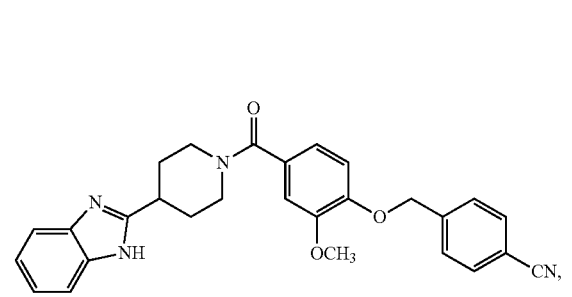

4-((4-(4-(1H-benzo[d]imidazol-2-yl)piperidine-1-carbonyl)-2-methoxyphenoxy)methyl)benzonitrile (AZ173)

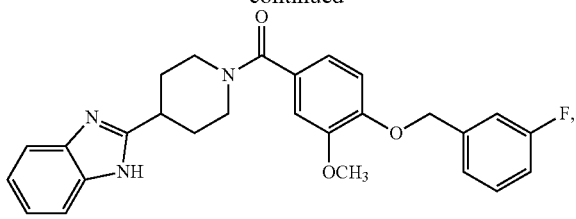

(4-(1H-benzo[d]imidazol-2-yl)piperidin-1-yl)(4-(3-fluorobenzyloxy)-3-methoxyphenyl)methanone (AZ177)

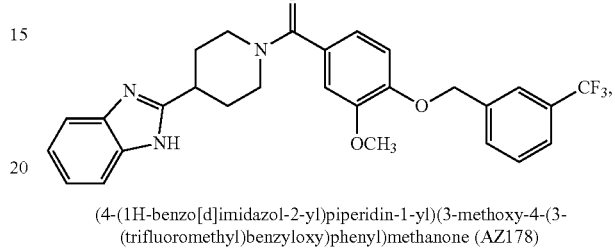

(4-(1H-benzo[d]imidazol-2-yl)piperidin-1-yl)(3-methoxy-4-(3-(trifluoromethyl)benzyloxy)phenyl)methanone (AZ178)

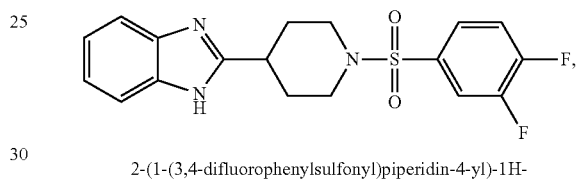

2-(1-(3,4-difluorophenylsulfonyl)piperidin-4-yl)-1H-benzo[d]imidazole (AZ190)

2-(1-(4-phenoxyphenylsulfonyl)piperidin-4-yl)-1H-benzo[d]imizadole (AZ192)

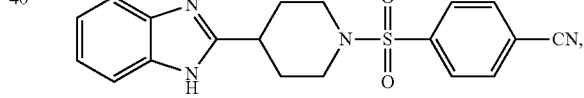

4-(4-(1H-benzo[d]imidazol-2-yl)piperidin-1-ylsulfonyl)benzonitrile (AZ193)

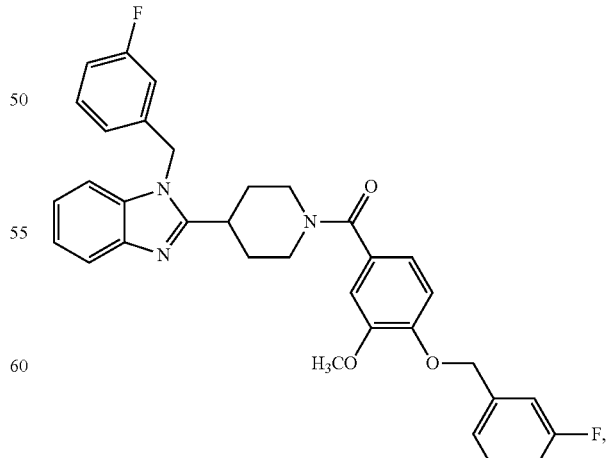

(4-(1-(3-fluorobenzyl)-1H-benzo[d]imidazol-2-yl)piperidin-1-yl)(4-(3-fluorobenzyloxy)-3-methoxyphenyl)methanone (AZ194)

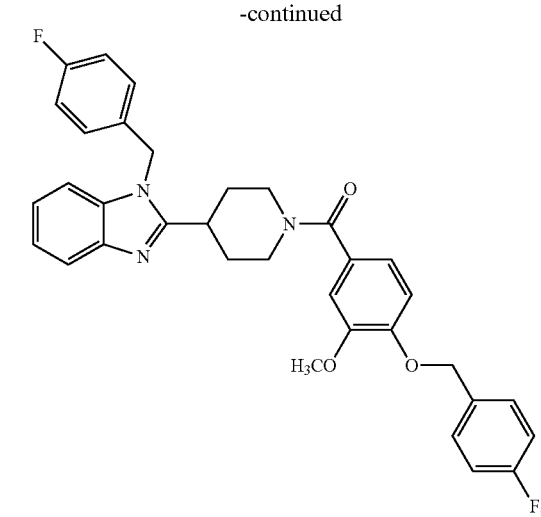

(4-(1-(4-fluorobenzyl)-1H-benzo[d]imidazol-2-yl)piperidin-1-yl)(4-(4-fluorobenzyloxy)-3-methoxyphenyl)methanone (AZ195)

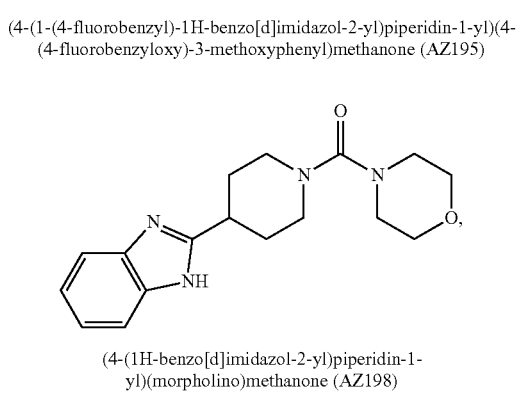

(4-(1H-benzo[d]imidazol-2-yl)piperidin-1-yl)(morpholino)methanone (AZ198)

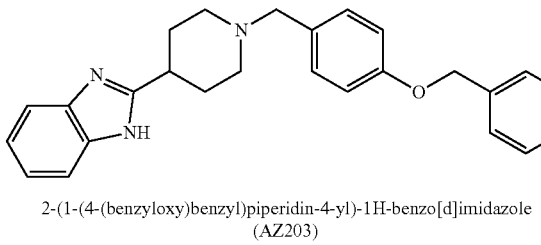

2-(1-(4-(benzyloxy)benzyl)piperidin-4-yl)-1H-benzo[d]imidazole (AZ203)

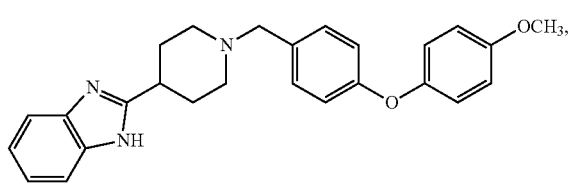

2-(1-(4-(4-methoxyphenoxy)benzyl)piperidin-4-yl)-1H-benzo[d]imidazole (AZ205)

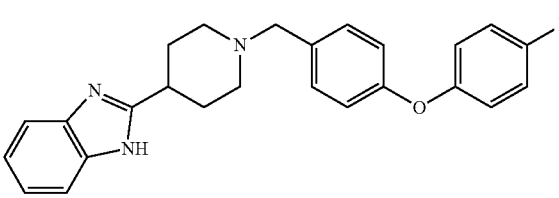

2-(1-(4-(4-fluorophenoxy)benzyl)piperidin-4-yl)-1H-benzo[d]imidazole (AZ206)

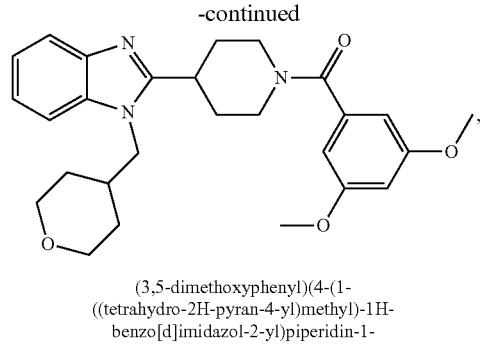

(3,5-dimethoxyphenyl)(4-(1-((tetrahydro-2H-pyran-4-yl)methyl)-1H-benzo[d]imidazol-2-yl)piperidin-1-yl)methanone

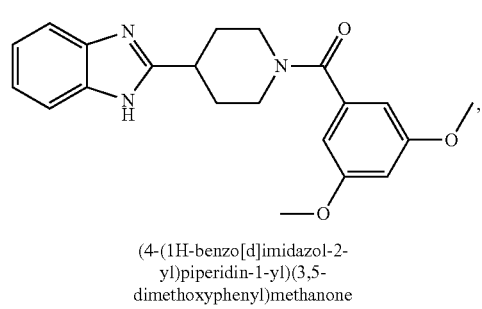

(4-(1H-benzo[d]imidazol-2-yl)piperidin-1-yl)(3,5-dimethoxyphenyl)methanone

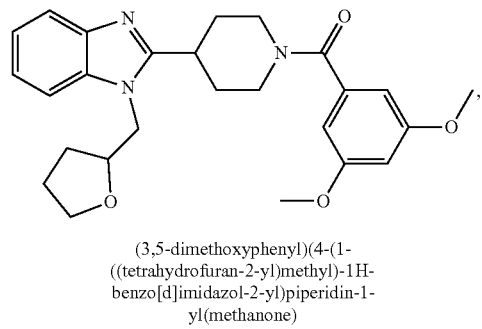

(3,5-dimethoxyphenyl)(4-(1-((tetrahydrofuran-2-yl)methyl)-1H-benzo[d]imidazol-2-yl)piperidin-1-yl(methanone)

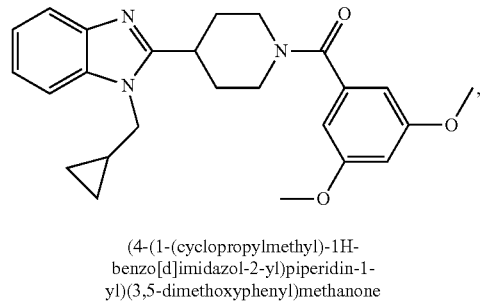

(4-(1-(cyclopropylmethyl)-1H-benzo[d]imidazol-2-yl)piperidin-1-yl)(3,5-dimethoxyphenyl)methanone

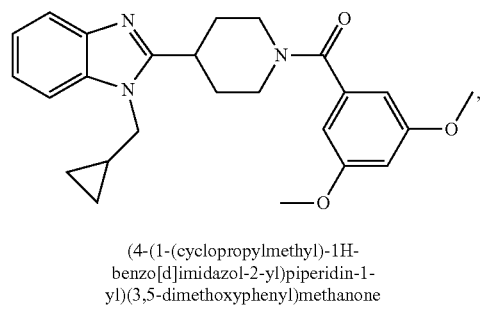

(4-(1-(cyclopropylmethyl)-1H-benzo[d]imidazol-2-yl)piperidin-1-yl)(3,5-dimethoxyphenyl)methanone -continued

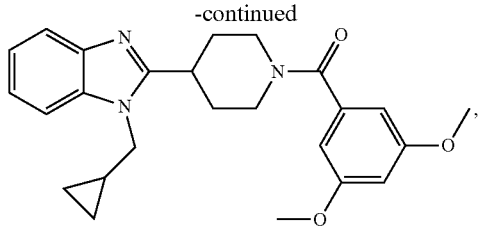

(4-(1-(cyclopropylmethyl)-1H-
benzo[d]imidazol-2-yl)piperidin-1-
yl)(3,5-dimethoxyphenyl)methanone

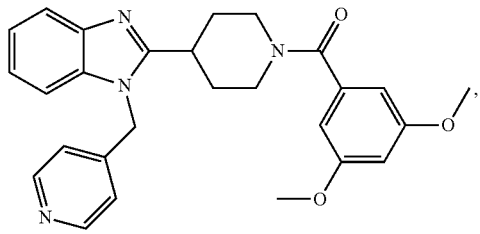

(3,5-dimethoxyphenyl)(4-(1-(pyridin-4-
ylmethyl)-1H-benzo[d]imidazol-2-
yl)piperidin-1-yl)methanone

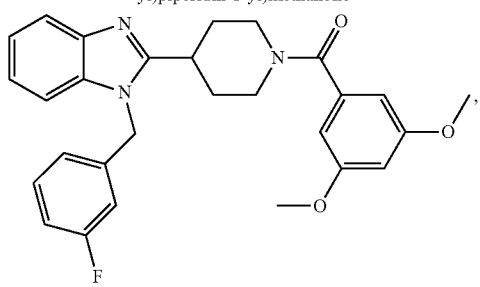

(3,5-dimethoxyphenyl)(4-(1-(3-
fluorobenzyl)-1H-benzo[d]imidazol-2-
yl)piperidin-1-yl)methanone

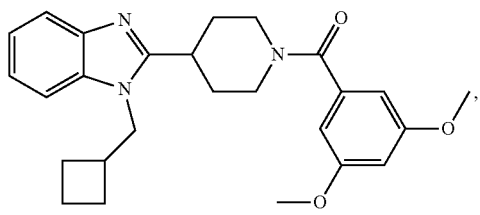

(4-(1-(cyclobutylmethyl)-1H-
benzo[d]imdazol-2-yl)piperidin-1-
yl)(3,5-dimethoxyphenyl)methanone

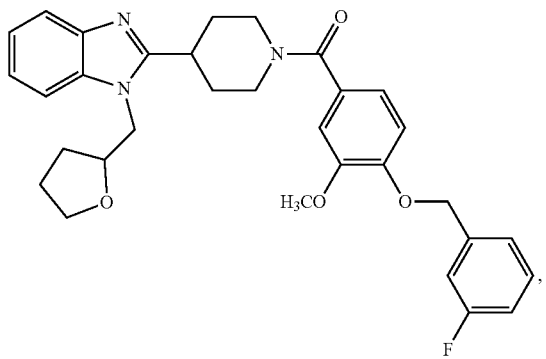

(4-((3-fluorobenzyl)oxy)-3-methoxyphenyl)(4-(1-
((tetrahydrofuran-2-yl)methyl)-1H-benzo[d]imidazol-2-
yl)piperidin-1-yl)methanone

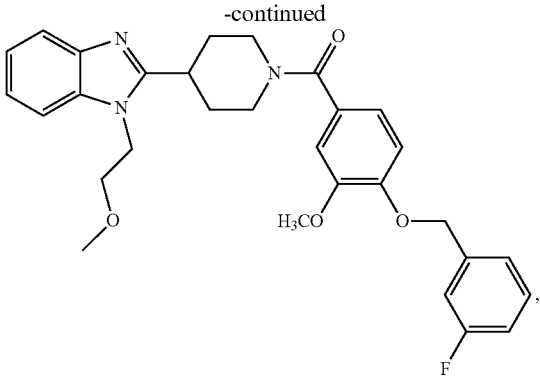

(4-((3-fluorobenzyl)oxy)-3-methoxyphenyl)(4-(1-(2-
methoxyethyl)-1H-benzo[d]imidazol-2-yl)piperidin-1-
yl)methanone

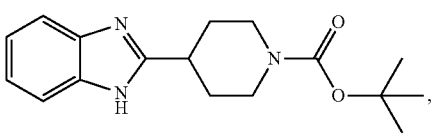

tert-butyl 4-(1H-benzo[d]imidazol-2-
yl)piperidine-1-carboxylate

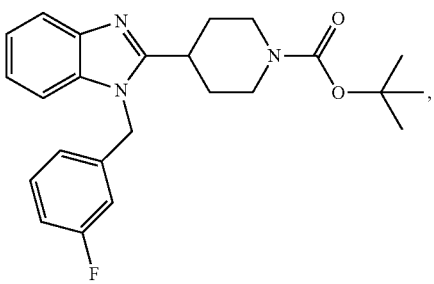

tert-butyl 4-(1-(3-fluorobenzyl)-1H-benzo[d]imidazol-2-yl)
piperidine-1-carboxylate

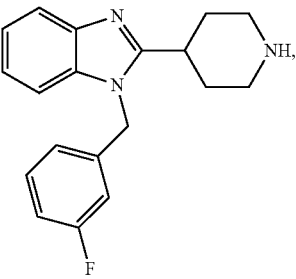

1-(3-fluorobenzyl)-2-(piperidin-4-yl)-
1H-benzo[d]imidazole

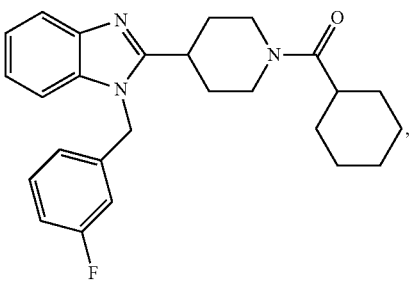

cyclohexyl(4-(1-(3-fluorobenzyl)-1H-benzo[d]imidazol-2-yl) piperidin-
1-yl)methanone

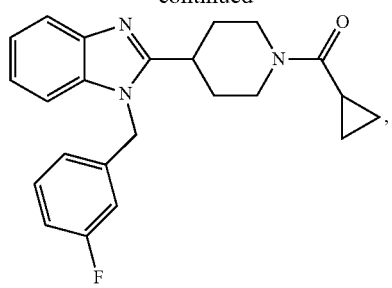

cyclopropyl(4-(1-(3-fluorobenzyl)-1H-benzo[d]
imidazol-2-yl) piperidin-1-yl)methanone

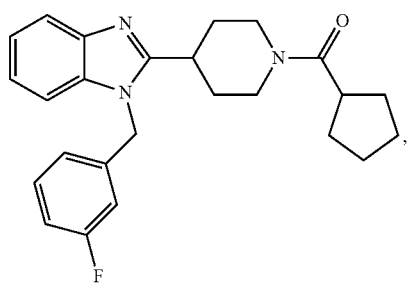

cyclopentyl(4-(1-(3-fluorobenzyl)-1H-benzo[d]imidazol-
2-yl) piperidin-1-yl)methanone

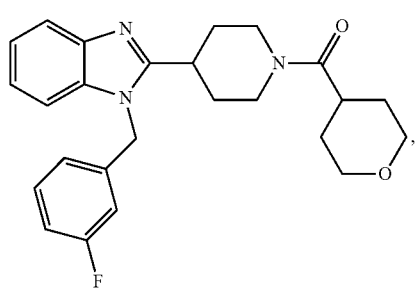

(4-(1-(3-fluorobenzyl)-1H-benzo[d]imidazol-2-yl)
piperidin-1-yl)(tetrahydro-2H-pyran-4-yl)methanone

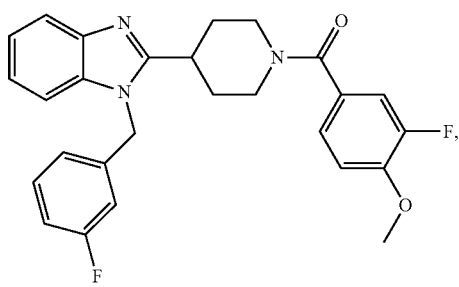

(3-fluoro-4-methoxyphenyl)(4-(1-(3-fluorobenzyl)-
1H-benzo[d]imidazole-2-yl)piperidin-1-
yl)methanone

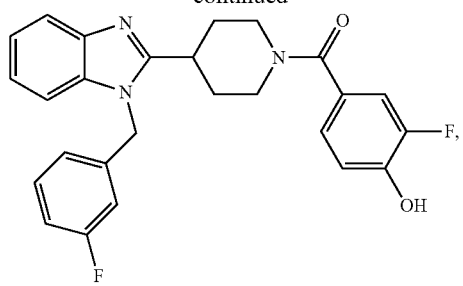

(3-fluoro-4-hydroxyphenyl)(4-(1-(3-fluorobenzyl)-
1H-benzo[d]imidazol-2-yl)piperidin-1-yl)
methanone

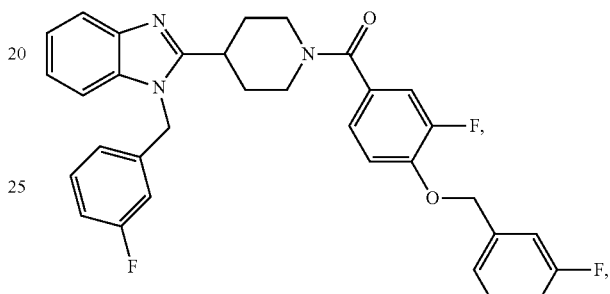

(3-fluoro-4-((3-fluorobenzyl)oxy)phenyl)(4-(1-(3-fluorobenzyl)-
1H-benzo[d]imidazol-2-yl(piperidin-1-yl)methanone

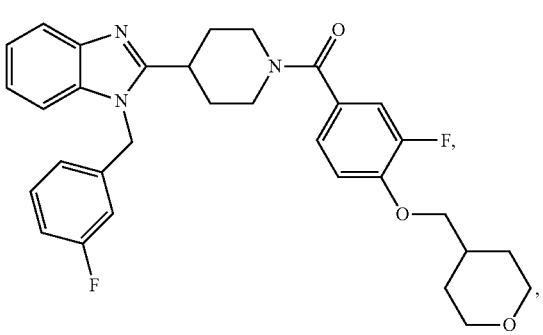

(3-fluoro-4-((tetrahydro-2H-pyran-4-yl)methoxy)phenyl)(4-(1-
(3-fluorobenzyl)-1H-benzo[d]imidazol-2-yl)piperidin-1-yl)
methanone

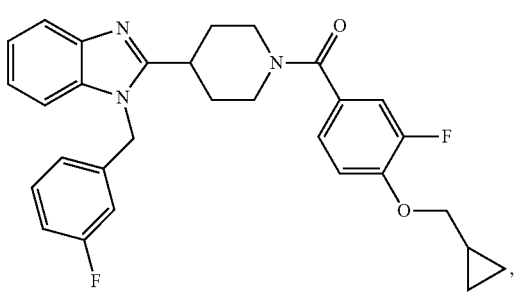

(4-(cyclopropylmethoxy)-3-fluorophenyl)(4-(1-(3-fluorobenzyl-
1H-benzo[d]imidazol-2-yl)piperidin-1-yl)methanone -continued

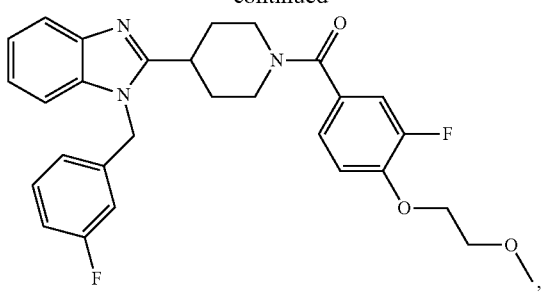

(3-fluoro-4-(2-methoxyethoxy)phenyl)(4-(1-(3-fluorobenzyl)-
1H-benzo[d]piperidin-1-yl)methanone

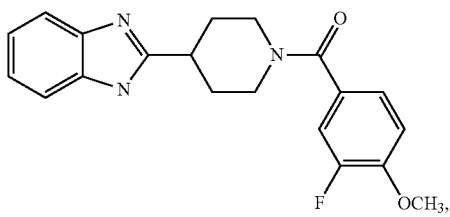

(4-(1H-benzo[d]imidazol-2-yl)piperidin-1-yl)(3-fluoro-
4-methoxyphenyl)methanone

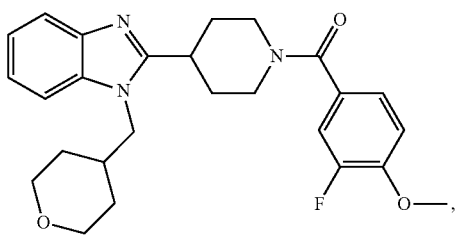

(3-fluoro-4-methoxyphenyl)(4-(1-
((tetrahydro-2H-pyran-4-yl)methyl)-1H-
benzo[d]imidazol-2-yl)piperidin-1-
yl)methanone

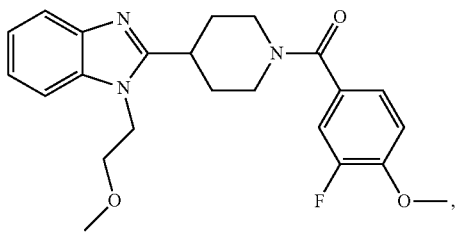

(3-fluoro-4-methoxyphenyl)(4-(1-(2-
methoxyethyl)-1H-benzo[d]imidazol-2-
yl)piperidin-1-yl)methanone

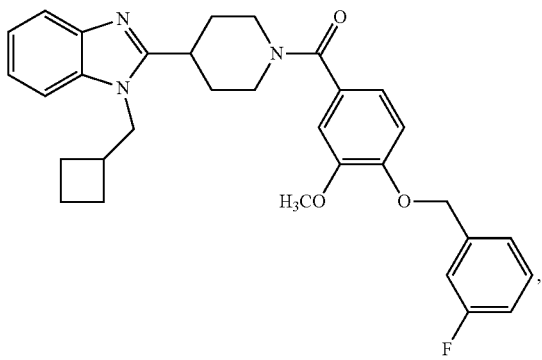

(4-(1-(cyclobutylmethyl)-1H-benzo[d]imidazol-2-yl)piperidin-1-
yl)(4-((3-fluorobenzyl)oxy)-3-methoxyphenyl)methanone

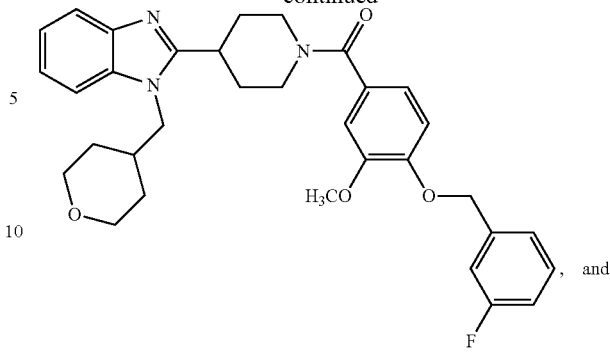

, and (4-((3-fluorobenzyl)oxy)-3-methoxyphenyl)(4-(1-((tetrahydro-
2H-pyran-4-yl)methyl)-1H-benzo[d]imidazol-2-yl)piperidin-1-
yl)methanone

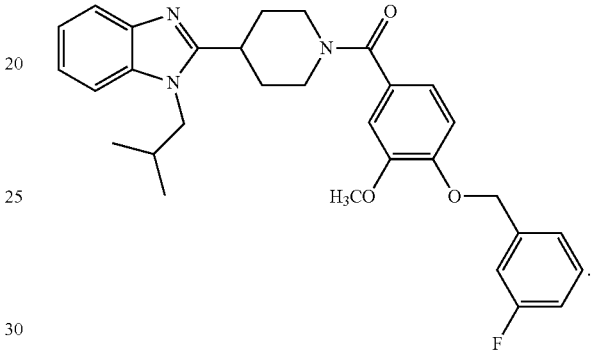

(4-((3-fluorobenzyl)oxy)-3-methoxyphenyl)(4-(1-isobutyl-1H-
benzo[d]imidazol-2-yl)piperidin-1-yl)methanone Moreover, the present invention provides pharmaceutical compositions comprising one or more of the compounds described herein.

The present invention further provides methods for inhibiting and/or alleviating itch and/or pain and/or anosmia and/or a migraine event related to Nav1.7 activity through administration of therapeutic amounts of one or more of the compounds described herein to a subject (e.g., a human patient) suffering from itch, pain (e.g., acute, inflammatory and/or neuropathic pain), anosmia, and/or a migraine event related to Nav1.7 activity. The methods are not limited to a particular type of itch, pain, anosmia, and/or a migraine event related to Navy 1.7 activity. In some embodiments, the pain related to Nav1.7 activity is neuropathic pain. In some embodiments, administration of such compounds results in inhibition of SUMOylation of CRMP2 resulting in antagonism of Nav1.7 activity. In some embodiments, such compounds are co-administered with one or more pain relief agents.

Accordingly, the present invention further provides methods for inducing endogenous opioid upregulation and/or expression through administration of therapeutic amounts of one or more of the compounds described herein. Such methods are not limited to upregulation of a particular type or kind of endogenous opioid. In some embodiments, the endogenous opioid is proenkephalin. In some embodiments, such methods are further used in treating a subject (e.g., a mammalian subject) (e.g., a human subject) suffering from itch and/or pain related to Nav1.7 activity (e.g., acute, inflammatory and/or neuropathic pain). The methods are not limited to a particular type of pain or itch related to Nav1.7 activity. In some embodiments, the pain related to Nav1.7 activity is neuropathic pain. In some embodiments, administration of such compounds results in inhibition of SUMOylation of CRMP2 resulting in antagonism of Nav1.7 activity. In some embodiments, administration of such compounds results in inhibition of SUMOylation of CRMP2 resulting in antagonism of Navy 1.7 activity through preventing binding between Ubc9 and a CRMP2 binding pocket characterized by one or more of the following CRMP2 amino acid residues: Lys23, Val25, Ser30, Tyr32, Met64, Ser319, Ser322, Trp366, Val370, Val371, Gly373, Lys374, Met375, Asp376, Glu377, Glu377, Gln379, Pro414, Asp415, Ser416, Val417, and Arg440. In some embodiments, such compounds are co-administered with one or more pain relief agents.

The present invention provides methods of treating, ameliorating, or preventing itch, anosmia, a migraine event, or pain related to Nav1.7 activity (e.g., acute, inflammatory and/or neuropathic pain) in a patient (e.g., a human patient) comprising administering to the patient a therapeutically effective amount of a pharmaceutical composition comprising one or more the compounds described herein.

The present invention provides methods of upregulating endogenous opioid (e.g., proenkephalin) expression and/or activity in a patient comprising administering to said patient (e.g., a human patient) a therapeutically effective amount of a pharmaceutical composition comprising one or more the compounds described herein.

Moreover, the present invention provides kits comprising one or more of such compounds. In some embodiments, the present invention provides kits comprising such a compound and instructions for administering the compound to a patient experiencing or at risk for experiencing itch and/or pain related to Nav1.7 activity (e.g., acute, inflammatory and neuropathic pain, and itch) and/or in need of endogenous opioid upregulation.

In certain embodiments, the present invention provides methods for the identification of compounds with a molecular weight in the range 400 to 750 which hinder (e.g., inhibit, prevent, diminish) binding between CRMP2 and Ubc9, comprising selecting compounds shown to have one or more of the following abilities:

a) form a hydrogen bonding interaction in which the compound accepts a hydrogen bond from the backbone NH— group of Glu377;

b) form a hydrogen bonding interaction in which the compound accepts a hydrogen bond from the sidechain —NH2 group of Lys23;

c) form a hydrogen bonding interaction in which the compound donates a hydrogen bond to the backbone CO— group of Gly373;

d) form a hydrogen bonding interaction in which the compound donates a hydrogen bond to the sidechain —COOH group of Glu377;

e) form a hydrogen bonding interaction in which the compound accepts a hydrogen bond from the sidechain guanidine group of Arg440;

f) form a hydrogen bonding interaction in which the compound donates a hydrogen bond to the sidechain COOH— group of Asp376;

g) form electrostatic interaction with the sidechain —NH2 group of Lys23; and h) form electrostatic interaction with the sidechain —COOH group of Asp376; and which are also able to form a Van der Waals interaction with a lipophilic binding region of a binding pocket such that one or more heavy atoms of the said compounds lie within a 6 Å range of any of the heavy atoms of the following CRMP2 residues which define the binding pocket: Lys23, Val25, Ser30, Tyr32, Met64, Ser319, Ser322, Trp366, Val370, Val371, Gly373, Lys374, Met375, Asp376, Glu377, Gln379, Pro414, Asp415, Ser416, Val417 and Arg440.

In some embodiments, compounds identified with such methods are further tested for the ability to inhibit binding between Ubc9 in a saturation transfer difference nuclear magnetic resonance (STD-NMR) assay.

In some embodiments, compounds identified with such methods are further tested for the ability to bind a CRMP2 binding pocket characterized by one or more of the following CRMP2 amino acid residues: Lys23, Val25, Ser30, Tyr32, Met64, Ser319, Ser322, Trp366, Val370, Val371, Gly373, Lys374, Met375, Asp376, Glu377, Glu377, Gln379, Pro414, Asp415, Ser416, Val417, and Arg440.

In some embodiments, compounds identified with such methods are further tested for the ability to inhibit interaction between CRMP2 and Ubc9.

BRIEF DESCRIPTION OF THE DRAWINGS

FIGS. 5-24 provide modeling images separately depicting compounds described herein (AZ145, AZ159, AZ160, AZ161, AZ162, AZ168, AZ170, AZ172, AZ173, AZ177, AZ178, AZ190, AZ192, AZ193, AZ194, AZ195, AZ198, AZ203, AZ205, and AZ206) within the CRMP2 binding pocket and the positioning of relevant amino acids within the CRMP2 binding pocket around the respective compound.

DEFINITIONS

Figure 1:
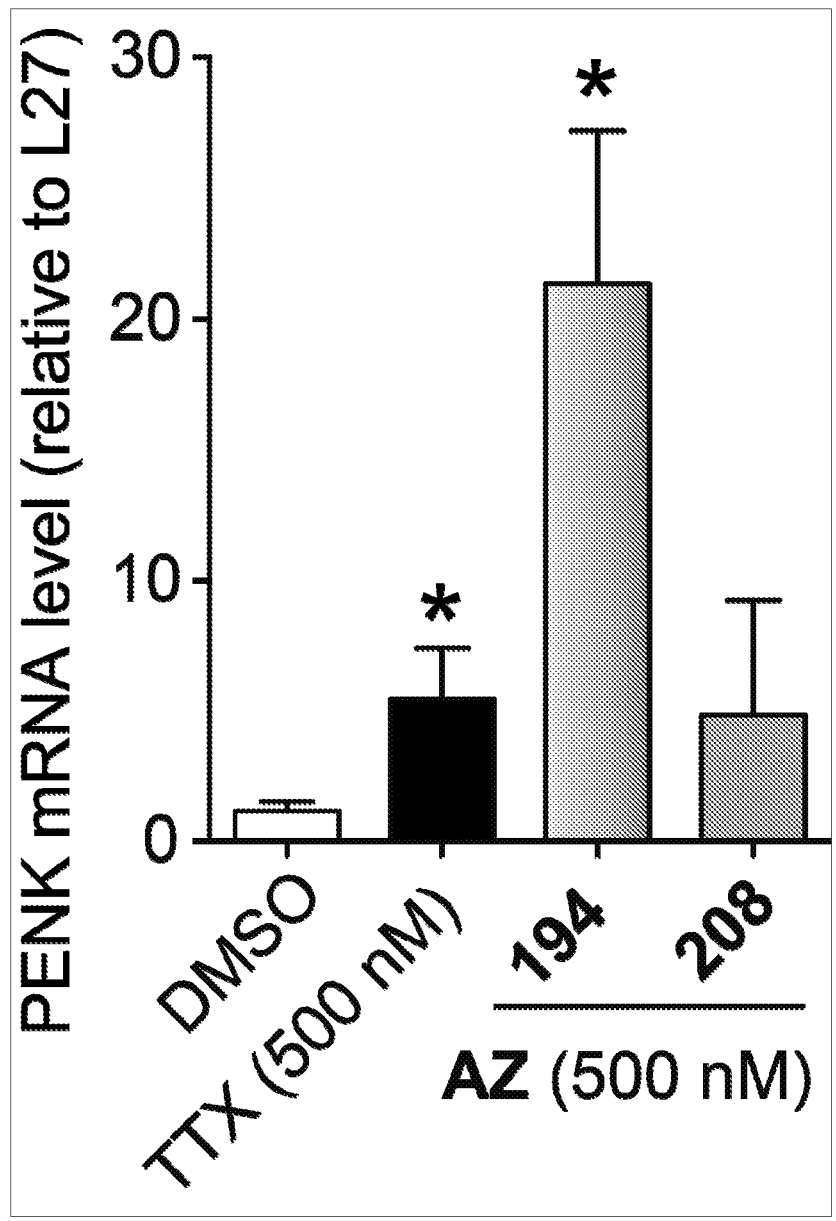
FIG. 1: demonstrates that blocking Nay channels with TTX or AZ194 upregulates Penk expression. Exposure (6 hr) to TTX or AZ194, but not AZ208, increased Penk mRNA is cultured rat DRG neurons (n=4 per group). Data is normalized to L27 ribosomal RNA.

As used herein the term "SUMOylation" refers to the post-translational modifications of cellular proteins by the small ubiquitin-like modifier (SUMO) family of proteins. The SUMOylation requires multiple steps that are catalyzed by three types of SUMOylation enzymes: activating enzyme E1 (made up of two subunits, SAE1 and SAE2/Uba2), conjugating enzyme E2 (Ubc9), and one of approximately ten E3 ligases.

The term "prodrug" as used herein, refers to a pharmacologically inactive derivative of a parent "drug" molecule that requires biotransformation (e.g., either spontaneous or enzymatic) within the target physiological system to release, or to convert (e.g., enzymatically, physiologically, mechanically, electromagnetically) the prodrug into the active drug. Prodrugs are designed to overcome problems associated with stability, water solubility, toxicity, lack of specificity, or limited bioavailability. Exemplary prodrugs comprise an active drug molecule itself and a chemical masking group (e.g., a group that reversibly suppresses the activity of the drug). Some prodrugs are variations or derivatives of compounds that have groups cleavable under metabolic conditions. Prodrugs can be readily prepared from the parent compounds using methods known in the art, such as those described in A Textbook of Drug Design and Development, Krogsgaard-Larsen and H. Bundgaard (eds.), Gordon & Breach, 1991, particularly Chapter 5: "Design and Applications of Prodrugs"; Design of Prodrugs, H. Bundgaard (ed.), Elsevier, 1985; Prodrugs: Topical and Ocular Drug Delivery, K. B. Sloan (ed.), Marcel Dekker, 1998; Methods in Enzymology, K. Widder et al. (eds.), Vol. 42, Academic Press, 1985, particularly pp. 309-396; Burger's Medicinal Chemistry and Drug Discovery, 5th Ed., M. Wolff (ed.), John Wiley & Sons, 1995, particularly Vol. 1 and pp. 172-178 and pp. 949-982; Pro-Drugs as Novel Delivery Systems, T. Higuchi and V. Stella (eds.), Am. Chem. Soc., 1975; and Bioreversible Carriers in Drug Design, E. B. Roche (ed.), Elsevier, 1987.

Exemplary prodrugs become pharmaceutically active in vivo or in vitro when they undergo solvolysis under physiological conditions or undergo enzymatic degradation or other biochemical transformation (e.g., phosphorylation, hydrogenation, dehydrogenation, glycosylation). Prodrugs often offer advantages of water solubility, tissue compatibility, or delayed release in the mammalian organism. (See e.g., Bundgard, Design of Prodrugs, pp. 7-9, 21-24, Elsevier, Amsterdam (1985); and Silverman, The Organic Chemistry of Drug Design and Drug Action, pp. 352-401, Academic Press, San Diego, Calif. (1992)). Common prodrugs include acid derivatives such as esters prepared by reaction of parent acids with a suitable alcohol (e.g., a lower alkanol) or esters prepared by reaction of parent alcohol with a suitable carboxylic acid, (e.g., an amino acid), amides prepared by reaction of the parent acid compound with an amine, basic groups reacted to form an acylated base derivative (e.g., a lower alkylamide), or phosphorus-containing derivatives, e.g., phosphate, phosphonate, and phosphoramidate esters, including cyclic phosphate, phosphonate, and phosphoramidate (see, e.g., US Patent Application Publication No. US 2007/0249564 A1; herein incorporated by reference in its entirety).

The term "pharmaceutically acceptable salt" as used herein, refers to any salt (e.g., obtained by reaction with an acid or a base) of a compound of the present invention that is physiologically tolerated in the target animal (e.g., a mammal). Salts of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, mesylate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

The term "solvate" as used herein, refers to the physical association of a compound of the invention with one or more solvent molecules, whether organic or inorganic. This physical association often includes hydrogen bonding. In certain instances, the solvate is capable of isolation, for example, when one or more solvate molecules are incorporated in the crystal lattice of the crystalline solid. "Solvate" encompasses both solution-phase and isolable solvates. Exemplary solvates include hydrates, ethanolates, and methanolates.

The term "therapeutically effective amount," as used herein, refers to that amount of the therapeutic agent sufficient to result in amelioration of one or more symptoms of a disorder, or prevent advancement of a disorder, or cause regression of the disorder. For example, with respect to the treatment of pain related to Nav1.7 activity, in one embodiment, a therapeutically effective amount will refer to the amount of a therapeutic agent that decreases the amount of pain experienced by a patient by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

The term "pharmaceutically acceptable carrier" or "pharmaceutically acceptable vehicle" encompasses any of the standard pharmaceutical carriers, solvents, surfactants, or vehicles. Suitable pharmaceutically acceptable vehicles include aqueous vehicles and nonaqueous vehicles. Standard pharmaceutical carriers and their formulations are described in Remington's Pharmaceutical Sciences, Mack Publishing Co., Easton, Pa., 19th ed. 1995.

DETAILED DESCRIPTION OF THE INVENTION

Experiments conducted during the course of developing embodiments for the present invention investigated the concept that inhibiting SUMOylation of CRMP2 would result in inhibition of Nav1.7 activity. Moreover, such experiments investigated the concept that such inhibition of Nav1.7 activity would further result in treating, ameliorating, or preventing itch and/or pain related to Nav1.7 activity (e.g., acute, inflammatory and/or neuropathic pain) in a patient (e.g., a human patient). Such experiments resulted in the generation of a new class of small-molecules having a piperidinyl-benzoimidazole structure that inhibit SUMOylation of CRMP2, thereby inhibiting Nav1.7 activity, and as such, inhibit or alleviate itch and/or pain related to Nav1.7 activity (e.g., acute, inflammatory, and/or neuropathic pain).

Experiments conducted during the course of developing embodiments for the present invention further determined that such small-molecules having a piperidinyl-benzoimidazole are capable of upregulating endogenous opioid expression (e.g., mRNA expression) within a mammalian subject. Indeed, such experiments demonstrated that administration of such compounds

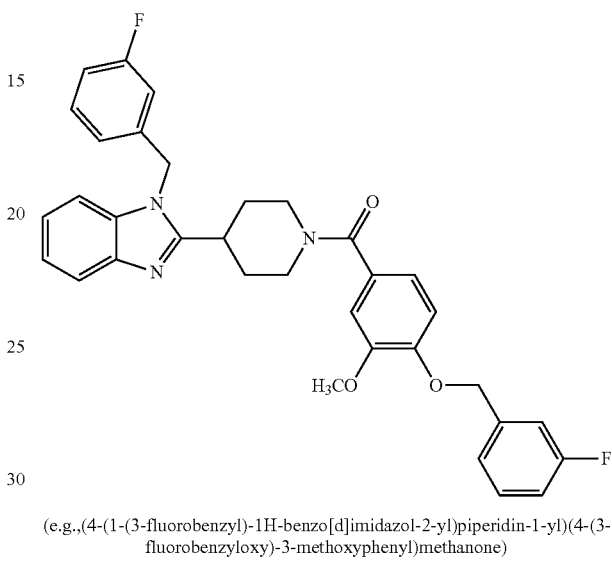

(e.g.,(4-(1-(3-fluorobenzyl)-1H-benzo[d]imidazol-2-yl)piperidin-1-yl)(4-(3-fluorobenzyloxy)-3-methoxyphenyl)methanone)

resulted in upregulation of proenkephalin mRNA levels simultaneous with inhibition of SUMOylation of CRMP2.

Experiments conducted during the course of developing embodiments for the conjugating enzyme Ubc9 (see, Example III). Specifically, such experiments demonstrated the ability of specific small molecule compounds described herein (e.g., AZ145, AZ159, AZ160, AZ161, AZ162, AZ168, AZ170, AZ172, AZ173, AZ177, AZ178, AZ190, AZ192, AZ193, AZ194, AZ195, AZ198, AZ203, AZ205, and AZ206) to bind with CRMP2 through this CRMP2 binding pocket. Such results further indicated that such binding with CRMP2 through the identified CRMP2 binding pocket will inhibit binding between Ubc9 and CRMP2, thereby inhibiting downstream activity dependent upon binding between Ubc9 and CRMP2 (e.g., CRMP2 SUMOylation, Nav1.7 protein expression and activity, pain related to Nav1.7 protein expression and activity). As shown in such FIGS. 5-24, the following amino acids within CRMP2 were shown to be associated with the CRMP2 binding pocket: Lys23, Val25, Ser30, Tyr32, Met64, Ser319, Ser322, Trp366, Val370, Val371, Gly373, Lys374, Met375, Asp376, Glu377, Glu377, Gln379, Pro414, Asp415, Ser416, Val417, and Arg440.

Accordingly, the present invention relates to compounds which function as inhibitors of Nav1.7 activity through inhibiting SUMOylation of CRMP2. The present invention further relates to compounds which function as upregulators of endogenous opioids (e.g., proenkephalin).

The invention further relates to methods of treating, ameliorating, or preventing pain related to Nav1.7 activity in a patient through administering to the patient a compound that inhibits Nav1.7 activity through inhibiting SUMOylation of CRMP2. Pain related to Nav1.7 activity includes, but is not limited to, acute, inflammatory and/or neuropathic pain. The invention further relates to methods of treating, ameliorating, or preventing pain in a subject through administering to the patient a compound that induces endogenous opioid (e.g., proenkephalin) activity and/or expression.

In some embodiments, such compounds are able to inhibit or alleviate such pain and/or increase susceptibility to the pain-relieving effects of other types of therapy through docking within a CRMP2 binding pocket characterized by one or more of the following CRMP2 amino acid residues (Lys23, Val25, Ser30, Tyr32, Met64, Ser319, Ser322, Trp366, Val370, Val371, Gly373, Lys374, Met375, Asp376, Glu377, Glu377, Gln379, Pro414, Asp415, Ser416, Val417, and Arg440) thereby preventing and/or inhibiting binding between CRMP2 and Ubc9, which thereby prevents SUMOylation of CRMP2.

In a particular embodiment, the present invention provides small molecule compounds having a piperidinyl-benzoimidazole structure encompassed within Formula I:

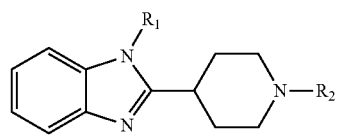

or Formula II:

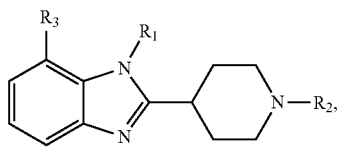

including pharmaceutically acceptable salts, solvates, and/or prodrugs thereof.

Formulas I and II are not limited to a particular chemical moiety for R1, R2 and R3. In some embodiments, the particular chemical moiety for R1, R2 and R3 independently include any chemical moiety that permits the resulting compound to prevent engagement between SUMO and CRMP2. In some embodiments, the particular chemical moiety for R1, R2 and R3 independently include any chemical moiety that permits the resulting compound to prevent SUMOylation of CRMP2. In some embodiments, the particular chemical moiety for R1, R2 and R3 independently include any chemical moiety that permits the resulting compound to indirectly inhibit Nav1.7 related activity. In some embodiments, the particular chemical moiety for R1, R2 and R3 independently include any chemical moiety that permits the resulting compound to inhibit or alleviate itch and/or pain related to Nav1.7 activity (e.g., neuropathic pain). In some embodiments, the particular chemical moiety for R1, R2 and R3 independently include any chemical moiety that permits the resulting compound to inhibit Nav1.7 related activity through preventing SUMOylation of CRMP2, and as such, inhibit or alleviate itch and/or pain related to Nav1.7 activity (e.g., neuropathic pain). In some embodiments, the particular chemical moiety for R1, R2 and R3 independently include any chemical moiety that permits the resulting compound to induce endogenous opioid (e.g., proenkephalin) expression and/or activity. In some embodiments, the particular chemical moiety for R1, R2 and R3 independently include any chemical moiety that permits the resulting compound to bind and/or dock within a CRMP2 binding pocket characterized by one or more of the following CRMP2 amino acid residues: Lys23, Val25, Ser30, Tyr32, Met64, Ser319, Ser322, Trp366, Val370, Val371, Gly373, Lys374, Met375, Asp376, Glu377, Glu377, Gln379, Pro414, Asp415, Ser416, Val417, and Arg440. In some embodiments, the particular chemical moiety for R1, R2 and R3 independently include any chemical moiety that permits the resulting compound to inhibit binding and/or docking of Ubc9 within a CRMP2 binding pocket characterized by one or more of the following CRMP2 amino acid residues: Lys23, Val25, Ser30, Tyr32, Met64, Ser319, Ser322, Trp366, Val370, Val371, Gly373, Lys374, Met375, Asp376, Glu377, Glu377, Gln379, Pro414, Asp415, Ser416, Val417, and Arg440.

Such compounds are not limited to a particular chemical moiety for R1. In some embodiments, R1 is Hydrogen,

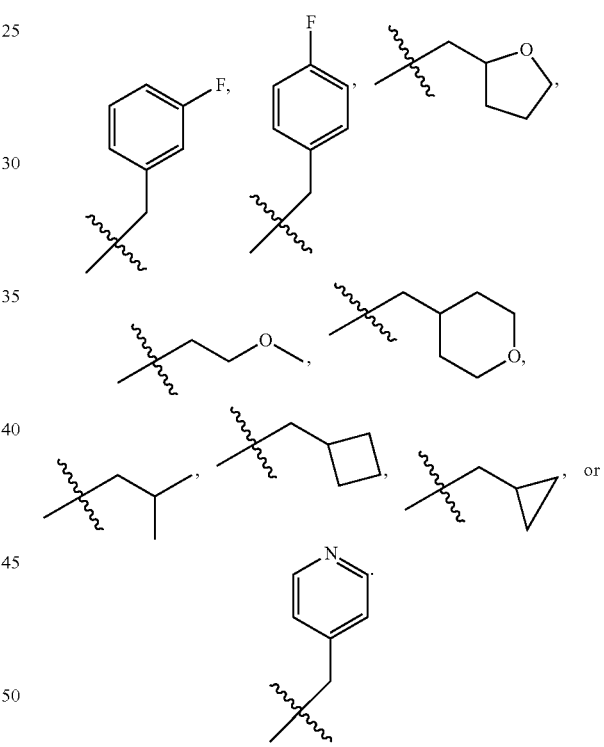

Such compounds are not limited to a particular chemical moiety for R2. In some embodiments, R2 is Hydrogen,

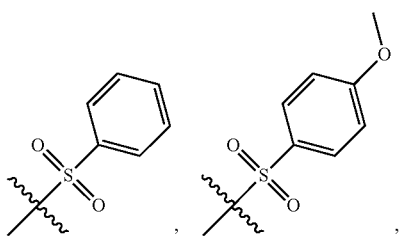

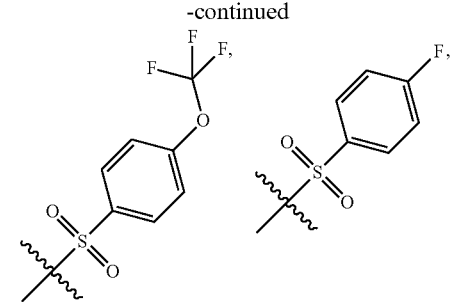
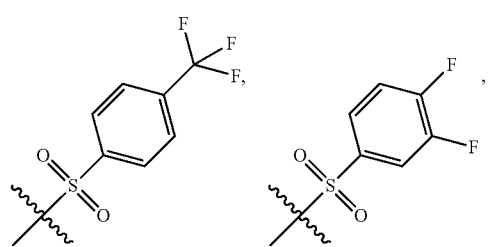
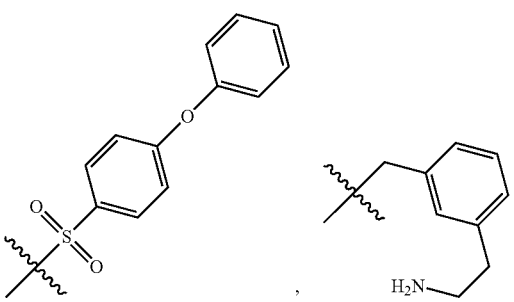
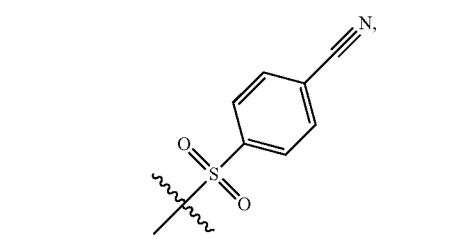
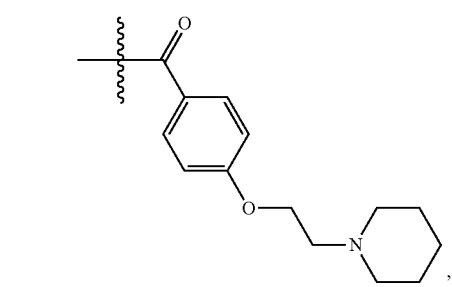
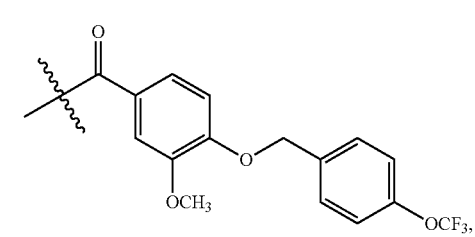
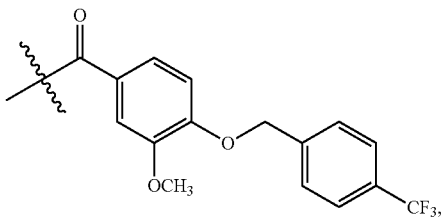
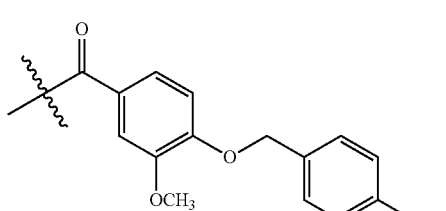
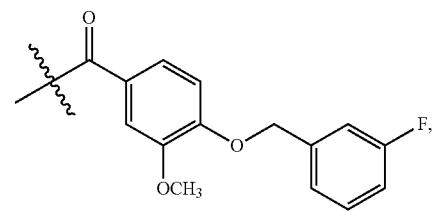
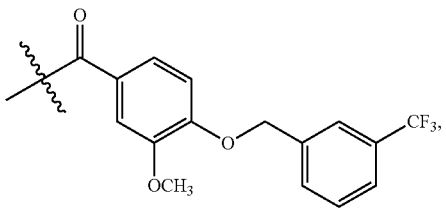
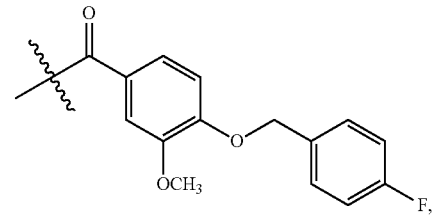
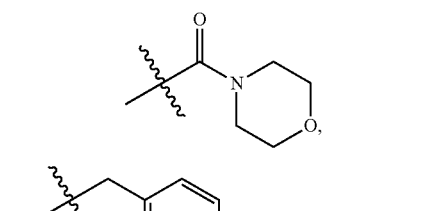
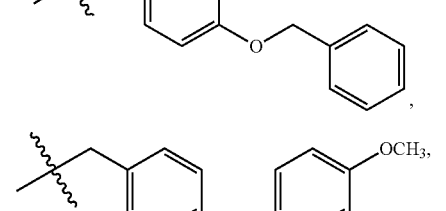
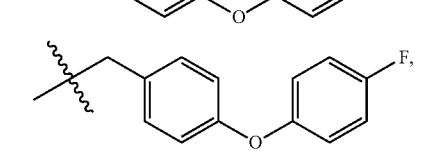

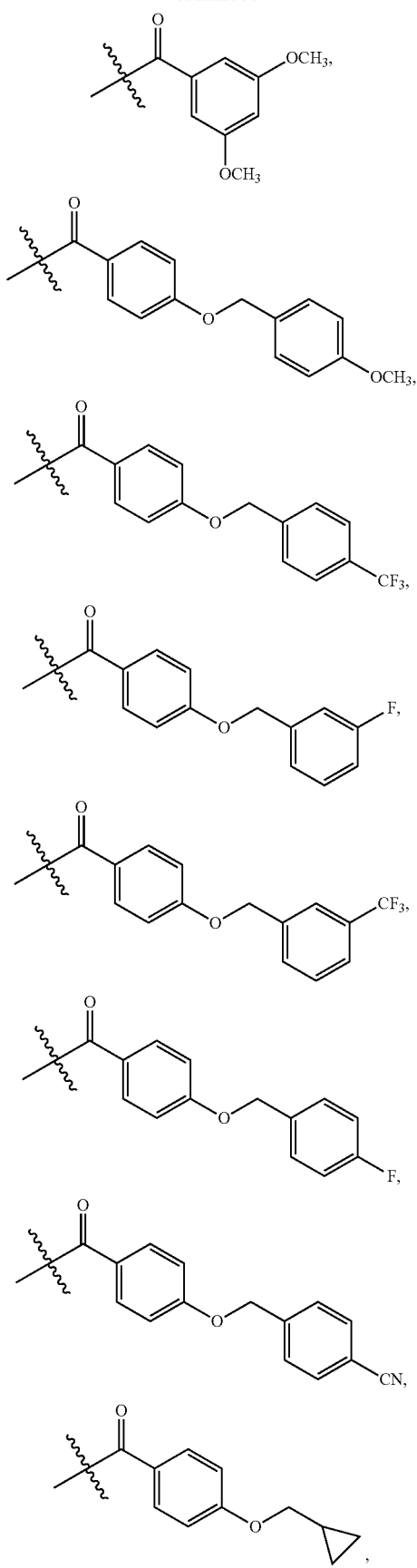
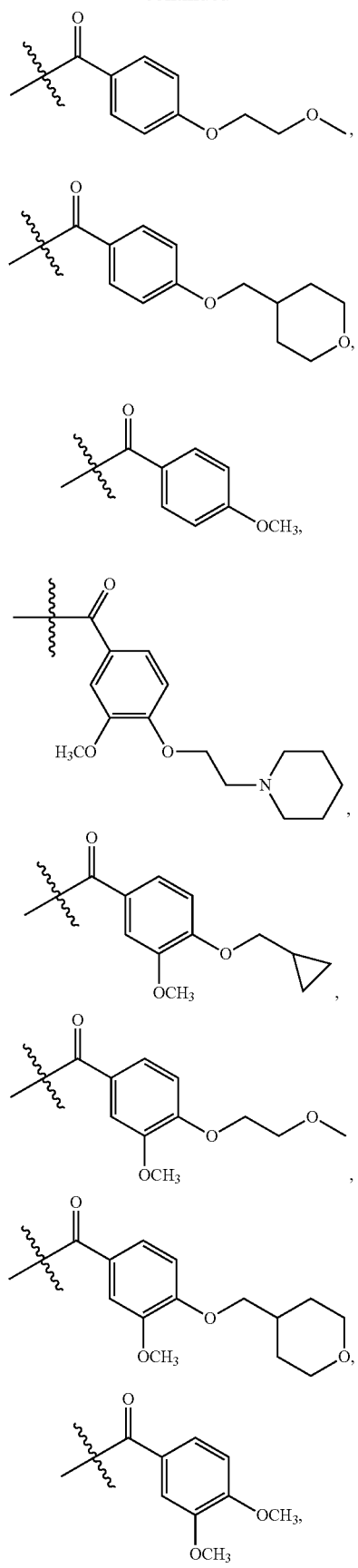

-continued
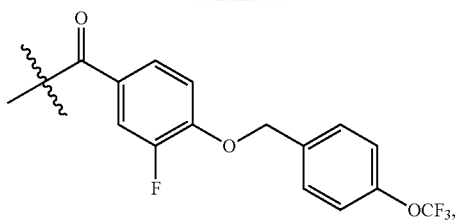
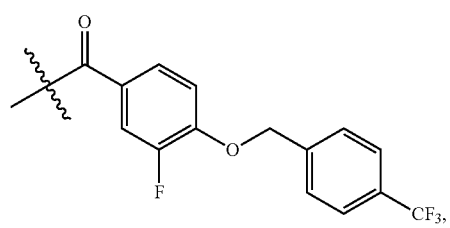
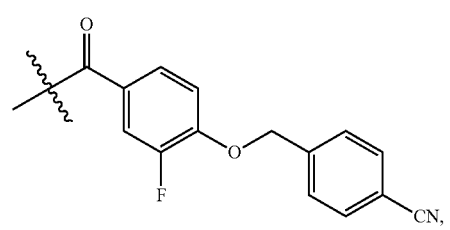
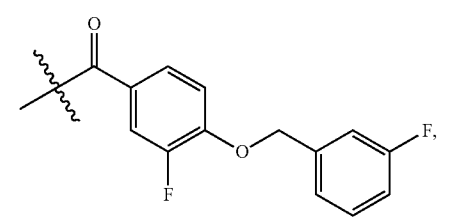
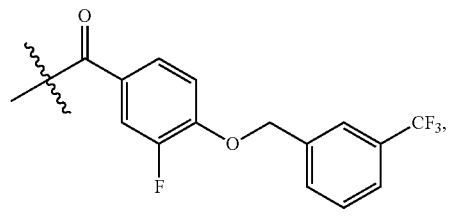
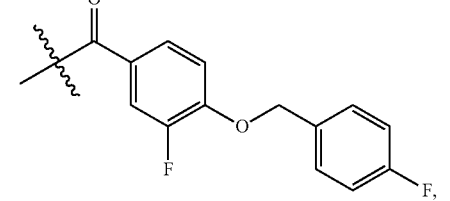
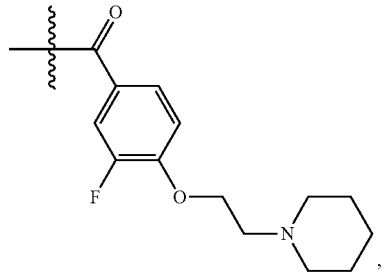
-continued
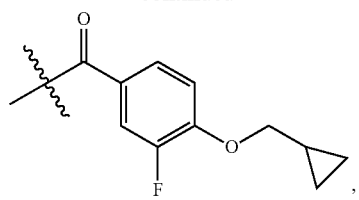
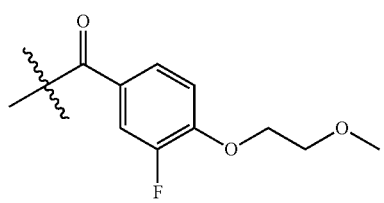
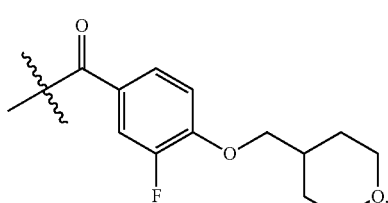
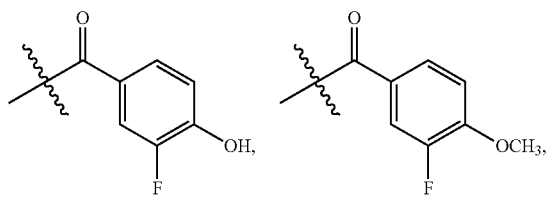
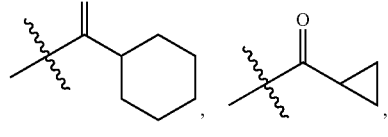
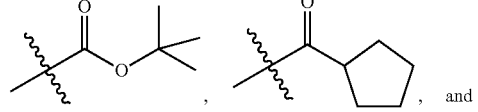
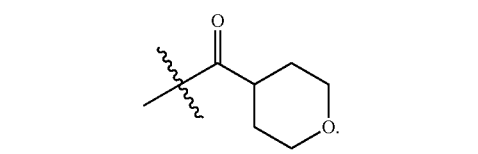
Such compounds are not limited to a particular chemical moiety for R3. In some embodiments, R3 is Hydrogen or CH3.
In some embodiments, the following compounds are contemplated for Formulas I and II:
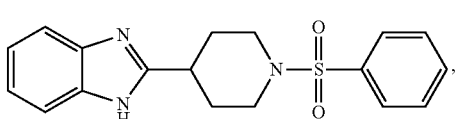
2-(1-(phenylsulfonyl)piperidin-4-yl)-
1H-benzo[d]imidazole (AZ158)

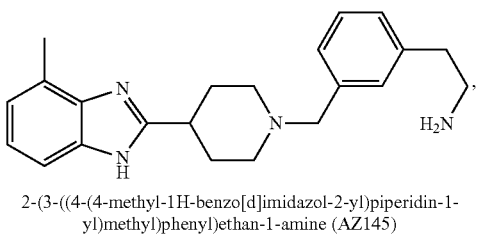

2-(3-((4-(4-methyl-1H-benzo[d]imidazol-2-yl)piperidin-1-yl)methyl)phenyl)ethan-1-amine (AZ145)

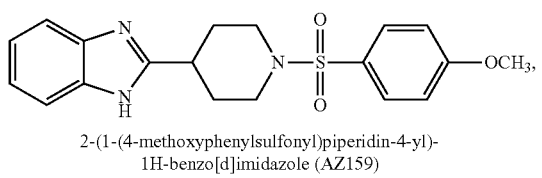

2-(1-(4-methoxyphenylsulfonyl)piperidin-4-yl)-1H-benzo[d]imidazole (AZ159)

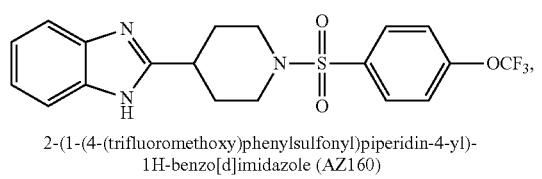

2-(1-(4-(trifluoromethoxy)phenylsulfonyl)piperidin-4-yl)-1H-benzo[d]imidazole (AZ160)

2-(1-(4-fluorophenylsulfonyl)piperidin-4-yl)-1H-benzo[d]imidazole (AZ161)

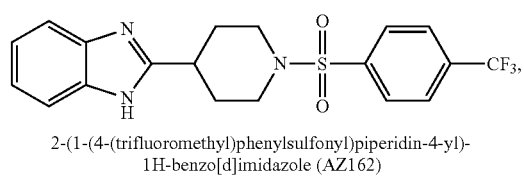

2-(1-(4-(trifluoromethyl)phenylsulfonyl)piperidin-4-yl)-1H-benzo[d]imidazole (AZ162)

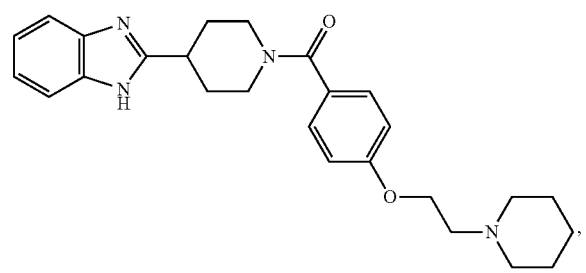

(4-(1H-benzo[d]imidazol-2-yl)piperidin-1-yl)(4-(2-(piperidin-1-yl)ethoxy)phenyl)methanone (AZ168)

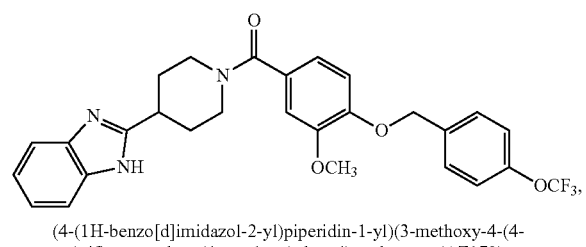

(4-(1H-benzo[d]imidazol-2-yl)piperidin-1-yl)(3-methoxy-4-(4-(trifluoromethoxy)benzyloxy)phenyl)methanone (AZ170)

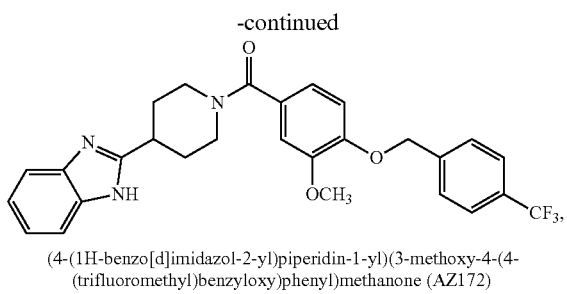

(4-(1H-benzo[d]imidazol-2-yl)piperidin-1-yl)(3-methoxy-4-(4-(trifluoromethyl)benzyloxy)phenyl)methanone (AZ172)

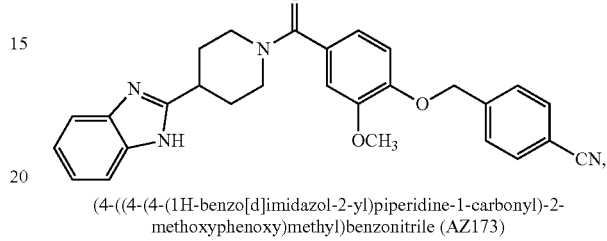

(4-((4-(4-(1H-benzo[d]imidazol-2-yl)piperidine-1-carbonyl)-2-methoxyphenoxy)methyl)benzonitrile (AZ173)

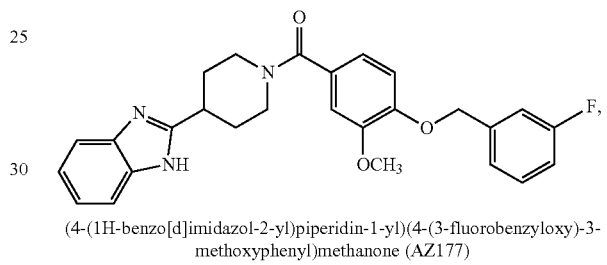

(4-(1H-benzo[d]imidazol-2-yl)piperidin-1-yl)(4-(3-fluorobenzyloxy)-3-methoxyphenyl)methanone (AZ177)

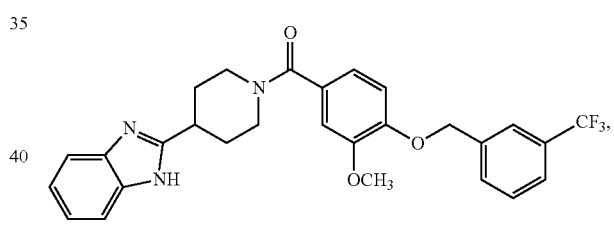

(4-(1H-benzo[d]imidazol-2-yl)piperidin-1-yl)(3-methoxy-4-(3-(trifluoromethyl)benzyloxy)phenyl)methanone (AZ178)

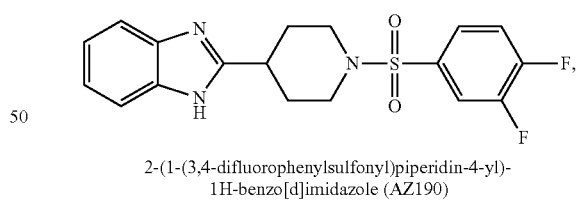

2-(1-(3,4-difluorophenylsulfonyl)piperidin-4-yl)-1H-benzo[d]imidazole (AZ190)

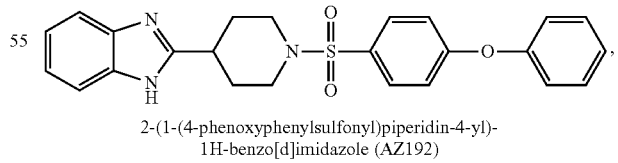

2-(1-(4-phenoxyphenylsulfonyl)piperidin-4-yl)-1H-benzo[d]imidazole (AZ192)

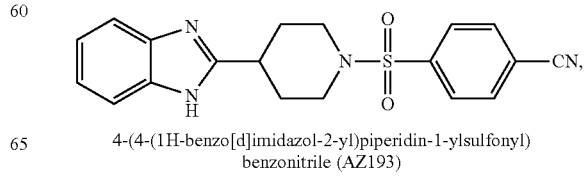

4-(4-(1H-benzo[d]imidazol-2-yl)piperidin-1-ylsulfonyl)benzonitrile (AZ193)

-continued

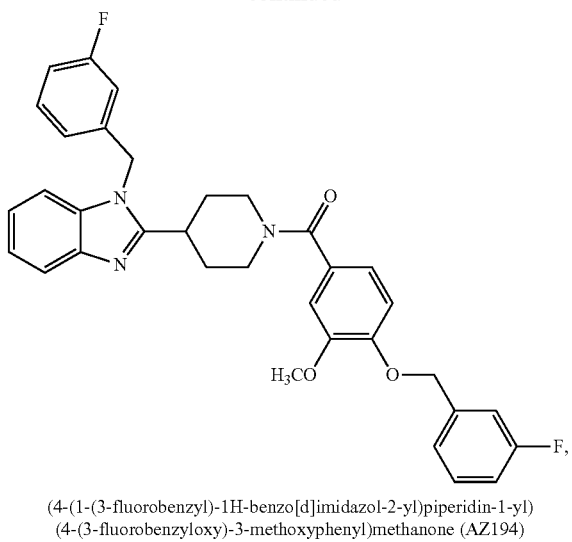

(4-(1-(3-fluorobenzyl)-1H-benzo[d]imidazol-2-yl)piperidin-1-yl)
(4-(3-fluorobenzyloxy)-3-methoxyphenyl)methanone (AZ194)

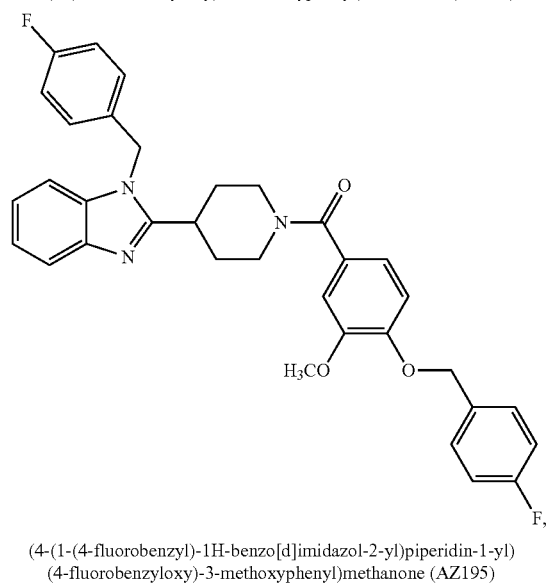

(4-(1-(4-fluorobenzyl)-1H-benzo[d]imidazol-2-yl)piperidin-1-yl)
(4-fluorobenzyloxy)-3-methoxyphenyl)methanone (AZ195)

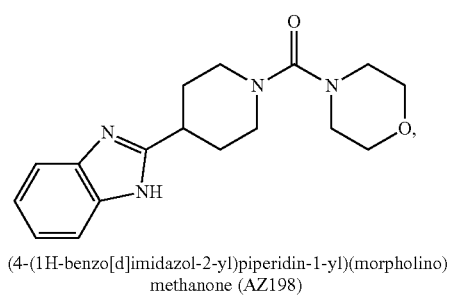

(4-(1H-benzo[d]imidazol-2-yl)piperidin-1-yl)(morpholino)
methanone (AZ198)

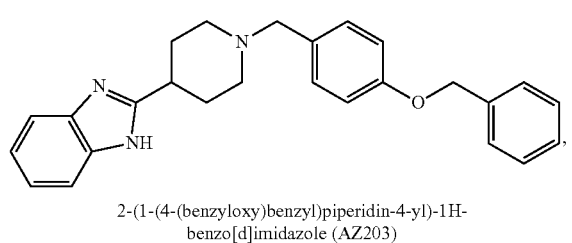

2-(1-(4-(benzyloxy)benzyl)piperidin-4-yl)-1H-
benzo[d]imidazole (AZ203)

-continued

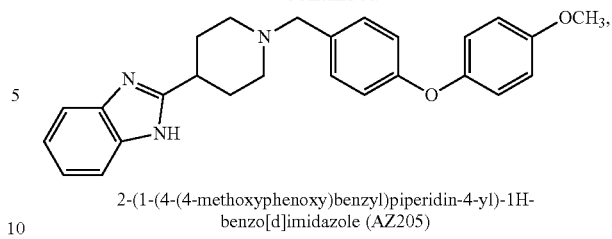

2-(1-(4-(4-methoxyphenoxy)benzyl)piperidin-4-yl)-1H-
benzo[d]imidazole (AZ205)

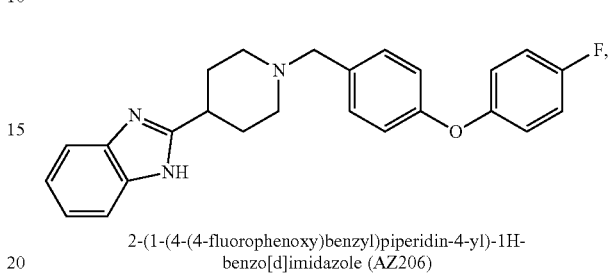

2-(1-(4-(4-fluorophenoxy)benzyl)piperidin-4-yl)-1H-
benzo[d]imidazole (AZ206)

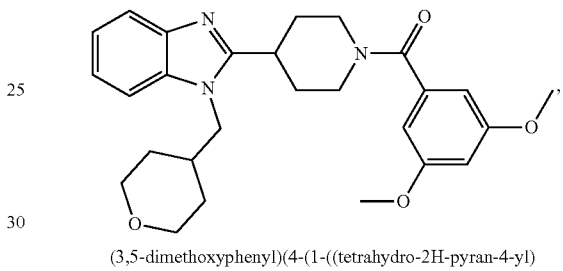

(3,5-dimethoxyphenyl)(4-(1-((tetrahydro-2H-pyran-4-yl)
methyl)-1H-benzo[d]imidazol-2-yl)piperidin-1-yl)methanone

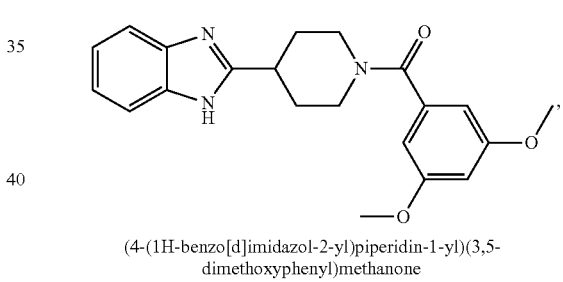

(4-(1H-benzo[d]imidazol-2-yl)piperidin-1-yl)(3,5-
dimethoxyphenyl)methanone

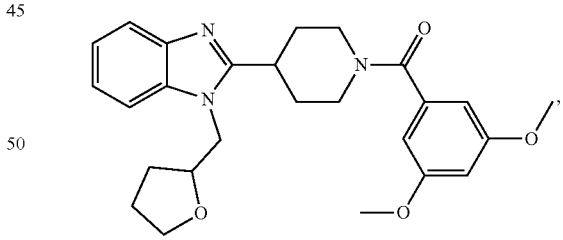

(3,5-dimethoxyphenyl)(4-(1-((tetrahydrofuran-2-yl)
methyl)-1H-benzo[d]imidazol-2-yl)piperidin-1-yl)methanone

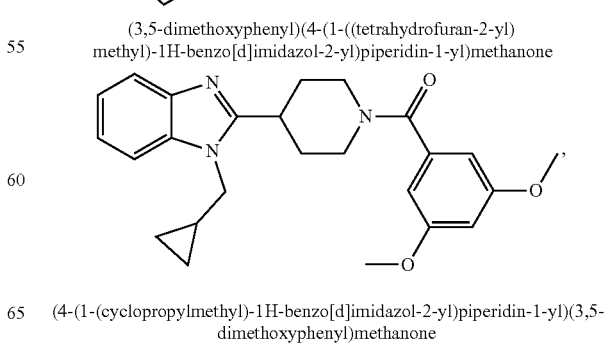

(4-(1-(cyclopropylmethyl)-1H-benzo[d]imidazol-2-yl)piperidin-1-yl)(3,5-
dimethoxyphenyl)methanone -continued

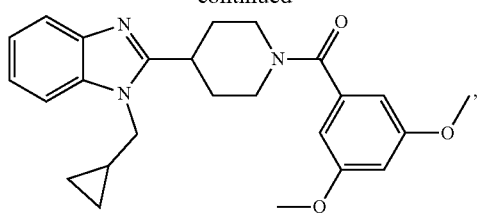

(4-(1-(cyclopropylmethyl)-1H-benzo[d]imidazol-2-yl)piperidin-1-yl)(3,5-dimethoxyphenyl)methanone

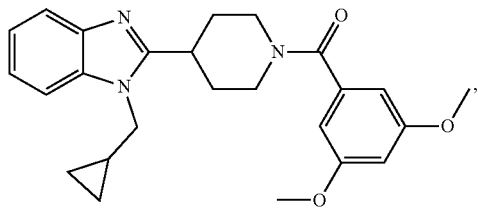

(4-(1-(cyclopropylmethyl)-1H-benzo[d]imidazol-2-yl)piperidin-1-yl)(3,5-dimethoxyphenyl)methanone

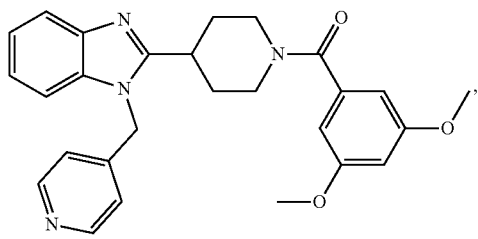

(3,5-dimethoxyphenyl)(4-(1-(pyridin-4-ylmethyl)-1H-benzo[d]imidazol-2-yl)piperidin-1-yl)methanone

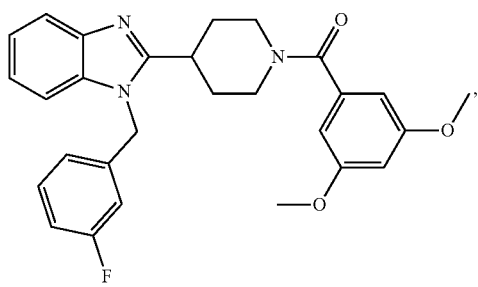

(3,5-dimethoxyphenyl)(4-(1-(3-fluorobenzyl)-1H-benzo[d]imidazol-2-yl)piperidin-1-yl)methanone

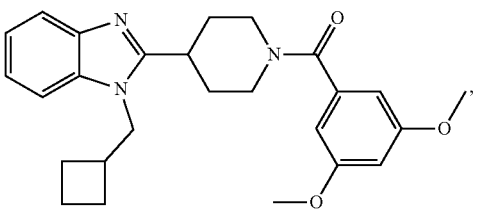

(4-(1-(cyclobutylmethyl)-1H-benzo[d]imidazol-2-yl)piperidin-1-yl)(3,5-dimethoxyphenyl)methanone -continued

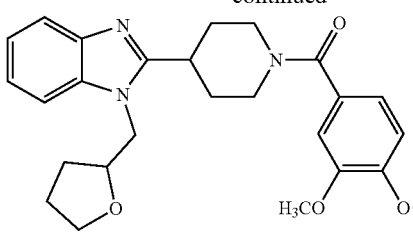

(4-((3-fluorobenzyl)oxy)-3-methoxyphenyl)(4-(1-((tetrahydrofuran-2-yl)methyl)-1H-benzo[d]imidazol-2-yl)piperidin-1-yl)methanone

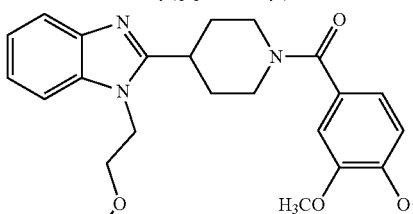

(4-((3-fluorobenzyl)oxy)-3-methoxyphenyl)(4-(1-(2-methoxyethyl)-1H-benzo[d]imidazol-2-yl)piperidin-1-yl)methanone

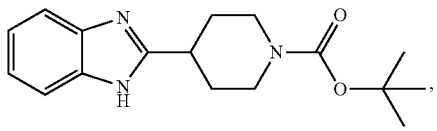

tert-butyl 4-(1H-benzo[d]imidazol-2-yl)piperidine-1-carboxylate

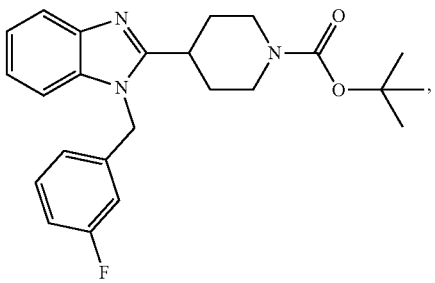

tert-butyl 4-(1-(3-fluorobenzyl)-1H-benzo[d]imidazol-2-yl)piperidine-1-carboxylate

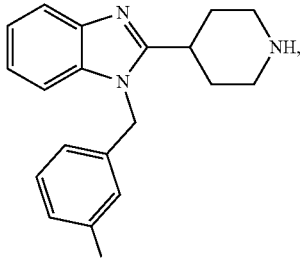

1-(3-fluorobenzyl)-2-(piperidin-4-yl)-1H-benzo[d]imidazole

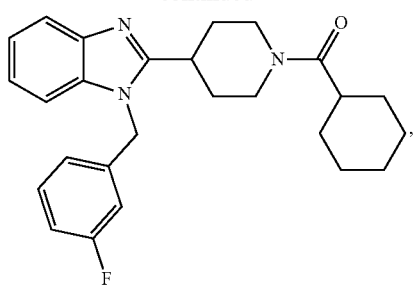

cyclohexyl(4-(1-(3-fluorobenzyl)-1H-benzo[d]imidazol-2-yl)
piperidin-1-yl)methanone

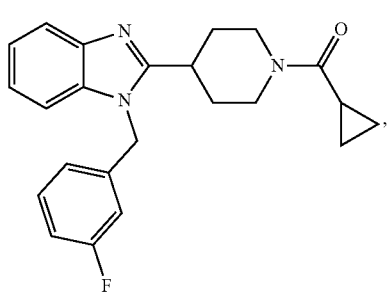

cyclopropyl(4-(1-(3-fluorobenzyl)-1H-benzo[d]imidazol-2-yl)
piperidin-1-yl)methanone

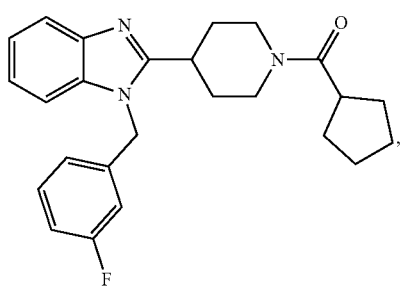

cyclopentyl(4-(1-(3-fluorobenzyl)-1H-benzo[d]imidazol-2-yl)
piperidin-1-yl)methanone

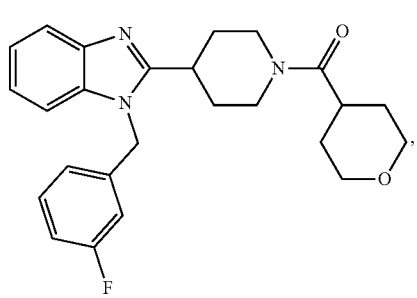

(4-(1-(3-fluorobenzyl)-1H-benzo[d]imidazol-2-yl)
piperidin-1-yl)(tetrahydro-2H-pyran-4-yl)methanone

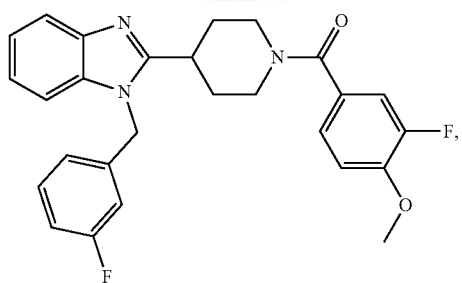

(3-fluoro-4-methoxyphenyl)(4-(1-(3-fluorobenzyl)-1H-benzo[d]
imidazol-2-yl)piperidin-1-yl)methanone

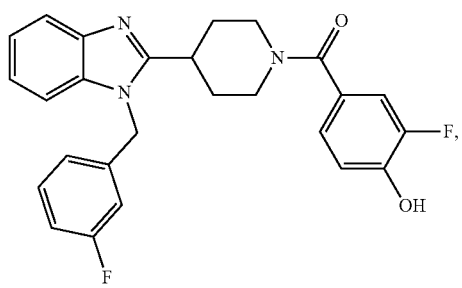

(3-fluoro-4-hydroxyphenyl)(4-(1-(3-fluorobenzyl)-1H-benzo[d]
imidazol-2-yl)piperidin-1-yl)methanone

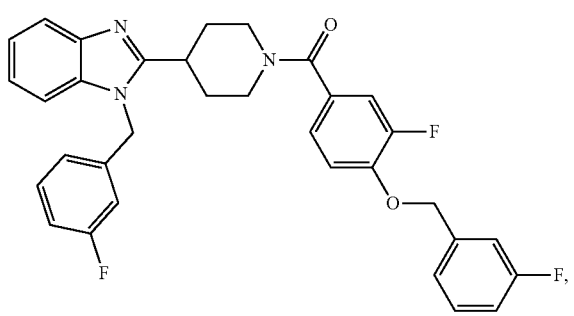

(3-fluoro-4-((3-fluorobenzyl)oxy)phenyl)(4-(1-(3-fluorobenzyl)-1H-
benzo[d]imidazol-2-yl)piperidin-1-yl)methanone

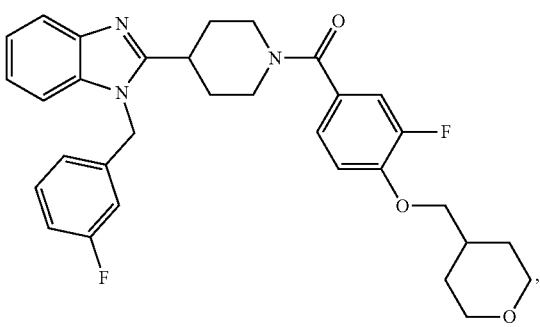

(3-fluoro-4-((tetrahydro-2H-pyran-4-yl)methoxy)phenyl)(4-(1-(3-
fluorobenzyl)-1H-benzo[d]imidazol-2-yl)piperidin-1-yl)methanone

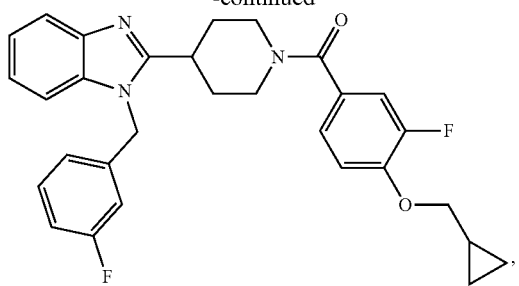

(4-(cyclopropylmethoxy-3-fluorophenyl)(4-(1-(3-fluorobenzyl)-1H-benzo[d]imidazol-2-yl)piperidin-1-yl)methanone

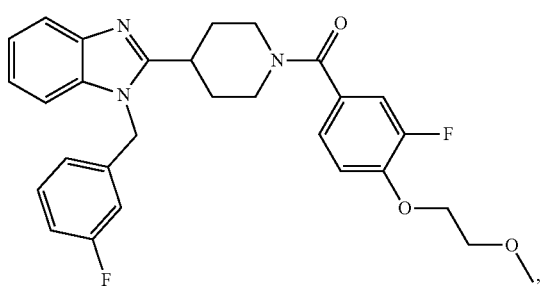

(3-fluoro-4-(2-methoxyethoxy)phenyl)(4-(1-(3-fluorobenzyl)-1H-benzo[d]imidazol-2-yl)piperidin-1-yl)methanone

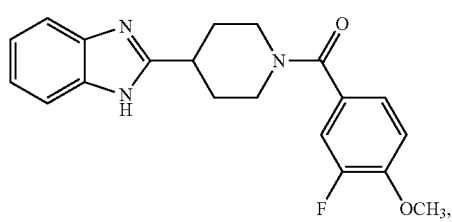

(4-(1H-benzo[d]imidazol-2-yl)piperidin-1-yl)(3-fluoro-4-methoxyphenyl)methanone

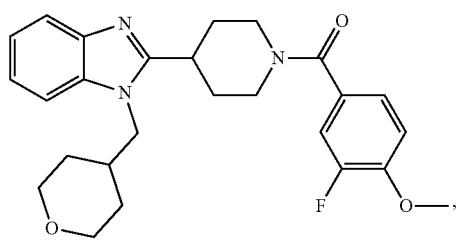

(3-fluoro-4-methoxyphenyl)(4-(1-((tetrahydro-2H-pyran-4-yl)methyl)-1H-benzo[d]imidazol-2-yl)piperidin-1-yl)methanone

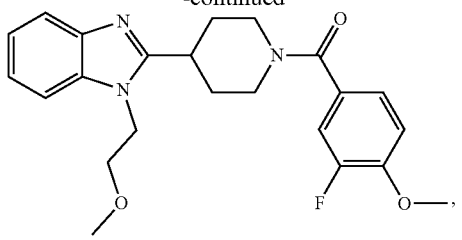

(3-fluoro-4-methoxyphenyl)(4-(1-(2-methoxyethyl)-1H-benzo[d]imidazol-2-yl)piperidin-1-yl)methanone

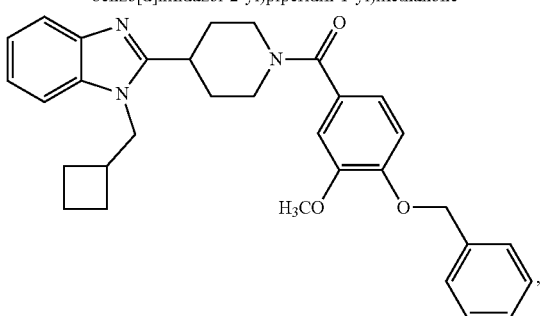

(4-(1-(cyclobutylmethyl)-1H-benzo[d]imidazol-2-yl)piperidin-1-yl)(4-((3-fluorobenzyl)oxy)-3-methoxyphenyl)methanone

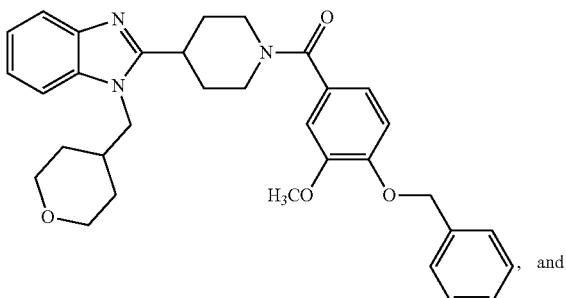

(4-((3-fluorobenzyl)oxy)-3-methoxyphenyl)(4-(1-((tetrahydro-2H-pyran-4-yl)methyl)-1H-benzo[d]imidazol-2-yl)piperidin-1-yl)methanone

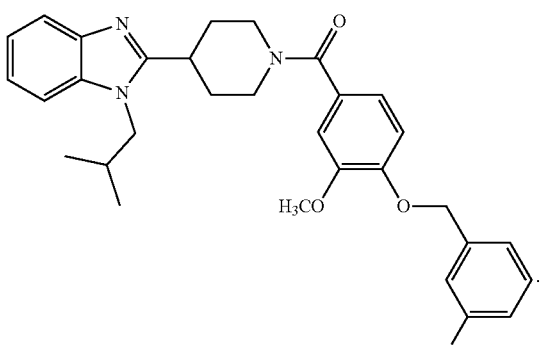

(4-((3-fluorobenzyl)oxy)-3-methoxyphenyl)(4-(1-isobutyl-1H-benzo[d]imidazol-2-yl)piperidin-1-yl)methanone Tables 1, 2, 3, 4, 5 and 6 show additional structure arrangements for the piperidinyl-benzoimidazole compounds described herein.

TABLE 1

Structures of CRMP2 SUMOylation inhibitors

| Compound | R₅ | R₆ | R₇ |
|---|---|---|---|
| AZ168 | —H | —O-CH₂CH₂-piperidinyl | —H |
| AZ170 | —H | —O-CH₂-(4-OCF₃-phenyl) | —OCH₃ |
| AZ172 | —H | —O-CH₂-(4-CF₃-phenyl) | —OCH₃ |
| AZ173 | —H | —O-CH₂-(4-CN-phenyl) | —OCH₃ |
| AZ177 | —H | —O-CH₂-(3-F-phenyl) | —OCH₃ |
| AZ178 | —H | —O-CH₂-(3-CF₃-phenyl) | —OCH₃ |
| AZ194 | —CH₂-(3-F-phenyl) | —O-CH₂-(3-F-phenyl) | —OCH₃ |
| AZ195 | —CH₂-(4-F-phenyl) | —O-CH₂-(4-F-phenyl) | —OCH₃ |

TABLE 1-continued

Structures of CRMP2 SUMOylation inhibitors

| Compound | R₅ | R₆ | R₇ |
|---|---|---|---|
| AZ218 | tetrahydrofuran-2-ylmethyl | 3-fluorobenzyloxy | —OCH₃ |
| AZ219 | 2-methoxyethyl | 3-fluorobenzyloxy | —OCH₃ |
| AZ231 | (tetrahydropyran-4-yl)methyl | 3-fluorobenzyloxy | —OCH₃ |
| AZ232 | isobutyl | 3-fluorobenzyloxy | —OCH₃ |
| AZ233 | cyclobutylmethyl | 3-fluorobenzyloxy | —OCH₃ |
| AZ225 | 3-fluorobenzyl | 3-fluorobenzyloxy | —F |
| AZ226 | 3-fluorobenzyl | cyclopropylmethoxy | —F |
| AZ227 | 3-fluorobenzyl | 2-methoxyethoxy | —F |
| AZ228 | —H | —OCH₃ | —F |

TABLE 1-continued

Structures of CRMP2 SUMOylation inhibitors

| Compound | R$_5$ | R$_6$ | R$_7$ |
|---|---|---|---|
| AZ230 | -CH$_2$CH$_2$OCH$_3$ | —OCH$_3$ | —F |
| AZ229 | -CH$_2$-(tetrahydropyran-4-yl) | —OCH$_3$ | —F |
| AZ0715 | -CH$_2$-(3-fluorophenyl) | -OCH$_2$-(tetrahydropyran-4-yl) | —F |

TABLE 2

Structures of CRMP2 SUMOylation inhibitors

| Compound | R$_8$ | R$_9$ |
|---|---|---|
| AZ158 | —H | —H |
| AZ159 | —OCH$_3$ | —H |
| AZ160 | —OCF$_3$ | —H |
| AZ161 | —F | —H |
| AZ162 | —CF$_3$ | —H |
| AZ190 | —F | —F |
| AZ192 | —O-phenyl | —H |
| AZ193 | —CN | —H |

TABLE 3

Structures of CRMP2 SUMOylation inhibitors

| Compound | R$_{10}$ |
|---|---|
| AZ203 | —O-CH$_2$-phenyl |
| AZ205 | —O-(4-methoxyphenyl) |
| AZ206 | —O-(4-fluorophenyl) |

TABLE 4

Structures of CRMP2 SUMOylation inhibitors

| Compound | R$_{11}$ |
|---|---|
| AZ209 | 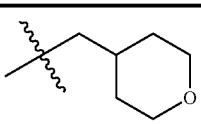 |
| AZ210 | 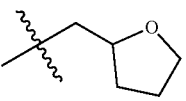 [SMILES: *CC1CCCO1] |
| AZ211 | 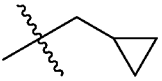 |
| AZ212 |  |
| AZ213 | 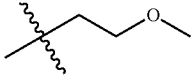 [SMILES: *CCOC] |
| AZ214 | 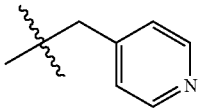 [SMILES: *Cc1ccncc1] |
| AZ215 | 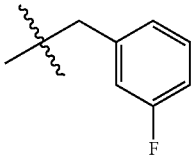 [SMILES: *Cc1cccc(F)c1] |
| AZ216 |  |
| AZ217 | H |

TABLE 5

Structures of CRMP2 SUMOylation inhibitors

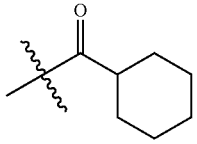 [SMILES: *C(=O)C1CCCCC1]

| Compound | R$_{12}$ |
|---|---|
| AZ220 | 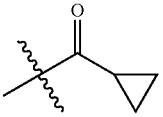 [SMILES: *C(=O)C1CC1] |

TABLE 5-continued

Structures of CRMP2 SUMOylation inhibitors

| Compound | R$_{12}$ |
|---|---|
| AZ221 | 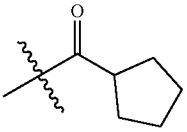 [SMILES: *C(=O)C1CCCC1] |
| AZ222 | 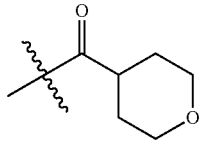 [SMILES: *C(=O)C1CCOCC1] |
| AZ223 | 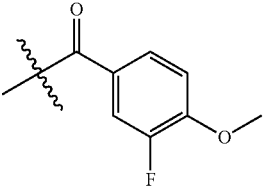 [SMILES: *C(=O)c1ccc(OC)c(F)c1] |
| AZ224 | |

TABLE 6

Structure of CRMP2 SUMOylation inhibitor

AZ198 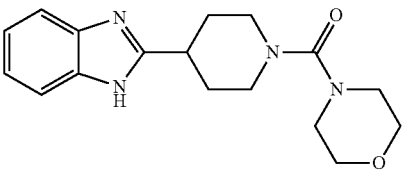 [SMILES: O=C(N1CCOCC1)N1CCC(c2nc3ccccc3[nH]2)CC1]

In some embodiments, the compositions and methods of the present invention are used to treat pain related to Nav1.7 activity in a patient (e.g., a mammalian patient including, but not limited to, humans and veterinary animals) through inhibiting CRMP2 SUMOylation. In some embodiments, the compositions and methods of the present invention are used to treat pain related to Nav1.7 activity in a patient (e.g., a mammalian patient including, but not limited to, humans and veterinary animals) through inhibiting CRMP2 SUMOylation via preventing and/or hindering and/or inhibiting binding between Ubc9 and CRMP2. Pain related to Nav1.7 activity includes, but is not limited to, acute, inflammatory and/or neuropathic pain.

In some embodiments, the compositions and methods of the present invention are used to induce endogenous opioid expression and/or activity in a subject. Such compounds are not limited to inducing expression and/or activity of a specific type of endogenous opioid (e.g., proenkephalin).

Some embodiments of the present invention provide methods for administering an effective amount of a compound of the invention and at least one additional pain relieving agent. Such embodiments are not limited to a particular type of an additional pain relieving agent.

In some embodiments, the pain relieving agents include, but are not limited to, analgesic drugs and respective antagonists. Examples of analgesic drugs include, but are not limited to, paracetamol and Non-steroidal anti-inflammatory drugs (NSAIDs), COX-2 inhibitors, opiates and morphonimimetics, and specific analgesic agents.

Examples of NSAIDs include, but are not limited to, salicylates (e.g., Acetylsalicylic acid (Aspirin), Amoxiprin, Benorylate/Benorilate, Choline magnesium salicylate, Diflunisal, Ethenzamide, Faislamine, Methyl salicylate, Magnesium salicylate, Salicyl salicylate, Salicylamide), arylalkanoic acids (e.g., Diclofenac, Aceclofenac, Acemethacin, Alclofenac, Bromfenac, Etodolac, Indometacin, Nabumetone, Oxametacin, Proglumetacin, Sulindac, Tolmetin), 2-arylpropionic acids (profens) (e.g., Ibuprofen, Alminoprofen, Benoxaprofen, Carprofen, Dexibuprofen, Dexketoprofen, Fenbufen, Fenoprofen, Flunoxaprofen, Flurbiprofen, Ibuproxam, Indoprofen, Ketoprofen, Ketorolac, Loxoprofen, Naproxen, Oxaprozin, Pirprofen, Suprofen, Tiaprofenic acid), N-arylanthranilic acids (fenamic acids) (e.g., Mefenamic acid, Flufenamic acid, Meclofenamic acid, Tolfenamic acid), pyrazolidine derivatives (e.g., Phenylbutazone, Ampyrone, Azapropazone, Clofezone, Kebuzone, Metamizole, Mofebutazone, Oxyphenbutazone, Phenazone, Sulfinpyrazone), oxicams (e.g., Piroxicam, Droxicam, Lornoxicam, Meloxicam, Tenoxicam), sulphonanilides (e.g., nimesulide), licofelone, and omega-3 fatty acids.

Examples of COX-2 inhibitors include, but are not limited to Celecoxib, Etoricoxib, Lumiracoxib, Parecoxib, Rofecoxib, Valdecoxib.

Examples of opiates include, but are not limited to, natural opiates (e.g., alkaloids contained in the resin of the opium poppy including morphine, codeine and thebaine), semi-synthetic opiates (e.g., created from the natural opioids, such as hydromorphone, hydrocodone, oxycodone, oxymorphone, desomorphine, diacetylmorphine (Heroin), nicomorphine, dipropanoylmorphine, diamorphine, benzylmorphine, Buprenorphine, Nalbuphine, Pentazocine, meperidine, diamorphine, and ethylmorphine), fully synthetic opioids (e.g., such as fentanyl, pethidine, Oxycodone, Oxymorphone, methadone, tramadol, Butorphanol, Levorphanol, and propoxyphene), and endogenous opioid peptides (e.g., produced naturally in the body, such as endorphins, enkephalins, dynorphins, and endomorphins).

Examples of analgesics include, but are not limited to, tricyclic antidepressants (e.g., amitriptyline, carbamazepine, gabapentin, and pregabalin), Tetrahydrocannabinol, ketamine, clonidine, α2-adrenoreceptor agonists, mexiletine, Orphenadrine, cyclobenzaprine, scopolamine, atropine, gabapentin, first-generation antidepressants and other drugs possessing anticholinergic and/or antispasmodic.

In some embodiments, pain relieving agents include anesthetic drugs. Examples of anesthetic drugs include, but are not limited to, local anesthetics (e.g., procaine, amethocaine, cocaine, lidocaine, prilocaine, bupivacaine, levobupivacaine, ropivacaine, dibucaine), inhaled anesthetics (e.g., Desflurane, Enflurane, Halothane, Isoflurane, Nitrous oxide, Sevoflurane, Xenon), intravenous anesthetics (e.g., Barbiturates (e.g., amobarbital (Amytal), pentobarbital (Nembutal), secobarbital (Seconal), Phenobarbital, Methohexital, Thiopental, Methylphenobarbital, Metharbital, Barbexaclone)), Benzodiazepines (e.g., alprazolam, bromazepam (Lexotan), chlordiazepoxide (Librium), Clobazam, Clonazepam, Clorazepate, Diazepam, Midazolam, Lorazepam, Nitrazepam, temazepam, nimetazepam, Estazolam, Flunitrazepam, oxazepam (Serax), temazepam (Restoril, Normison, Planum, Tenox, and Temaze), Triazolam), Etomidate, Ketamine, Propofol).

In some embodiments, pain relieving agents include anticonvulsant drugs. Examples of anticonvulsant drugs include, but are not limited to, aldehydes (e.g., paraldehyde), aromatic allylic alcohols (e.g., stiripentol), barbiturates (e.g., amobarbital (Amytal), pentobarbital (Nembutal), secobarbital (Seconal), Phenobarbital, Methohexital, Thiopental, Methylphenobarbital, Metharbital, Barbexaclone), benzodiazepines (e.g., alprazolam, bromazepam (Lexotan), chlordiazepoxide (Librium), Clobazam, Clonazepam, Clorazepate, Diazepam, Midazolam, Lorazepam, Nitrazepam, temazepam, nimetazepam, Estazolam, Flunitrazepam, oxazepam (Serax), temazepam (Restoril, Normison, Planum, Tenox, and Temaze), Triazolam), bromides (e.g., potassium bromide), carbamates (e.g., felbamate), carboxamides (e.g., carbamazepine, oxcarbazepine), fatty acids (e.g., valproates (e.g., valproic acid, sodium valproate, and divalproex sodium), Vigabatrin, Progabide, Tiagabine), fructose derivatives (e.g., topiramate), gaba analogs (e.g., gabapentin, pregabalin), hydantoins (e.g., Ethotoin, Phenytoin, Mephenytoin, Fosphenytoin), Oxazolidinediones (e.g., paramethadione, trimethadione, ethadione), priopionates (e.g., primidone), pyrrolidines (e.g., brivaracetam, levetiracetam, seletracetam), succinimides (e.g., Ethosuximide, Phensuximide, Mesuximide), sulfonamides (e.g., Acetazolamide, Sulthiame, Methazolamide, Zonisamide), triazines (e.g., lamotrigine), ureas (e.g., pheneturide, phenacemide), and valproylamdies (amide derivatives of valproate) (e.g., valpromide, valnoctamide).

In some embodiments, pain relieving agents include muscle relaxant drugs. Examples of muscle relaxant drugs include, but are not limited to, depolarizing muscle relaxants (e.g., Succinylcholine), short acting non-depolarizing muscle relaxants (e.g., Mivacurium, Rapacuronium), intermediate acting non-depolarizing muscle relaxants (e.g., Atracurium, Cisatracurium, Rocuronium, Vecuronium), and long acting non-depolarizing muscle relaxants (e.g., Alcuronium, Doxacurium, Gallamine, Metocurine, Pancuronium, Pipecuronium, d-Tubocurarine).

In some embodiments of the present invention, a compound of the invention and one or more pain relieving agents are administered to an animal under one or more of the following conditions: at different periodicities, at different durations, at different concentrations, by different administration routes, etc. In some embodiments, the compound and the additional pain relieving agent are administered concurrently but on different schedules.

Compositions within the scope of this invention include all compositions wherein the compounds of the present invention are contained in an amount which is effective to achieve its intended purpose. While individual needs vary, determination of optimal ranges of effective amounts of each component is within the skill of the art. Typically, the compounds may be administered to mammals, e.g. humans, orally at a dose of 0.0025 to 50 mg/kg, or an equivalent amount of the pharmaceutically acceptable salt thereof, per day of the body weight of the mammal being treated for disorders responsive to induction of apoptosis. In one embodiment, about 0.01 to about 25 mg/kg is orally administered to treat, ameliorate, or prevent such disorders. For intramuscular injection, the dose is generally about one-half of the oral dose. For example, a suitable intramuscular dose would be about 0.0025 to about 25 mg/kg, or from about 0.01 to about 5 mg/kg.

The unit oral dose may comprise from about 0.01 to about 1000 mg, for example, about 0.1 to about 100 mg of the compound. The unit dose may be administered one or more times daily as one or more tablets or capsules each containing from about 0.1 to about 10 mg, conveniently about 0.25 to 50 mg of the compound or its solvates.

In a topical formulation, the compound may be present at a concentration of about 0.01 to 100 mg per gram of carrier. In a one embodiment, the compound is present at a concentration of about 0.07-1.0 mg/ml, for example, about 0.1-0.5 mg/ml, and in one embodiment, about 0.4 mg/ml.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. The preparations, particularly those preparations which can be administered orally or topically and which can be used for one type of administration, such as tablets, dragees, slow release lozenges and capsules, mouth rinses and mouth washes, gels, liquid suspensions, hair rinses, hair gels, shampoos and also preparations which can be administered rectally, such as suppositories, as well as suitable solutions for administration by intravenous infusion, injection, topically or orally, contain from about 0.01 to 99 percent, in one embodiment from about 0.25 to 75 percent of active compound(s), together with the excipient.

The pharmaceutical compositions of the invention may be administered to any patient which may experience the beneficial effects of the compounds of the invention. Foremost among such patients are mammals, e.g., humans, although the invention is not intended to be so limited. Other patients include veterinary animals (cows, sheep, pigs, horses, dogs, cats and the like).

The compounds and pharmaceutical compositions thereof may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are in one embodiment dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension include, for example, sodium carboxymethyl cellulose, sorbitol, and/or dextran. Optionally, the suspension may also contain stabilizers.

The topical compositions of this invention are formulated in one embodiment as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The carriers may be those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762; each herein incorporated by reference in its entirety.

Ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight. Lotions may be conveniently prepared by dissolving the active ingredient, in a suitable high molecular weight alcohol such as propylene glycol or polyethylene glycol.

One of ordinary skill in the art will readily recognize that the foregoing represents merely a detailed description of certain preferred embodiments of the present invention. Various modifications and alterations of the compositions and methods described above can readily be achieved using expertise available in the art and are within the scope of the invention.

EXAMPLES

The following examples are illustrative, but not limiting, of the compounds, compositions, and methods of the present invention. Other suitable modifications and adaptations of the variety of conditions and parameters normally encountered in clinical therapy and which are obvious to those skilled in the art are within the spirit and scope of the invention.

Example I

This example describes synthetic routes for the piperidinyl-benzoimidazole compounds described herein.

The following abbreviations are used: 1-Hydroxybenzotriazole (HOBt); Dichloromethane (DCM); Ethyl acetate (EtOAc); Methanol (MeOH); 2-(1H-benzotriazol-1-yl)-1,1,3,3-tetramethyluronium hexafluorophosphate (HBTU); N,N-diisopropylethylamine (DIPEA); N,N-dimethylformamide (DMF); Ethanol (EtOH); Triethylamine (Et$_3$N); Thin layer chromatography (TLC); Nuclear magnetic resonance (NMR); 1-Ethyl-3-(3-dimethylaminopropyl)carbodiimide (EDC) and 1-[Bis(dimethylamino)methylene]-1H-1,2,3-triazolo[4,5-b]pyridinium 3-oxid hexafluorophosphate (HATU).

All the chemicals were purchased from commercial vendors. All the solvents were obtained from Fischer Scientific. Purifications were performed either by flash chromatography with silica gel (230/400 mesh, Fisher Scientific) or Combiflash Rf+ Lumen system (Teledyne ISCO Corp.) with prepacked silica gel universal Rf cartridges. All anhydrous reactions were carried out under positive pressure of nitrogen. HPLC-MS analyses were performed on an Agilent 1100 series instrument with a Zorbax C18 reverse-phase column. HRMS results were obtained on an apex-Qe instrument. All 1H-NMR and 13C-NMR spectra were recorded on a BRUKER AVANCE-III 400 MHz NMR instrument, using deuterated solvents. The spectra are reported in ppm and referenced to deuterated DMSO (2.49 ppm for 1H, 39.5 ppm for 13C) or deuterated chloroform (7.26 ppm for 1H, 77 ppm for 13C). High-resolution mass spectra (HRMS) were acquired on a Bruker 9.4 T Apex-Qh FTICR mass spectrometer. All compounds were analyzed for purity by HPLC using either MS or UV absorbance detectors. All final compounds showed ≥95% purity.

Synthesis of 4-(2-(piperidin-1-yl)ethoxy benzoic acid

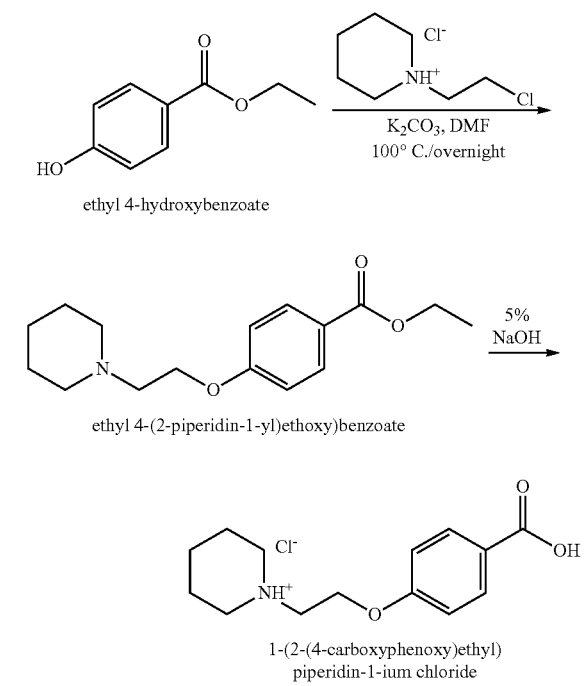

In a round bottomed flask equipped with nitrogen inlet and magnetic stir bar, potassium carbonate (2.91 g, 21.09 mmol), ethyl 4-hydroxybenzoate (1 g, 6.03 mmol) and DMF (6 mL) were added. The mixture was stirred for 30 minutes and then, 4-(2-chloroethyl)piperidine hydrochloride (1.88 g, 10.25 mmol) was added. Mixture was heated to 100° C. overnight and then, water (100 mL) was added to the cooled reaction mixture. Aqueous was extracted with ethyl acetate (3×40 mL). The combined organic layers were evaporated and the, dried in vacuo to obtain 1.58 g of ethyl 4-(2-(piperidin-1-yl)ethoxy)benzoate.

$^1$H NMR (400 MHz, Chloroform-d) δ 7.92 (dd, J=17.6, 8.9 Hz, 2H), 6.84 (dd, J=11.9, 8.9 Hz, 2H), 4.31 (qd, J=7.1, 3.6 Hz, 2H), 4.13 (t, J=6.0 Hz, 2H), 2.78 (t, J=6.0 Hz, 2H), 2.62-2.33 (m, 4H), 1.62-1.54 (m, 4H), 1.49-1.39 (m, 3H), 1.35 (td, J=7.1, 2.1 Hz, 3H).

In a round bottomed flask equipped with nitrogen inlet and magnetic stir bar, a solution of ethyl 4-(2-(piperidin-1-yl)ethoxy)benzoate (1.58 g, 5.7 mmol) in methanol (25 mL) was added. To the above solution, 8 mL of 5% NaOH solution was added and the reaction was stirred overnight. Methanol was evaporated and 15 mL cold water was added to the residue. The precipitated solid was filtered, washed with 5 mL water and the, dried in vacuo to give 1.36 g of 1-(2-(4-carboxyphenoxy)ethyl)piperidin-1-ium chloride $^1$H NMR (400 MHz, Chloroform-d) δ 7.93 (d, J=8.9 Hz, 2H), 6.85 (d, J=8.9 Hz, 2H), 6.30 (bs, 1H), 4.84 (bs, 1H), 4.32 (q, J=7.1 Hz, 2H), 3.86 (bs, 1H), 2.07-1.53 (m, 4H), 1.36 (t, J=7.1 Hz, 2H). HPLC-MS: Expected: 250; Found: 250.

Synthesis of (4-(1H-benzo[d]imidazol-2-yl)piperidin-1-yl)(4-(2-(piperidin-1-yl)ethoxy)phenyl)methanone (AZ168)

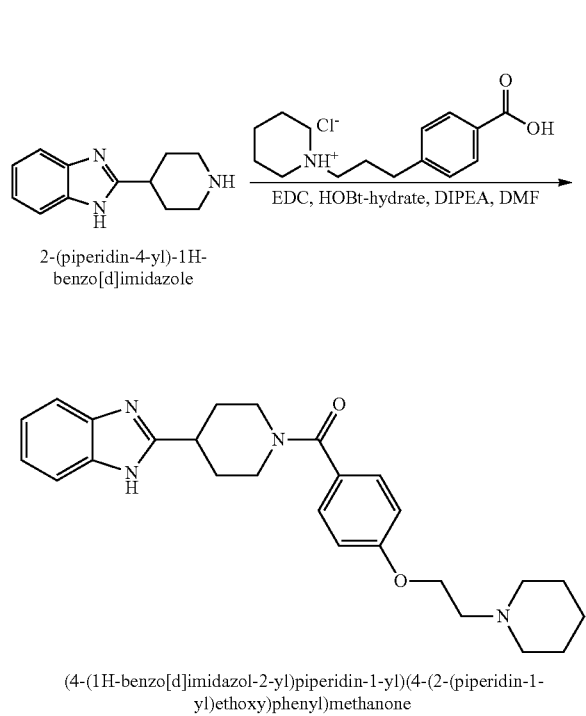 [SMILES: c1ccc2[nH]c(C3CCNCC3)nc2c1 ; O=C(O)c1ccc(CCC[NH+]2CCCCC2)cc1 ; [Cl-] ; O=C(c1ccc(OCCN2CCCCC2)cc1)N1CCC(c2nc3ccccc3[nH]2)CC1]

(4-(1H-benzo[d]imidazol-2-yl)piperidin-1-yl)(4-(2-(piperidin-1-yl)ethoxy)phenyl)methanone In a round bottomed flask equipped with a magnetic stir bar and a nitrogen inlet, a mixture of 1-(2-(4-carboxyphenoxy)ethyl)piperidin-1-ium chloride, EDC hydrochloride (138 g, 0.72 mmol) and HOBt-hydrate (110 mg, 0.72 mmol) and DIPEA (0.21 mL, 1.21 mmol) in 10 mL acetonitrile were added. The mixture was then stirred at room temperature for one hour. To the above solution, 2-(piperidin-4-yl)-1H-benzo[d]imidazole (121 mg, 0.6 mmol) was added. The mixture was stirred at room temperature overnight. To the reaction mixture water was added. Precipitate was filtered, washed with CH$_3$CN and then dried in vacuo yielding 123 mg of the crude. The crude was washed with water and then dried in vacuo to give 50 mg (19%) of (4-(1H-benzo[d]imidazol-2-yl)piperidin-1-yl)(4-(2-(piperidin-1-yl)ethoxy)phenyl)methanone as tan color solid.

$^1$H NMR (400 MHz, DMSO-d6) δ 12.23 (bs, 1H), 7.57-7.40 (m, 2H), 7.38 (d, J=8.8 Hz, 2H), 7.16-7.07 (m, 2H), 7.00 (d, J=8.8 Hz, 2H), 4.11 (t, J=5.9 Hz, 2H), 3.27-3.01 (m, 4H), 2.67 (t, J=5.9 Hz, 2H), 2.44-2.42 (m, 4H), 2.10-1.87 (m, 2H), 1.81 (qd, J=12.0, 4.1 Hz, 2H), 1.51 (p, J=5.5 Hz, 4H), 1.39 (p, J=6 Hz, 1H).

$^{13}$C NMR (101 MHz, DMSO-d6) δ 169.42, 162.71, 159.79, 157.67, 143.32, 134.61, 129.20, 128.54, 122.04, 118.82, 114.59, 111.28, 66.09, 57.72, 54.82, 36.18, 32.10-30.06 (m), 25.99, 24.36.

HRMS: Found=MH$^+$=433.25980 (theoretical MH$^+$=433.25980)

Synthesis of ethyl 4-hydroxy-3 methoxybenzoate

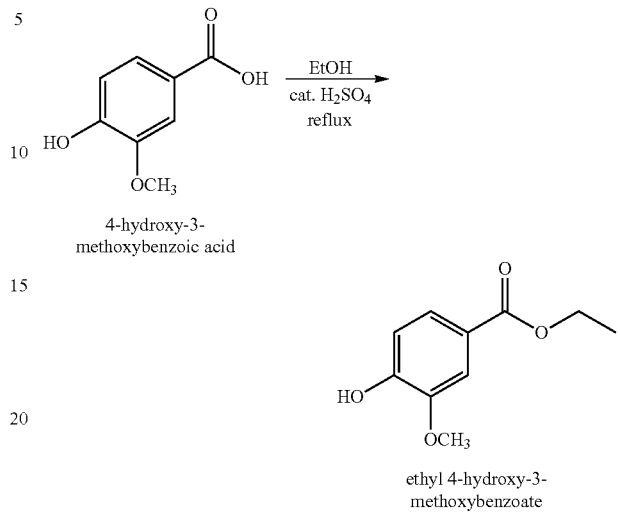

In a round bottomed flask equipped with a nitrogen inlet and a magnetic stir bar, a solution of 4-hydroxy-3-methoxybenzoic acid (10 g, 59.49 mmol) in EtOH (400 mL) was added. To the above solution 600 mg (6.11 mmol) of conc. H$_2$SO$_4$ was added. The mixture was then stirred at reflux temperature for 48 h. The solution was rotary evaporated. Water (100 mL) was then added to the residue and a greenish oily compound separates out. The greenish oil was then separated and then dried in vacuo to 11.45 g (98%) of ethyl 4-hydroxy-3-methoxybenzoate.

1H NMR (400 MHz, Chloroform-d) δ 7.62 (dd, J=8.5, 2.1 Hz, 1H), 7.53 (d, J=1.8 Hz, 1H), 6.91 (d, J=8.6 Hz, 1H), 4.33 (q, J=7.1 Hz, 2H), 3.91 (s, 3H), 1.36 (t, J=7.3 Hz, 3H). HPLC-MS: Expected: 197 (MH+); Found: 197

Synthesis of 3-methoxy-4-((4-(trifluoromethoxy)benzyl)oxy)benzoyl chloride

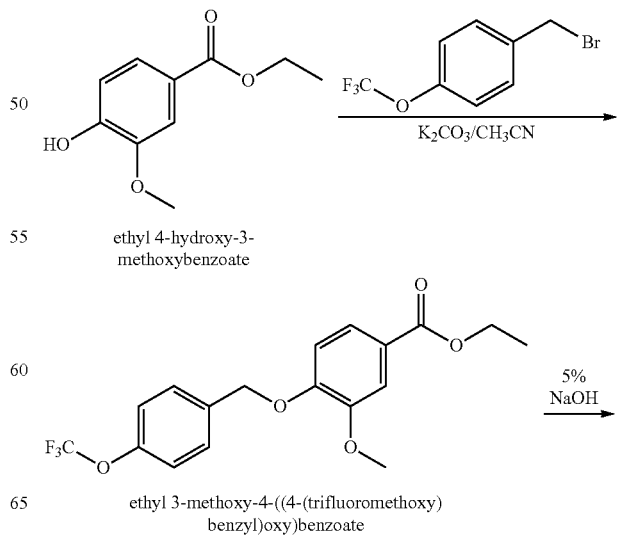

Synthesis of 4-(1H-benzo[d]imidazol-2-yl)piperidin-1-yl)(3-methoxy-4-((4-(trifluoromethoxy)benzyl)oxy)phenyl)methanone (AZ170)

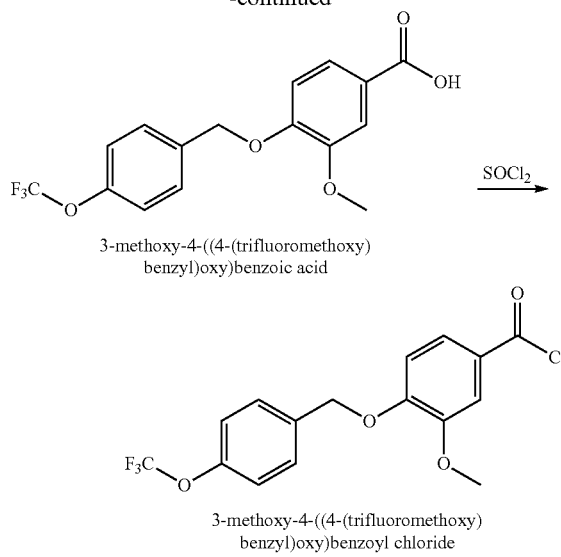

3-methoxy-4-((4-(trifluoromethoxy)benzyl)oxy)benzoic acid 3-methoxy-4-((4-(trifluoromethoxy)benzyl)oxy)benzoyl chloride

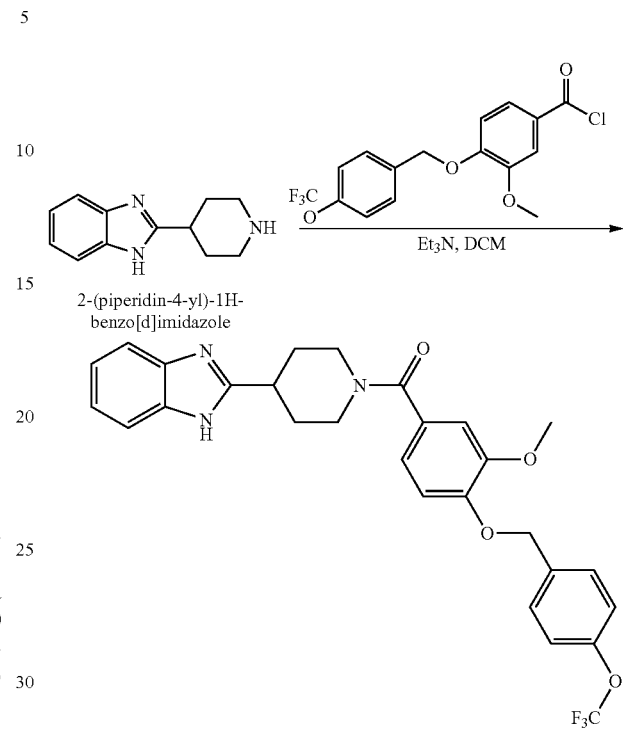

2-(piperidin-4-yl)-1H-benzo[d]imidazole (4-(1H-benzo[d]imidazol-2-yl)piperidin-1-yl)(3-methoxy-4-((4-(trifluoromethoxy)benzyl)oxy)phenyl)methanone In a round bottomed flask with nitrogen inlet and magnetic stir bar, potassium carbonate (1.86 g, 13.46 mmol), ethyl 4-hydroxy-3-methoxybenzoate (1.2 g, 6.12 mmol) and acetonitrile (26 mL) were added. Mixture was stirred for 30 minutes before 1-(bromomethyl)-4-(trifluoromethoxy)benzene (1.72 g, 6.74 mmol) was added. Reaction was heated to reflux overnight and then, cooled to room temperature. Water 100 mL was added and the aqueous mixture was extracted with ethyl acetate (3×50 mL). The combined organic layers were evaporated and then dried to get 2.26 g of ethyl 3-methoxy-4-((4-(trifluoromethoxy)benzyl)oxy)benzoate.

1H NMR (400 MHz, Chloroform-d) δ 7.61 (ddd, J=8.4, 2.0, 0.8 Hz, 1H), 7.56 (s, 1H), 7.45 (d, J=8.9 Hz, 2H), 7.21 (d, J=8.1 Hz, 2H), 6.86 (d, J=8.4 Hz, 1H), 4.33 (q, J=7.4 Hz, 1H), 3.92 (s, 7H), 1.36 (t, J=7.1 Hz, 2H).

In a round bottomed flask equipped with nitrogen inlet and magnetic stir bar, a solution of ethyl 3-methoxy-4-((4-(trifluoromethoxy)benzyl)oxy)benzoate (2.26 g, 6.10 mmol) in methanol (25 mL) was added. To the above solution, 9 mL of 5% NaOH solution was added. The reaction was stirred at room temperature overnight. Methanol was evaporated and 15 mL cold water was added to it. Aqueous layer was acidified with 6 N HCl, the precipitate was filtered, washed with cold water and dried to obtain 2.09 g of 3-methoxy-4-((4-(trifluoromethoxy)benzyl)oxy)benzoic acid.

1H NMR (400 MHz, Chloroform-d) δ 7.58 (dd, J=15.1, 1.9 Hz, 2H), 7.45 (d, J=8.7 Hz, 2H), 7.21 (d, J=8.6 Hz, 2H), 6.87 (d, J=8.5 Hz, 1H), 5.17 (s, 2H), 3.87 (s, 3H).

HPLC-MS (negative mode): Expected: 341 (M−1); found: 341.

In a round bottomed flask equipped with nitrogen inlet and magnetic stir bar, 3-methoxy-4-((4-(trifluoromethoxy)benzyl)oxy)benzoic acid (563 mg, 1.65 mmol) and thionyl chloride (3 mL, 41.35 mmol) were added. Reaction mixture was heated to 110° C. for 2 hours and then, additional thionyl chloride (2 mL, 27.57 mmol) was added. After the reaction is complete, thionyl chloride was co-evaporated with toluene to get 463 mg of 3-methoxy-4-((4-(trifluoromethoxy)benzyl)oxy)benzoyl chloride as desired product.

In a round bottomed flask equipped with a nitrogen inlet and a magnetic stir bar, 3-methoxy-4-((4-(trifluoromethoxy)benzyl)oxy)benzoyl chloride (156 mg, 0.43 mmol), 2-(piperidin-4-yl)-1H-benzo[d]imidazole (87 mg, 0.43 mmol) and Et$_3$N (0.13 mL, 0.93 mmol) in CH$_2$Cl$_2$ (5 mL) were added. The reaction mixture was filtered and 44 mg of the starting material was recovered as a beige color solid. The filtrate was washed with H$_2$O and the aqueous was extracted with CH$_2$Cl$_2$. The organic layer was dried over Na$_2$SO$_4$, filtered and then concentrated using rotary evaporator. The crude was purified using preparatory TLC with 70% EtOAc in hexanes to give 47 mg (21%) of the pure and desired product. Yield is 43%

$^1$H NMR (400 MHz, Chloroform-d) δ 10.83 (s, 1H), 7.67 (d, J=6.6 Hz, 1H), 7.42 (d, J=8.7 Hz, 2H), 7.26 (d, J=8.4 Hz, 1H), 7.19 (d, J=8.7 Hz, 4H), 6.98 (d, J=1.9 Hz, 1H), 6.89 (dd, J=8.2, 1.9 Hz, 1H), 6.79 (d, J=8.3 Hz, 1H), 5.08 (s, 2H), 3.77 (s, 3H), 3.16 (tt, J=12.5, 4.5 Hz, 1H), 3.10-2.94 (m, 2H), 2.14-2.04 (m, 2H), 2.01-1.85 (m, 4H).

$^{13}$C NMR (101 MHz, Chloroform-d) δ 170.44, 156.42, 149.66, 149.33, 148.90, 142.84, 135.18, 133.81, 128.98, 128.59, 128.47, 123.09-121.55 (m), 121.30, 120.90, 119.69, 118.90 (d, J=44.1 Hz), 113.16 (d, J=15.0 Hz), 111.09 (d, J=11.7 Hz), 110.68 (d, J=49.7 Hz), 70.13, 56.10, 36.85, 36.76, 30.95.

HRMS: Found MH$^+$=156.1946 (Theoretically: MH$^+$=526.1948)

Synthesis of 3-methoxy-4-((4-(trifluoromethyl)benzyl)oxy)benzoic acid

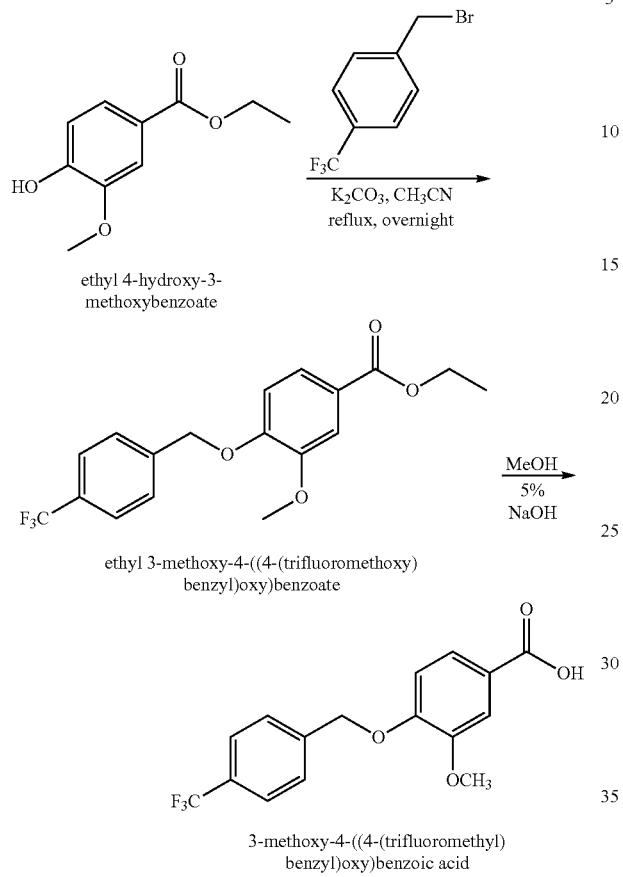

ethyl 4-hydroxy-3-methoxybenzoate ethyl 3-methoxy-4-((4-(trifluoromethoxy)benzyl)oxy)benzoate 3-methoxy-4-((4-(trifluoromethyl)benzyl)oxy)benzoic acid In a round bottomed flask equipped with a nitrogen inlet and a magnetic stir bar, potassium carbonate (1.86 g, 13.46 mmol), ethyl 4-hydroxy-3-methoxybenzoate (1.2 g, 6.12 mmol) and CH₃CN (26 mL) were added. The mixture was stirred for 30 minutes before 1-(bromomethyl)-3-(trifluoromethyl)benzene (1.59 g, 6.65 mmol) was added. The mixture was then stirred at reflux temperature for overnight hours. The reaction mixture was rotary evaporated. Water (100 mL) was then added to the residue and the aqueous was then extracted with EtOAc (50 mL×3). The combined organic layers were evaporated and then dried in vacuo yielding 2.08 g (96%) of ethyl 3-methoxy-4-((3-(trifluoromethyl)benzyl)oxy)benzoate as beige solid.

¹H NMR (400 MHz, Chloroform-d) δ 7.80-7.39 (m, 6H), 6.83 (d, J=8.4 Hz, 1H), 5.24 (s, 2H), 4.33 (q, J=7.1 Hz, 2H), 3.93 (s, 3H), 1.36 (t, J=7.1 Hz, 3H).

In a round bottomed flask equipped with a nitrogen inlet and a magnetic stir bar, a solution of ethyl 3-methoxy-4-((4-(trifluoromethyl)benzyl)oxy)benzoate (2.17 g, 6.12 mmol) in MeOH (28 mL) was added. To the above solution 9 mL of 5% NaOH was added. The reaction mixture was stirred at room temperature for overnight. The mixture was rotary evaporated and 20 mL of cold water was added. The aqueous was acidified with 6 N HCl. The precipitate was filtered and the solid, washed with 5 mL of water and then dried in vacuo to give 1.78 g (89%) of 3-methoxy-4-((4-(trifluoromethyl)benzyl)oxy)benzoic acid as white colored solid.

¹H NMR (400 MHz, Chloroform-d) δ 7.71-7.48 (m, 6H), 6.84 (d, J=8.4 Hz, 1H), 5.25 (s, 2H), 3.93 (s, 3H).

Synthesis of (4-(1H-benzo[d]imidazol-2-yl)piperidin-1-yl)(3-methoxy-4-((4-(trifluoromethyl)benzyl)oxy)phenyl)methanone (AZ172)

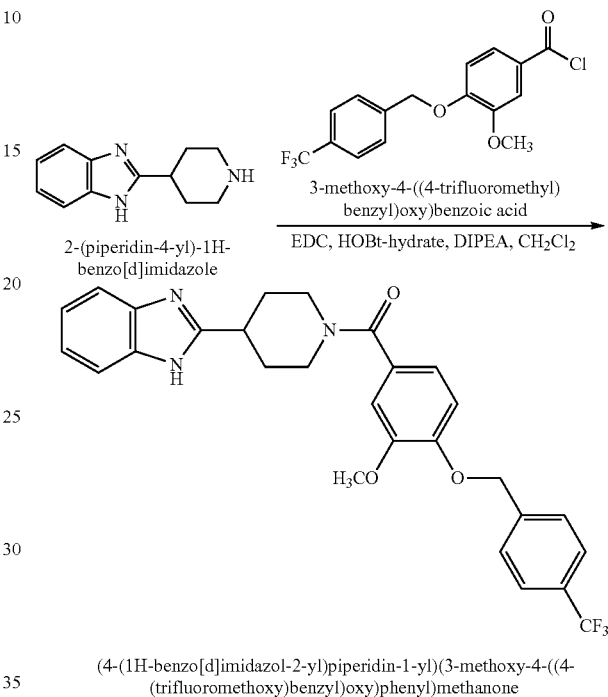

2-(piperidin-4-yl)-1H-benzo[d]imidazole 3-methoxy-4-((4-trifluoromethyl)benzyl)oxy)benzoic acid (4-(1H-benzo[d]imidazol-2-yl)piperidin-1-yl)(3-methoxy-4-((4-(trifluoromethoxy)benzyl)oxy)phenyl)methanone In a round bottomed flask equipped with a magnetic stir bar and a nitrogen inlet, a mixture of 3-methoxy-4-((4-(trifluoromethyl)benzyl)oxy)benzoic acid (255 mg, 0.78 mmol), EDC hydrochloride (374 g, 1.95 mmol), HOBT-hydrate (299 mg, 1.95 mmol) and DIEPA (0.27 mL, 3.14 mmol) in 2 mL DMF was added. The mixture was then stirred at room temperature for an hour. To the above solution, 2-(piperidin-4-yl)-1H-benzo[d]imidazole (157 mg, 0.78 mmol) was added. The mixture was stirred at room temperature for 16 h. The mixture was dissolved in water, basified to pH 10 with saturated Na₂CO₃ (aq), and the aqueous was extracted with CH₂Cl₂. The organic layer was then removed by rotary evaporation and the crude was purified by column chromatography. The desired product was eluted with 10% of MeOH in CH₂Cl₂ to give 20 mg (5%) of (4-(1H-benzo[d]imidazol-2-yl)piperidin-1-yl)(3-methoxy-4-((4 (trifluoromethyl)benzyl)oxy)phenyl)methanone.

¹H NMR (400 MHz, Chloroform-d) δ 10.27 (s, 1H), 7.61 (d, J=8.1 Hz, 2H), 7.51 (d, J=8.0 Hz, 2H), 7.19 (q, J=7.1 Hz, 2H), 7.00 (d, J=1.9 Hz, 1H), 6.90 (dd, J=8.2, 1.9 Hz, 1H), 6.78 (d, J=8.3 Hz, 1H), 5.17 (s, 2H), 3.82 (s, 3H), 3.23-2.96 (m, 3H), 2.12-2.09 (m, 2H), 2.02-1.86 (m, 3H), 1.23 (m, 1H). (2 proton peak may be was covered by the CDCl3 peak)

¹³C NMR (101 MHz, Chloroform-d) δ 170.36, 156.25, 149.63, 149.11, 140.59, 130.66, 130.34, 130.02, 129.69, 128.78, 127.62-126.52 (m), 125.69-125.48 (m), 122.36, 119.70, 113.08, 111.13, 72.24-65.68 (m), 56.02 (d, J=15.2 Hz), 36.78 (d, J=5.0 Hz).

HRMS MH⁺=510.20006 (Theoretically=510.19990)

Synthesis of
4-((4-cyanobenzyl)oxy)-3-methoxybenzoyl chloride

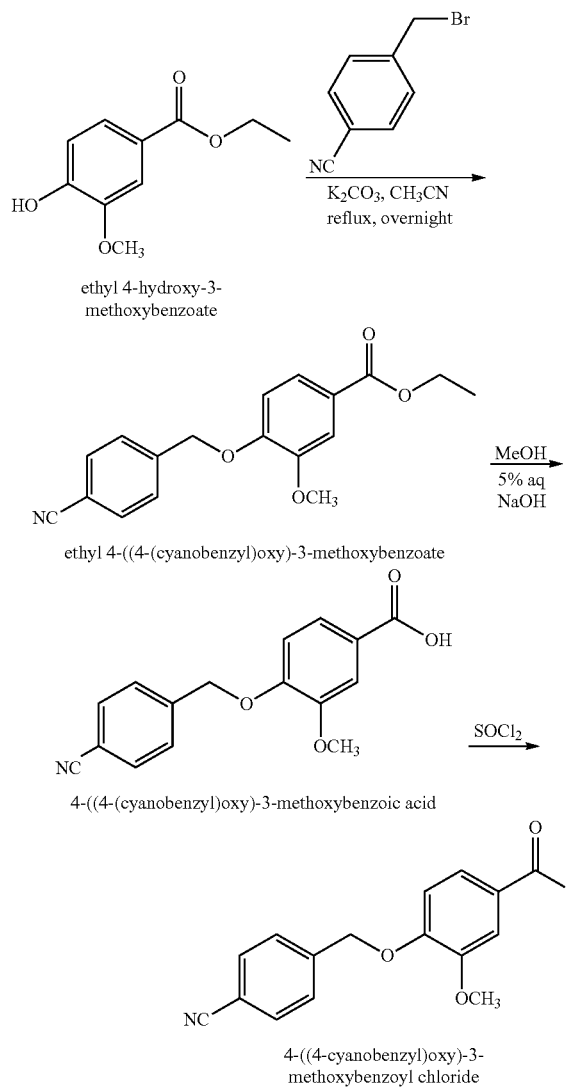

In a round bottomed flask equipped with a nitrogen inlet and a magnetic stir bar, potassium carbonate (1.86 g, 13.46 mmol), ethyl 4-hydroxy-3-methoxybenzoate (1.2 g, 6.12 mmol) and CH$_3$CN (26 mL) was added. The mixture was stirred for 30 minutes before 4-(bromomethyl)benzonitrile (1.32 g, 6.73 mmol) was added. The mixture was then stirred at reflux temperature overnight. The reaction mixture was rotary evaporated. Water (100 mL) was then added to the residue and the aqueous was then extracted with EtOAc (3×50 mL). The combined organic layers were evaporated and then dried in vacuo yielding 2.04 g (96%) of ethyl 4-((4-cyanobenzyl)oxy)-3-methoxybenzoate as product.

1H NMR (400 MHz, Chloroform-d) δ 7.80-7.35 (m, 6H), 6.82 (d, J=8.4 Hz, 1H), 5.24 (s, 2H), 4.34 (q, J=7.1 Hz, 2H), 3.93 (s, 3H), 1.36 (t, J=7.1 Hz, 3H).

In a round bottomed flask equipped with a nitrogen inlet and a magnetic stir bar, a solution of ethyl 4-((4-cyanobenzyl)oxy)-3-methoxybenzoate (2.04 g, 6.12 mmol) in MeOH (28 mL) was added. To the above, 9 mL of 5% NaOH solution was added. The reaction mixture was stirred at room temperature for overnight. The mixture was rotary evaporated and 20 mL of cold water was added. The aqueous was acidified with 6 N HCl. The precipitate was filtered and the solid, washed with 5 mL of water and then dried in vacuo to give 1.28 g of 4-((4-cyanobenzyl)oxy)-3-methoxybenzoic acid as pure and desired product.

¹H NMR (400 MHz, Chloroform-d) δ 7.65 (dt, J=6.3, 1.4 Hz, 2H), 7.61-7.56 (m, 1H), 7.56-7.50 (m, 3H), 7.24 (t, J=1.7 Hz, 1H), 5.22 (s, 2H), 3.92 (s, 3H).

HPLC-MS (negative mode): Expected: 282 (M−1); Found: 282.

In a 25-mL round bottomed flask equipped with nitrogen inlet and a magnetic stir bar, 300 mg of 4-((4-cyanobenzyl)oxy)-3-methoxybenzoic acid (1.76 mmol), thionyl chloride (3.2 ml, 44.1 mmol) was added. The mixture was stirred at 110° C. for 2 h before additional thionyl chloride (2.1 ml, 28.95 mmol) was added. The reaction mixture was stirred at reflux overnight. Excess thionyl chloride was co-evaporated with toluene to give 451 mg of 4-((4-cyanobenzyl)oxy)-3-methoxybenzoyl chloride. The compound was used in the next step.

Synthesis of 4-((4-(4-(1H-benzo[d]imidazol-2-yl)piperidine-1-carbonyl)-2-methoxyphenoxy)methyl)benzonitrile (AZ173)

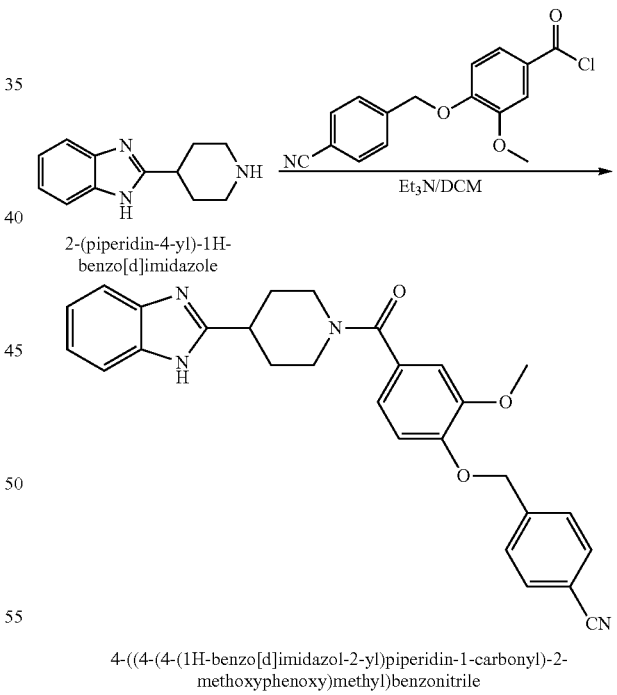

4-((4-(4-(1H-benzo[d]imidazol-2-yl)piperidin-1-carbonyl)-2-methoxyphenoxy)methyl)benzonitrile In a round bottomed flask equipped with a nitrogen inlet and a magnetic stir bar, 4-((4-cyanobenzyl)oxy)-3-methoxybenzoyl chloride (142 mg, 0.47 mmol), 2-(piperidin-4-yl)-1H-benzo[d]imidazole (95 mg, 0.47 mmol) and Et$_3$N (0.14 mL, 1.00 mmol) in CH$_2$Cl$_2$ (5 mL) was added. The reaction mixture was filtered and 46 mg of the starting material was recovered as a beige color solid. The filtrate was washed with H$_2$O and the aqueous was extracted with CH$_2$Cl$_2$. The organic layer was dried over Na₂SO₄, filtered and then concentrated using rotary evaporator. The crude was purified using preparatory TLC with 70% EtOAc in hexanes to give 80 mg (36%) of the pure and desired product.

¹H NMR (400 MHz, Chloroform-d) δ 7.63 (d, J=8.0 Hz, 2H), 7.50 (d, J=8.1 Hz, 2H), 7.74-7.44 (m, 2H), 7.17 (dq, J=7.0, 3.8 Hz, 2H), 6.99 (s, 1H), 6.87 (dd, J=8.2, 1.4 Hz, 1H), 6.75 (d, J=8.2 Hz, 1H), 5.15 (s, 2H), 4.86-4.40 (m, 1H), 3.80 (s, 3H), 3.30-2.79 (m, 4H), 2.17-2.03 (m, 2H), 2.01-1.87 (m, 2H).

¹³C NMR (101 MHz, Chloroform-d) δ 170.33, 156.37, 149.66, 148.90, 142.00, 132.61, 132.26, 128.97, 127.62, 127.27, 122.47, 122.25, 119.62, 118.62, 113.21 (d, J=13.3 Hz), 111.74, 111.10, 111.05, 69.93, 69.58, 56.01 (d, J=22.6 Hz), 36.70 (d, J=5.2 Hz).

HRMS Found=MH⁺=467.20775 (Theoretically=467.20777)

Synthesis of (4-(1H-benzo[d]imidazol-2-yl)piperidin-1-yl)(4-hydroxy-3-methoxyphenyl)methanone

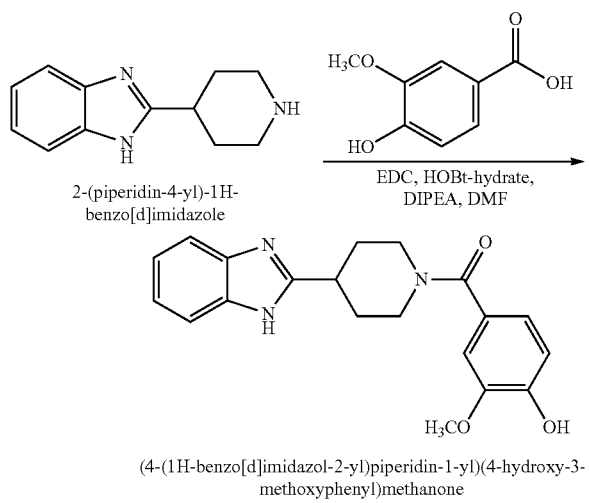

In a round bottomed flask equipped with a magnetic stir bar and a nitrogen inlet, a mixture of vanillic acid (501 mg, 2.98 mmol), EDC hydrochloride (571 g, 2.98 mmol) and HOBt-hydrate (456 mg, 2.98 mmol) and DIPEA (0.86 mL, 8.97 mmol) in 18 mL DMF were added. The mixture was then stirred at room temperature for one hour. To the above solution, 2-(piperidin-4-yl)-1H-benzo[d]imidazole (600 mg, 2.98 mmol) was added. The mixture was stirred at room temperature for overnight. To the reaction mixture water was added, precipitate was filtered and dried in vacuo yielding 724 mg of (4-(1H-benzo[d]imidazol-2-yl)piperidin-1-yl)(4-hydroxy-3-methoxyphenyl)methanone as crude product. To the crude product, CH₂Cl₂ was added, white precipitate formed was filtered and then dried in vacuo to give 334 mg (32%) of the desired product.

¹H NMR (400 MHz, DMSO-d6) δ 12.19 (s, 1H), 9.40 (s, 1H), 7.50 (d, J=8.0 Hz, 1H), 7.38 (d, J=7.6 Hz, 1H), 7.19-7.02 (m, 2H), 6.93 (s, 1H), 6.89-6.64 (m, 2H), 3.75 (s, 3H+1H masked), 3.20-2.94 (m, 4H), 2.10-1.88 (m, 2H), 1.75 (q, J=13.5, 13.0 Hz, 2H).

Synthesis of (4-(1H-benzo[d]imidazol-2-yl)piperidin-1-yl)(4-((3-fluorobenzyl)oxy)-3-methoxyphenyl)methanone (AZ177) and (4-(1-(3-fluorobenzyl)-1H-benzo[d]imidazol-2-yl)piperidin-1-yl)(4-((3-fluorobenzyl)oxy)-3-methoxyphenyl)methanone (AZ194)

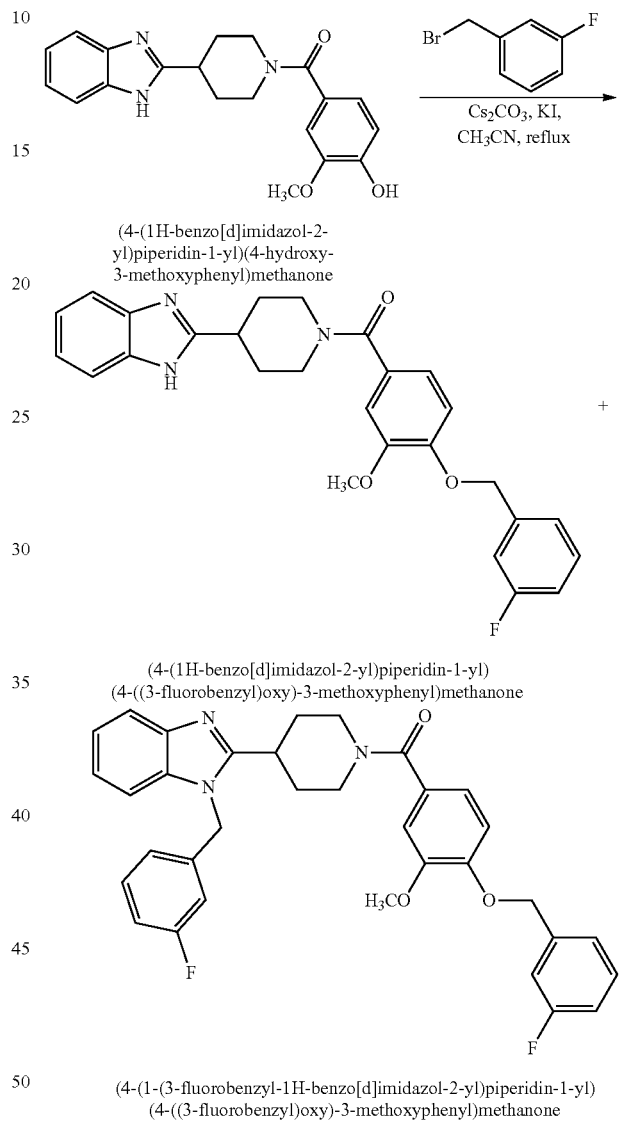

In a round bottomed flask equipped with a magnetic stir bar and a nitrogen inlet, a mixture of (4-(1H-benzo[d]imidazol-2-yl)piperidin-1-yl)(4-hydroxy-3-methoxyphenyl)methanone (165 mg, 0.47 mmol), Cs₂CO₃ (230 mg, 0.71 mmol) and KI (16 mg, 0.1 mmol) in 10 mL CH₃CN was added. The mixture was then stirred at room temperature for 10 mins. To the above solution, 1-(bromomethyl)-3-fluorobenzene (89 mg, 0.47 mmol) was added. The mixture was refluxed overnight. The reaction mixture was filtered and the filtrate was rotary evaporated. The residue was dissolved in CH₂Cl₂ (15 mL) and washed with H₂O (25 mL). The aqueous layer was extracted with CH₂Cl₂ (15 mL×2). The combined organic layers were dried over Na₂SO₄, filtered, rotary evaporated and then dried in vacuo. The crude was purified by column chromatography and the product was eluted with 0-2% MeOH in CH$_2$Cl$_2$ to give 104 mg of (4-(1-(3-fluorobenzyl)-1H-benzo[d]imidazol-2-yl)piperidin-1-yl)(4-((3-fluorobenzyl)oxy)-3-methoxyphenyl)methanone (39%) and 64 mg (30%) of (4-(1H-benzo[d]imidazol-2-yl)piperidin-1-yl)(4-((3-fluorobenzyl)oxy)-3-methoxyphenyl)methanone.

(4-(1H-benzo[d]imidazol-2-yl)piperidin-1-yl)(4-((3-fluorobenzyl)oxy)-3-methoxyphenyl)methanone $^1$H NMR (400 MHz, Chloroform-d) δ 11.07 (s, 1H), 7.65 (bs, 1H), 7.29 (td, J=8.0, 5.9 Hz, 1H), 7.22-7.08 (m, 4H), 6.97 (d, J=1.8 Hz, 2H), 6.86 (dd, J=8.2, 1.9 Hz, 1H), 6.75 (d, J=8.3 Hz, 1H), 5.09 (s, 2H), 4.67 (bs, 1H), 3.77 (s, 3H), 3.28-2.84 (m, 3H), 2.36-1.60 (m, 5H).

$^{13}$C NMR (101 MHz, Chloroform-d) δ 170.46, 164.17, 161.75, 156.50, 149.58, 149.24, 139.06 (d, J=7.4 Hz), 130.20 (d, J=8.2 Hz), 128.45, 122.54 (d, J=3.1 Hz), 119.67, 115.03, 114.82, 114.14, 113.92, 113.02, 110.98, 70.10, 55.99 (d, J=5.9 Hz), 36.84

HRMS: MH$^+$=460.20307 (Theoretical 460.20310)

(4-(1-(3-fluorobenzyl)-1H-benzo[d]imidazol-2-yl)piperidin-1-yl)(4-((3-fluorobenzyl)oxy)-3-methoxyphenyl)methanone $^1$H NMR (400 MHz, Chloroform-d) δ 7.77 (d, J=7.9 Hz, 1H), 7.36-7.09 (m, 7H), 7.00 (d, J=1.8 Hz, 1H), 6.99-6.94 (m, 2H), 6.91 (dd, J=8.2, 1.9 Hz, 1H), 6.81 (d, J=8.3 Hz, 1H), 6.77 (d, J=8.4 Hz, 1H), 6.71 (d, J=9.6 Hz, 1H), 5.37 (s, 2H), 5.14 (s, 2H), 3.89 (s, 3H), 3.89 (bs, 1H, seen as a broad base under the singlet), 3.11-2.84 (m, 4H), 2.18-2.03 (m, 2H), 1.94-1.76 (m, 2H).

$^{13}$C NMR (101 MHz, Chloroform-d) δ 170.22, 164.39, 164.20, 161.93, 161.75, 156.65, 149.55, 148.95, 142.46, 139.26 (d, J=7.1 Hz), 138.52 (d, J=6.8 Hz), 134.97, 130.82 (d, J=8.1 Hz), 130.15 (d, J=8.1 Hz), 128.94, 122.89, 122.50, 121.46, 119.68, 119.61, 115.13 (d, J=21.0 Hz), 114.95, 114.04 (d, J=22.3 Hz), 113.30-112.60 (m), 111.07, 109.50, 56.05, 46.24, 34.68, 31.05.

HRMS: MH$^+$=568.24237 (Theoretical: 568.24062)

Synthesis of 3-methoxy-4-((3-(trifluoromethyl)benzyl)oxy)benzoyl chloride

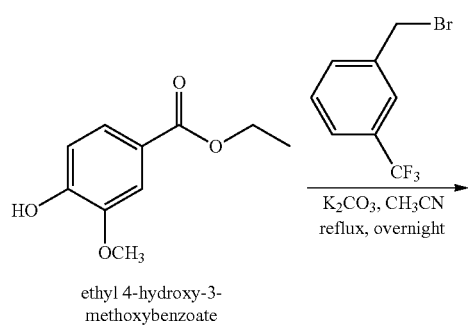

ethyl 4-hydroxy-3-methoxybenzoate

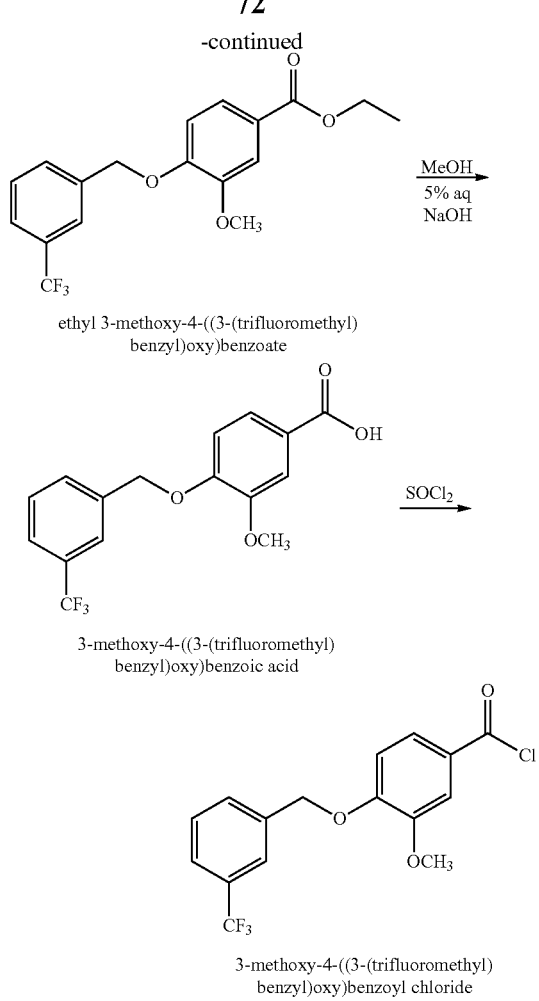

In a round bottomed flask equipped with a nitrogen inlet and a magnetic stir bar, potassium carbonate (1.86 g, 13.46 mmol), ethyl 4-hydroxy-3-methoxybenzoate (1.2 g, 6.12 mmol) and CH$_3$CN (26 mL) were added. The mixture was stirred for 30 minutes before 1-(bromomethyl)-3-(trifluoromethyl)benzene (1.59 g, 6.65 mmol) was added. The mixture was then stirred at reflux temperature overnight. The reaction mixture was rotary evaporated. Water (100 mL) was then added to the residue and the aqueous was then extracted with EtOAc (3×50 mL). The combined organic layers were evaporated and then dried in vacuo yielding 2.08 g (96%) of ethyl 3-methoxy-4-((3-(trifluoromethyl)benzyl)oxy)benzoate as product.

1H NMR (400 MHz, Chloroform-d) δ 7.69 (s, 1H), 7.63 (d, J=2.0 Hz, 1H), 7.60 (d, J=2.0 Hz, 1H), 7.57 (d, J=2.0 Hz, 1H), 7.56 (s, 1H), 7.48 (t, J=7.7 Hz, 1H), 6.87 (d, J=8.4 Hz, 1H), 5.22 (s, 2H), 4.34 (q, J=7.1 Hz, 2H), 3.93 (s, 3H), 1.36 (t, J=7.1 Hz, 3H).

HPLC-MS: Expected: 355 (MH+); Found: 355.

In a round bottomed flask equipped with a nitrogen inlet and a magnetic stir bar, a solution of ethyl 3-methoxy-4-((3-(trifluoromethyl)benzyl)oxy)benzoate (2.04 g, 5.88 mmol) in MeOH (28 mL) was added. To the above, 8 mL of 5% NaOH solution was added. The reaction mixture was stirred at room temperature for overnight. The mixture was rotary evaporated and 20 mL of cold water was added. The aqueous was acidified with 6 N HCl. The precipitate was filtered and the solid, washed with 5 mL of water and then dried in vacuo to give 1.67 g of 3-methoxy-4-((3-(trifluoromethyl)benzyl)oxy)benzoic acid as pure and desired product.

1H NMR (400 MHz, Methanol-d4) δ 7.77 (s, 1H), 7.71 (d, J=6.7 Hz, 1H), 7.69-7.47 (m, 4H), 7.07 (dd, J=8.4, 2.7 Hz, 1H), 5.24 (s, 2H), 3.88 (s, 3H).

In a 25-mL round bottomed flask equipped with nitrogen inlet and a magnetic stir bar, 300 mg of 3-methoxy-4-((3-(trifluoromethyl)benzyl)oxy)benzoic acid (0.83 mmol), thionyl chloride (1.5 mL, 20.68 mmol) was added. The mixture was stirred at 110° C. for 2 h before additional thionyl chloride (1.0 mL, 13.78 mmol) was added. The reaction mixture was stirred at reflux overnight. Excess thionyl chloride was co-evaporated with toluene to give 292 mg of 3-methoxy-4-((3-(trifluoromethyl)benzyl)oxy)benzoyl chloride. The compound was used in the next step.

Synthesis of (4-(1H-benzo[d]imidazol-2-yl)piperidin-1-yl)(3-methoxy-4-((3-(trifluoromethyl)benzyl)oxy)phenyl)methanone (AZ178)

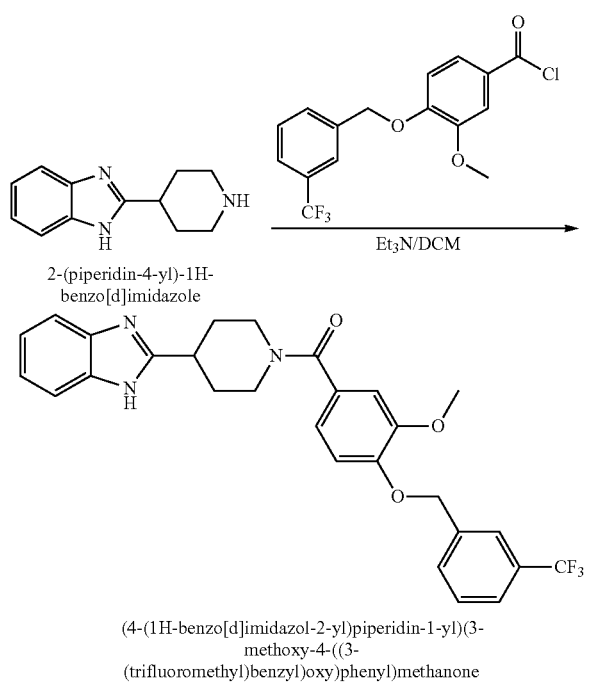

(4-(1H-benzo[d]imidazol-2-yl)piperidin-1-yl)(3-methoxy-4-((3-(trifluoromethyl)benzyl)oxy)phenyl)methanone In a round bottomed flask equipped with a nitrogen inlet and a magnetic stir bar, 3-methoxy-4-((3-(trifluoromethyl)benzyl)oxy)benzoyl chloride (143 mg, 0.415 mmol), 2-(piperidin-4-yl)-1H-benzo[d]imidazole (83.5 mg, 0.415 mmol) and Et$_3$N (0.15 mL, 1.08 mmol) in CH$_2$Cl$_2$ (5 mL) was added. The reaction mixture was stirred for 5 h. Water 10 mL was added to the reaction mixture was filtered and the aqueous was extracted with CH$_2$Cl$_2$. The organic layer was dried over Na$_2$SO$_4$, filtered and then concentrated using rotary evaporator. The crude was purified using preparatory TLC with 5% MeOH in CH$_2$Cl$_2$ to give 68 mg (32%) of (4-(1H-benzo[d]imidazol-2-yl)piperidin-1-yl)(3-methoxy-4-((3-(trifluoromethyl)benzyl)oxy)phenyl)methanone.

$^1$H NMR (400 MHz, Chloroform-d) δ 7.67 (s, 1H), 7.61-7.53 (m, 2H), 7.50-7.42 (m, 3H), 7.17 (dq, J=6.9, 3.9 Hz, 2H), 6.98 (s, 1H), 6.89 (d, J=8.3 Hz, 1H), 6.79 (d, J=8.2 Hz, 1H), 5.13 (s, 2H), 4.84-4.47 (m, 1H), 3.78 (s, 3H), 3.32-3.10 (m, 2H), 3.12-2.76 (m, 2H), 2.26-2.03 (m, 2H), 2.05-1.78 (m, 2H).

$^{13}$C NMR (101 MHz, Chloroform-d) δ 170.43, 156.43, 149.72, 149.20, 137.51, 130.72 (dd, J=39.6, 30.2 Hz), 129.13 (d, J=27.0 Hz), 128.76, 125.32, 124.90 (d, J=28.2 Hz), 123.99 (d, J=31.1 Hz), 122.34 (d, J=16.0 Hz), 119.68, 113.36 (d, J=5.9 Hz), 111.06 (d, J=2.9 Hz), 72.48-68.00 (m), 56.08, 55.87, 36.78, 36.72.

HRMS: MH$^+$=510.19997 (Theoretically=510.19990)

Synthesis of (4-(1-(4-fluorobenzyl)-1H-benzo[d]imidazol-2-yl)piperidin-1-yl)(4-((4-fluorobenzyl)oxy)-3-methoxyphenyl)methanone (AZ195)

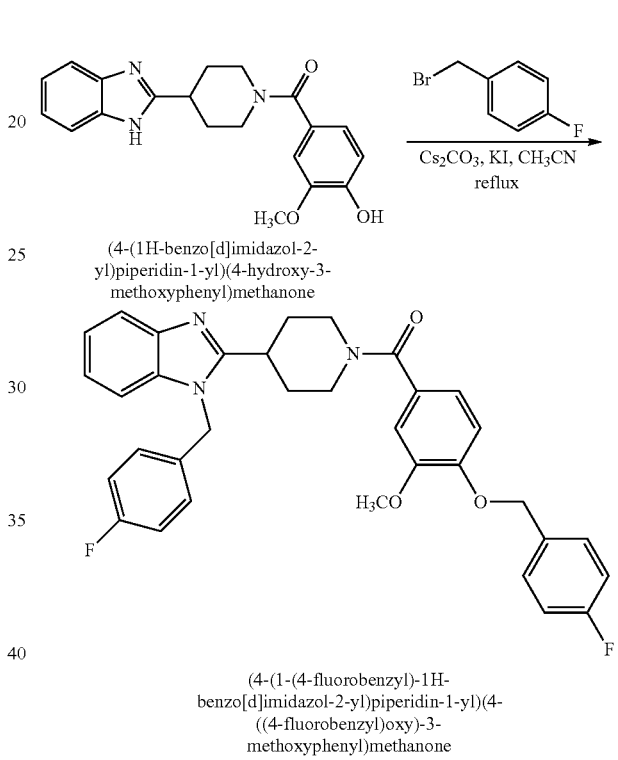

(4-(1-(4-fluorobenzyl)-1H-benzo[d]imidazol-2-yl)piperidin-1-yl)(4-((4-fluorobenzyl)oxy)-3-methoxyphenyl)methanone In a round bottomed flask equipped with a magnetic stir bar and a nitrogen inlet, a mixture of (4-(1H-benzo[d]imidazol-2-yl)piperidin-1-yl)(4-hydroxy-3-methoxyphenyl)methanone (165 mg, 0.47 mmol), Cs$_2$CO$_3$ (230 mg, 0.71 mmol) and KI (16 mg, 0.1 mmol) in 10 mL CH$_3$CN were added. The mixture was then stirred at room temperature for 10 mins. To the above solution, 1-(bromomethyl)-4-fluorobenzene (89 mg, 0.47 mmol) was added. The mixture was stirred at reflux for overnight. The reaction mixture was filtered and the filtrate was rotary evaporated. The residue was dissolved in CH$_2$Cl$_2$ (15 mL) and washed with water (25 mL). The aqueous layer was extracted with CH$_2$Cl$_2$ (15 mL×2). The combined organic layers were dried over Na$_2$SO$_4$, rotary evaporated and then dried in vacuo. The crude was purified using 5% MeOH in CH$_2$Cl$_2$ as an eluent to give 158 mg of (4-(1-(4-fluorobenzyl)-1H-benzo[d]imidazol-2-yl)piperidin-1-yl)(4-((4-fluorobenzyl)oxy)-3-methoxyphenyl)methanone.

$^1$H NMR (400 MHz, DMSO-d6) δ 7.59-7.53 (m, 1H), 7.47 (dd, J=8.1, 5.9 Hz, 2H), 7.43-7.35 (m, 1H), 7.20 (t, J=8.9 Hz, 2H), 7.16-7.08 (m, 6H), 7.05 (d, J=8.3 Hz, 1H), 6.98 (s, 1H), 6.93 (dd, J=8.2, 1.9 Hz, 1H), 5.52 (s, 2H), 5.06

(s, 2H), 3.76 (s, 3H), 3.76 (bs, 1H, seen as a broad base under the singlet), 3.18-2.88 (m, 4H), 1.90-1.62 (m, 4H). (2 proton peaks seems to be masked by DMSO peaks).

$^{13}$C NMR (101 MHz, Chloroform-d) δ 170.26, 156.66, 149.57, 149.09, 134.96, 132.35 (d, J=3.1 Hz), 131.64, 129.21, 129.13, 128.82, 127.65, 127.57, 122.84, 122.45, 119.69, 119.55, 116.23, 116.01, 115.61, 115.39, 113.06, 111.06, 109.56, 70.28, 56.06 (d, J=5.7 Hz), 46.12, 34.73, 31.05.

HRMS: MH$^+$=568.24051 (Theoretically=568.24062)

Synthesis of (4-(1H-benzo[d]imidazol-2-yl)piperidin-1-yl)(morpholino)methanone (AZ198)

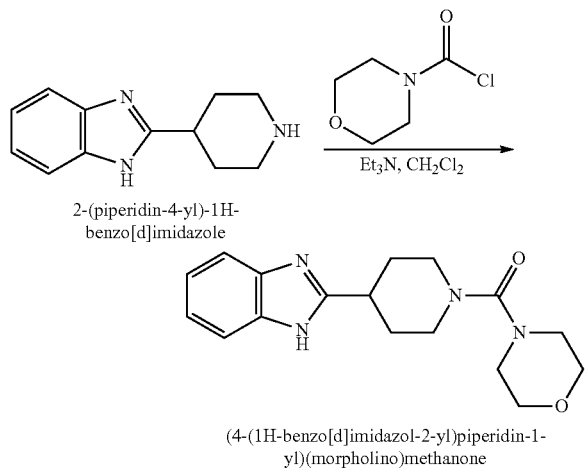

(4-(1H-benzo[d]imidazol-2-yl)piperidin-1-yl)(morpholino)methanone

In a round bottomed flask equipped with a nitrogen inlet and a magnetic stir bar, morphorlinylcarbonyl chloride (75 mg, 0.5 mmol), 2-(piperidin-4-yl)-1H-benzo[d]imidazole (100 mg, 0.50 mmol) and Et$_3$N (0.14 mL, 1.00 mmol) in CH$_2$Cl$_2$ (5 mL) was added. The reaction mixture was filtered and the precipitate was washed with CH$_2$Cl$_2$ and then dried in vacuo to give 95 mg (60%) of (4-(1H-benzo[d]imidazol-2-yl)piperidin-1-yl)(morpholino)methanone.

$^1$H NMR (400 MHz, DMSO-d6) δ 12.16 (s, 1H), 7.61-7.21 (m, 2H), 7.16-6.96 (m, 2H), 3.65 (d, J=12.9 Hz, 2H), 3.58-3.51 (m, 4H), 3.15-3.07 (m, 4H), 3.02 (tt, J=11.6, 3.9 Hz, 1H), 2.89 (t, J=11.3 Hz, 2H), 2.02-1.89 (m, 2H), 1.75 (qd, J=12.3, 4.7 Hz, 2H).

$^{13}$C NMR (101 MHz, DMSO-d6) δ 163.57, 157.94, 68.00-63.84 (m), 47.52, 46.47 (dd, J=34.1, 23.5 Hz), 36.33 (d, J=11.9 Hz), 30.65.

HRMS: MH$^+$=315.18142 (Theoretically=315.18155) and (M+Na)=337.16336 (Theoretically=337.16350)

Synthesis of 2-(1-(phenylsulfonyl)piperidin-4-yl)-1H-benzo[d]imidazole (AZ158)

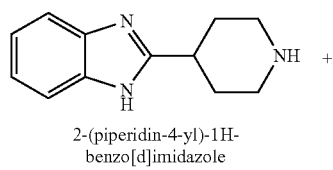

2-(piperidin-4-yl)-1H-benzo[d]imidazole

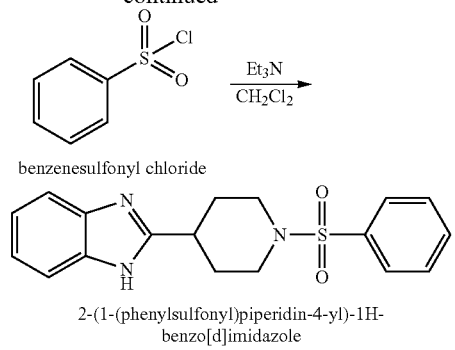

benzenesulfonyl chloride 2-(1-(phenylsulfonyl)piperidin-4-yl)-1H-benzo[d]imidazole In a round bottomed flask equipped with a nitrogen inlet and a magnetic stir bar, benzenesulfonyl chloride (207 mg, 1.2 mmol), 2-(piperidin-4-yl)-1H-benzo[d]imidazole (201 mg, 1 mmol) and Et$_3$N (0.28 mL, 2 mmol) in CH$_2$Cl$_2$ (5 mL) were added. The mixture was then stirred at room temperature for overnight. The precipitate was then filtered, washed with CH$_2$Cl$_2$ and the residue was dried in vacuo yielding 356 mg (100%) of the 2-(1-(phenylsulfonyl)piperidin-4-yl)-1H-benzo[d]imidazole as white solid.

$^1$H NMR (400 MHz, DMSO-d6) δ 12.14 (s, 1H), 7.77-7.60 (m, 5H), 7.47 (d, J=8.3 Hz, 1H), 7.36 (d, J=7.0 Hz, 1H), 7.12-7.02 (m, 2H), 3.69-3.61 (m, 2H), 2.90-2.79 (m, 1H), 2.44-2.39 (m, 2H), 2.12-2.03 (m, 2H), 1.87-1.75 (m, 2H).

$^{13}$C NMR (101 MHz, DMSO-d6) δ 157.17, 143.27, 135.95, 134.64, 133.59, 129.88, 127.92, 122.05, 121.31, 118.79, 111.30, 46.02, 34.86, 29.93.

HRMS: MH$^+$=342.12733 (Theoretically=342.12707)

Synthesis of 2-(1-((4-methoxyphenyl)sulfonyl)piperidin-4-yl)-1H-benzo[d]imidazole (AZ159)

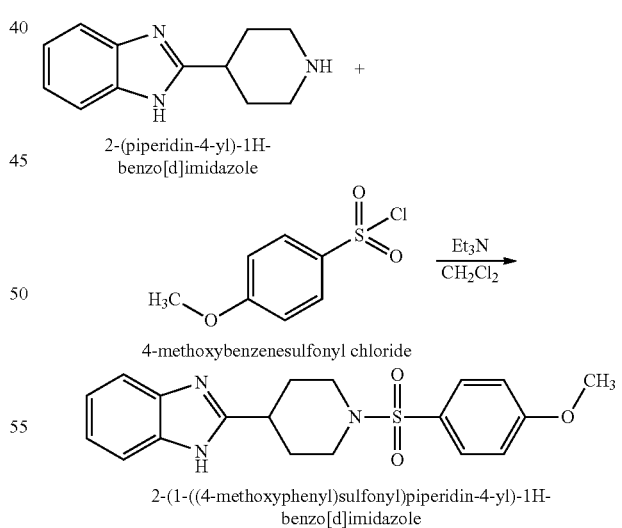

2-(1-((4-methoxyphenyl)sulfonyl)piperidin-4-yl)-1H-benzo[d]imidazole

In a round bottomed flask equipped with a nitrogen inlet and a magnetic stir bar, 4-methoxybenzenesulfonyl chloride (207 mg, 1 mmol), 2-(piperidin-4-yl)-1H-benzo[d]imidazole (200 mg, 1 mmol) and Et$_3$N (0.28 mL, 2 mmol) in CH$_2$Cl$_2$ (5 mL) was added. The mixture was then stirred at room temperature for overnight. The precipitate was then filtered, washed with CH$_2$Cl$_2$ and the residue was dried in vacuo yielding 295 mg (79%) of 2-(1-((4-methoxyphenyl)sulfonyl)piperidin-4-yl)-1H-benzo[d]imidazole.

$^{1}$H NMR (400 MHz, DMSO-d6) δ 12.14 (s, 1H), 7.68 (d, J=9.0 Hz, 2H), 7.48 (d, J=7.1 Hz, 1H), 7.36 (d, J=7.8 Hz, 1H), 7.14 (d, J=9.0 Hz, 2H), 7.11-7.03 (m, 2H), 3.83 (s, 3H), 3.62 (d, J=11.9 Hz, 2H), 2.87-2.79 (m, 1H), 2.44-2.34 (m, 2H), 2.07 (d, J=16.5 Hz, 2H), 1.86-1.76 (m, 2H)

$^{13}$C NMR (101 MHz, DMSO-d6) δ 163.09, 157.21, 143.27, 134.64, 130.17, 127.38, 122.04, 121.30, 118.78, 114.98, 111.26, 56.19, 46.02, 34.91, 29.88.

HRMS: MH$^{+}$=372.13764 (Theoretically=372.13764)

Synthesis of 2-(1-((4-(trifluoromethoxy)phenyl)sulfonyl)piperidin-4-yl)-1H-benzo[d]imidazole (AZ160)

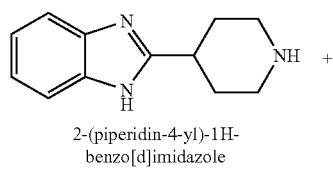

2-(piperidin-4-yl)-1H-benzo[d]imidazole

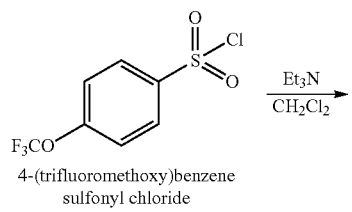

4-(trifluoromethoxy)benzene sulfonyl chloride

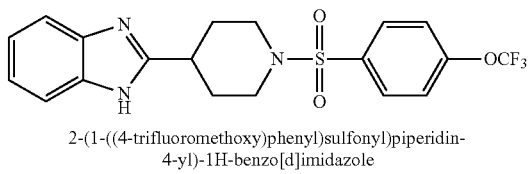

2-(1-((4-trifluoromethoxy)phenyl)sulfonyl)piperidin-4-yl)-1H-benzo[d]imidazole

In a round bottomed flask equipped with a nitrogen inlet and a magnetic stir bar, 4-trifluoromethoxybenzenesulfonyl chloride (313 mg, 1.2 mmol), 2-(piperidin-4-yl)-1H-benzo[d]imidazole (200 mg, 1 mmol) and Et$_3$N (0.28 mL, 2 mmol) in CH$_2$Cl$_2$ (5 mL) was added. The mixture was then stirred at room temperature for overnight. The precipitate was then filtered, washed with CH$_2$Cl$_2$ and the residue was dried in vacuo yielding 304 mg (71%) of 2-(1-((4-(trifluoromethoxy)phenyl)sulfonyl)piperidin-4-yl)-1H-benzo[d]imidazole.

$^{1}$H NMR (400 MHz, DMSO-d6) δ 12.16 (s, 1H), 7.89 (d, J=8.9 Hz, 2H), 7.62 (d, J=8.9 Hz, 2H), 7.47 (d, J=8.4 Hz, 1H), 7.36 (d, J=8.4 Hz, 1H), 7.11-7.03 (m, 2H), 3.67 (d, J=11.8 Hz, 2H), 2.93-2.83 (m, 1H), 2.54-2.48 (m, 2H), 2.13-2.03 (m, 2H), 1.88-1.74 (m, 2H).

$^{13}$C NMR (101 MHz, DMSO-d6) δ 157.15, 151.72, 143.25, 135.00, 134.63, 130.54, 122.02, 121.97, 121.31, 118.72, 111.26, 45.95, 34.70, 29.93.

HRMS: MH$^{+}$=426.10960 (Theoretically=426.10937)

Synthesis of 2-(1-((4-fluorophenyl)sulfonyl)piperidin-4-yl)-1H-benzo[d]imidazole (AZ161)

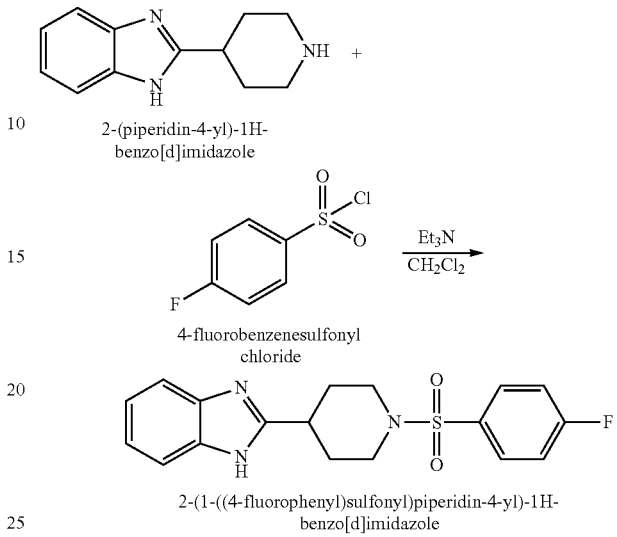

2-(1-((4-fluorophenyl)sulfonyl)piperidin-4-yl)-1H-benzo[d]imidazole

In a round bottomed flask equipped with a nitrogen inlet and a magnetic stir bar, 4-fluorobenzenesulfonyl chloride (195 mg, 1 mmol), 2-(piperidin-4-yl)-1H-benzo[d]imidazole (200 mg, 1 mmol) and Et$_3$N (0.28 mL, 2 mmol) in CH$_2$Cl$_2$ (5 mL) was added. The mixture was then stirred at room temperature for overnight. The precipitate was then filtered, washed with CH$_2$Cl$_2$ and the residue was dried in vacuo yielding 320 mg (89%) of 2-(1-((4-fluorophenyl)sulfonyl)piperidin-4-yl)-1H-benzo[d]imidazole.

$^{1}$H NMR (400 MHz, DMSO-d6) δ 12.15 (s, 1H), 7.82 (dd, J=8.7, 5.2 Hz, 2H), 7.49-7.45 (m, 3H), 7.36 (d, J=7.3 Hz, 1H), 7.07 (p, J=6.8 Hz, 2H), 3.65 (d, J=11.9 Hz, 3H), 2.91-2.80 (m, 1H), 2.42 (m, 2H), 2.08 (d, J=14.6 Hz, 1H), 1.87-1.74 (m, 2H)

$^{13}$C NMR (101 MHz, DMSO-d6) δ 166.27, 163.78, 157.16, 143.27, 132.37 (d, J=2.5 Hz), 130.97 (t, J=10.7 Hz), 122.05, 121.31, 118.90-118.57 (m), 117.06 (dd, J=22.5, 12.1 Hz), 111.26 (d, J=10.4 Hz), 45.97, 34.81, 29.92.

HRMS: MH$^{+}$=360.11784 (Theoretically=360.11765)

Synthesis of 2-(1-((4-(trifluoromethyl)phenyl)sulfonyl)piperidin-4-yl)-1H-benzo[d]imidazole (AZ162)

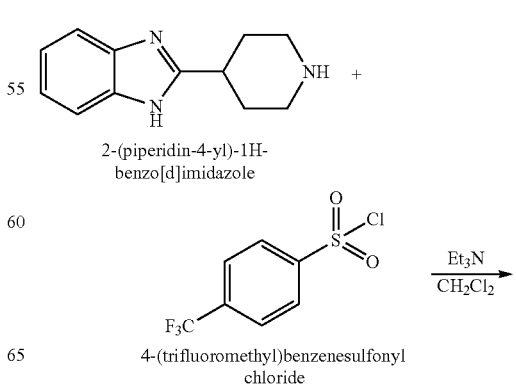

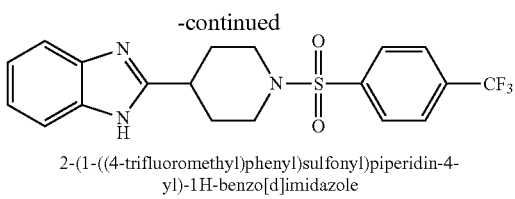

2-(1-((4-trifluoromethyl)phenyl)sulfonyl)piperidin-4-yl)-1H-benzo[d]imidazole

In a round bottomed flask equipped with a nitrogen inlet and a magnetic stir bar, 4-trifluoromethylbenzenesulfonyl chloride (294 mg, 1.2 mmol), 2-(piperidin-4-yl)-1H-benzo[d]imidazole (201 mg, 1 mmol) and Et$_3$N (0.28 mL, 2 mmol) in CH$_2$Cl$_2$ (5 mL) was added. The mixture was then stirred at room temperature for overnight. The precipitate was then filtered, washed with CH$_2$Cl$_2$ and the residue was dried in vacuo yielding 259 mg (63%) of 2-(1-((4-(trifluoromethyl)phenyl)sulfonyl)piperidin-4-yl)-1H-benzo[d]imidazole.

$^1$H NMR (400 MHz, DMSO-d6) δ 12.16 (s, 1H), 8.03-7.96 (m, 4H), 7.47 (d, J=8.0 Hz, 1H), 7.36 (d, J=7.0 Hz, 1H), 7.18-6.98 (m, 2H), 3.70 (d, J=11.9 Hz, 2H), 2.91-2.85 (m, 1H), 2.52 (t, J=11.6 Hz, 2H), 2.09 (d, J=13.5 Hz, 2H), 1.88-1.86 (m, 2H).

$^{13}$C NMR (101 MHz, DMSO-d6) δ 157.13, 143.24, 140.06, 134.63, 133.30, 132.98, 128.88, 127.08, 125.26, 122.07, 121.32, 118.73, 111.27, 45.94, 34.67, 29.96.

HRMS MH$^+$=410.11482 (Theoretically=410.11446)

Synthesis of 2-(1-((3,4-difluorophenyl)sulfonyl)piperidin-4-yl)-1H-benzo[d]imidazole (AZ190)

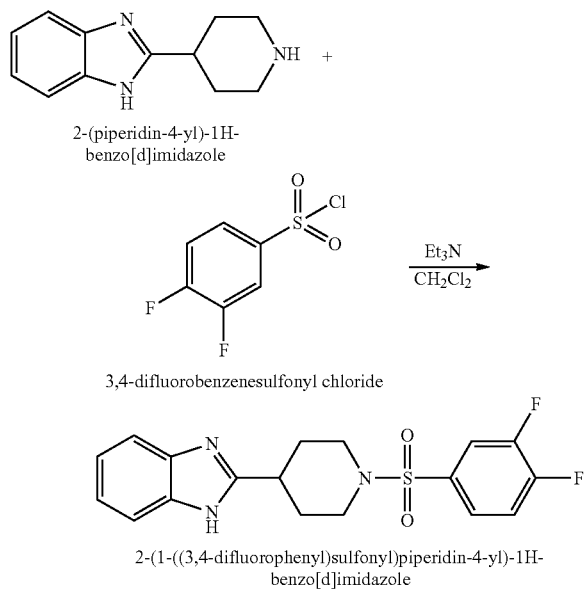

Into a round bottomed flask equipped with a nitrogen inlet and a magnetic stir bar, 3,4-difluorobenzenesulfonyl chloride (110 mg, 0.52 mmol), 2-(piperidin-4-yl)-1H-benzo[d]imidazole (100 mg, 0.49 mmol) and Et$_3$N (0.14 mL, 1 mmol) in CH$_2$Cl$_2$ (5 mL) was added. The mixture was then stirred at room temperature for overnight. The precipitate was then filtered, washed with CH$_2$Cl$_2$ and the residue was dried in vacuo yielding 120 mg (65%) of 2-(1-((3,4-difluorophenyl)sulfonyl)piperidin-4-yl)-1H-benzo[d]imidazole as white solid.

$^1$H NMR (400 MHz, DMSO-d6) δ 12.19 (s, 1H), 7.92 (ddd, J=9.7, 7.4, 2.2 Hz, 1H), 7.79-7.73 (m, 1H), 7.70-7.66 (m, 1H), 7.52 (d, J=6.8 Hz, 1H), 7.41 (d, J=7.0 Hz, 1H), 7.15-7.08 (m, 2H), 3.75-3.70 (m, 2H), 2.97-2.87 (m, 1H), 2.58 (td, J=11.8, 2.5 Hz, 2H), 2.13 (dd, J=13.5, 3.0 Hz, 2H), 1.94-1.79 (m, 2H).

$^{13}$C NMR (101 MHz, DMSO-d6) δ 157.17, 143.31, 134.68, 133.36, 125.87 (dd, J=8.1, 4.2 Hz), 122.10, 121.36, 119.40, 119.22, 118.78, 118.52, 117.98, 117.78, 46.02, 34.83, 29.96.

HRMS: MH$^+$=378.10806 (Theoretically=378.10823)

Synthesis of 2-(1-((4-phenoxyphenyl)sulfonyl)piperidin-4-yl)-1H-benzo[d]imidazole (AZ192)

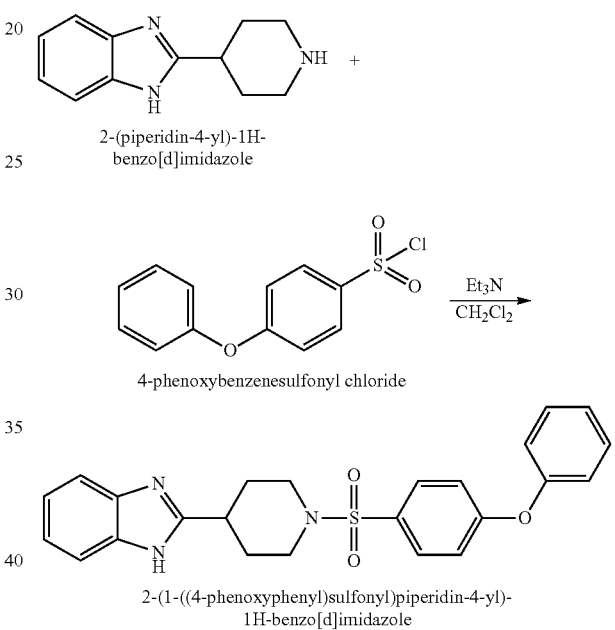

In a round bottomed flask equipped with a nitrogen inlet and a magnetic stir bar, 4-phenoxybenzenesulfonyl chloride (148 mg, 0.55 mmol), 2-(piperidin-4-yl)-1H-benzo[d]imidazole (110 mg, 0.55 mmol) and Et$_3$N (0.16 mL, 1.14 mmol) in CH$_2$Cl$_2$ (5 mL) was added. The mixture was then stirred at room temperature for overnight. The precipitate was then filtered, washed with CH$_2$Cl$_2$ and the residue was dried in vacuo yielding 132 mg (55%) of 2-(1-((4-phenoxyphenyl)sulfonyl)piperidin-4-yl)-1H-benzo[d]imidazole.

$^1$H NMR (400 MHz, DMSO-d6) δ 12.16 (s, 1H), 7.74 (d, J=8.8 Hz, 2H), 7.49-4.43 (m, 3H), 7.37 (d, J=7.3 Hz, 1H), 7.24 (t, J=7.4 Hz, 1H), 7.13 (d, J=8.8 Hz, 4H), 7.07 (q, J=7.3 Hz, 2H), 3.63 (d, J=12.0 Hz, 2H), 2.92-2.80 (m, 1H), 2.43 (m, 2H), 2.08 (d, J=13.1 Hz, 2H), 1.88-1.74 (m, 2H).

$^{13}$C NMR (101 MHz, DMSO-d6) δ 161.42, 157.21, 155.10, 143.26, 134.63, 130.99, 130.76, 130.59, 130.34, 129.78, 125.94-124.93 (m), 122.11, 121.37, 120.62 (d, J=12.4 Hz), 118.73 (d, J=24.1 Hz), 118.05 (d, J=12.9 Hz), 111.28 (d, J=22.4 Hz), 46.00, 34.85 (d, J=10.6 Hz), 29.89 (d, J=25.8 Hz).

HRMS: MH$^+$=434.15324 (Theoretically=434.15329)

Synthesis of 4-((4-(1H-benzo[d]imidazol-2-yl)piperidin-1-yl)sulfonyl)benzonitrile (AZ193)

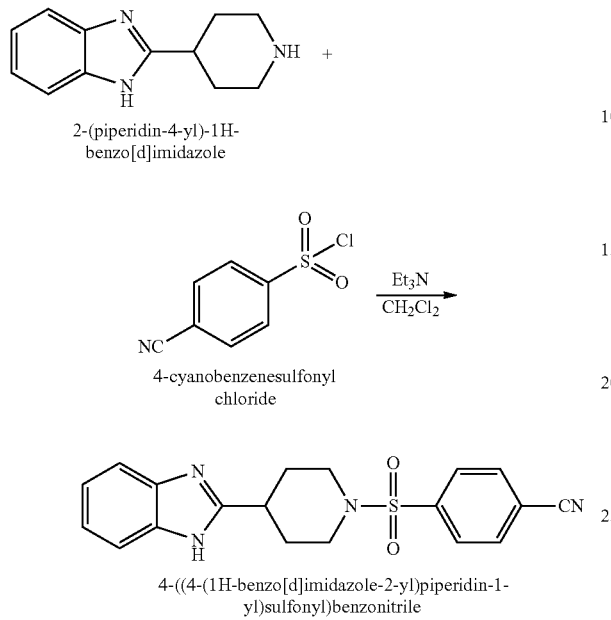

In a round bottomed flask equipped with a nitrogen inlet and a magnetic stir bar, 4-cyanobenzenesulfonyl chloride (111 mg, 0.55 mmol), 2-(piperidin-4-yl)-1H-benzo[d]imidazole (110 mg, 0.55 mmol) and Et$_3$N (0.16 mL, 1.14 mmol) in CH$_2$Cl$_2$ (5 mL) was added. The mixture was then stirred at room temperature for overnight. The precipitate was then filtered, washed with CH$_2$Cl$_2$ and the residue was dried in vacuo yielding 120 mg (60%) of 4-((4-(1H-benzo[d]imidazol-2-yl)piperidin-1-yl)sulfonyl)benzonitrile as white solid.

$^1$H NMR (400 MHz, DMSO-d6) δ 12.16 (s, 1H), 8.12 (d, J=8.7 Hz, 2H), 7.93 (d, J=8.7 Hz, 2H), 7.48 (d, J=6.9 Hz, 1H), 7.36 (d, J=7.0 Hz, 1H), 7.07 (p, J=7.1 Hz, 1H, meta coupling (J=1.3 Hz), 3.69 (dt, J=11.2, 2.9 Hz, 2H), 2.94-2.82 (m, 1H), 2.54 (td, J=11.8, 2.7 Hz, 2H), 2.08 (dd, J=13.7, 3.5 Hz, 2H), 1.80 (qd, J=11.6, 4.0 Hz, 2H).

$^{13}$C NMR (101 MHz, DMSO-d6) δ 157.10, 143.24, 140.36, 134.63, 134.01 (d, J=15.4 Hz), 128.61 (d, J=21.9 Hz), 122.09, 121.30, 118.74 (d, J=23.7 Hz), 118.10, 115.96, 111.28 (d, J=23.4 Hz), 45.92 (t, J=21.8 Hz), 34.72 (d, J=9.6 Hz), 29.94 (dd, J=15.3, 11.0 Hz).

HRMS: MH$^+$=367.1220) (Theoretically=367.12232)

Synthesis of 2-(1-(4-(benzyloxy)benzyl)piperidin-4-yl)-1H-benzo[d]imidazole (AZ203)

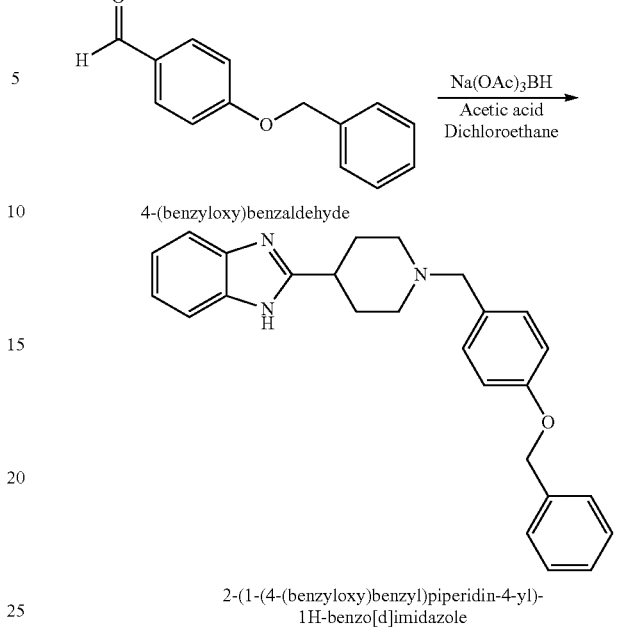

In a round bottomed flask equipped with a nitrogen inlet and a magnetic stir bar, 4-(benzyloxy)benzaldehyde (88 mg, 0.42 mmol), 2-(piperidin-4-yl)-1H-benzo[d]imidazole (100 mg, 0.50 mmol) in dichloroethane (3 mL) was added. To the above mixture AcOH (24 µL, 0.42 mmol) was added. The reaction was stirred for 1 hour at room temperature. To the mixture, Na(OAc)$_3$BH (264 mg, 1.25 mmol) was added in portion over a period of 2 hours. The reaction mixture was allowed to stir overnight at room temperature. The reaction mixture was poured into H$_2$O and the aqueous was extracted with CH$_2$Cl$_2$. The organic layer was dried over Na$_2$SO$_4$, filtered and then rotary evaporated. The crude was purified by preparatory TLC with 10% MeOH in CH$_2$Cl$_2$ to give 118 mg (60%) of 2-(1-(4-(benzyloxy)benzyl)piperidin-4-yl)-1H-benzo[d]imidazole as white solid.

$^1$H NMR (400 MHz, Chloroform-d) δ 7.54 (dt, J=6.7, 3.3 Hz, 2H), 7.42 (m, 2H), 7.37 (t, J=7.4 Hz, 2H), 7.34-7.30 (m, 1H), 7.27 (d, J=8.7 Hz, 2H), 7.19 (dt, J=6.7, 3.3 Hz, 2H), 6.94 (d, J=8.7 Hz, 2H), 5.05 (s, 2H), 3.68 (s, 2H), 3.24-3.10 (m, 2H), 3.12-2.97 (m, 1H), 2.40-2.17 (m, 2H), 2.07 (d, J=17.0 Hz, 4H).

$^{13}$C NMR (101 MHz, Chloroform-d) δ 158.72, 156.96, 138.17, 136.77, 131.52, 131.01, 128.88, 128.28, 127.72, 127.15, 126.59 (d, J=13.1 Hz), 122.47, 122.01, 114.86 (d, J=6.6 Hz), 71.09-67.89 (m), 61.59 (t, J=21.5 Hz), 52.47 (d, J=36.8 Hz), 35.98, 30.30-28.26 (m).

HRMS: MH+=398.2227 (Theoretically=398.2227)

Synthesis of 2-(1-(4-(4-methoxyphenoxy)benzyl)piperidin-4-yl)-1H-benzo[d]imidazole (AZ205)

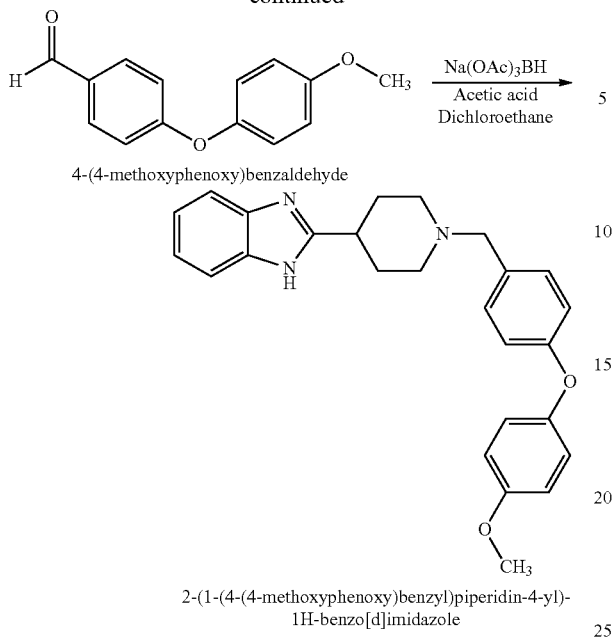

2-(1-(4-(4-methoxyphenoxy)benzyl)piperidin-4-yl)-1H-benzo[d]imidazole

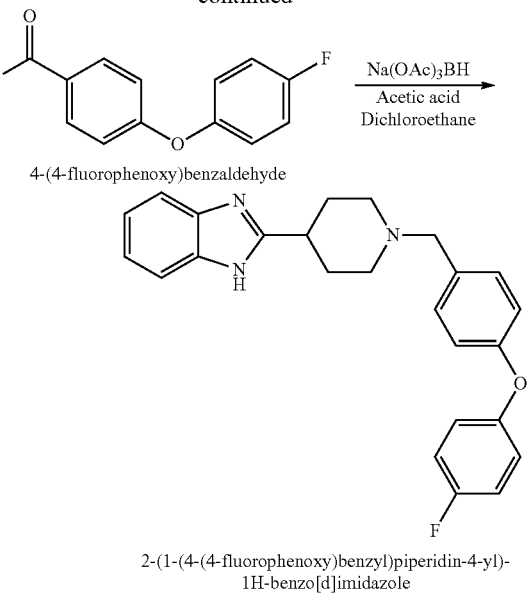

2-(1-(4-(4-fluorophenoxy)benzyl)piperidin-4-yl)-1H-benzo[d]imidazole

In a round bottomed flask equipped with a nitrogen inlet and a magnetic stir bar, 4-(4-methoxyphenoxy)benzaldehyde (190 mg, 0.83 mmol), 2-(piperidin-4-yl)-1H-benzo[d]imidazole (200 mg, 0.99 mmol) in dichloroethane (6 mL) was added. To the above mixture AcOH (48 μL, 0.82 mmol) was added. The reaction was stirred for 1 hour at room temperature. To the mixture, Na(OAc)$_3$BH (528 mg, 2.50 mmol) was added in portion over a period of 2 hours. The reaction mixture was allowed to stir overnight at room temperature. The reaction mixture was poured into H$_2$O and the aqueous was extracted with CH$_2$Cl$_2$. The organic layer was dried over Na$_2$SO$_4$, filtered and then rotary evaporated. The crude was purified by preparatory TLC with 10% MeOH in CH$_2$Cl$_2$ to give 240 mg (59%) of 2-(1-(4-(4-methoxyphenoxy)benzyl)piperidin-4-yl)-1H-benzo[d]imidazole.

$^1$H NMR (400 MHz, Chloroform-d) δ 8.35 (s, 1H), 7.53 (dt, J=6.3, 3.2 Hz, 2H), 7.28 (d, J=8.6 Hz, 2H), 7.18 (dt, J=6.0, 3.1 Hz, 2H), 6.97 (d, J=9.1 Hz, 2H), 6.92-6.85 (m, 2H), 3.83 (s, 2H), 3.79 (s, 3H), 3.33-3.12 (m, 3H), 2.51-2.27 (m, 4H), 2.04-2.02 (m, 2H).

$^{13}$C NMR (101 MHz, Chloroform-d) δ 159.30, 156.51, 156.26, 149.23, 137.80, 132.18, 131.62, 125.47, 122.63, 122.15, 121.32, 121.20, 117.30, 115.10, 114.93, 114.52, 60.77 (d, J=33.6 Hz), 55.53, 53.65-49.66 (m), 35.20 (d, J=11.6 Hz), 31.21-27.22 (m), 23.28-21.84 (m).

HRMS: MH+=414.2175 (Theoretically=414.2176)

Synthesis of 2-(1-(4-(4-fluorophenoxy)benzyl)piperidin-4-yl)-1H-benzo[d]imidazole (AZ206)

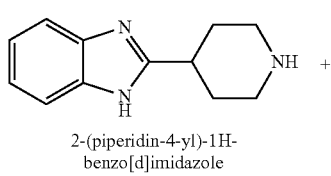

2-(piperidin-4-yl)-1H-benzo[d]imidazole

Into a round bottomed flask equipped with a nitrogen inlet and a magnetic stir bar, 4-(4-fluorophenoxy)benzaldehyde (176 mg, 0.83 mmol), 2-(piperidin-4-yl)-1H-benzo[d]imidazole (200 mg, 0.99 mmol) in dichloroethane (6 mL) was added. To the above mixture AcOH (48 μL, 0.82 mmol) was added. The reaction was stirred for 1 hour at room temperature. To the mixture, Na(OAc)$_3$BH (528 mg, 2.50 mmol) was added in portion over a period of 2 hours. The reaction mixture was allowed to stir overnight at room temperature. The reaction mixture was poured into H$_2$O and the aqueous was extracted with CH$_2$Cl$_2$. The organic layer was dried over Na$_2$SO$_4$, filtered and then rotary evaporated. The crude was purified by preparatory TLC with 10% MeOH in CH$_2$Cl$_2$ to give 293 mg (74%) of 2-(1-(4-(4-fluorophenoxy)benzyl)piperidin-4-yl)-1H-benzo[d]imidazole.

$^1$H NMR (400 MHz, Chloroform-d) δ 8.30 (s, 1H), 7.53 (dt, J=6.5, 3.3 Hz, 2H), 7.29 (d, J=8.5 Hz, 2H), 7.18 (dt, J=6.6, 3.6 Hz, 2H), 7.08-6.93 (m, 4H), 6.91 (d, J=8.5 Hz, 2H), 3.74 (s, 2H), 3.22-3.02 (m, 3H), 2.40-2.20 (m, 4H), 2.05-1.97 (m, 2H).

$^{13}$C NMR (101 MHz, Chloroform-d) δ 176.57, 160.25, 158.0, 157.84, 156.80, 152.17, 137.94, 131.94, 131.37, 127.84, 122.58, 122.09, 120.98 (dd, J=11.7, 8.3 Hz), 117.88, 116.41 (t, J=22.8 Hz), 115.09, 114.49, 62.80-58.09 (m), 54.49-50.01 (m), 35.57, 31.47-26.83 (m).

HRMS: MH+=402.1975 (Theoretically=402.1976)

Synthesis of (4-(1H-benzo[d]imidazol-2-yl)piperidin-1-yl)(3,5-dimethoxyphenyl)methanone (AZ217)

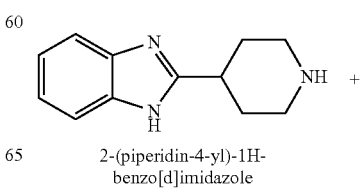

2-(piperidin-4-yl)-1H-benzo[d]imidazole

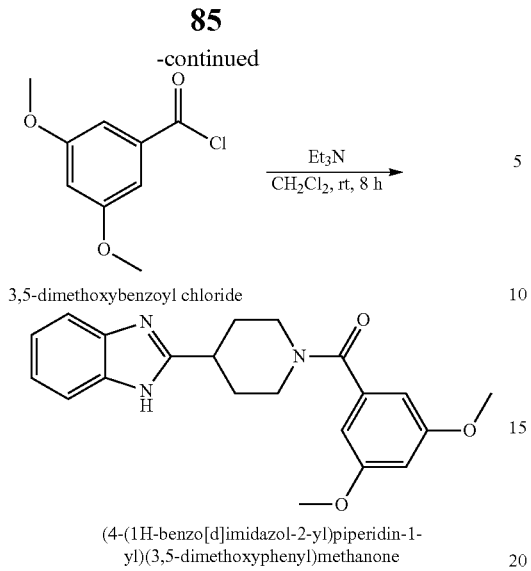

3,5-dimethoxybenzoyl chloride (4-(1H-benzo[d]imidazol-2-yl)piperidin-1-yl)(3,5-dimethoxyphenyl)methanone Into a round bottomed flask equipped with a nitrogen inlet and a magnetic stir bar, 2-(piperidin-4-yl)-1H-benzo[d]imidazole (3.12 g, 15.5 mmol), Et$_3$N (4.32 mL, 31 mmol) and 62 mL CH$_2$Cl$_2$ were added at 0° C. To the above solution 3,5-dimethoxybenzoyl chloride (3.11 g 15.5 mmol) was added slowly and continued to stir for 8 hours at room temperature. The reaction mixture was then rotary evaporated to give 5.7 g of beige color solid as crude. The crude was stirred in EtOAc for 30 minutes, filtered and the solid was washed with copious amount of EtOAc and the dried in vacuo to give 4.6 g (81%) of white solid.

$^1$H NMR (400 MHz, Chloroform-d) δ 11.02 (bs, 1H), 7.79-7.52 (m, 1H), 7.49-7.30 (m, 1H), 7.21 (dt, J=5.9, 2.5 Hz, 2H), 6.54 (d, J=2.3 Hz, 2H), 6.49 (t, J=2.3 Hz, 1H), 4.88-4.66 (m, 1H), 4.06-3.88 (m, 1H), 3.75 (s, 6H), 3.18 (ddq, J=11.5, 7.6, 3.7 Hz, 2H), 3.04-2.84 (m, 1H), 2.20-2.06 (m, 2H), 2.06-1.84 (m, 2H). $^{13}$C NMR (101 MHz, Chloroform-d) δ 170.31, 160.98, 156.34, 137.58, 122.31, 104.63, 101.63, 77.22, 55.46, 47.61, 42.08, 36.83, 31.45, 30.44. LCMS: Expected: 366 (M+H)$^+$; Found: 366. HRMS:—Found: 366.18102 (M+H)$^+$; Theoretically=366.18122.

Synthesis of (3,5-dimethoxyphenyl)(4-(1-((tetrahydro-2H-pyran-4-yl)methyl)-1H-benzo[d]imidazol-2-yl)piperidin-1-yl)methanone (AZ209)

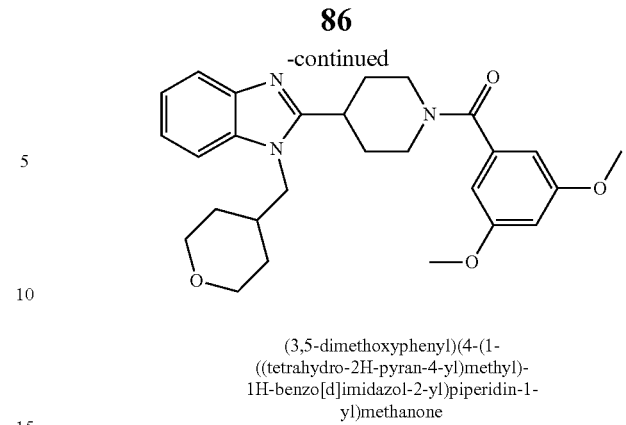

(3,5-dimethoxyphenyl)(4-(1-((tetrahydro-2H-pyran-4-yl)methyl)-1H-benzo[d]imidazol-2-yl)piperidin-1-yl)methanone Into a round bottomed flask equipped with a nitrogen inlet and a magnetic stir bar, (4-(1H-benzo[d]imidazol-2-yl)piperidin-1-yl)(3,5-dimethoxyphenyl)methanone (366 mg, 1 mmol), NaH (60% in oil, 87 mg, 2.18 mmol) and 2.6 mL DMF were added and stirred at room temperature for 2 hours. Solution of 4-(bromomethyl)tetrahydro-2H-pyran (269 mg, 1.5 mmol) in 0.2 mL of DMF was then slowly added to the above solution. The reaction mixture was then allowed to stir at 80° C. for 4 hours. DI water was then added to the reaction mixture and stirred for 15 minutes. The sticky solid formed was filtered and washed with water. The solid was purified using the combiflash purification system with 0-5% MeOH in CH$_2$Cl$_2$ to give 209 mg (45%) of white solid as the pure and desired compound.

$^1$H NMR (400 MHz, Chloroform-d) δ 7.84-7.71 (m, 1H), 7.39-7.31 (m, 1H), 7.31-7.25 (m, 2H), 6.59 (d, J=2.3 Hz, 2H), 6.52 (t, J=2.3 Hz, 1H), 4.89 (bs, 1H), 4.07 (d, J=7.5 Hz, 2H), 4.05-3.95 (m, 2H), 3.84 (s, 6H), 3.51 (d, J=4.8 Hz, 2H), 3.34 (td, J=11.5, 2.9 Hz, 2H), 3.17-3.04 (m, 2H), 2.95 (dd, J=29.1, 0.6 Hz, 1H), 2.18 (dddd, J=16.1, 12.6, 8.6, 3.2 Hz, 2H), 2.10-1.82 (m, 2H), 1.63-1.40 (m, 4H), 1.19 (q, J=5.5 Hz, 1H). $^{13}$C NMR (101 MHz, Chloroform-d) δ 170.06, 160.90, 156.70, 142.48, 137.85, 134.90, 122.46, 122.22, 119.51, 109.70, 104.59, 101.83, 67.36, 55.54, 50.84, 49.27, 36.06, 34.59, 30.82. (one aliphatic peak seems to be hidden in the solvent peak region). LCMS: Expected: 464 (M+H)$^+$; Found: 464. HRMS:—Found: 464.25518 (M+H)$^+$; Theoretically=464.25438.

Synthesis of (3,5-dimethoxyphenyl)(4-(1-((tetrahydrofuran-2-yl)methyl)-1H-benzo[d]imidazol-2-yl)piperidin-1-yl)methanone (AZ210)

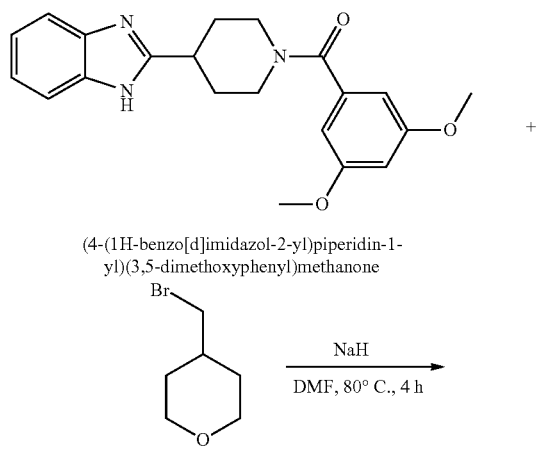

(4-(1H-benzo[d]imidazol-2-yl)piperidin-1-yl)(3,5-dimethoxyphenyl)methanone

+

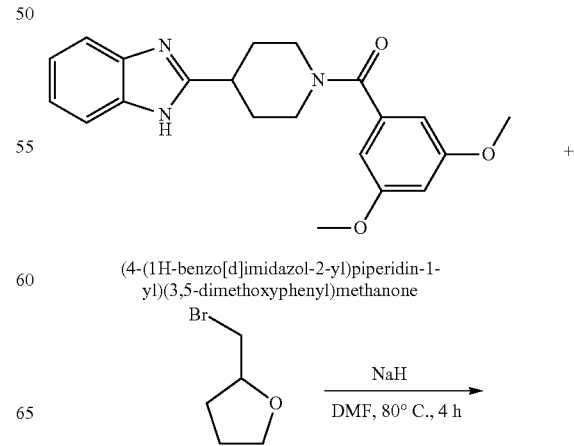

(4-(1H-benzo[d]imidazol-2-yl)piperidin-1-yl)(3,5-dimethoxyphenyl)methanone

+

-continued

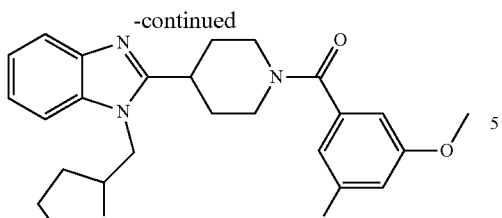

(3,5-dimethoxyphenyl)(4-(1-((tetrahydrofuran-2-yl)methyl)-1H benzo[d]imidazol-2-yl)piperidin-1-yl)methanone Into a round bottomed flask equipped with a nitrogen inlet and a magnetic stir bar, (4-(1H-benzo[d]imidazol-2-yl)piperidin-1-yl)(3,5-dimethoxyphenyl)methanone (366 mg, 1 mmol), NaH (60% in oil, 87 mg, 2.18 mmol) and 2.6 mL DMF were added and stirred at room temperature for 2 hours. Solution of 2-(bromomethyl)tetrahydrofuran (248 mg, 1.5 mmol) in 0.2 mL of DMF was then slowly added to the above solution. The reaction mixture was then allowed to stir at 80° C. for 4 hours. DI water was then added to the reaction mixture and stirred for 15 minutes. The sticky solid formed was filtered and washed with water. The solid was purified using the combiflash purification system with 0-5% MeOH in CH$_2$Cl$_2$ to give 223 mg (50%) of white solid as the pure and desired compound.

$^1$H NMR (400 MHz, Chloroform-d) δ 7.77 (s, 1H), 7.36 (dt, J=6.8, 3.6 Hz, 1H), 7.31-7.25 (m, 2H), 6.60 (d, J=2.2 Hz, 2H), 6.51 (t, J=2.3 Hz, 1H), 4.99-4.79 (m, 1H), 4.42-4.30 (m, 1H), 4.30-4.18 (m, 2H), 4.10-3.93 (m, 1H), 3.84 (s, 6H), 3.89-3.79 (m, 1H), 3.79-3.70 (m, 1H), 3.32 (t, J=7.7 Hz, 1H), 3.27-3.04 (m, 1H), 3.05-2.82 (m, 1H), 2.33-1.81 (m, 6H), 1.80-1.53 (m, 2H). $^{13}$C NMR (101 MHz, Chloroform-d) δ 170.04, 160.88, 138.04, 122.46, 119.28, 109.65, 104.56, 101.84, 77.66, 77.23, 68.27, 55.57, 34.43, 31.21, 29.19, 25.69. LCMS: Expected: 450 (M+H)$^+$; Found: 450. HRMS:—Found: 450.23948 (M+H)$^+$; Theoretically=; 450.23873.

Synthesis of (4-(1-(cyclopropylmethyl)-1H-benzo[d]imidazol-2-yl)piperidin-1-yl)(3,5-dimethoxyphenyl)methanone (AZ211)

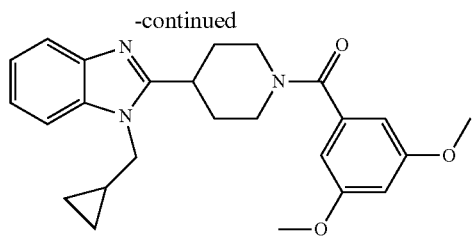

(4-(1-(cyclopropylmethyl)-1H-benzo[d]imidazol-2-yl)piperidin-1-yl)(3,5-dimethoxyphenyl)methanone Into a round bottomed flask equipped with a nitrogen inlet and a magnetic stir bar, (4-(1H-benzo[d]imidazol-2-yl)piperidin-1-yl)(3,5-dimethoxyphenyl)methanone (366 mg, 1 mmol), NaH (60% in oil, 87 mg, 2.18 mmol) and 2.6 mL DMF were added and stirred at room temperature for 2 hours. Solution of (bromomethyl)cyclopropane (203 mg, 1.5 mmol) in 0.2 mL of DMF was then slowly added to the above solution. The reaction mixture was then allowed to stir at 80° C. for 4 hours. Water was then added to the reaction mixture and stirred for 15 minutes. The sticky solid formed was filtered and washed with water. The solid was purified using the combiflash purification system with 0-5% MeOH in CH$_2$Cl$_2$ to give 201 mg (48%) of white solid as the pure and desired compound.

$^1$H NMR (400 MHz, Chloroform-d) δ 7.82-7.70 (m, 1H), 7.43-7.33 (m, 1H), 7.31-7.21 (m, 2H), 6.59 (d, J=2.3 Hz, 2H), 6.51 (t, J=2.3 Hz, 1H), 4.87 (bs, 1H), 4.10 (d, J=6.5 Hz, 2H), 4.01-3.93 (bs, 1H), 3.84 (s, 6H), 3.14 (tt, J=11.2, 3.9 Hz, 2H), 2.99 (bs, 1H), 2.19 (qd, J=12.3, 11.9, 4.2 Hz, 2H), 1.96-1.72 (m, 2H), 1.36-1.12 (m, 1H), 0.67 (q, J=5.4 Hz, 2H), 0.44 (q, J=5.4 Hz, 2H). $^{13}$C NMR (101 MHz, Chloroform-d) δ 170.04, 160.89, 156.39, 142.55, 137.94, 135.02, 122.34, 122.03, 119.37, 109.67, 104.58, 101.81, 77.23, 55.54, 47.59, 34.62, 31.39, 11.64, 4.45. LCMS: Expected: 420 (M+H)$^+$; Found: 420. HRMS:—Found: 420.22864 (M+H)$^+$; Theoretically=420.22817.

Synthesis of (3,5-dimethoxyphenyl)(4-(1-isobutyl-1H-benzo[d]imidazol-2-yl)piperidin-1-yl)methanone (AZ212)

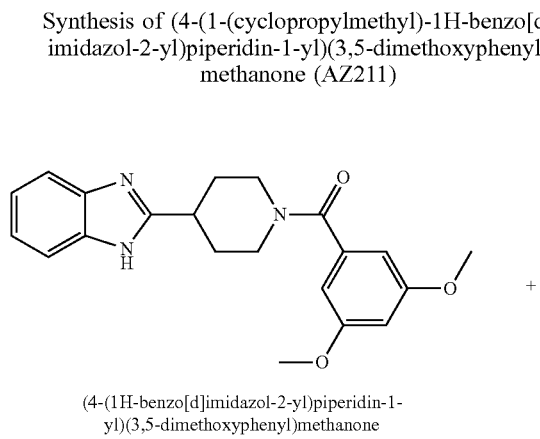

(4-(1H-benzo[d]imidazol-2-yl)piperidin-1-yl)(3,5-dimethoxyphenyl)methanone

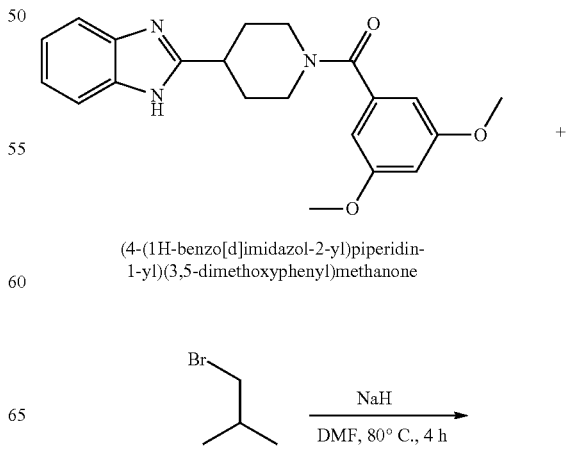

(4-(1H-benzo[d]imidazol-2-yl)piperidin-1-yl)(3,5-dimethoxyphenyl)methanone

-continued

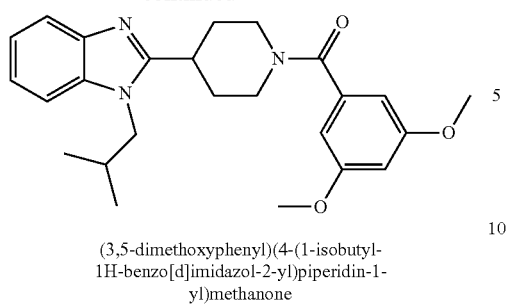

(3,5-dimethoxyphenyl)(4-(1-isobutyl-1H-benzo[d]imidazol-2-yl)piperidin-1-yl)methanone Into a round bottomed flask equipped with a nitrogen inlet and a magnetic stir bar, (4-(1H-benzo[d]imidazol-2-yl)piperidin-1-yl)(3,5-dimethoxyphenyl)methanone (366 mg, 1 mmol), NaH (60% in oil, 87 mg, 2.18 mmol) and 2.6 mL DMF were added and stirred at room temperature for 2 hours. Solution of 1-bromo-2-methylpropane (206 mg, 1.5 mmol) in 0.2 mL of DMF was then slowly added to the above solution. The reaction mixture was then allowed to stir at 80° C. for 4 hours. Water was then added to the reaction mixture and stirred for 15 minutes. The sticky solid formed was filtered and washed with water. The solid was purified using the combiflash purification system with 0-5% MeOH in $CH_2Cl_2$ to give 210 mg (50%) of white solid as the pure and desired compound.

$^1$H NMR (400 MHz, Chloroform-d) δ 7.81-7.69 (m, 1H), 7.37-7.31 (m, 1H), 7.30-7.24 (m, 2H), 6.59 (d, J=2.3 Hz, 2H), 6.52 (t, J=2.3 Hz, 1H), 4.89 (bs, 1H), 4.01 (bs, 1H), 3.98 (d, J=7.6 Hz, 2H), 3.84 (s, 6H), 3.52 (s, 1H), 3.11 (tt, J=11.3, 3.9 Hz, 2H), 3.05-2.89 (m, 1H), 2.34-2.12 (m, 2H), 2.13-1.73 (m, 2H), 1.01 (d, J=6.7 Hz, 6H). $^{13}$C NMR (101 MHz, Chloroform-d) δ 170.03, 160.89, 156.77, 142.50, 137.94, 135.04, 122.25, 122.00, 119.37, 109.87, 104.84, 101.82, 55.55, 50.94, 34.62, 29.38, 20.28. LCMS: Expected: 422 (M+H)$^+$; Found: 422. HRMS:—Found: 422.24438 (M+H)$^+$; Theoretically=422.24382.

Synthesis of (3,5-dimethoxyphenyl)(4-(1-(2-methoxyethyl)-1H-benzo[d]imidazol-2-yl)piperidin-1-yl)methanone (AZ213)

-continued

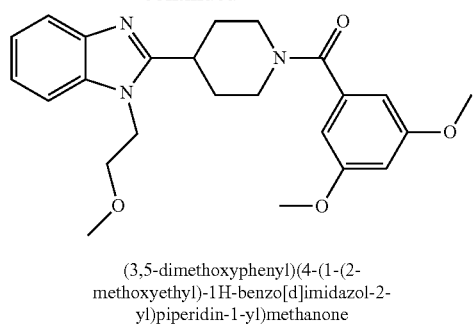

(3,5-dimethoxyphenyl)(4-(1-(2-methoxyethyl)-1H-benzo[d]imidazol-2-yl)piperidin-1-yl)methanone Into a round bottomed flask equipped with a nitrogen inlet and a magnetic stir bar, (4-(1H-benzo[d]imidazol-2-yl)piperidin-1-yl)(3,5-dimethoxyphenyl)methanone (366 mg, 1 mmol), NaH (60% in oil, 87 mg, 2.18 mmol) and 2.6 mL DMF were added and stirred at room temperature for 2 hours. Solution of 1-bromo-2-methoxyethane (208 mg, 1.5 mmol) in 0.2 mL of DMF was then slowly added to the above solution. The reaction mixture was then allowed to stir at 80° C. for 4 hours. Water was then added to the reaction mixture and stirred for 15 minutes. The sticky solid formed was filtered and washed with water. The solid was purified using the combiflash purification system with 0-5% MeOH in $CH_2Cl_2$ to give 307 mg (72%) of white solid as the pure and desired compound.

$^1$H NMR (400 MHz, Chloroform-d) δ 7.90-7.65 (m, 1H), 7.37-7.31 (m, 1H), 7.30-7.22 (m, 2H), 6.59 (d, J=2.3 Hz, 2H), 6.51 (t, J=2.3 Hz, 1H), 4.87 (bs, 1H), 4.37 (t, J=5.3 Hz, 2H), 4.03 (bs, 1H), 3.83 (s, 6H), 3.72 (t, J=5.3 Hz, 2H), 3.28 (s, 3H), 3.28-3.21 (m, 1H), 3.06 (m, 2H), 2.19-2.06 (m, 3H), 1.96 (bs, 1H). $^{13}$C NMR (101 MHz, Chloroform-d) δ 170.01, 160.87, 157.51, 142.63, 138.05, 134.55, 122.32, 119.46, 109.24, 104.57, 101.79, 70.62, 59.19, 55.54, 43.72, 34.28. LCMS: Expected: 424 (M+H)$^+$; Found: 424. HRMS:—Found: 424.22374 (M+H)$^+$; Theoretically=424.22308.

Synthesis of (3,5-dimethoxyphenyl)(4-(1-(pyridin-4-ylmethyl)-1H-benzo[d]imidazol-2-yl)piperidin-1-yl)methanone (AZ214)

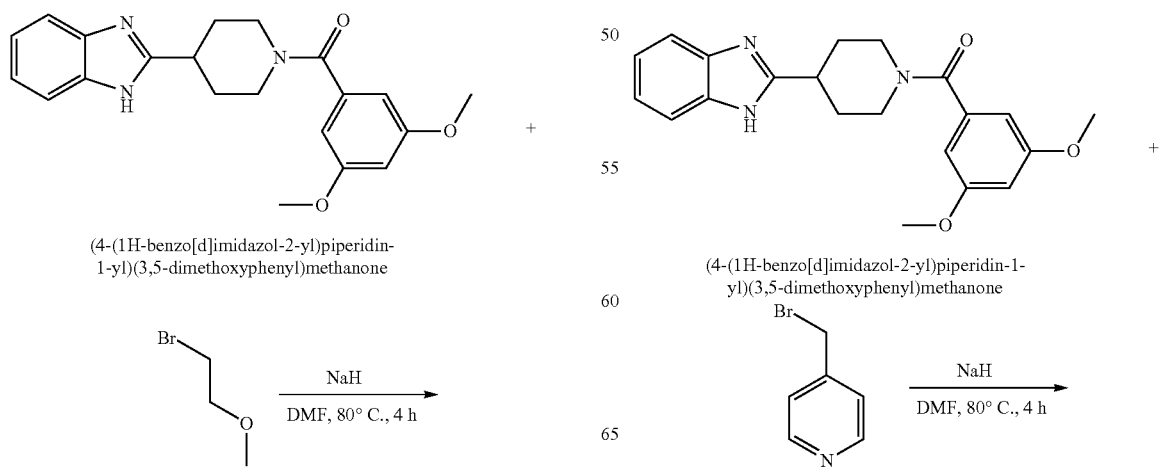

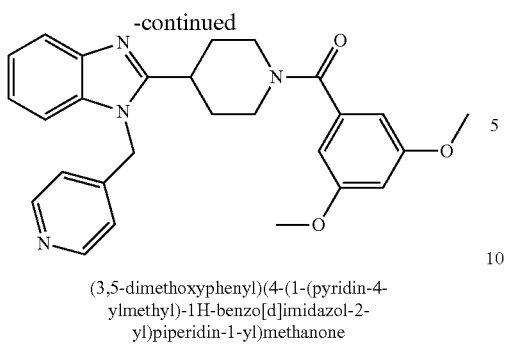

(3,5-dimethoxyphenyl)(4-(1-(pyridin-4-ylmethyl)-1H-benzo[d]imidazol-2-yl)piperidin-1-yl)methanone Into a round bottomed flask equipped with a nitrogen inlet and a magnetic stir bar, (4-(1H-benzo[d]imidazol-2-yl)piperidin-1-yl)(3,5-dimethoxyphenyl)methanone (366 mg, 1 mmol), NaH (60% in oil, 87 mg, 2.18 mmol) and 2.6 mL DMF were added and stirred at room temperature for 2 hours. Solution of 4-(bromomethyl)pyridine hydrobromide (379 mg, 1.5 mmol) in 0.2 mL of DMF was then slowly added to the above solution. The reaction mixture was then allowed to stir at 80° C. for 4 hours. Water was then added to the reaction mixture and stirred for 15 minutes. The sticky solid formed was filtered and washed with water. The solid was purified using the combiflash purification system with 0-5% MeOH in CH$_2$Cl$_2$ to give 301 mg (66%) of white solid as the pure and desired compound.

$^1$H NMR (400 MHz, Chloroform-d) δ 8.58 (d, J=6.0 Hz, 2H), 7.83 (d, J=7.9 Hz, 1H), 7.40-7.30 (m, 1H), 7.26 (td, J=7.6, 1.1 Hz, 1H), 7.16 (d, J=8.1 Hz, 1H), 6.94 (d, J=6.1 Hz, 2H), 6.55 (d, J=2.3 Hz, 2H), 6.50 (t, J=2.3 Hz, 1H), 5.43 (s, 2H), 4.81 (bs, 1H), 4.16-3.89 (m, 1H), 3.82 (d, J=0.9 Hz, 6H), 3.02 (ddt, J=11.4, 7.5, 3.8 Hz, 2H), 2.93 (bs, 1H), 2.21-2.08 (m, 2H), 1.96 (s, 1H), 1.86 (s, 1H). $^{13}$C NMR (101 MHz, Chloroform-d) δ 170.06, 160.91, 156.50, 150.64, 144.94, 137.74, 134.80, 123.00 (d, J=33.5 Hz), 120.74, 119.79, 109.39, 104.58, 101.75, 55.53, 36.72, 36.51, 34.52, 31.45. LCMS: Expected: 457 (M+H)$^+$; Found: 457.

HRMS:—Found: 457.22397 (M+H)$^+$; Theoretically=457.22342.

Synthesis of (3,5-dimethoxyphenyl)(4-(1-(3-fluorobenzyl)-1H-benzo[d]imidazol-2-yl)piperidin-1-yl)methanone (AZ215)

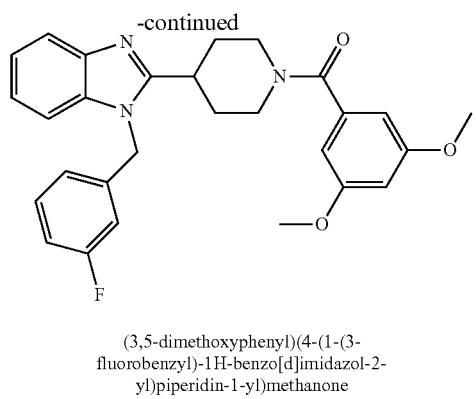

(3,5-dimethoxyphenyl)(4-(1-(3-fluorobenzyl)-1H-benzo[d]imidazol-2-yl)piperidin-1-yl)methanone Into a round bottomed flask equipped with a nitrogen inlet and a magnetic stir bar, (4-(1H-benzo[d]imidazol-2-yl)piperidin-1-yl)(3,5-dimethoxyphenyl)methanone (366 mg, 1 mmol), NaH (60% in oil, 87 mg, 2.18 mmol) and 2.6 mL DMF were added and stirred at room temperature for 2 hours. Solution of 1-(bromomethyl)-3-fluorobenzene (284 mg, 1.5 mmol) in 0.2 mL of DMF was then slowly added to the above solution. The reaction mixture was then allowed to stir at 80° C. for 4 hours. Water was then added to the reaction mixture and stirred for 15 minutes. The sticky solid formed was filtered and washed with water. The solid was purified using the combiflash purification system with 0-5% MeOH in CH$_2$Cl$_2$ to give 203 mg (43%) of white solid as the pure and desired compound.

$^1$H NMR (400 MHz, Chloroform-d) δ 7.82 (ddd, J=7.9, 1.3, 0.8 Hz, 1H), 7.35-7.27 (m, 2H), 7.25 (dd, J=6.8, 1.2 Hz, 2H), 7.01 (tdd, J=8.4, 2.7, 1.1 Hz, 1H), 6.82 (ddd, J=7.8, 1.7, 0.9 Hz, 1H), 6.75 (dt, J=9.3, 2.0 Hz, 1H), 6.56 (d, J=2.3 Hz, 2H), 6.50 (t, J=2.3 Hz, 1H), 5.41 (s, 2H), 4.81 (bs, 1H), 4.04-3.87 (m, 1H), 3.83 (s, 6H), 3.06 (tt, J=11.3, 3.8 Hz, 2H), 3.00-2.79 (m, 1H), 2.18-2.03 (m, 2H), 2.04-1.72 (m, 2H). $^{13}$C NMR (101 MHz, Chloroform-d) δ 170.02, 160.88, 156.64, 142.52, 138.60, 137.86, 135.02, 130.89, 122.92, 122.52, 121.46, 119.66, 115.17 (d, J=21.0 Hz), 113.10 (d, J=22.3 Hz), 109.50, 104.57, 101.78, 55.52, 46.29, 34.69. LCMS: Expected: 474 (M+H)$^+$; Found: 474. HRMS:—Found: 474.21917 (M+H)$^+$; Theoretically=474.21875.

Synthesis of (4-(1-(cyclobutylmethyl)-1H-benzo[d]imidazol-2-yl)piperidin-1-yl)(3,5-dimethoxyphenyl)methanone (AZ216)

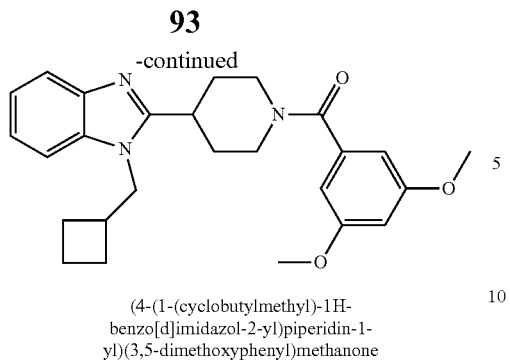

(4-(1-(cyclobutylmethyl)-1H-
benzo[d]imidazol-2-yl)piperidin-1-
yl)(3,5-dimethoxyphenyl)methanone Into a round bottomed flask equipped with a nitrogen inlet and a magnetic stir bar, (4-(1H-benzo[d]imidazol-2-yl)piperidin-1-yl)(3,5-dimethoxyphenyl)methanone (366 mg, 1 mmol), NaH (60% in oil, 87 mg, 2.18 mmol) and 2.6 mL DMF were added and stirred at room temperature for 2 hours. Solution of (bromomethyl)cyclobutane (224 mg, 1.5 mmol) in 0.2 mL of DMF was then slowly added to the above solution. The reaction mixture was then allowed to reflux for 4 hours. Water was then added to the reaction mixture and stirred for 15 minutes. The reaction mixture was then allowed to stir at 80° C. for 4 hours. The solid was purified using the combiflash purification system with 0-5% MeOH in $CH_2Cl_2$ to give 219 mg (51%) of white solid as the pure and desired compound.

$^1$H NMR (400 MHz, Chloroform-d) δ 7.78-7.71 (m, 1H), 7.42-7.33 (m, 1H), 7.26 (ddt, J=6.2, 2.4, 1.1 Hz, 2H), 6.59 (s, 2H), 6.51 (s, 1H), 4.89 (bs, 1H), 4.19 (d, J=6.9 Hz, 2H), 4.11-3.98 (m, 1H), 3.83 (s, 6H), 3.12 (tt, J=11.2, 3.9 Hz, 2H), 2.99 (bs, 1H), 2.91-2.74 (m, 1H), 2.24-2.11 (m, 2H), 2.12-1.96 (m, 2H), 1.96-1.69 (m, 6H). $^{13}$C NMR (101 MHz, Chloroform-d) δ 170.02, 160.89, 156.52, 142.49, 137.95, 135.07, 122.25, 121.99, 119.32, 109.71, 104.58, 101.82, 55.54, 48.37, 36.24, 34.60, 31.35, 26.58, 18.27. LCMS: Expected: 434 (M+H)$^+$; Found: 434. HRMS:—Found: 434.24401 (M+H)$^+$; Theoretically=434.24382.

Synthesis of (4-(1H-benzo[d]imidazol-2-yl)piperidin-1-yl)(4-((3-fluorobenzyl)oxy)-3-methoxyphenyl)methanone (AZ177)

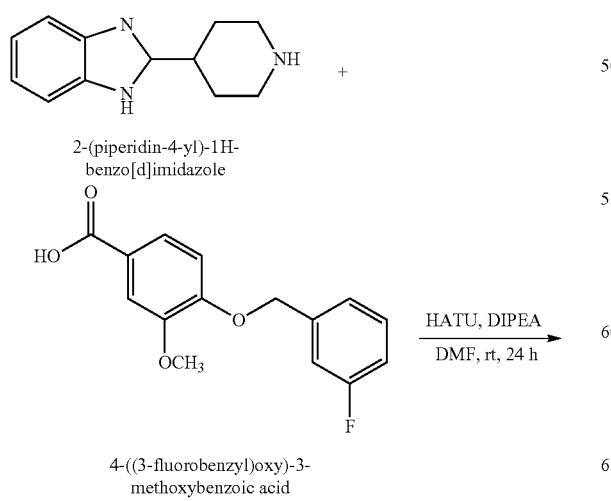

2-(piperidin-4-yl)-1H-
benzo[d]imidazole 4-((3-fluorobenzyl)oxy)-3-
methoxybenzoic acid HATU, DIPEA
DMF, rt, 24 h

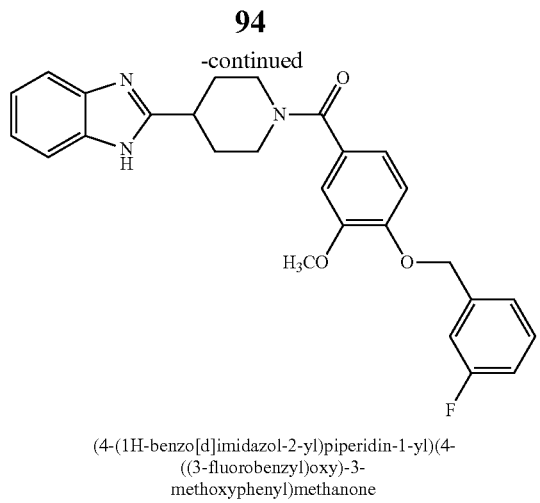

(4-(1H-benzo[d]imidazol-2-yl)piperidin-1-yl)(4-
((3-fluorobenzyl)oxy)-3-
methoxyphenyl)methanone Into a round bottomed flask equipped with a magnetic stir bar and a nitrogen inlet, a mixture of 4-((3-fluorobenzyl)oxy)-3-methoxybenzoic acid (1.14 g, 4.13 mmol), HATU (3.14 g, 8.26 mmol) and DIPEA (2.16 mL, 12.4 mmol) in 5 mL DMF was added. To the above solution, 2-(piperidin-4-yl)-1H-benzo[d]imidazole (1 g, 4.97 mmol) was added. The mixture was stirred at room temperature for 24 h. To the mixture sat. aq. NaHCO$_3$ solution was added and the aqueous was extracted with $CH_2Cl_2$ (×3). The combined organic layers were dried over Na$_2$SO$_4$, filtered, removed by rotary evaporation and the crude was purified by combiflash column chromatography and the desired product was eluted with 5% MeOH in $CH_2Cl_2$ to give 406 mg (18%) of white solid as the pure and desired compound.

$^1$H NMR (400 MHz, Chloroform-d) δ 11.07 (s, 1H), 7.65 (bs, 1H), 7.29 (td, J=8.0, 5.9 Hz, 1H), 7.22-7.08 (m, 4H), 6.97 (d, J=1.8 Hz, 2H), 6.86 (dd, J=8.2, 1.9 Hz, 1H), 6.75 (d, J=8.3 Hz, 1H), 5.09 (s, 2H), 4.67 (bs, 1H), 3.77 (s, 3H), 3.28-2.84 (m, 3H), 2.36-1.60 (m, 5H).

$^{13}$C NMR (101 MHz, Chloroform-d) δ 170.46, 164.17, 161.75, 156.50, 149.58, 149.24, 139.06 (d, J=7.4 Hz), 130.20 (d, J=8.2 Hz), 128.45, 122.54 (d, J=3.1 Hz), 119.67, 115.03, 114.82, 114.14, 113.92, 113.02, 110.98, 70.10, 55.99 (d, J=5.9 Hz), 36.84. LCMS: Expected: 460 (M+H)$^+$; Found: 460.

Synthesis of (4-((3-fluorobenzyl)oxy)-3-methoxyphenyl)(4-(1-((tetrahydrofuran-2-yl)methyl)-1H-benzo[d]imidazol-2-yl)piperidin-1-yl)methanone (AZ218)

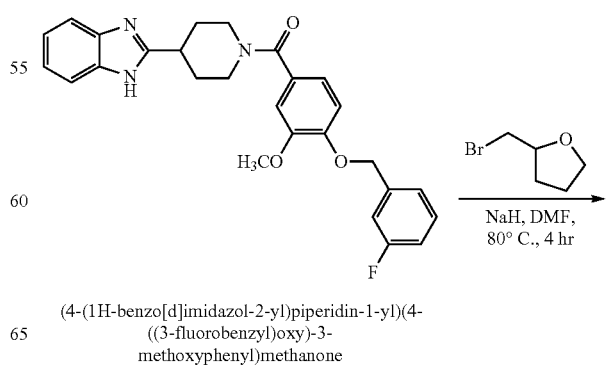

(4-(1H-benzo[d]imidazol-2-yl)piperidin-1-yl)(4-
((3-fluorobenzyl)oxy)-3-
methoxyphenyl)methanone NaH, DMF,
80° C., 4 hr

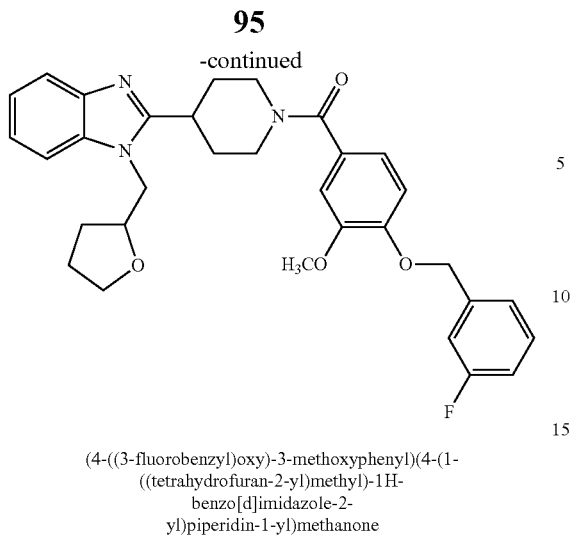

(4-((3-fluorobenzyl)oxy)-3-methoxyphenyl)(4-(1-((tetrahydrofuran-2-yl)methyl)-1H-benzo[d]imidazole-2-yl)piperidin-1-yl)methanone Into a round bottomed flask equipped with a nitrogen inlet and a magnetic stir bar, tert-butyl (4-(1H-benzo[d]imidazol-2-yl)piperidin-1-yl)(4-((3-fluorobenzyl)oxy)-3-methoxyphenyl)methanone (140 mg, 0.3 mmol), NaH (60% in oil, 27 mg, 0.68 mmol) and 1 mL DMF were added at 0° C. and then stirred at room temperature for 2 hours. Solution of 2-(bromomethyl)tetrahydrofuran (74.26 mg, 0.74 mmol) was then slowly added to the above solution. The reaction mixture was then allowed to stir at 80° C. for 5 hours. DI water was then added to the reaction mixture and stirred for 15 minutes. The sticky solid was then filtered and then washed with water to give the crude product. The crude solid was purified using the combiflash purification system with 2-5% MeOH in CH$_2$Cl$_2$ to give 60 mg (36%) of white solid as the pure and desired compound.

$^1$H NMR (400 MHz, Chloroform-d) δ 7.78 (s, 1H), 7.42-7.31 (m, 2H), 7.28-7.26 (m, 2H), 7.25-7.16 (m, 2H), 7.08 (d, J=1.8 Hz, 1H), 7.06-6.96 (m, 2H), 6.87 (d, J=8.2 Hz, 1H), 5.19 (s, 2H), 4.93-4.61 (bs, 1H), 4.46-4.28 (m, 2H), 4.31-4.15 (m, 2H), 3.96 (s, 3H), 3.87-3.70 (m, 2H), 3.32 (t, J=11.2 Hz, 1H), 3.06 (bs, 2H), 2.19 (bs, 2H), 2.13-1.81 (m, 5H), 1.63 (dq, J=12.0, 8.0 Hz, 1H). $^{13}$C NMR (101 MHz, Chloroform-d) δ 170.28, 164.24, 161.80, 157.47, 149.61, 148.96, 139.36 (d, J=7.3 Hz), 130.17 (d, J=8.3 Hz), 129.22, 122.58 (d, J=2.9 Hz), 119.78, 119.24, 114.86 (d, J=21.1 Hz), 114.09 (d, J=22.1 Hz), 113.19, 111.18, 109.65, 77.66, 70.20 (d, J=1.9 Hz), 68.27, 56.16, 53.44, 47.37, 34.47, 31.28, 29.20, 25.69. LCMS: Expected: 544 (M+H)$^+$; Found: 544. HRMS:—Found: 544.26187 (M+H)$^+$; Theoretically=544.64685.

Synthesis of (4-((3-fluorobenzyl)oxy)-3-methoxyphenyl)(4-(1-(2-methoxyethyl)-1H-benzo[d]imidazol-2-yl)piperidin-1-yl)methanone (AZ219)

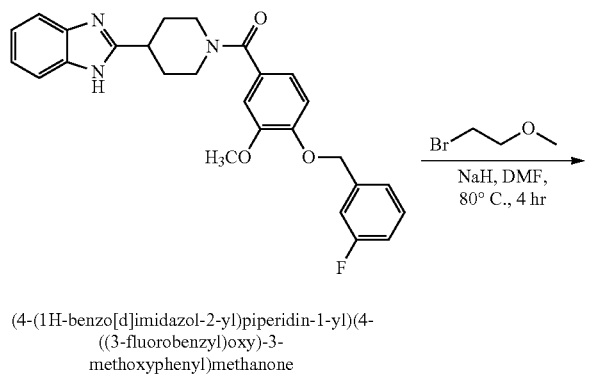

(4-(1H-benzo[d]imidazol-2-yl)piperidin-1-yl)(4-((3-fluorobenzyl)oxy)-3-methoxyphenyl)methanone

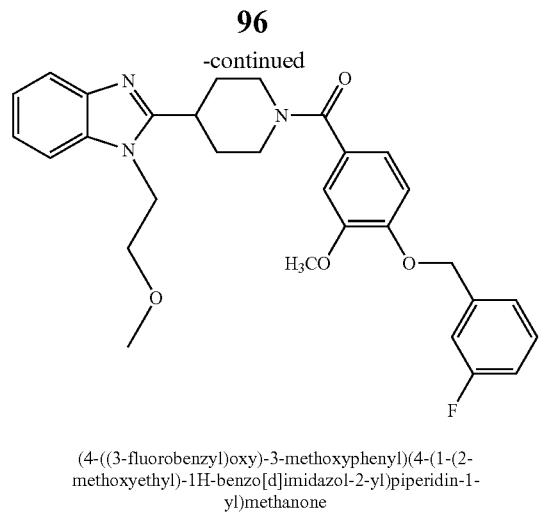

(4-((3-fluorobenzyl)oxy)-3-methoxyphenyl)(4-(1-(2-methoxyethyl)-1H-benzo[d]imidazol-2-yl)piperidin-1-yl)methanone Into a round bottomed flask equipped with a nitrogen inlet and a magnetic stir bar, tert-butyl (4-(1H-benzo[d]imidazol-2-yl)piperidin-1-yl)(4-((3-fluorobenzyl)oxy)-3-methoxyphenyl)methanone (266 mg, 0.58 mmol), NaH (60% in oil, 51 mg, 1.28 mmol) and 1.5 mL DMF were added at 0° C. and then stirred at room temperature for 2 hours. Solution of 1-bromo-2-methoxyethane (121 mg, 0.87 mmol) was then slowly added to the above solution. The reaction mixture was then allowed to stir at 80° C. for 5 hours. water was then added to the reaction mixture and stirred for 15 minutes. The sticky solid was then filtered and then washed with water to give the crude product. The crude solid was purified using the combiflash purification system with 2-5% MeOH in CH$_2$Cl$_2$ to give 77 mg (26%) of white solid as the pure and desired compound.

$^1$H NMR (400 MHz, Chloroform-d) δ 7.80-7.70 (m, 1H), 7.40-7.31 (m, 2H), 7.31-7.24 (m, 2H), 7.24-7.16 (m, 2H), 7.07 (d, J=1.9 Hz, 1H), 7.02 (dd, J=8.5, 1.9 Hz, 1H), 6.99 (dd, J=8.2, 1.9 Hz, 1H), 6.87 (d, J=8.2 Hz, 1H), 5.18 (s, 2H), 4.83 (d, J=48.6 Hz, 1H), 4.37 (t, J=5.3 Hz, 2H), 3.95 (s, 3H), 3.71 (t, J=5.2 Hz, 2H), 3.28 (s, 3H), 3.27-3.23 (m, 1H), 3.18-2.88 (m, 2H), 2.15 (qd, J=12.6, 3.7 Hz, 2H), 2.03 (bs, 3H). $^{13}$C NMR (101 MHz, Chloroform-d) δ 170.25, 164.24, 161.79, 157.55, 149.28 (d, J=65.0 Hz), 142.59, 139.32, 134.55, 130.17 (d, J=8.2 Hz), 129.22, 124.53-120.46 (m), 119.59 (d, J=34.0 Hz), 114.86 (d, J=21.1 Hz), 114.09 (d, J=22.1 Hz), 113.18, 111.18, 109.28, 77.26, 70.61, 70.19 (d, J=1.9 Hz), 59.19, 56.13, 43.72, 34.31, 31.31. LCMS: Expected: 518 (M+H)$^+$; Found: 518. HRMS:—Found: 518.24643 (M+H)$^+$; Theoretically=518.60885.

Synthesis of tert-butyl 4-(1H-benzo[d]imidazol-2-yl)piperidine-1-carboxylate

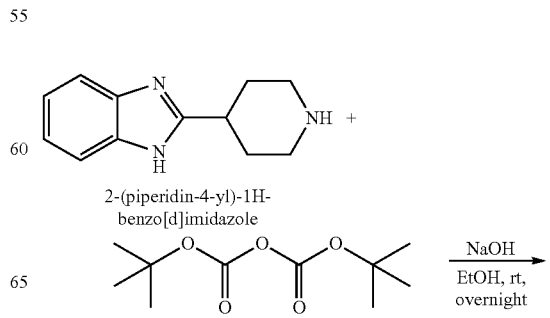

2-(piperidin-4-yl)-1H-benzo[d]imidazole

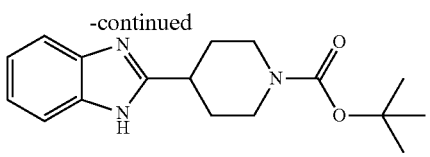

tert-butyl 4-(1H-benzo[d]imidazole-2-yl)piperidine-1-carboxylate

Into a round bottom flask equipped with a nitrogen inlet and a magnetic stir bar, 2-(piperidin-4-yl)-1H-benzo[d]imidazole (5 g, 24.8 mmol), 1 M NaOH (aq) (57 mL, 57 mmol) and EtOH (19 mL) were added at 0° C. Boc anhydride (10.84 g, 49.7 mmol) was slowly added to the reaction mixture. The reaction was warmed to room temperature and allowed to stir at room temperature for overnight. The reaction mixture was filtered and then dried in vacuo. The solid was washed with copious amount of water, followed by washing with 1:1 Et$_2$O-hexanes and then dried in vacuo to give 7.3 g (49%) of the pure and desired compound.

$^1$H NMR (400 MHz, Chloroform-d) δ 10.61 (s, 1H), 7.79-7.66 (m, 1H), 7.46-7.37 (m, 1H), 7.37-7.19 (m, 2H), 4.26 (bs, 2H), 3.14 (tt, J=11.8, 3.7 Hz, 1H), 2.90 (bs, 2H), 2.30-1.82 (m, 4H), 1.50 (d, J=2.5 Hz, 9H). $^{13}$C NMR (101 MHz, Chloroform-d) δ 157.00, 154.75, 142.97, 133.81, 122.58, 122.02, 119.02, 110.69, 79.93, 36.98, 28.47, 28.15. LCMS: Expected: 302 (M+H)$^+$; Found: 302.

Synthesis of tert-butyl 4-(1-(3-fluorobenzyl)-1H-benzo[d]imidazol-2-yl)piperidine-1-carboxylate

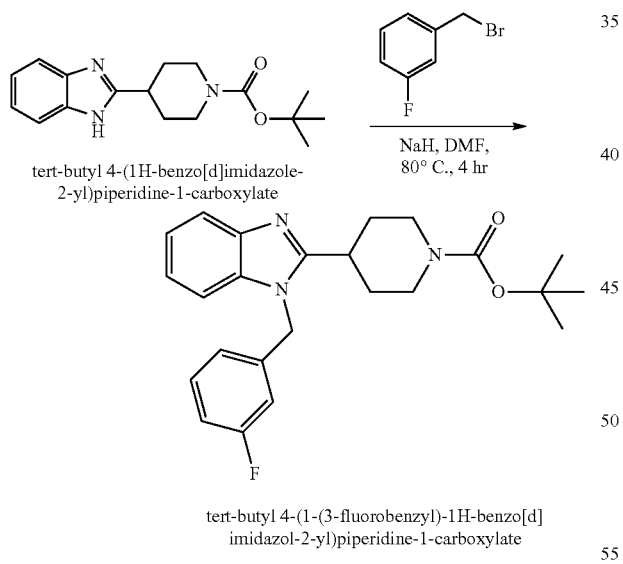

tert-butyl 4-(1-(3-fluorobenzyl)-1H-benzo[d]imidazol-2-yl)piperidine-1-carboxylate Into a round bottomed flask equipped with a nitrogen inlet and a magnetic stir bar, tert-butyl 4-(1H-benzo[d]imidazol-2-yl)piperidine-1-carboxylate (1.72 g, 5.71 mmol), NaH (60% in oil, 500 mg, 12.5 mmol) and 15 mL DMF were added at 0° C. and then stirred at room temperature for 2 hours. Solution of 1-(bromomethyl)-3-fluorobenzene (1.62 g, 8.57 mmol) in 1 mL of DMF was then slowly added to the above solution. The reaction mixture was then allowed to reflux for overnight hours. Saturated solution of NaHCO$_3$ was then added to the reaction mixture and stirred for 15 minutes. The aqueous was extracted with EtOAc (×3). The crude solid was purified using the combiflash purification system with 2-5% MeOH in CH$_2$Cl$_2$ to give 2 g (86%) of white solid as the pure and desired compound.

$^1$H NMR (400 MHz, Chloroform-d) δ 7.80 (ddd, J=7.9, 1.3, 0.7 Hz, 1H), 7.33-7.17 (m, 4H), 6.99 (tdd, J=8.4, 2.6, 0.9 Hz, 1H), 6.81 (ddt, J=7.6, 1.7, 0.9 Hz, 1H), 6.74 (dt, J=9.4, 2.0 Hz, 1H), 5.38 (s, 2H), 4.25 (bs, 2H), 3.02-2.87 (m, 1H), 2.80 (bs, 2H), 2.03 (bs, 2H), 1.81 (d, J=13.6 Hz, 2H), 1.48 (s, 9H). $^{13}$C NMR (101 MHz, Chloroform-d) δ 164.42, 161.96, 157.20, 154.50, 142.59, 138.65 (d, J=6.9 Hz), 135.03, 130.78 (d, J=8.2 Hz), 122.55 (d, J=37.2 Hz), 121.51 (d, J=3.0 Hz), 119.62, 115.06 (d, J=21.2 Hz), 113.09 (d, J=22.4 Hz), 109.49, 79.60, 46.24 (d, J=2.1 Hz), 34.72, 30.83, 28.44. LCMS: Expected: 410 (M+H)$^+$; Found: 410.

Synthesis of 1-(3-fluorobenzyl)-2-(piperidin-4-yl)-1H-benzo[d]imidazole

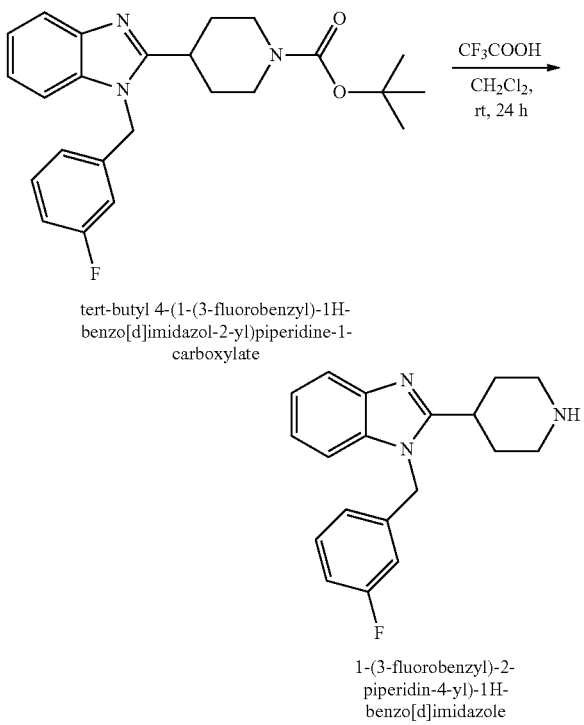

1-(3-fluorobenzyl)-2-piperidin-4-yl)-1H-benzo[d]imidazole

Into a round bottom flask equipped with a nitrogen inlet and a magnetic stir bar, a solution of tert-butyl 4-(1-(3-fluorobenzyl)-1H-benzo[d]imidazol-2-yl)piperidine-1-carboxylate (2.0 g, 4.88 mmol) in CH$_2$Cl$_2$ (10 mL) was. To the above solution CF$_3$COOH (3 mL) was slowly added to the reaction mixture. The reaction was stirred at room temperature for overnight. Saturated solution of NaHCO$_3$ was then slowly added to the reaction mixture. The aqueous was extracted with CH$_2$Cl$_2$ (×3). The combined organic layer was then dried over Na$_2$SO$_4$, filtered and then dried in vacuo to give 1.51 g (100%) of the pure and desired compound. $^1$H NMR (400 MHz, Chloroform-d) δ 7.83 (d, J=8.2 Hz, 1H), 7.38-7.15 (m, 4H), 7.00 (td, J=8.2, 2.0 Hz, 1H), 6.81 (d, J=8.3 Hz, 1H), 6.73 (d, J=9.3 Hz, 1H), 5.83 (bs, 1H), 5.40 (s, 2H), 3.56 (dt, J=13.3, 4.6 Hz, 2H), 3.16 (tt, J=9.0, 4.1 Hz, 1H), 3.02 (ddd, J=13.3, 10.0, 3.5 Hz, 2H), 2.25-2.00 (m, 4H). $^{13}$C NMR (101 MHz, Chloroform-d) δ 164.44, 161.98, 156.10, 142.39, 138.51, 135.04, 130.86 (d, J=8.3 Hz), 122.81 (d, J=47.4 Hz), 121.48, 119.70, 115.17 (d, J=21.2 Hz), 113.06 (d, J=22.6 Hz), 109.57, 46.31 (d, J=2.0 Hz), 43.63, 32.26, 28.85.
LCMS: Expected: 310 (M+H)$^+$; Found: 310.

Synthesis of cyclohexyl(4-(1-(3-fluorobenzyl)-1H-benzo[d]imidazol-2-yl)piperidin-1-yl)methanone (AZ220)

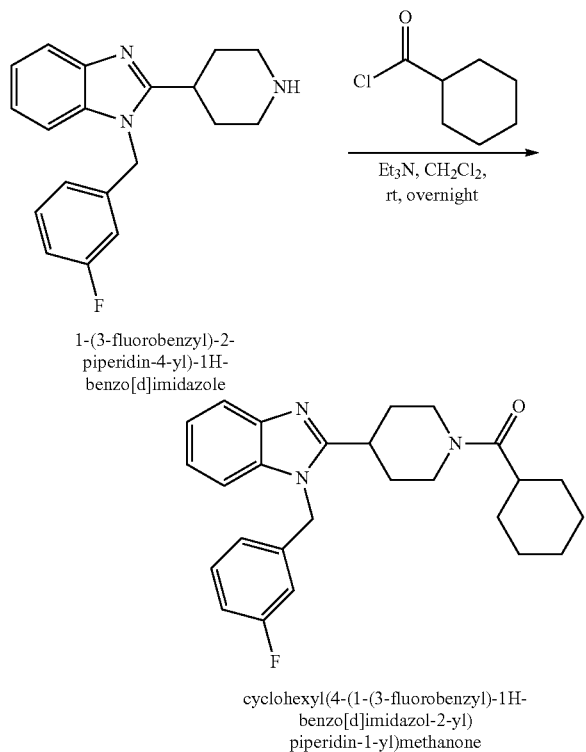

1-(3-fluorobenzyl)-2-piperidin-4-yl)-1H-benzo[d]imidazole cyclohexyl(4-(1-(3-fluorobenzyl)-1H-benzo[d]imidazol-2-yl)piperidin-1-yl)methanone Into a round bottom flask equipped with a nitrogen inlet and a magnetic stir bar, 1-(3-fluorobenzyl)-2-(piperidin-4-yl)-1H-benzo[d]imidazole (200 mg, 0.65 mmol), Et$_3$N (0.18 mL, 1.26 mmol) and CH$_2$Cl$_2$ (5 mL) were added. cyclohexanecarbonyl chloride (95 mg, 0.65 mmol) was added to the reaction mixture. The reaction was stirred at room temperature overnight. Water (15 mL) was added to the reaction mixture, the layers were separated and the aqueous was extracted with CH$_2$Cl$_2$ (10 mL×3). The combined organic layer was dried over Na$_2$SO$_4$, filtered, dried in vacuo to give the crude product. The crude product was purified using combiflash column and the desired product was eluted with 2% MeOH in CH$_2$Cl$_2$ to give 158 mg (58%) of the pure and desired compound.

$^1$H NMR (400 MHz, Chloroform-d) δ 7.81 (ddd, J=7.9, 1.3, 0.7 Hz, 1H), 7.36-7.29 (m, 2H), 7.28-7.17 (m, 2H), 7.02 (tdd, J=8.4, 2.6, 0.9 Hz, 1H), 6.82 (ddq, J=7.6, 1.7, 0.8 Hz, 1H), 6.75 (dt, J=9.4, 2.0 Hz, 1H), 5.41 (s, 2H), 4.75 (d, J=13.5 Hz, 1H), 4.09 (d, J=13.7 Hz, 1H), 3.12 (t, J=12 Hz, 1H), 2.51 (tt, J=11.5, 3.3 Hz, 1H), 2.65 (t, J=12 Hz, 1H), 2.51 (tt, J=11.5, 3.3 Hz, 1H), 2.21-2.12 (m, 1H), 2.03-1.69 (m, 8H), 1.55 (q, J=11.7 Hz, 2H), 1.39-1.15 (m, 3H). $^{13}$C NMR (101 MHz, Chloroform-d) δ 174.44, 164.45, 161.98, 156.79, 142.53, 138.56, 135.03, 130.83 (d, J=8.3 Hz), 122.66 (d, J=39.0 Hz), 121.49 (d, J=3.0 Hz), 119.67, 115.13 (d, J=21.2 Hz), 113.09 (d, J=22.3 Hz), 109.50, 46.28, 45.22, 41.46, 40.50, 34.82, 31.22 (d, J=15.4 Hz), 29.48 (d, J=44.1 Hz), 25.88 (d, J=2.3 Hz). LCMS: Expected: 420 (M+H)$^+$; Found: 420. HRMS:—Found: 420.24515 (M+H)$^+$; Theoretically=420.24457.

Synthesis of cyclopropyl(4-(1-(3-fluorobenzyl)-1H-benzo[d]imidazol-2-yl)piperidin-1-yl)methanone (AZ221)

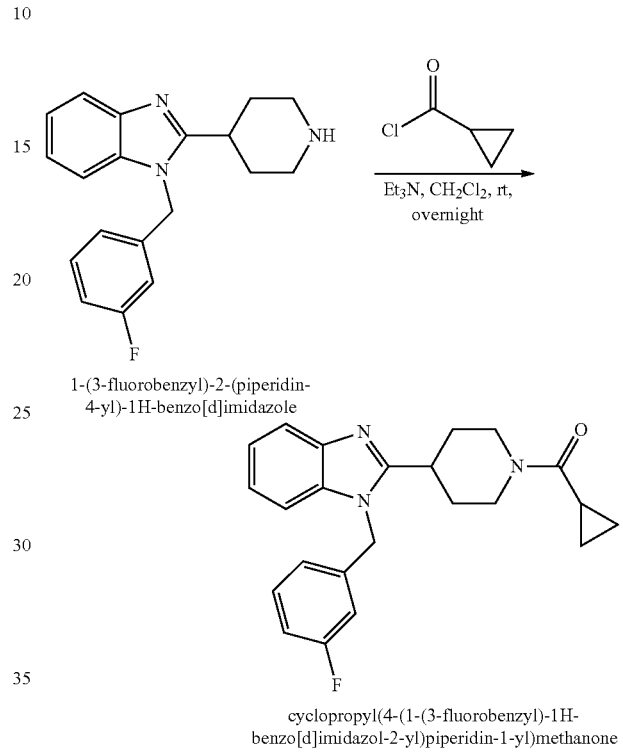

1-(3-fluorobenzyl)-2-(piperidin-4-yl)-1H-benzo[d]imidazole cyclopropyl(4-(1-(3-fluorobenzyl)-1H-benzo[d]imidazol-2-yl)piperidin-1-yl)methanone Into a round bottom flask equipped with a nitrogen inlet and a magnetic stir bar, 1-(3-fluorobenzyl)-2-(piperidin-4-yl)-1H-benzo[d]imidazole (200 mg, 0.65 mmol), Et$_3$N (0.18 mL, 1.26 mmol) and CH$_2$Cl$_2$ (5 mL) were added. Cyclopropanecarbonyl chloride (68 mg, 0.65 mmol) was added to the reaction mixture. The reaction was stirred at room temperature overnight. Water (15 mL) was added to the reaction mixture, the layers were separated and the aqueous was extracted with CH$_2$Cl$_2$ (10 mL×3). The combined organic layer was dried over Na$_2$SO$_4$, filtered, dried in vacuo to give the crude product. The crude product was purified using combiflash column and the desired product was eluted with 2% MeOH in CH$_2$Cl$_2$ to give 110 mg (45%) of the pure and desired compound.

$^1$H NMR (400 MHz, Chloroform-d) δ 7.81 (ddd, J=7.9, 1.3, 0.7 Hz, 1H), 7.35-7.18 (m, 4H), 7.01 (tdd, J=8.4, 2.6, 0.9 Hz, 1H), 6.82 (ddq, J=7.7, 1.7, 0.8 Hz, 1H), 6.75 (dt, J=9.4, 2.0 Hz, 1H), 5.42 (s, 2H), 4.71 (d, J=13.0 Hz, 1H), 4.39 (d, J=18.3 Hz, 1H), 3.22 (t, J=12.9 Hz, 1H), 3.06 (tt, J=11.2, 4.0 Hz, 1H), 2.73 (t, J=12.9 Hz, 1H), 2.33-2.14 (m, 1H), 1.94-1.75 (m, 3H), 1.78 (tt, J=8.0, 4.7 Hz, 1H), 1.02 (dd, J=7.9, 2.1 Hz, 2H), 0.78 (dd, J=7.9, 2.1 Hz, 2H). $^{13}$C NMR (101 MHz, Chloroform-d) δ 171.75, 164.45, 161.99, 156.82, 142.55, 138.60 (d, J=7.0 Hz), 135.03, 130.83 (d, J=8.3 Hz), 122.65 (d, J=38.9 Hz), 121.49 (d, J=3.0 Hz), 119.67, 115.13 (d, J=21.2 Hz), 113.09 (d, J=22.4 Hz), 109.50, 46.28, 34.78, 31.05, 11.02, 7.31. LCMS: Expected: 378 (M+H)$^+$, 400

(M+Na)⁺; Found: 378 and 400. HRMS:—Found: 378.19799 (M+H)⁺; Theoretically=378.19762.

Synthesis of cyclopentyl(4-(1-(3-fluorobenzyl)-1H-benzo[d]imidazol-2-yl)piperidin-1-yl)methanone (AZ222)

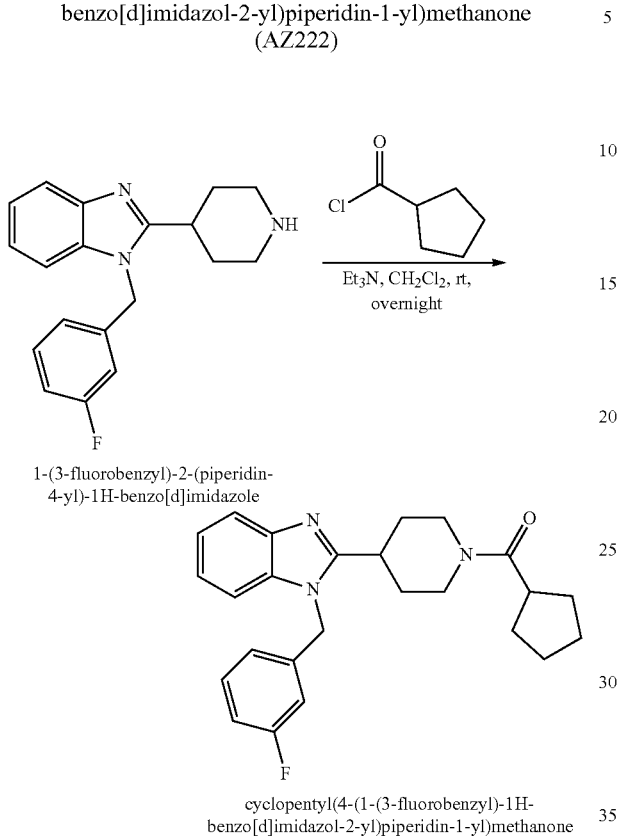

1-(3-fluorobenzyl)-2-(piperidin-4-yl)-1H-benzo[d]imidazole cyclopentyl(4-(1-(3-fluorobenzyl)-1H-benzo[d]imidazol-2-yl)piperidin-1-yl)methanone Into a round bottom flask equipped with a nitrogen inlet and a magnetic stir bar, 1-(3-fluorobenzyl)-2-(piperidin-4-yl)-1H-benzo[d]imidazole (200 mg, 0.65 mmol), Et₃N (0.18 mL, 1.26 mmol) and CH₂Cl₂ (5 mL) were added. Cyclopentanecarbonyl chloride (86 mg, 0.65 mmol) was added to the reaction mixture. The reaction was stirred at room temperature overnight. Water (15 mL) was added to the reaction mixture, the layers were separated and the aqueous was extracted with CH₂Cl₂ (10 mL×3). The combined organic layer was dried over Na₂SO₄, filtered, dried in vacuo to give the crude product. The crude product was purified using combiflash column and the desired product was eluted with 2% MeOH in CH₂Cl₂ to give 147 mg (56%) of the pure and desired compound.

¹H NMR (400 MHz, Chloroform-d) δ 7.83 (d, J=7.7 Hz, 1H), 7.35-7.22 (m, 4H), 7.03 (td, J=8.4, 2.5 Hz, 1H), 6.82 (ddd, J=7.7, 1.7, 0.9 Hz, 1H), 6.75 (d, J=9.4 Hz, 1H), 5.42 (s, 2H), 4.74 (d, J=13.5 Hz, 1H), 4.09 (d, J=13.5 Hz, 1H), 4.05 (d, J=12.8 Hz, 2H), 3.48 (td, J=11.8, 2.2 Hz, 2H), 3.16 (t, J=12.9 Hz, 1H), 3.05 (t, J=12.9 Hz, 1H), 2.78 (ddt, J=11.3, 7.5, 3.8 Hz, 1H), 2.69 (t, J=12.4 Hz, 1H), 2.32-2.14 (m, 1H), 2.07-1.75 (m, 5H), 1.65 (t, J=17.1 Hz, 2H). ¹³C NMR (101 MHz, Chloroform-d) δ 174.39, 164.45, 161.99, 156.71, 138.47, 134.90, 130.86 (d, J=8.2 Hz), 122.81 (d, J=37.5 Hz), 121.48 (d, J=3.0 Hz), 119.56, 115.19 (d, J=21.2 Hz), 113.09 (d, J=22.4 Hz), 109.56, 53.44, 46.33, 45.30, 41.67, 41.11, 34.85, 31.07, 30.18 (d, J=40.9 Hz), 26.04. LCMS: Expected: 406 (M+H)⁺, 428 (M+Na)⁺; Found: 406 and 428. HRMS:—Found: 406.22953 (M+H)⁺; Theoretically=406.22892.

Synthesis (4-(1-(3-fluorobenzyl)-1H-benzo[d]imidazol-2-yl)piperidin-1-yl)(tetrahydro-2H-pyran-4-yl)methanone (AZ223)

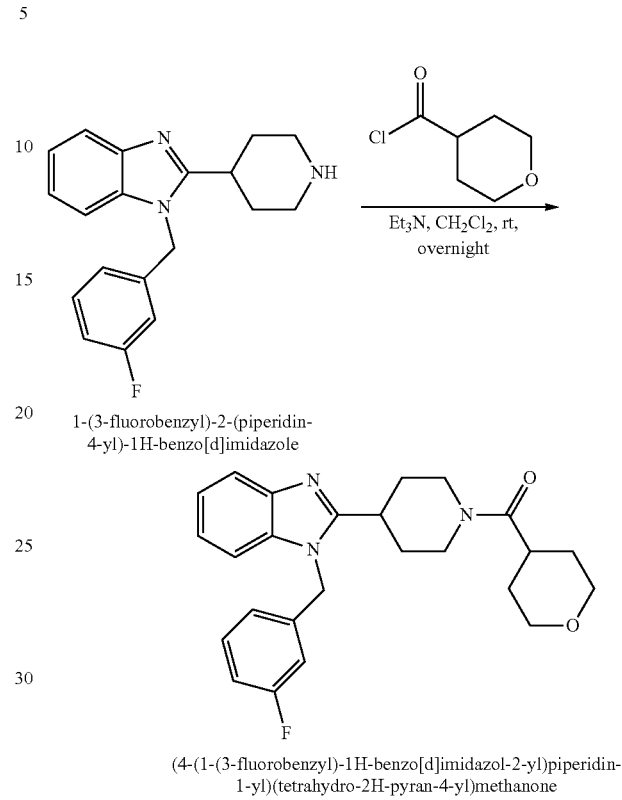

1-(3-fluorobenzyl)-2-(piperidin-4-yl)-1H-benzo[d]imidazole (4-(1-(3-fluorobenzyl)-1H-benzo[d]imidazol-2-yl)piperidin-1-yl)(tetrahydro-2H-pyran-4-yl)methanone Into a round bottom flask equipped with a nitrogen inlet and a magnetic stir bar, 1-(3-fluorobenzyl)-2-(piperidin-4-yl)-1H-benzo[d]imidazole (200 mg, 0.65 mmol), Et₃N (0.18 mL, 1.26 mmol) and CH₂Cl₂ (5 mL) were added. Tetrahydro-2H-pyran-4-carbonyl chloride (97 mg, 0.65 mmol) was added to the reaction mixture. The reaction was stirred at room temperature overnight. Water (15 mL) was added to the reaction mixture, the layers were separated and the aqueous was extracted with CH₂Cl₂ (10 mL×3). The combined organic layer was dried over Na₂SO₄, filtered, dried in vacuo to give the crude product. The crude product was purified using combiflash column and the desired product was eluted with 2% MeOH in CH₂Cl₂ to give 82 mg (30%) of the pure and desired compound.

¹H NMR (400 MHz, Chloroform-d) δ 7.83 (d, J=7.7 Hz, 1H), 7.35-7.22 (m, 4H), 7.03 (td, J=8.4, 2.5 Hz, 1H), 6.82 (ddd, J=7.7, 1.7, 0.9 Hz, 1H), 6.75 (d, J=9.4 Hz, 1H), 5.42 (s, 2H), 4.74 (d, J=13.5 Hz, 1H), 4.05 (d, J=12.5 Hz, 3H), 3.48 (t, J=10.7 Hz, 2H), 3.16 (t, J=12.9 Hz, 1H), 3.05 (d, J=11.2 Hz, 1H), 2.78 (tt, J=11.3, 3.8 Hz, 1H), 2.69 (t, J=12.4 Hz, 1H), 2.20 (bs, 1H), 2.03-1.78 (m, 5H), 1.65 (t, J=17.1 Hz, 2H). ¹³C NMR (101 MHz, Chloroform-d) δ 172.66, 164.46, 162.00, 156.43, 130.91 (d, J=8.2 Hz), 121.47 (d, J=3.0 Hz), 119.49, 115.27 (d, J=20.5 Hz), 113.10 (d, J=22.4 Hz), 109.61, 67.28, 46.38, 45.17, 41.61, 37.62, 34.69, 31.03, 29.16 (d, J=32.6 Hz). LCMS: Expected: 422 (M+H)⁺, 444 (M+Na)⁺; Found: 422 and 444. HRMS:—Found: 422.2429 (M+H)⁺; Theoretically=422.22383.

Synthesis of (3-fluoro-4-methoxyphenyl)(4-(1-(3-fluorobenzyl)-1H-benzo[d]imidazol-2-yl)piperidin-1-yl)methanone (AZ224)

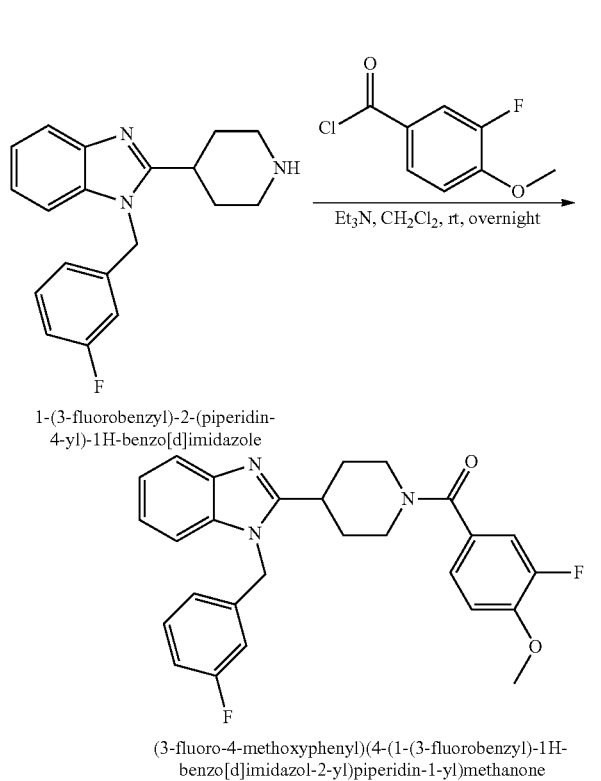

1-(3-fluorobenzyl)-2-(piperidin-4-yl)-1H-benzo[d]imidazole (3-fluoro-4-methoxyphenyl)(4-(1-(3-fluorobenzyl)-1H-benzo[d]imidazol-2-yl)piperidin-1-yl)methanone 2-(piperidin-4-yl)-1H-benzo[d]imidazole (900 mg, 2.91 mmol), Et$_3$N (0.81 mL, 5.67 mmol) and CH$_2$Cl$_2$ (15 mL) were added. 3-fluoro-4-methoxybenzoyl chloride (603 mg, 3.20 mmol) was added to the reaction mixture. The reaction was stirred at room temperature overnight. Water (30 mL) was added to the reaction mixture, the layers were separated and the aqueous was extracted with CH$_2$Cl$_2$ (20 mL×3). The combined organic layer was dried over Na$_2$SO$_4$, filtered, dried in vacuo to give the crude product. The crude product was purified using combiflash column and the desired product was eluted with 2% MeOH in CH$_2$Cl$_2$ to give 826 mg (62%) of the pure and desired compound.

$^1$H NMR (400 MHz, Chloroform-d) δ 7.85 (d, J=7.8 Hz, 1H), 7.39-7.19 (m, 6H), 7.01 (dt, J=12.2, 7.3 Hz, 2H), 6.82 (ddd, J=7.7, 1.7, 0.9 Hz, 1H), 6.76 (d, J=9.2 Hz, 1H), 5.43 (s, 2H), 4.96-4.35 (m, 1H), 4.48-4.01 (m, 1H), 3.94 (s, 3H), 3.09 (ddt, J=11.0, 6.9, 3.7 Hz, 2H), 3.00 (bs, 1H), 2.26-2.08 (m, 2H), 1.90 (d, J=13.3 Hz, 2H). $^{13}$C NMR (101 MHz, Chloroform-d) δ 169.12, 164.45, 161.99, 156.42, 153.10, 150.63, 149.00 (d, J=10.7 Hz), 130.92 (d, J=8.2 Hz), 128.31 (d, J=5.5 Hz), 123.76 (d, J=3.7 Hz), 123.22, 121.48 (d, J=3.1 Hz), 119.46, 115.54 (d, J=19.6 Hz), 115.29 (d, J=21.1 Hz), 113.22, 113.05-112.92 (m), 109.64, 56.29, 46.40, 34.66, 30.95. LCMS: Expected: 462 (M+H)$^+$, 484 (M+Na)$^+$; Found: 462 and 484. HRMS:—Found: 462.19962 (M+H)$^+$; Theoretically=462.19876.

Synthesis of (3-fluoro-4-hydroxyphenyl)(4-(1-(3-fluorobenzyl)-1H-benzo[d]imidazol-2-yl)piperidin-1-yl)methanone

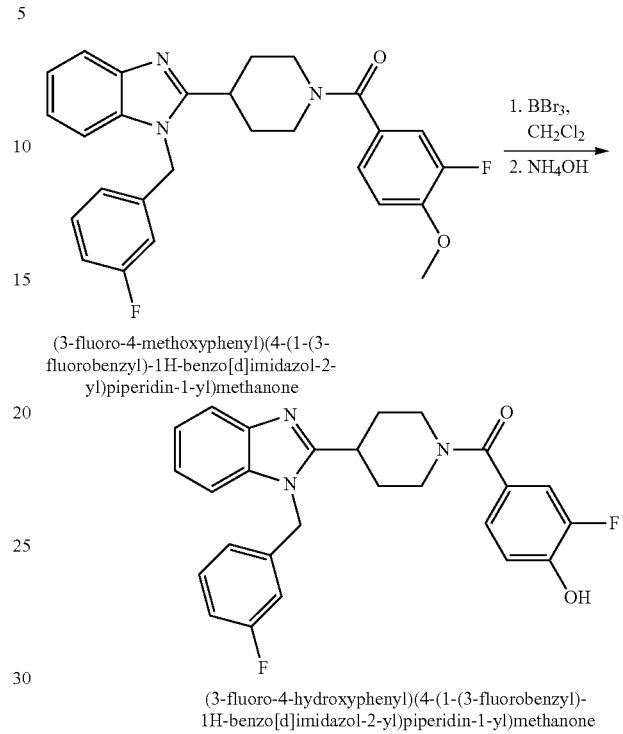

(3-fluoro-4-methoxyphenyl)(4-(1-(3-fluorobenzyl)-1H-benzo[d]imidazol-2-yl)piperidin-1-yl)methanone (3-fluoro-4-hydroxyphenyl)(4-(1-(3-fluorobenzyl)-1H-benzo[d]imidazol-2-yl)piperidin-1-yl)methanone Into a round bottom flask equipped with a nitrogen inlet and a magnetic stir bar, a solution of (3-fluoro-4-methoxyphenyl)(4-(1-(3-fluorobenzyl)-1H-benzo[d]imidazol-2-yl)piperidin-1-yl)methanone (745 mg, 1.61 mmol) in CH$_2$Cl$_2$ (75 mL) was added. To the above solution, BBr$_3$ (1.5 mL, 15.23 mmol) was slowly added at 0° C. The reaction mixture was warmed to room temperature and then stirred for 2 hours (the reaction was monitored by TLC). The reaction mixture was cooled to 0° C. before 30 mL of 30% NH$_4$OH (aq) was added slowly (pH=9). The reaction was then warmed to room temperature and stirred for 2 hours. The reaction mixture was then poured into a separatory funnel and the layers were separated. The aqueous was then extracted with CH$_2$Cl$_2$ (25 mL×3). The combined organic layers were separated and then dried in vacuo to give 700 mg (97%) of the desired compound that was pure enough to be used in the step.

$^1$H NMR (400 MHz, Chloroform-d) δ 7.84 (ddd, J=7.9, 1.4, 0.7 Hz, 1H), 7.28-7.24 (m, 4H), 7.19 (dd, J=10.8, 1.9 Hz, 1H), 7.09 (ddd, J=8.3, 2.0, 0.7 Hz, 1H), 7.06-6.98 (m, 2H), 6.83 (ddd, J=7.7, 1.7, 0.9 Hz, 1H), 6.78 (dd, J=9.2, 2.2 Hz, 1H), 5.47 (s, 2H), 3.23-3.05 (m, 1H), 2.98 (bs, 2H), 2.29-2.05 (m, 3H), 1.95-1.72 (m, 3H). $^{13}$C NMR (101 MHz, Chloroform-d) δ 169.45, 164.44, 161.97, 156.45, 152.21, 149.81, 146.17 (d, J=13.4 Hz), 138.10 (d, J=6.9 Hz), 134.49, 130.97 (d, J=8.3 Hz), 127.35, 124.01 (d, J=3.2 Hz), 123.51, 123.20, 121.53 (d, J=3.0 Hz), 119.10, 117.76, 115.40 (dd, J=20.3, 8.5 Hz), 113.16 (d, J=22.4 Hz), 109.83, 46.52, 34.62, 30.84. LCMS: Expected: 448 (M+H)$^+$; Found: 448.

Synthesis of (3-fluoro-4-((3-fluorobenzyl)oxy)phenyl)(4-(1-(3-fluorobenzyl)-1H-benzo[d]imidazol-2-yl)piperidin-1-yl)methanone (AZ225)

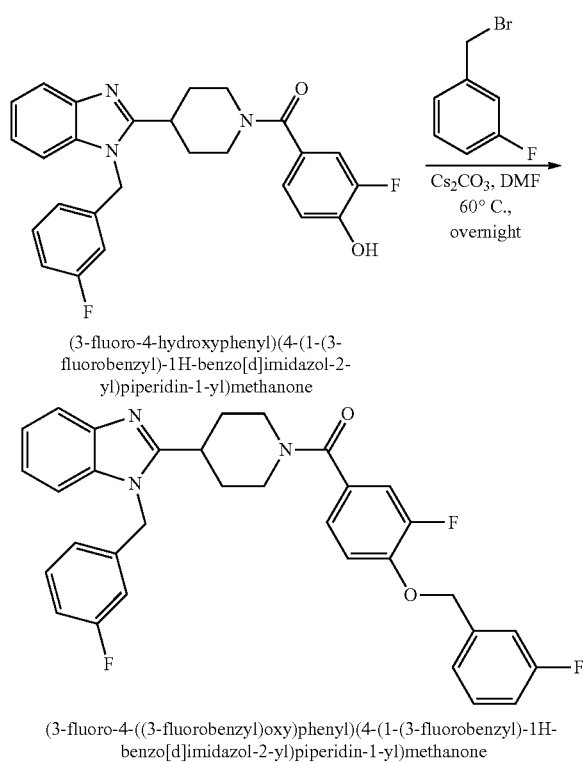

(3-fluoro-4-hydroxyphenyl)(4-(1-(3-fluorobenzyl)-1H-benzo[d]imidazol-2-yl)piperidin-1-yl)methanone (3-fluoro-4-((3-fluorobenzyl)oxy)phenyl)(4-(1-(3-fluorobenzyl)-1H-benzo[d]imidazol-2-yl)piperidin-1-yl)methanone Into a round bottom flask equipped with a nitrogen inlet and a magnetic stir bar, a solution of (3-fluoro-4-hydroxyphenyl)(4-(1-(3-fluorobenzyl)-1H-benzo[d]imidazol-2-yl)piperidin-1-yl)methanone (150 mg, 0.335 mmol) and $Cs_2CO_3$ (218 mg, 0.67 mmol) in DMF (1.5 mL) was added. To the above solution, a solution of 1-(bromomethyl)-3-fluorobenzene (69 mg, 0.365 mmol) was added. The reaction mixture was stirred at 60° C. overnight. Water (20 mL) was added to the reaction mixture aqueous was then extracted with $CH_2Cl_2$ (15 mL×3). The combined organic layers were separated and then dried in vacuo and the crude was purified using combiflash column chromatography. Excess 1-(bromomethyl)-3-fluorobenzene was removed with 30% EtOAc in Hexanes and the pure and desired product was eluted with 0-1% MeOH in $CH_2Cl_2$ to give 72 mg (39%) of yellow color solid.

$^1$H NMR (400 MHz, Chloroform-d) δ 7.83 (d, J=7.6 Hz, 1H), 7.41-7.29 (m, 3H), 7.28-7.15 (m, 6H), 7.13-6.90 (m, 3H), 6.82 (ddq, J=7.7, 1.7, 0.8 Hz, 1H), 6.75 (ddd, J=9.4, 2.5, 1.7 Hz, 1H), 5.42 (s, 2H), 5.18 (s, 2H), 5.04-3.52 (m, 2H), 3.46-2.82 (m, 3H), 2.15 (q, J=12.6 Hz, 2H), 1.89 (d, J=13.5 Hz, 2H). $^{13}$C NMR (101 MHz, Chloroform-d) δ 168.94 (d, J=1.8 Hz), 164.33 (d, J=23.4 Hz), 161.87 (d, J=21.7 Hz), 156.47, 153.47, 151.00, 147.72 (d, J=10.6 Hz), 138.58 (d, J=7.3 Hz), 138.45, 134.87, 130.89 (d, J=8.3 Hz), 130.28 (d, J=8.3 Hz), 129.14 (d, J=5.7 Hz), 123.65 (d, J=3.6 Hz), 123.10, 122.71 (d, J=3.0 Hz), 121.48 (d, J=3.0 Hz), 119.54, 115.80 (d, J=19.8 Hz), 115.46-114.92 (m), 114.20 (d, J=22.3 Hz), 113.10 (d, J=22.4 Hz), 109.60, 77.24, 70.44 (d, J=1.9 Hz), 46.35, 34.60, 31.43. LC-MS: Expected: 556 (M+H)$^+$, Found: 556. HRMS:—Found: 556.22218 (M+H)$^+$; Theoretically=556.22064.

Synthesis of (3-fluoro-4-((tetrahydro-2H-pyran-4-yl)methoxy)phenyl)(4-(1-(3-fluorobenzyl)-1H-benzo[d]imidazol-2-yl)piperidin-1-yl)methanone (AZ0715)

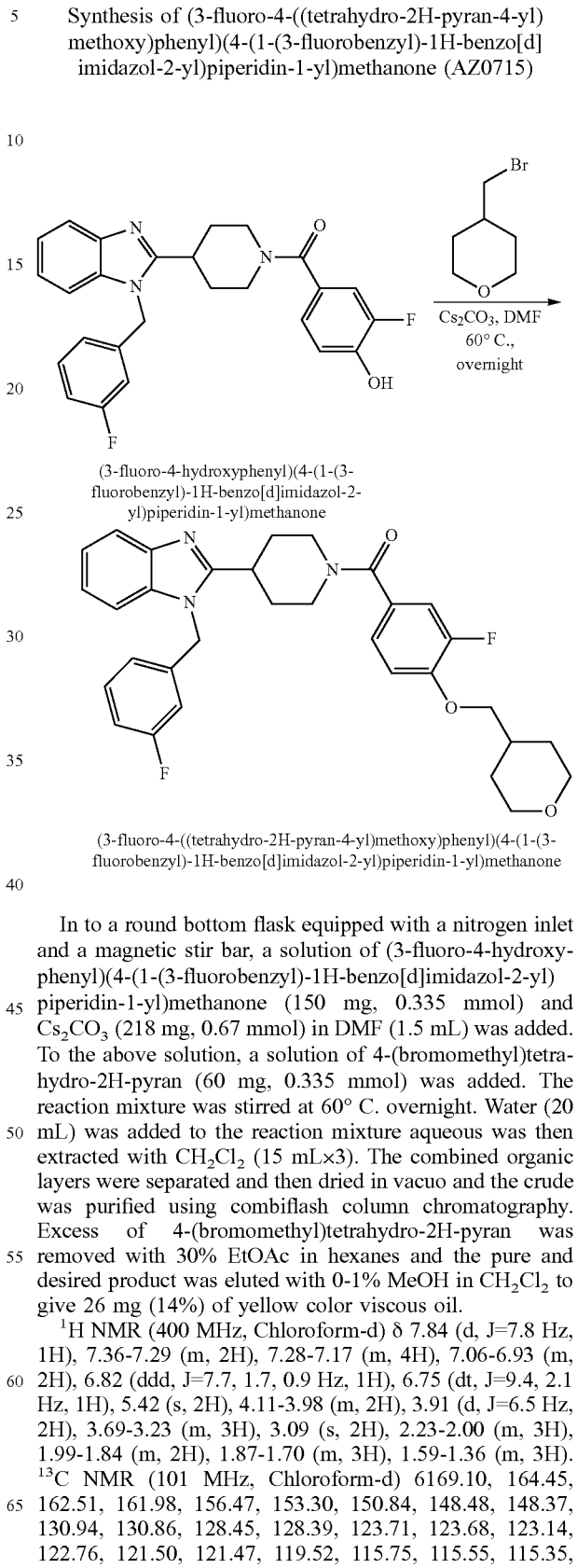

(3-fluoro-4-hydroxyphenyl)(4-(1-(3-fluorobenzyl)-1H-benzo[d]imidazol-2-yl)piperidin-1-yl)methanone (3-fluoro-4-((tetrahydro-2H-pyran-4-yl)methoxy)phenyl)(4-(1-(3-fluorobenzyl)-1H-benzo[d]imidazol-2-yl)piperidin-1-yl)methanone In to a round bottom flask equipped with a nitrogen inlet and a magnetic stir bar, a solution of (3-fluoro-4-hydroxyphenyl)(4-(1-(3-fluorobenzyl)-1H-benzo[d]imidazol-2-yl)piperidin-1-yl)methanone (150 mg, 0.335 mmol) and $Cs_2CO_3$ (218 mg, 0.67 mmol) in DMF (1.5 mL) was added. To the above solution, a solution of 4-(bromomethyl)tetrahydro-2H-pyran (60 mg, 0.335 mmol) was added. The reaction mixture was stirred at 60° C. overnight. Water (20 mL) was added to the reaction mixture aqueous was then extracted with $CH_2Cl_2$ (15 mL×3). The combined organic layers were separated and then dried in vacuo and the crude was purified using combiflash column chromatography. Excess of 4-(bromomethyl)tetrahydro-2H-pyran was removed with 30% EtOAc in hexanes and the pure and desired product was eluted with 0-1% MeOH in $CH_2Cl_2$ to give 26 mg (14%) of yellow color viscous oil.

$^1$H NMR (400 MHz, Chloroform-d) δ 7.84 (d, J=7.8 Hz, 1H), 7.36-7.29 (m, 2H), 7.28-7.17 (m, 4H), 7.06-6.93 (m, 2H), 6.82 (ddd, J=7.7, 1.7, 0.9 Hz, 1H), 6.75 (dt, J=9.4, 2.1 Hz, 1H), 5.42 (s, 2H), 4.11-3.98 (m, 2H), 3.91 (d, J=6.5 Hz, 2H), 3.69-3.23 (m, 3H), 3.09 (s, 2H), 2.23-2.00 (m, 3H), 1.99-1.84 (m, 3H), 1.87-1.70 (m, 3H), 1.59-1.36 (m, 3H). $^{13}$C NMR (101 MHz, Chloroform-d) 6169.10, 164.45, 162.51, 161.98, 156.47, 153.30, 150.84, 148.48, 148.37, 130.94, 130.86, 128.45, 128.39, 123.71, 123.68, 123.14, 122.76, 121.50, 121.47, 119.52, 115.75, 115.55, 115.35, 115.14, 114.28, 114.26, 113.21, 112.99, 109.61, 73.88, 67.53 (d, J=2.8 Hz), 49.85, 46.36, 35.04, 34.64, 31.43, 30.65, 29.58. LC-MS: Expected: 546 (M+H)+, Found: 546.

Synthesis of (4-(cyclopropylmethoxy)-3-fluorophenyl)(4-(1-(3-fluorobenzyl)-1H-benzo[d]imidazol-2-yl)piperidin-1-yl)methanone (AZ226)

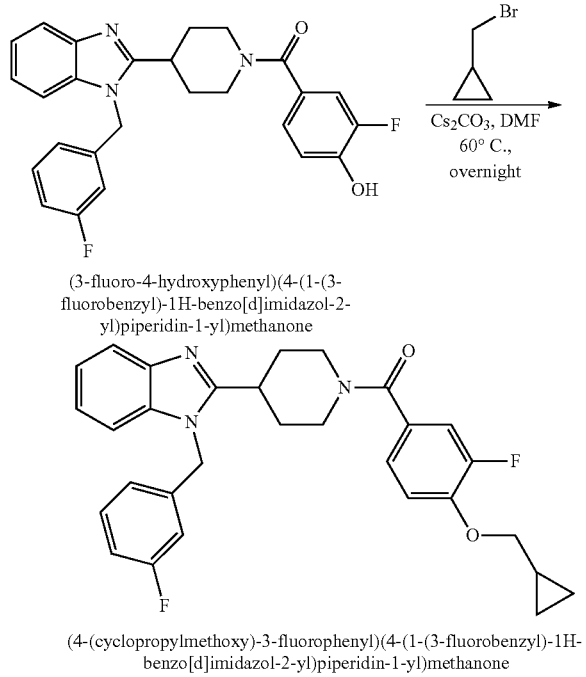

(3-fluoro-4-hydroxyphenyl)(4-(1-(3-fluorobenzyl)-1H-benzo[d]imidazol-2-yl)piperidin-1-yl)methanone (4-(cyclopropylmethoxy)-3-fluorophenyl)(4-(1-(3-fluorobenzyl)-1H-benzo[d]imidazol-2-yl)piperidin-1-yl)methanone Into a round bottom flask equipped with a nitrogen inlet and a magnetic stir bar, a solution of (3-fluoro-4-hydroxyphenyl)(4-(1-(3-fluorobenzyl)-1H-benzo[d]imidazol-2-yl)piperidin-1-yl)methanone (150 mg, 0.335 mmol) and $Cs_2CO_3$ (218 mg, 0.67 mmol in DMF (1.5 mL) was added. To the above solution, a solution of (bromomethyl)cyclopropane (46 mg, 0.340 mmol) was added. The reaction mixture was stirred at 60° C. overnight. Water (20 mL) was added to the reaction mixture aqueous was then extracted with $CH_2Cl_2$ (15 mL×3). The combined organic layers were separated and then dried in vacuo and the crude was purified using combiflash column chromatography. The excess (bromomethyl)cyclopropane was removed with 30% EtOAc in hexanes and the pure and desired product was eluted with 0-1% MeOH in $CH_2Cl_2$ to give 65 mg (39%) of yellow viscous oil.

$^1$H NMR (400 MHz, Chloroform-d) δ 7.83 (d, J=7.6 Hz, 1H), 7.36-7.13 (m, 6H), 7.08-6.90 (m, 2H), 6.82 (d, J=7.8 Hz, 1H), 6.75 (d, J=10.4 Hz, 1H), 5.42 (s, 2H), 5.07-3.95 (m, 2H), 3.92 (d, J=7.0 Hz, 2H), 3.10-2.90 (m, 2H), 2.20-2.10 (m, 2H), 1.89 (d, J=13.8 Hz, 2H), 1.45-1.06 (m, 2H), 0.69 (q, J=6.0, 5.4 Hz, 2H), 0.39 (q, J=6.0, 5.4 Hz, 2H). $^{13}$C NMR (101 MHz, Chloroform-d) δ 170.79-167.73 (m), 163.35-162.02 (m), 153.36, 148.48, 146.10, 142.55, 138.06, 134.73, 130.88 (d, J=8.3 Hz), 128.32, 123.67 (d, J=4.1 Hz), 123.08, 122.65, 121.48 (d, J=3.0 Hz), 119.54, 115.63 (d, J=19.7 Hz), 114.63, 113.10 (d, J=22.5 Hz), 109.59, 74.31, 46.35, 36.49, 31.43, 10.14, 3.34. LC-MS: Expected: 502 (M+H)$^+$, Found: 502. HRMS:—Found: 502.23122 (M+H)$^+$; Theoretically=502.23006.

Synthesis of (3-fluoro-4-(2-methoxyethoxy)phenyl)(4-(1-(3-fluorobenzyl)-1H-benzo[d]imidazol-2-yl)piperidin-1-yl)methanone (AZ227)

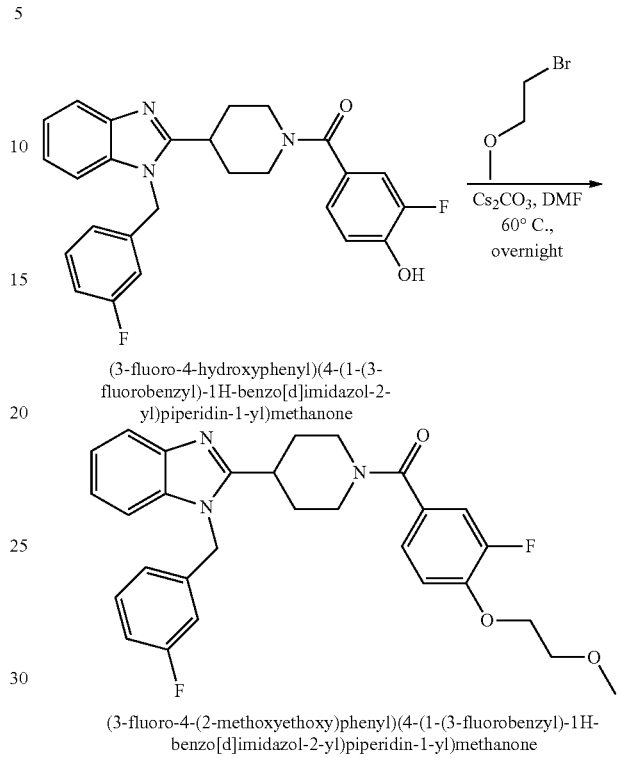

(3-fluoro-4-hydroxyphenyl)(4-(1-(3-fluorobenzyl)-1H-benzo[d]imidazol-2-yl)piperidin-1-yl)methanone (3-fluoro-4-(2-methoxyethoxy)phenyl)(4-(1-(3-fluorobenzyl)-1H-benzo[d]imidazol-2-yl)piperidin-1-yl)methanone Into a round bottom flask equipped with a nitrogen inlet and a magnetic stir bar, a solution of (3-fluoro-4-hydroxyphenyl)(4-(1-(3-fluorobenzyl)-1H-benzo[d]imidazol-2-yl)piperidin-1-yl)methanone (150 mg, 0.335 mmol) and $Cs_2CO_3$ (218 mg, 0.67 mmol in DMF (1.5 mL) was added. To the above solution, a solution of 1-bromo-2-methoxyethane (47 mg, 0.340 mmol) was added. The reaction mixture was stirred at 60° C. overnight. Water (20 mL) was added to the reaction mixture aqueous was then extracted with $CH_2Cl_2$ (15 mL×3). The combined organic layers were separated and then dried in vacuo and the crude was purified using combiflash column chromatography. The excess 1-bromo-2-methoxyethane was removed with 30% EtOAc in hexanes and the pure and desired product was eluted with 0-1% MeOH in $CH_2Cl_2$ to give 116 mg (68%) of yellow viscous oil.

$^1$H NMR (400 MHz, Chloroform-d) δ 7.81 (ddd, J=7.9, 1.3, 0.8 Hz, 1H), 7.37-7.14 (m, 6H), 7.05-6.94 (m, 2H), 6.81 (ddt, J=7.7, 1.7, 0.9 Hz, 1H), 6.77-6.69 (m, 1H), 5.41 (s, 2H), 5.08-4.25 (m, 2H), 4.31-4.16 (m, 2H), 3.88-3.70 (m, 1H), 3.46 (s, 3H), 3.21-2.90 (m, 3H), 2.27-2.05 (m, 2H), 1.88 (d, J=13.3 Hz, 2H). 1 missing (could be hidden behind the tall —OCH$_3$ peak). $^{13}$C NMR (101 MHz, Chloroform-d) δ 169.02 (d, J=1.8 Hz), 164.42, 162.50, 161.96, 153.37, 150.91, 148.20 (d, J=10.6 Hz), 142.33, 138.52 (d, J=6.9 Hz), 134.97, 130.86 (d, J=8.3 Hz), 128.82, 128.52 (d, J=5.7 Hz), 123.61 (d, J=3.7 Hz), 122.97, 122.57, 121.49 (d, J=3.0 Hz), 119.59, 116.10-114.55 (m), 113.08 (d, J=22.4 Hz), 109.57, 70.77, 68.97, 59.31, 46.29 (d, J=2.1 Hz), 36.47, 31.41. LC-MS: Expected: 506 (M+H)$^+$, Found: 506. HRMS:—Found: 506.22605 (M+H)$^+$; Theoretically=506.22497.

Synthesis of (4-(1H-benzo[d]imidazol-2-yl)piperidin-1-yl)(3-fluoro-4-methoxyphenyl)methanone (AZ228)

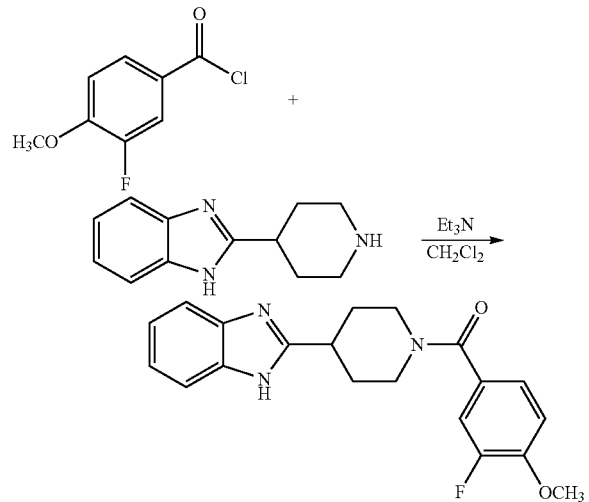

Into a round bottom flask equipped with a nitrogen inlet and a magnetic stir bar, 2-(piperidin-4-yl)-1H-benzo[d]imidazole (2.5 g, 12.42 mmol), Et$_3$N (1.8 mL, 12.56 mmol) and CH$_2$Cl$_2$ (50 mL) were added at 0° C. 3-fluoro-4-methoxybenzoyl chloride (2.34 g, 12.41 mmol) was slowly added to the reaction mixture. The reaction was warmed to room temperature and allowed to stir at room temperature for 10 minutes. The solid formed was filtered and then dried in vacuo. The solid was washed with copious amount of CH$_2$Cl$_2$ and then dried in vacuo to give 3.10 g (71%) of the pure and desired compound.

$^1$H NMR (400 MHz, DMSO-d6) δ 12.21 (s, 1H), 7.54 (d, J=8.7 Hz, 1H), 7.43 (d, J=6.9 Hz, 1H), 7.34-7.29 (m, 1H), 7.29-7.20 (m, 2H), 7.19-7.06 (m, 2H), 4.41 (bs, 1H), 3.90 (s, 3H+1H (hidden)), 3.19 (m, 3H), 2.08 (m, 2H), 1.82 (qd, J=11.9, 4.0 Hz, 2H). $^{13}$C NMR (101 MHz, DMSO-d6) δ 168.13, 157.64, 152.59, 150.15, 148.55 (d, J=10.3 Hz), 143.42, 134.69, 129.11 (d, J=5.8 Hz), 124.26 (d, J=3.6 Hz), 121.69 (d, J=72.5 Hz), 118.78, 115.41 (d, J=19.1 Hz), 114.02 (d, J=2.1 Hz), 111.31, 56.58, 36.11. LCMS: Expected: 354 (M+H)$^+$; Found: 354. HRMS:—Found: 354.16166 (M+H)$^+$; Theoretically=354.16123.

Synthesis of (3-fluoro-4-methoxyphenyl)(4-(1-((tetrahydro-2H-pyran-4-yl)methyl)-1H-benzo[d]imidazol-2-yl)piperidin-1-yl)methanone (AZ229)

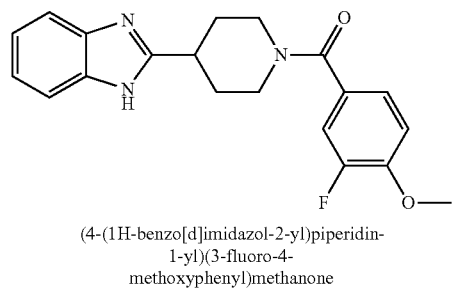

(4-(1H-benzo[d]imidazol-2-yl)piperidin-1-yl)(3-fluoro-4-methoxyphenyl)methanone

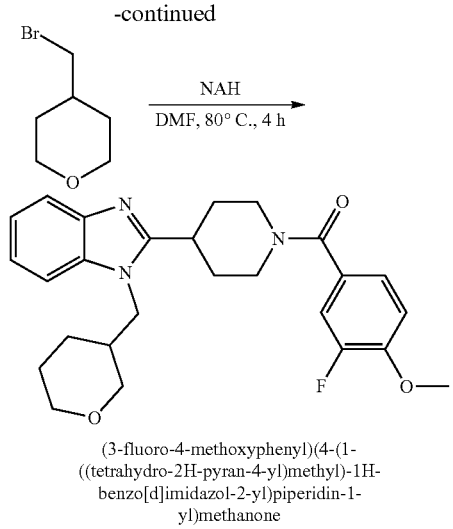

(3-fluoro-4-methoxyphenyl)(4-(1-((tetrahydro-2H-pyran-4-yl)methyl)-1H-benzo[d]imidazol-2-yl)piperidin-1-yl)methanone Into a round bottomed flask equipped with a nitrogen inlet and a magnetic stir bar, (4-(1H-benzo[d]imidazol-2-yl)piperidin-1-yl)(3-fluoro-4-methoxyphenyl)methanone (250 mg, 0.71 mmol), NaH (60% in oil, 62 mg, 1.55 mmol) and 2 mL DMF were added and stirred at room temperature for 2 hours. Solution of 4-(bromomethyl)tetrahydro-2H-pyran (190 mg, 1.06 mmol) in 0.2 mL of DMF was then slowly added to the above solution. The reaction mixture was then allowed to reflux for 4 hours. Water was then added to the reaction mixture and stirred for 15 minutes. The sticky solid formed was filtered and washed with water. The solid was purified using the combiflash purification system with 2-5% MeOH in CH$_2$Cl$_2$ to give 100 mg (31%) of white solid as the pure and desired compound.

$^1$H NMR (400 MHz, Chloroform-d) δ 7.78 (d, J=6.5 Hz, 1H), 7.42-7.33 (m, 1H), 7.33-7.21 (m, 4H), 7.00 (t, J=8.4 Hz, 1H), 5.32 (s, 2H), 4.08 (d, J=7.3 Hz, 2H), 4.01 (dd, J=12.3, 3.6 Hz, 2H), 3.94 (s, 3H), 3.34 (td, J=11.5, 2.9 Hz, 2H), 3.19-2.96 (m, 3H), 2.34-2.11 (m, 3H), 1.99 (d, J=13.6 Hz, 2H), 1.65-1.38 (m, 4H). $^{13}$C NMR (101 MHz, Chloroform-d) δ 169.12, 156.58, 149.06, 128.38, 123.80, 119.44, 115.56 (d, J=19.9 Hz), 112.99, 109.78, 67.34, 56.30, 53.45, 49.32, 36.04, 34.54, 31.29, 30.81. LCMS: Expected: 452 (M+H)$^+$; Found: 452.

HRMS:—Found: 452.23518 (M+H)$^+$; Theoretically=452.23440.

Synthesis of (3-fluoro-4-methoxyphenyl)(4-(1-(2-methoxyethyl)-1H-benzo[d]imidazol-2-yl)piperidin-1-yl)methanone (AZ230)

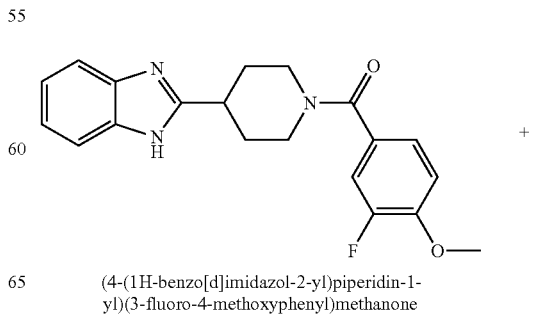

(4-(1H-benzo[d]imidazol-2-yl)piperidin-1-yl)(3-fluoro-4-methoxyphenyl)methanone

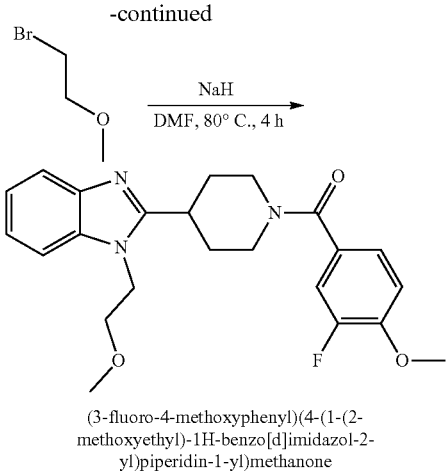

(3-fluoro-4-methoxyphenyl)(4-(1-(2-methoxyethyl)-1H-benzo[d]imidazol-2-yl)piperidin-1-yl)methanone

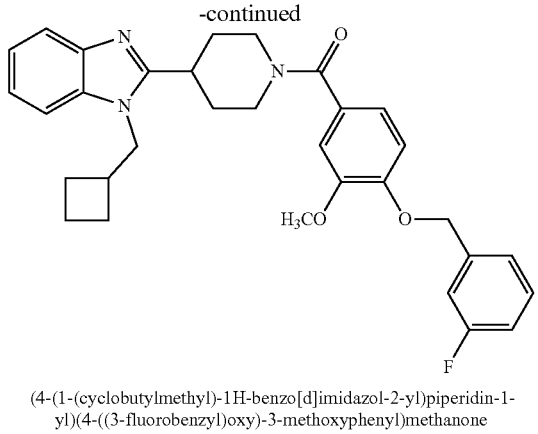

(4-(1-(cyclobutylmethyl)-1H-benzo[d]imidazol-2-yl)piperidin-1-yl)(4-((3-fluorobenzyl)oxy)-3-methoxyphenyl)methanone Into a round bottomed flask equipped with a nitrogen inlet and a magnetic stir bar, (4-(1H-benzo[d]imidazol-2-yl)piperidin-1-yl)(3-fluoro-4-methoxyphenyl)methanone (250 mg, 0.71 mmol), NaH (60% in oil, 62 mg, 1.55 mmol) and 2 mL DMF were added and stirred at room temperature for 2 hours. Solution of 1-bromo-2-methoxyethane (147 mg, 1.06 mmol) in 0.2 mL of DMF was then slowly added to the above solution. The reaction mixture was then allowed to reflux for 4 hours. Water was then added to the reaction mixture and stirred for 15 minutes. The sticky solid formed was filtered and washed with water. The solid was purified using the combiflash purification system with 2-5% MeOH in $CH_2Cl_2$ to give 60 mg (21%) of white solid as the pure and desired compound.

$^1$H NMR (400 MHz, Chloroform-d) δ 7.79 (dd, J=6.5, 2.6 Hz, 1H), 7.38-7.31 (m, 1H), 7.32-7.22 (m, 4H), 7.00 (t, J=8.4 Hz, 1H), 4.95-4.64 (m, 1H), 4.38 (t, J=5.2 Hz, 2H), 3.94 (s, 3H), 3.72 (t, J=5.2 Hz, 2H), 3.28 (s, 3H), 3.20-2.97 (m, 2H), 2.34-2.10 (m, 2H), 2.07 (d, J=0.6 Hz, 3H). $^{13}$C NMR (101 MHz, Chloroform-d) δ 169.11, 157.40, 153.10, 150.64, 148.93 (d, J=10.6 Hz), 134.41, 128.53 (d, J=5.8 Hz), 123.76 (d, J=3.6 Hz), 122.41 (d, J=16.4 Hz), 119.35, 115.55 (d, J=19.6 Hz), 112.96 (d, J=2.1 Hz), 109.33, 70.55, 60.41, 56.29, 43.80, 34.24, 31.22, 21.07, 14.21. LCMS: Expected: 412 (M+H)$^+$; Found: 412. HRMS:—Found: 412.20374 (M+H)$^+$; Theoretically=412.20310.

Synthesis of (4-(1-(cyclobutylmethyl)-1H-benzo[d]imidazol-2-yl)piperidin-1-yl)(4-((3-fluorobenzyl)oxy)-3-methoxyphenyl)methanone (AZ233)

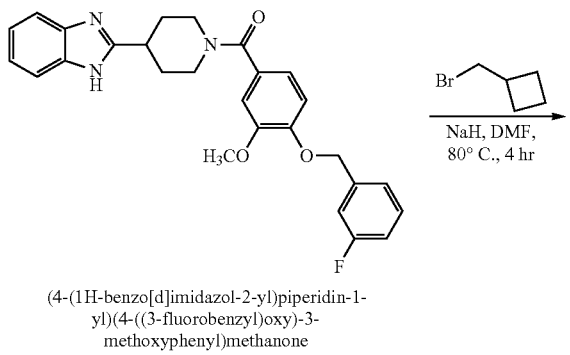

(4-(1H-benzo[d]imidazol-2-yl)piperidin-1-yl)(4-((3-fluorobenzyl)oxy)-3-methoxyphenyl)methanone Into a round bottomed flask equipped with a nitrogen inlet and a magnetic stir bar, tert-butyl (4-(1H-benzo[d]imidazol-2-yl)piperidin-1-yl)(4-((3-fluorobenzyl)oxy)-3-methoxyphenyl)methanone (250 mg, 0.54 mmol), NaH (60% in oil, 45 mg, 1.13 mmol) and 1.5 mL DMF were added at 0° C. and then stirred at room temperature for 2 hours. Solution of (bromomethyl)cyclobutane (112 mg, 0.75 mmol) was then slowly added to the above solution. The reaction mixture was then allowed to stir at 80° C. for 5 hours. water was then added to the reaction mixture and stirred for 15 minutes. Water was added to the reaction mixture and the aqueous was extracted with EtOAc (×3). The combined organic layer was dried over anhydrous $Na_2SO_4$, filtered, rotary evaporated and then dried in vacuo. The crude solid was purified using the combiflash purification system with 2-3% MeOH in $CH_2Cl_2$ to give 92 mg (32%) of white solid as the pure and desired compound.

$^1$H NMR (400 MHz, Chloroform-d) δ 7.82-7.72 (m, 1H), 7.43-7.32 (m, 2H), 7.28 (dd, J=5.1, 3.9 Hz, 2H), 7.25-7.14 (m, 2H), 7.08 (d, J=1.9 Hz, 1H), 7.06-6.96 (m, 2H), 6.87 (d, J=8.2 Hz, 1H), 5.19 (s, 2H), 4.95-4.27 (m, 1H), 4.20 (d, J=7.0 Hz, 2H), 3.96 (s, 3H), 3.22-2.99 (m, 3H), 2.88-2.73 (m, 1H), 2.37-2.12 (m, 2H), 2.13-1.75 (m, 9H). $^{13}$C NMR (101 MHz, Chloroform-d) δ 170.29, 164.24, 162.49, 161.80, 149.66, 149.03, 139.36 (d, J=7.3 Hz), 130.16 (d, J=8.2 Hz), 129.12, 122.58 (d, J=3.0 Hz), 119.79, 119.15, 114.85 (d, J=21.1 Hz), 114.08 (d, J=22.1 Hz), 113.24, 111.23, 109.81, 70.23, 70.21, 56.17, 48.46, 36.46, 36.19, 31.32, 26.57, 18.26. LCMS: Expected: 528 (M+H)$^+$; Found: 528. HRMS:—Found: 528.26735 (M+H)$^+$; Theoretically=528.6570.

(4-((3-fluorobenzyl)oxy)-3-methoxyphenyl)(4-(1-((tetrahydro-2H-pyran-4-yl)methyl)-1H-benzo[d]imidazol-2-yl)piperidin-1-yl)methanone (AZ231)

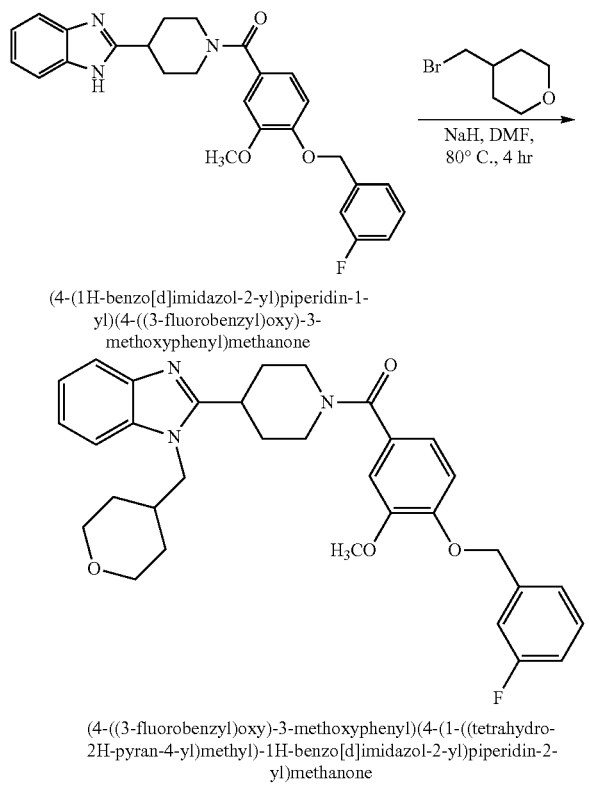

Into a round bottomed flask equipped with a nitrogen inlet and a magnetic stir bar, tert-butyl (4-(1H-benzo[d]imidazol-2-yl)piperidin-1-yl)(4-((3-fluorobenzyl)oxy)-3-methoxyphenyl)methanone (250 mg, 0.54 mmol), NaH (60% in oil, 45 mg, 1.13 mmol) and 1.5 mL DMF were added at 0° C. and then stirred at room temperature for 2 hours. Solution of 4-(bromomethyl)tetrahydro-2H-pyran (134 mg, 0.75 mmol) was then slowly added to the above solution. The reaction mixture was then allowed to stir at 80° C. for 5 hours. water was then added to the reaction mixture and stirred for 15 minutes. Water was added to the reaction mixture and the aqueous was extracted with EtOAc (×3). The combined organic layer was dried over anhydrous $Na_2SO_4$, filtered, rotary evaporated and then dried in vacuo. The crude solid was purified using the combiflash purification system with 2-3% MeOH in $CH_2Cl_2$ to give 240 mg (79%) of white solid as the pure and desired compound.

$^1$H NMR (400 MHz, Chloroform-d) δ 7.81-7.75 (m, 1H), 7.40-7.29 (m, 4H), 7.25-7.17 (m, 2H), 7.08 (d, J=1.9 Hz, 1H), 7.06-6.97 (m, 2H), 6.88 (d, J=8.2 Hz, 1H), 5.19 (s, 2H), 4.83-4.24 (bs, 1H), 4.08 (d, J=7.4 Hz, 2H), 4.04-3.97 (m, 2H), 3.96 (s, 3H), 3.34 (td, J=11.5, 2.9 Hz, 2H), 3.20-2.99 (m, 3H), 2.34-2.09 (m, 3H), 2.08-1.90 (m, 2H), 1.65 (bs, 1H), 1.60-1.36 (m, 4H). $^1$H NMR (400 MHz, Chloroform-d) δ 7.81-7.75 (m, 1H), 7.40-7.29 (m, 4H), 7.25-7.17 (m, 2H), 7.08 (d, J=1.9 Hz, 1H), 7.06-6.97 (m, 2H), 6.88 (d, J=8.2 Hz, 1H), 5.19 (s, 2H), 4.83-4.24 (bs, 1H), 4.08 (d, J=7.4 Hz, 2H), 4.04-3.97 (m, 2H), 3.96 (s, 3H), 3.34 (td, J=11.5, 2.9 Hz, 2H), 3.20-2.99 (m, 3H), 2.34-2.09 (m, 3H), 2.08-1.90 (m, 2H), 1.65 (bs, 1H), 1.60-1.36 (m, 4H). LCMS: Expected: 558 (M+H)$^+$; Found: 558. HRMS:—Found: 558.27810 (M+H)$^+$; Theoretically=558.27626.

(4-((3-fluorobenzyl)oxy)-3-methoxyphenyl)(4-(1-isobutyl-1H-benzo[d]imidazol-2-yl)piperidin-1-yl)methanone (AZ232)

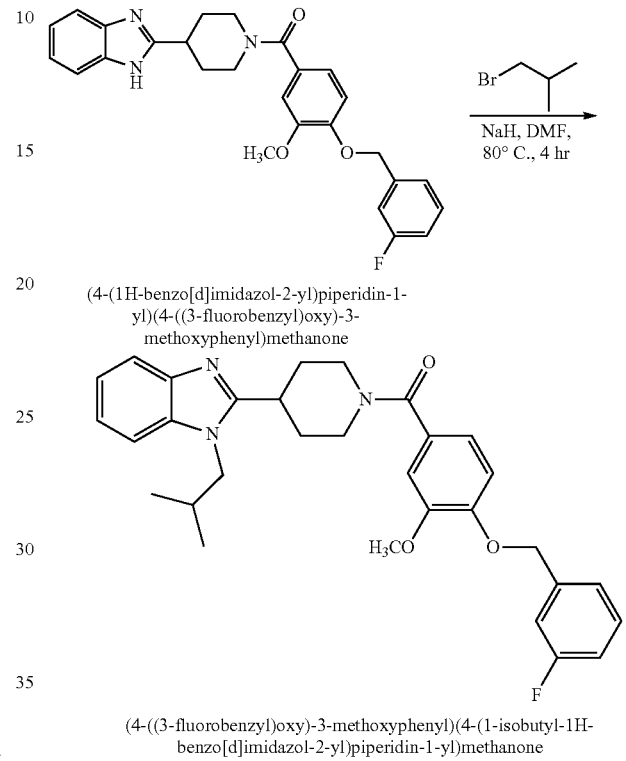

Into a round bottomed flask equipped with a nitrogen inlet and a magnetic stir bar, tert-butyl (4-(1H-benzo[d]imidazol-2-yl)piperidin-1-yl)(4-((3-fluorobenzyl)oxy)-3-methoxyphenyl)methanone (250 mg, 0.54 mmol), NaH (60% in oil, 45 mg, 1.13 mmol) and 1.5 mL DMF were added at 0° C. and then stirred at room temperature for 2 hours. Solution of 1-bromo-2-methylpropane (103 mg, 0.75 mmol) was then slowly added to the above solution. The reaction mixture was then allowed to stir at 80° C. for 5 hours. water was then added to the reaction mixture and stirred for 15 minutes. Water was added to the reaction mixture and the aqueous was extracted with EtOAc (×3). The combined organic layer was dried over anhydrous $Na_2SO_4$, filtered, rotary evaporated and then dried in vacuo. The crude solid was purified using the combiflash purification system with 2-3% MeOH in $CH_2Cl_2$ to give 141 mg (50%) of white solid as the pure and desired compound.

$^1$H NMR (400 MHz, Chloroform-d) δ 7.83-7.73 (m, 1H), 7.41-7.32 (m, 2H), 7.32-7.24 (m, 2H), 7.25-7.16 (m, 2H), 7.09 (d, J=1.8 Hz, 1H), 7.05-6.99 (m, 2H), 6.88 (d, J=8.2 Hz, 1H), 5.19 (s, 2H), 4.93-4.12 (m, 1H), 3.99 (d, J=7.6 Hz, 2H), 3.96 (s, 3H), 3.22-2.98 (m, 3H), 2.36-2.10 (m, 3H), 1.99 (d, J=13.4 Hz, 2H), 1.64 (bs, 1H), 1.01 (d, J=6.7 Hz, 6H).

$^{13}$C NMR (101 MHz, Chloroform-d) δ 170.33, 164.25, 161.80, 149.67, 149.04, 139.36 (d, J=7.4 Hz), 130.16 (d, J=8.1 Hz), 129.09, 122.58 (d, J=3.0 Hz), 119.82, 114.86 (d, J=21.2 Hz), 114.25, 114.09 (d, J=22.2 Hz), 113.26, 111.24, 110.04, 70.22 (d, J=2.0 Hz), 56.20, 53.42, 51.08, 34.69, 31.23, 29.36, 20.25. LCMS: Expected: 516 (M+H)⁺; Found: 516. HRMS:—Found: 516.26730 (M+H)⁺; Theoretically=516.26570.

Example II

Recognizing that loss of Nav1.7 likely leads to analgesia through upregulation of endogenous opioids (see, e.g., Minett M S, et al. (2012) Nature communications 3: 791), experiments were conducted to determine if the piperidinyl-benzoimidazole compounds described herein are capable of engaging the opioid system. Notably, it was shown that AZ194, but not AZ208

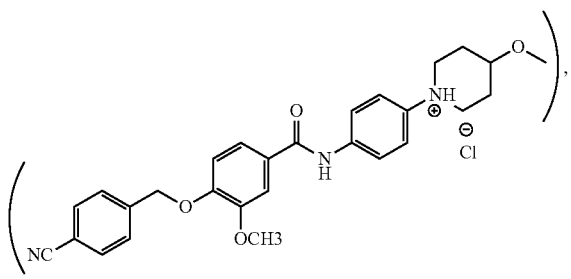 [SMILES: COc1cc(C(=O)Nc2ccc([NH+]3CCC(OC)CC3)cc2)ccc1OCc1ccc(C#N)cc1 ; [Cl-]]

upregulates mRNA levels for proenkephalin (see, FIG. 1).

Figure 2:
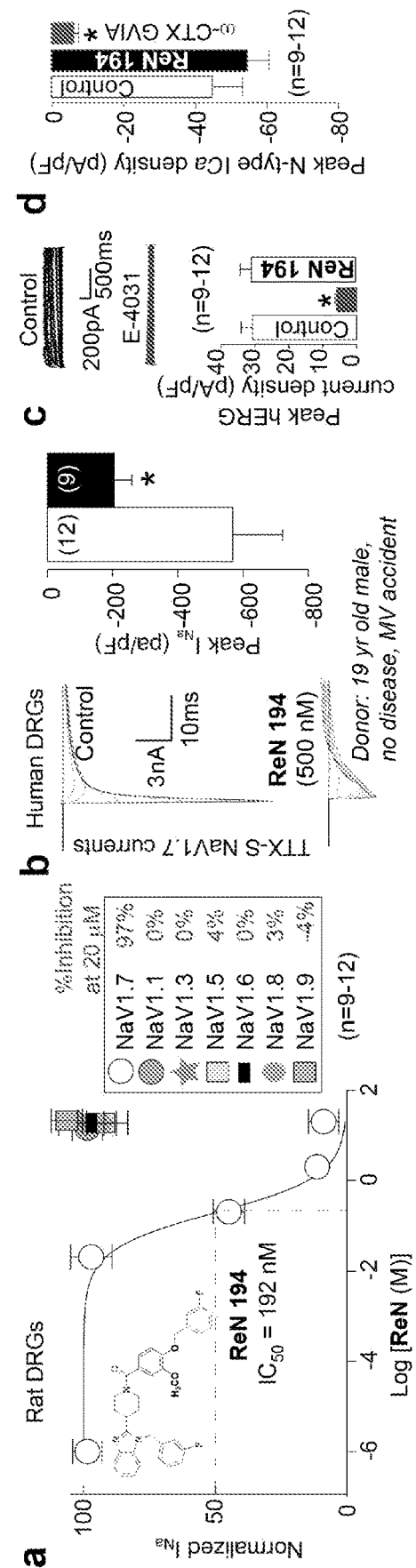
FIG. 2: shows that ReN 194 inhibits NaV1.7 with nanomolar potency without affecting other NaV1.x, hERG, and CaV2.2 channels. (a) concentration-response curve of inhibition of NaV1.7 from rat DRGs by ReN 194 (structure shown). At the highest concentration of 20 μM, the other NaV1.x channels tested (see box for legend) were not affected. (b) ReN 194 (500 nM) reduced TTX-S NaV1.7 currents (traces) in human DRGs by ~66%. (c) ReN 194 (20 μM) did not affect hERG $K^+$ currents (traces) in hEK293 cells, which were inhibited by the well-known hERG blocker E-4031 (1 μM). (d) ReN 194 (20 μM) did not affect peak CaV2.2 currents in DRGs, which were inhibited by the well-known CaV2.2-selective blocker co-conotoxin GVIA (1 μM).

AZ/ReNs 155, 170, 194, 205, and 206 were tested in whole-cell patch clamp electrophysiology in rat DRG neurons with ReN 194/aka AZ194 being also tested in human DRGs (FIG. 2). ReN 194 was tested extensively against the other NaV channels as well as hERG and CaV2.2 and showed no inhibition of these channels.

Figure 3:
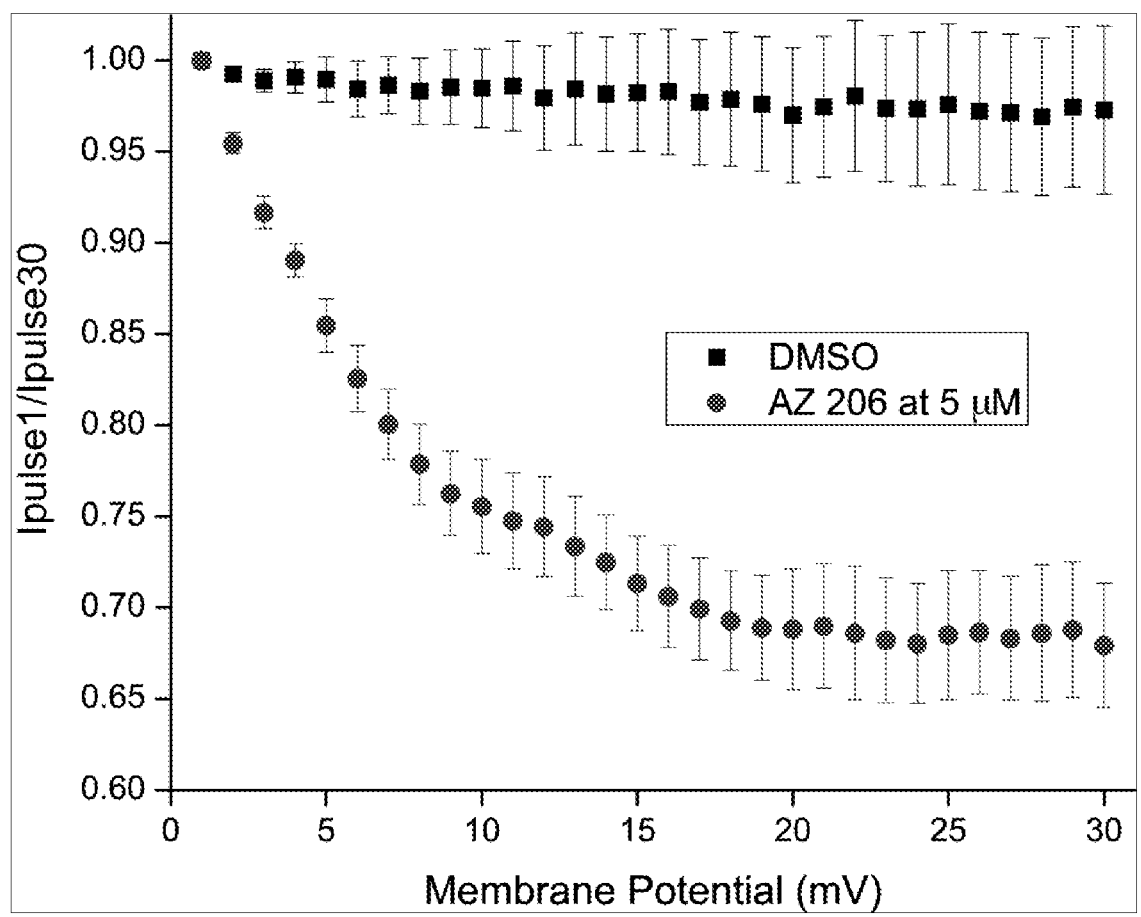
FIG. 3: Summary of average frequency (use)-dependent decrease in current amplitude over time (±SEM) produced by ReN 206 5 μM (circles). Control DRG neurons were treated with 0.03% DMSO (squares). Thirty, identical test pulses were applied at 10 Hz. The difference in available current was calculated by dividing the peak current at any given pulse (pulseN) by the peak current in response to the initial pulse (pulsei). Data are from 5-6 cells per condition.

FIG. 3 shows that ReN 206 appears to be a use-dependent inhibitor of NaV channels. The ability to block Na⁺ currents in an activity- or use-dependent manner is a useful property for drugs since it allows for preferential decreases in sodium channel availability during high—(i.e., hyperexcitable 'pain' neurons) but not low-frequency firing.

Figure 4:
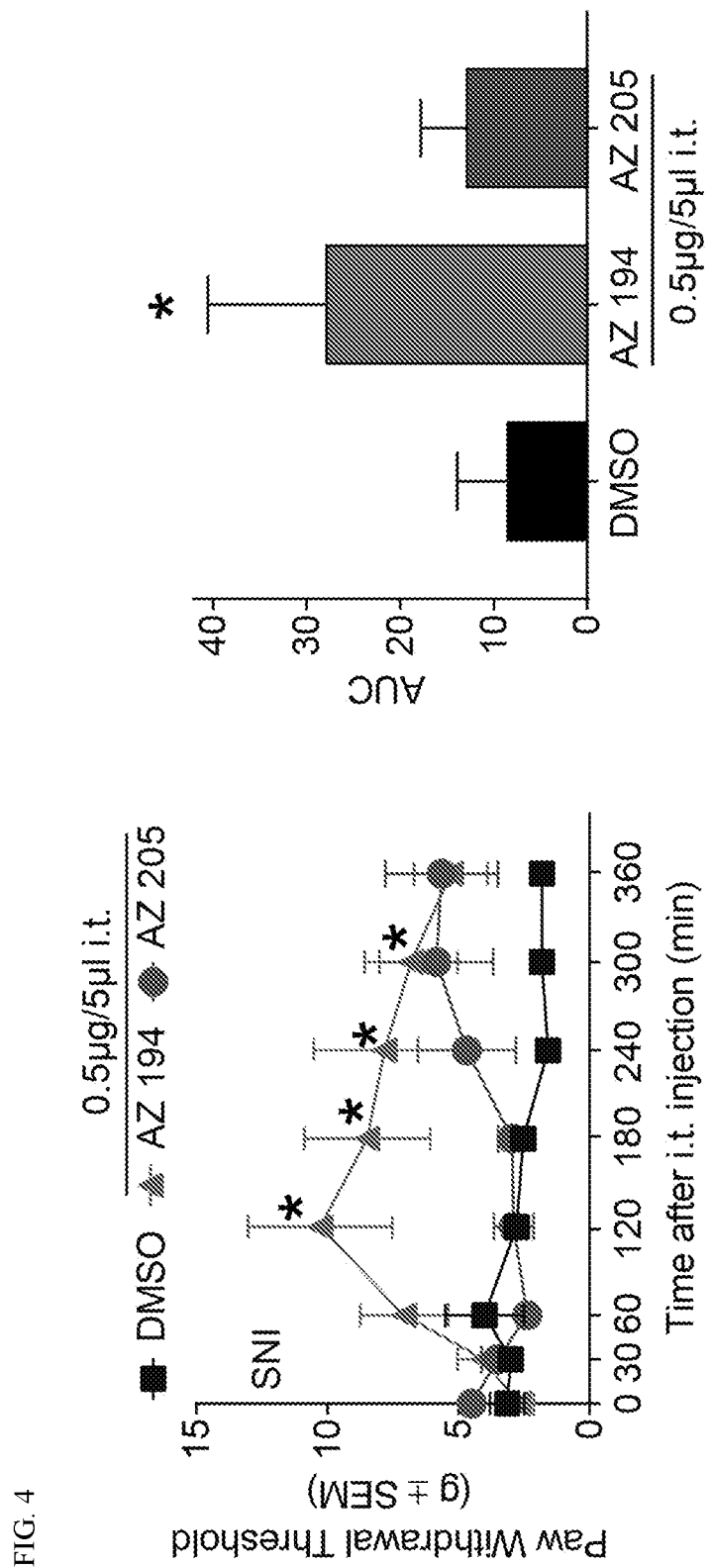
FIG. 4: AZ194 reduces spared nerve injury (SNI) induced nociceptive behaviors. Rats received spared nerve injury (SNI) on the left hind paw. Left panel: Paw withdrawal thresholds (PWTs) were significantly decreased 24 hours after incision. Intrathecal injection (i.t.) of AZ194 significantly reversed PWTs at the indicated times (n=5-8; *p<0.05; two-way ANOVA with a Bonferroni post hoc test) where time was treated as "within subjects" factor, whereas treatment was treated as "between" subjects factor. Right panel: Area under the curve (AUC), using the trapezoid method, for PWT (summary for data shown in the time course on the left) are shown. *p<0.05, one-way analysis of variance with Dunnett's post hoc analysis. Error bars represent mean±s.e.m. Injection of AZ194, but not AZ205, (0.5 μg/5 μl) significantly reversed PWTs (n=5-8; *p<0.05; 2-way ANOVA with a Bonferroni post hoc test).
Figure 5:
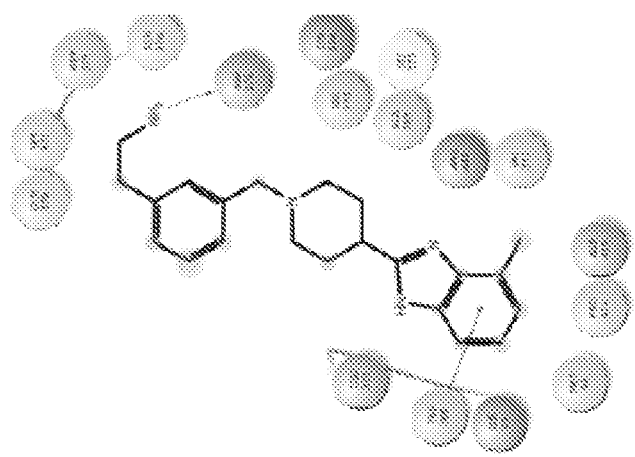
Figure 7:
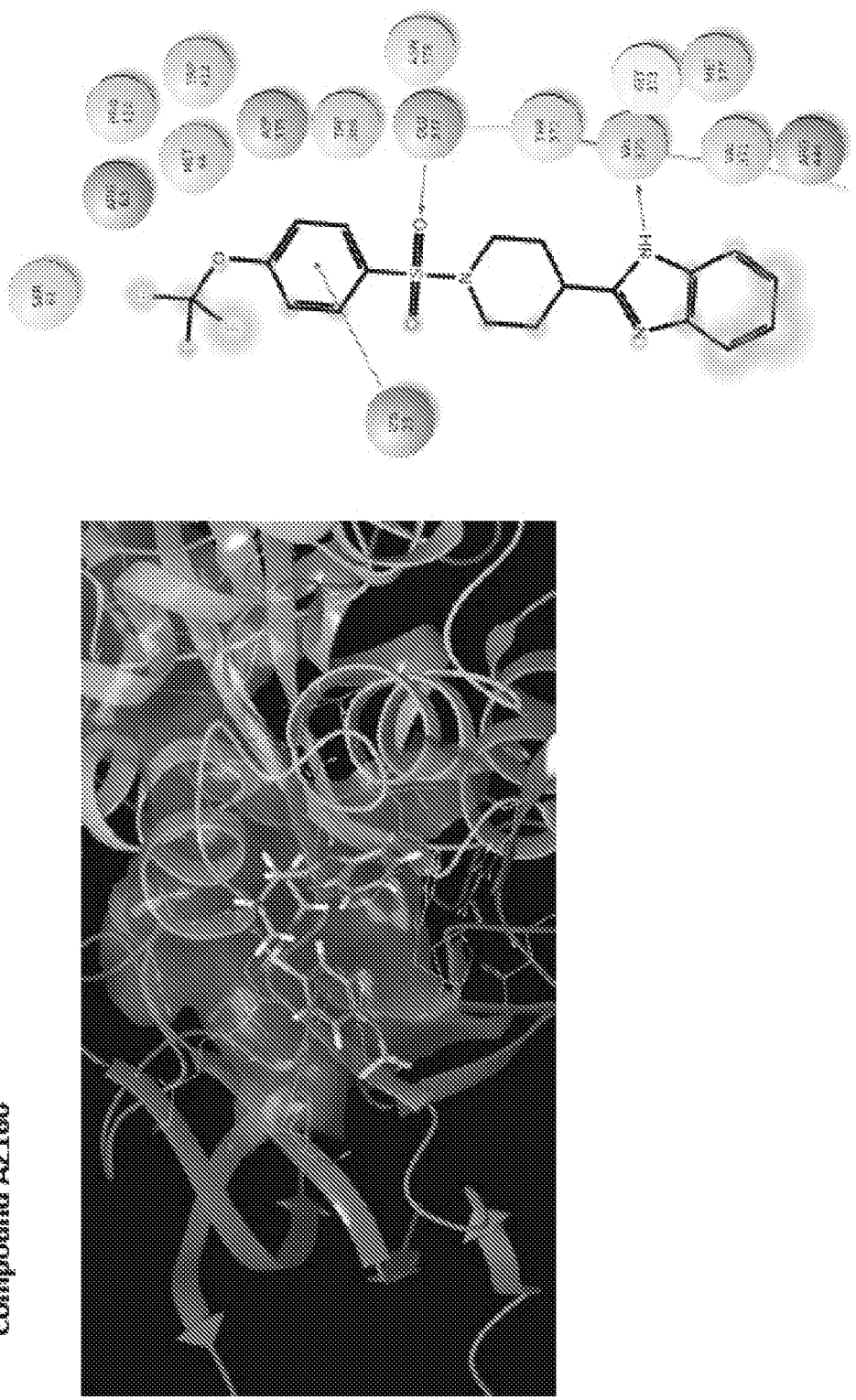
Figure 8:
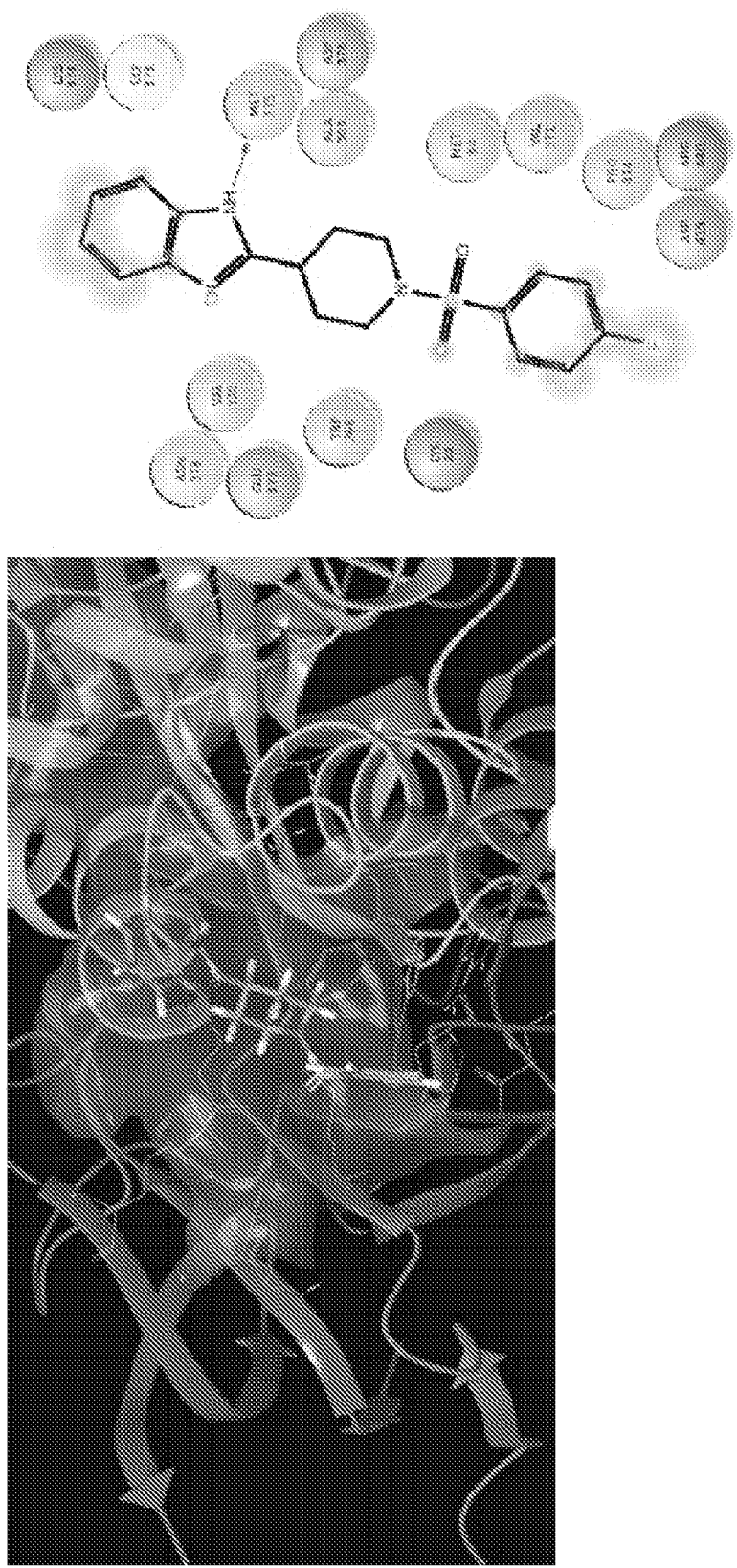
Figure 10:
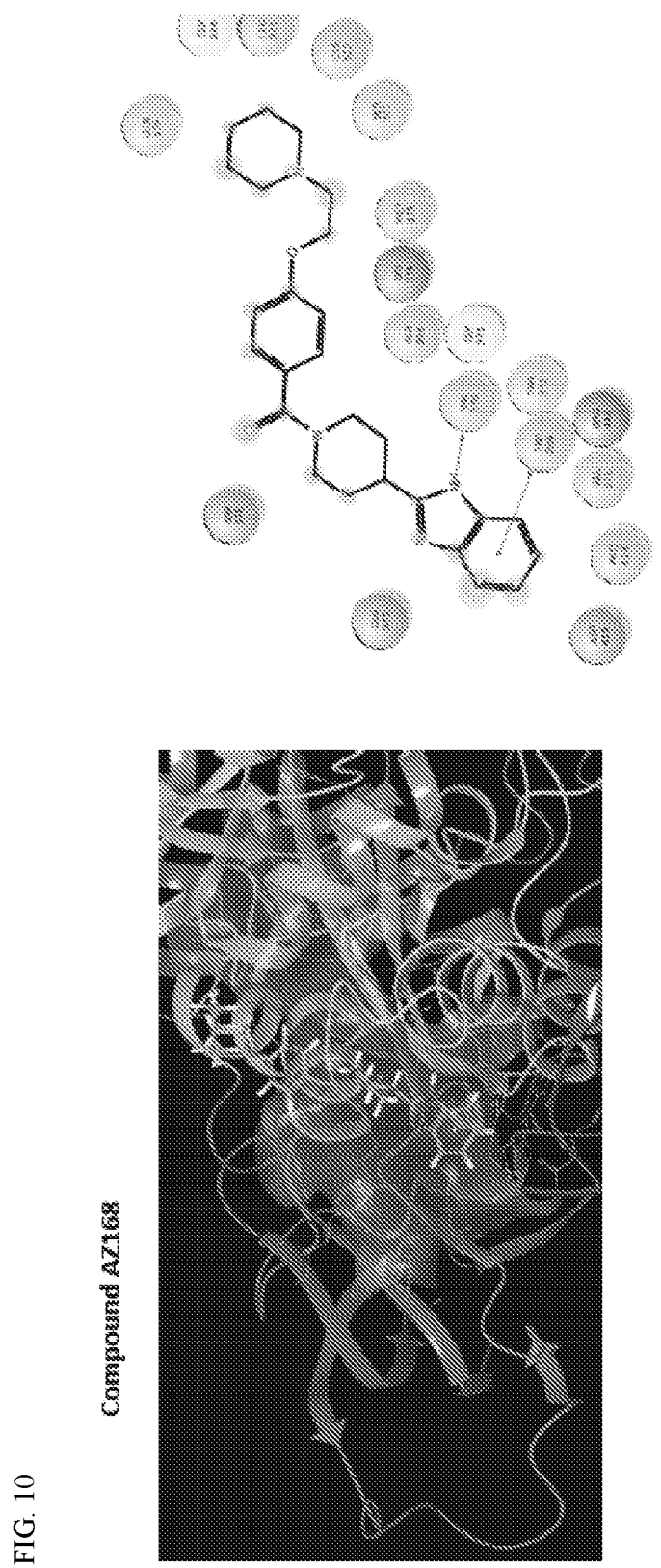
Figure 11:
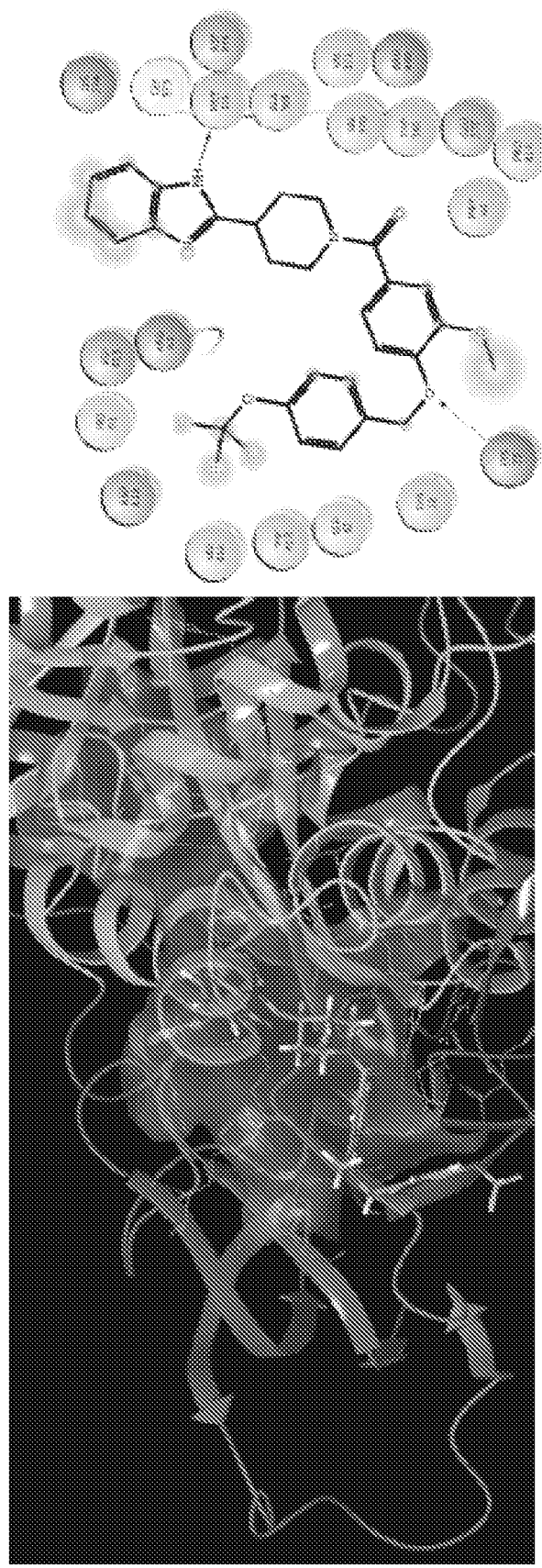
Figure 21:
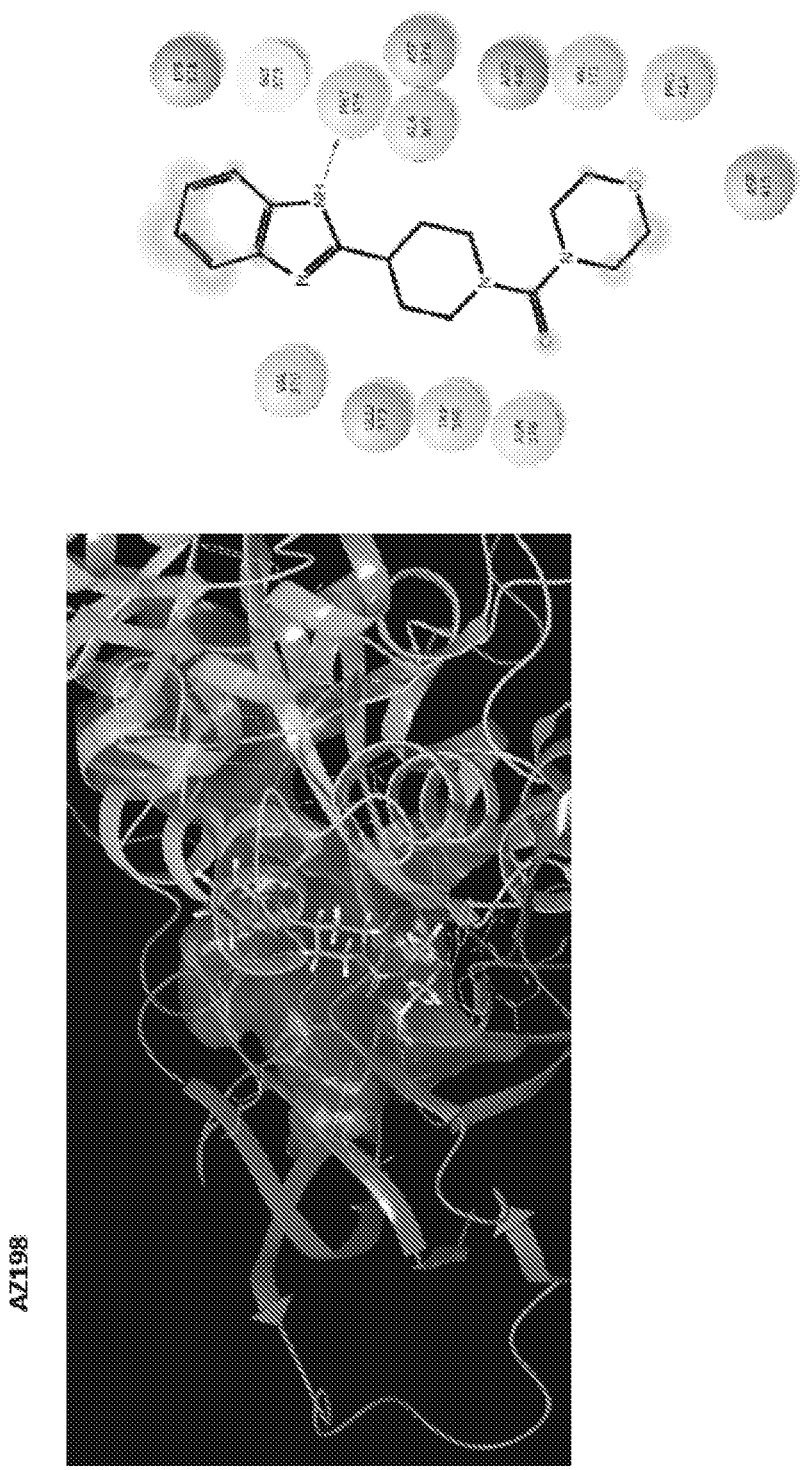
Figure 22:
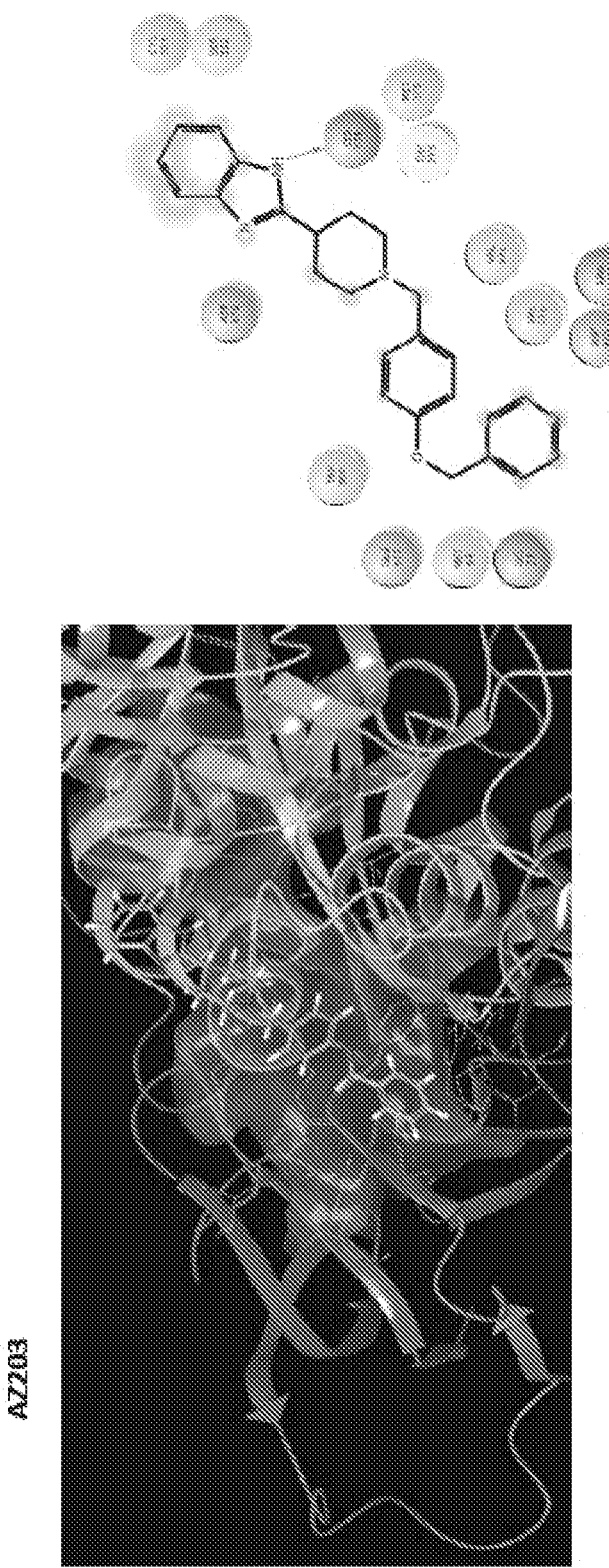
Figure 23:
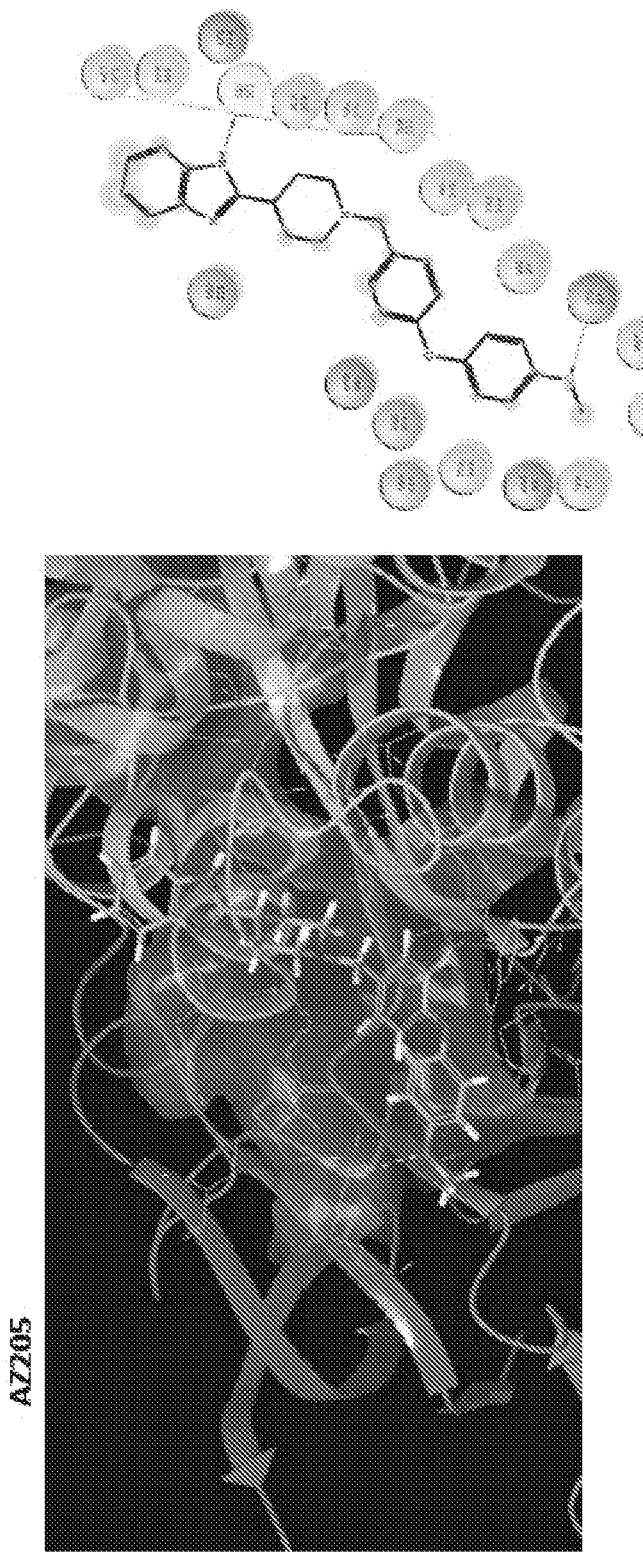

AZ194 was evaluated for efficacy in the spared nerve injury (SNI) model (see, e.g., Decosterd I, & Woolf C J (2000) Pain 87: 149-158) of neuropathic pain. SNI significantly reduced paw withdrawal thresholds (PWTs) 7-9 days post injury (FIG. 4A). Spinal administration of AZ194 significantly increased PWTs over post-baseline SNI-values at 2-4 hr post-injection (FIG. 4A). In contrast, vehicle-treatment did not increase PWTs compared to post-baseline SNI values (FIG. 4A). Such experiments also determined the AUC to assess effects over the full experimental duration. AUC analysis confirmed the reversal of mechanical allodynia compared to vehicle-treated injured animals (FIG. 4B).

Spared Nerve Injury (SNI).

Under isoflurane anesthesia (5% induction, 2.5% maintenance in 2 L/min air), skin on the lateral surface of the left hind thigh was incised. The biceps femoris muscle was bluntly dissected to expose the three terminal branches of the sciatic nerve (see, e.g., Decosterd I, & Woolf C J (2000) Pain 87: 149-158). Briefly, the common peroneal and tibial branches were tightly ligated with 4-0 silk and axotomized 2.0 mm distal to the ligation. Sham animals underwent the same operation; however the nerves were exposed and not ligated. Closure of the incision was made in two layers. The muscle was sutured once with 5-0 absorbable suture and skin was auto-clipped. Animals were allowed to recover for 5-7 days before any testing.

Example III

This example describes the identification and characterization of a binding pocket within CRMP2 wherein the E2 ubiquitin-conjugating enzyme Ubc9 engages (e.g., binds, docks) with CRMP2. In addition, this example demonstrates the ability of specific small molecule compounds to bind with CRMP2 through the identified CRMP2 binding pocket and not with Ubc9.

Molecular docking studies were performed using Schrodinger-Glide molecular modeling software. Briefly, x-ray structure of CRMP2 (5UQC) was used for modeling studies. Docking grid (10 Å×10 Å×10 Å) was created using Glide program around LYS374 residue. Docking studies were performed using Glide-XP docking program and poses were analyzed using glide poses viewer.

FIGS. 5-24 provides modeling images separately depicting compounds described herein (AZ145, AZ159, AZ160, AZ161, AZ162, AZ168, AZ170, AZ172, AZ173, AZ177, AZ178, AZ190, AZ192, AZ193, AZ194, AZ195, AZ198, AZ203, AZ205, and AZ206) within the CRMP2 binding pocket and the positioning of relevant amino acids within the CRMP2 binding pocket around the respective compound.

Such results indicate that a compound with a molecular weight in the range 400 to 750 having the following two characteristics would have structural characteristics consistent with having the ability to dock (e.g., bind, engage, etc.) within the identified CRMP2 binding pocket:

1) one or more of the following abilities:
   a) the ability to form a hydrogen bonding interaction in which the compound accepts a hydrogen bond from the backbone NH— group of Glu377;
   b) the ability to form a hydrogen bonding interaction in which the compound accepts a hydrogen bond from the sidechain —NH2 group of Lys23;
   c) the ability to form a hydrogen bonding interaction in which the compound donates a hydrogen bond to the backbone CO— group of Gly373;
   d) the ability to form a hydrogen bonding interaction in which the compound donates a hydrogen bond to the sidechain —COOH group of Glu377;
   e) the ability to form a hydrogen bonding interaction in which the compound accepts a hydrogen bond from the sidechain guanidine group of Arg440;
   f) the ability to form a hydrogen bonding interaction in which the compound donates a hydrogen bond to the sidechain COOH— group of Asp376;
   g) the ability to form electrostatic interaction with the sidechain —NH2 group of Lys23; and
   h) the ability to form electrostatic interaction with the sidechain —COOH group of Asp376; and 2) the ability to form a Van der Waals interaction with a lipophilic binding region of a binding pocket such that one or more heavy atoms of the compound lie within a 6 Å range of any of the heavy atoms of the following CRMP2 residues which define the identified binding pocket: Lys23, Val25, Ser30, Tyr32, Met64, Ser319, Ser322, Trp366, Val370, Val371, Gly373, Lys374, Met375, Asp376, Glu377, Gln379, Pro414, Asp415, Ser416, Val417 and Arg440.

As shown in such FIGS. 5-24, the following amino acids within CRMP2 are associated with the CRMP2 binding pocket: Lys23, Val25, Ser30, Tyr32, Met64, Ser319, Ser322, Trp366, Val370, Val371, Gly373, Lys374, Met375, Asp376, Glu377, Glu377, Gln379, Pro414, Asp415, Ser416, Val417, and Arg440.

Figure 25:
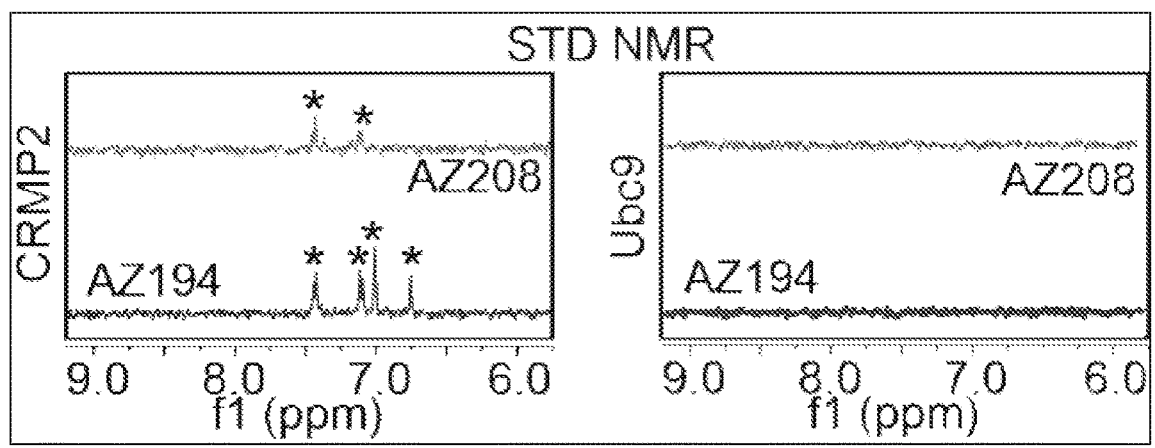
FIG. 25 shows that the AZ194 binds with CRMP2 but not Ubc9.

FIG. 25 shows that the AZ194 binds with CRMP2 but not Ubc9. 1D $^1$H STD NMR showing on-resonance spectrum for CRMP2 with probe AZ194. Asterisks correspond to protons. No binding was observed to Ubc9. NMR was performed on an AVANCE III 400 Mhz specrometer equipped with a Bruker PABBO 400S1 probe and SampleJet carousel that can hold up to 96 NMR tubes. The on-resonance excitation was set at 0.81 ppm (to irradiate protein methyl groups) and off-resonance set to 30 ppm. A 15 ms spin-lock was used to suppress the protein signal, followed by the double PFG spin echo to remove residual water signal. Spectra processing and analysis were performed with Topspin3.1 and MestReNova 7.1.

Example IV

This example demonstrates that targeting CRMP2 SUMOylation decreases pre-synapticNav1.7 localization.

Figure 26:
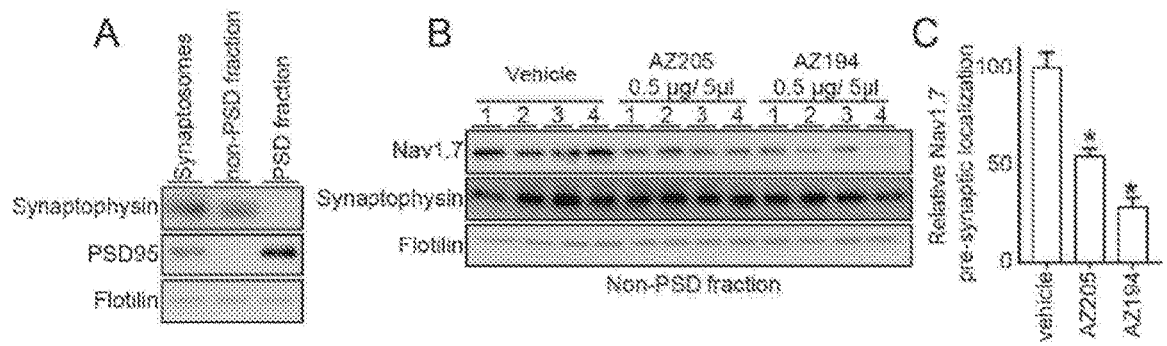
FIG. 26: Targeting CRMP2 SUMOylation decreases pre-synapticNav1.7 localization. (A) Immunoblots showing the integrity of the synaptic fractionation from lombar dorsal horn of the spinal cord. The non-PSD fraction was enriched in the pre-synaptic marker Synaptophysin and the PSD fraction was enriched in the post-synaptic marker PSD95. Flotilin is used as a loading control. (B) Immunoblots showing the pre-synaptic Nav1.7 levels in the lombar dorsal horn of the spinal cord, 2 hours after in trathecal administration of the indicated compounds. Flotilin is used as a loading control. (C) Bar graph showing decreased Nav1.7 localization at the pre-synaptic sites in the lombar dorsal horn of the spinal cord, 2 hours after intrathecal administration of the indicated compounds. Nav1.7 levels were normalized to the loading control Flotilin and to the pre-synaptic marker Synaptophysin. Mean±s.e.m.,*$p<0.05$, non-parametric One-Way ANOVA.

FIG. 26A presents immunoblots showing the integrity of the synaptic fractionation from lombar dorsal horn of the spinal cord. The non-PSD fraction was enriched in the pre-synaptic marker Synaptophysin and the PSD fraction was enriched in the post-synaptic marker PSD95. Flotilin is used as a loading control.

FIG. 26B presents immunoblots showing the pre-synaptic Nav1.7 levels in the lombar dorsal horn of the spinal cord, 2 hours after in trathecal administration of the indicated compounds. Flotilin is used as a loading control.

FIG. 26C presents a bar graph showing decreased Nav1.7 localization at the pre-synaptic sites in the lombar dorsal horn of the spinal cord, 2 hours after intrathecal administration of the indicated compounds. Nav1.7 levels were normalized to the loading control Flotilin and to the pre-synaptic marker Synaptophysin. Mean±s.e.m.,*p<0.05, non-parametric One-Way ANOVA.

Example V

Figure 27:
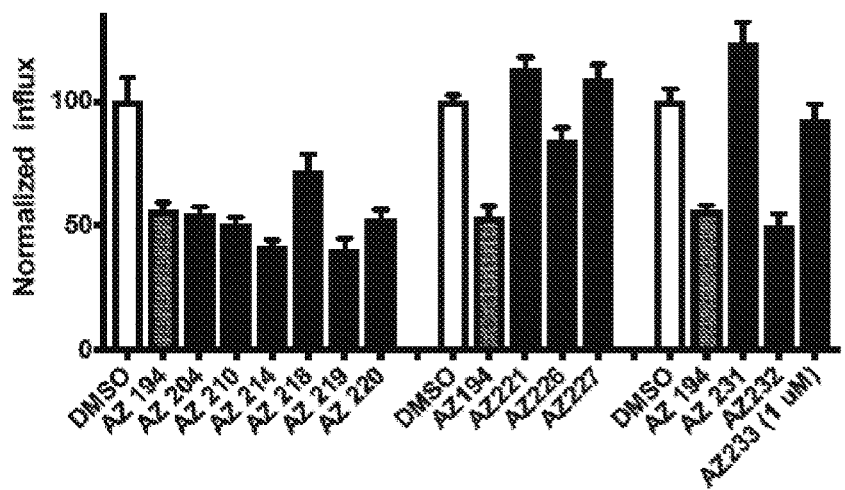
FIG. 27: Assessing inhibition of sodium in flux by AZ compounds. Primary rat sensory neurons were loaded with Fura2-AM and triggered to open Na+ channels with 30 µM veratradine in the absence (Control, 0.01% DMSO) or presence of 5 µM (or 1 µM for AZ233) of the indicated compounds. Bar graphs represent normalized fluorescence means±s.e.m. from at least 391 cells per condition from 4 separate rats. The prototypical CRMP2 SUMOylation inhibitor (AZ194) was tested in each experiment.
Figure 28:
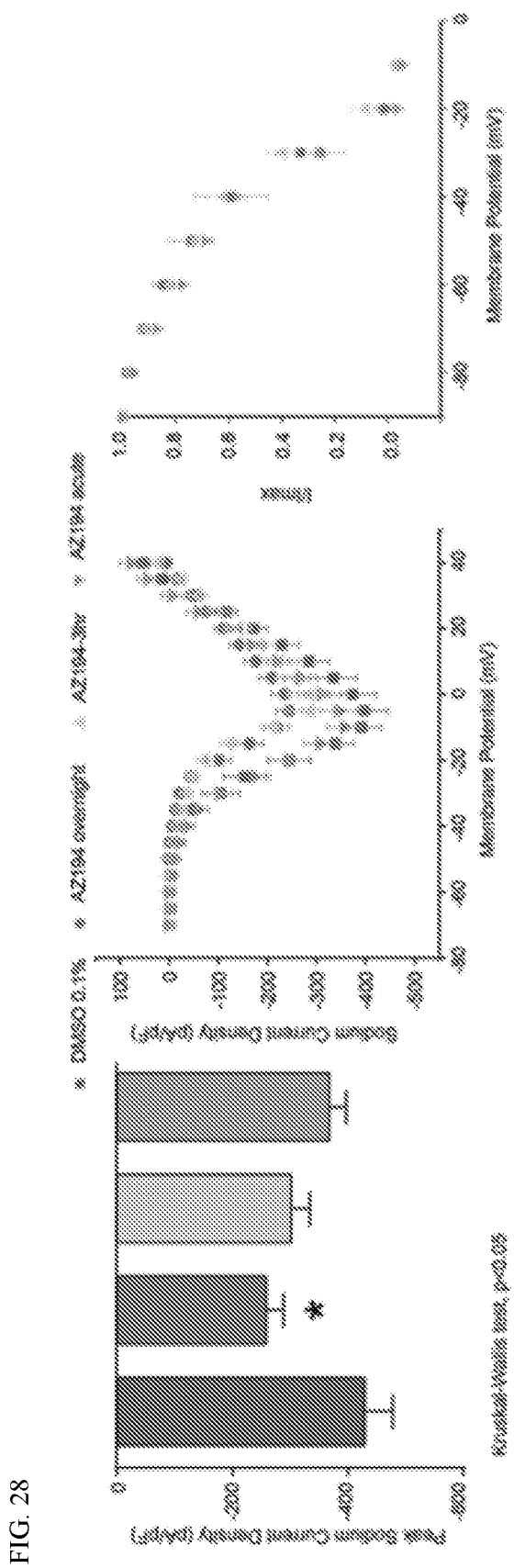
FIG. 28: AZ194 does not directly block NaV1.7 channels. Primary rat sensory neurons were incubated for the indicated times with DMSO 0.1% or 5 mM AZ194. Left: Bar graphs represent normalized peak sodium current density±s.e.m. from at least 14 cells per condition from 3 separate rats.*$p<0.05$, Kruskal-Wallis test. Middle: current voltage relationship of sodium currents from rat sensory neurons incubated for the indicated times with DMSO 0.1% or 5 mM AZ194. Right: biophysical properties of inactivation were not altered by AZ194 at any of the time points versus control.

This example describes the assessment of inhibition of sodium in flux by AZ compounds (FIG. 27). Primary rat sensory neurons were loaded with Fura2-AM and triggered to open Na+ channels with 30 µM veratradine in the absence (Control, 0.01% DMSO) or presence of 5 µM (or 1 µM for AZ233) of the indicated compounds. Bar graphs represent normalized fluorescence means±s.e.m. from at least 391 cells per condition from 4 separate rats. The prototypical CRMP2 SUMOylation inhibitor (AZ194) was tested in each experiment.

Example VI

This example demonstrates that AZ194 does not directly block NaV1.7 channels. Primary rat sensory neurons were incubated for the indicated times with DMSO 0.1% or 5 mM AZ194. FIG. 27 Left side shows Bar graphs represent normalized peak sodium current density±s.e.m. from at least 14 cells per condition from 3 separate rats.*p<0.05, Kruskal-Wallis test. FIG. 27 Middle shows current voltage relationship of sodium currents from rat sensory neurons incubated for the indicated times with DMSO 0.1% or 5 mM AZ194. FIG. 27 Right side shows biophysical properties of inactivation were not altered by AZ194 at any of the time points versus control.

Having now fully described the invention, it will be understood by those of skill in the art that the same can be performed within a wide and equivalent range of conditions, formulations, and other parameters without affecting the scope of the invention or any embodiment thereof. All patents, patent applications and publications cited herein are fully incorporated by reference herein in their entirety.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. A compound having Formula I:

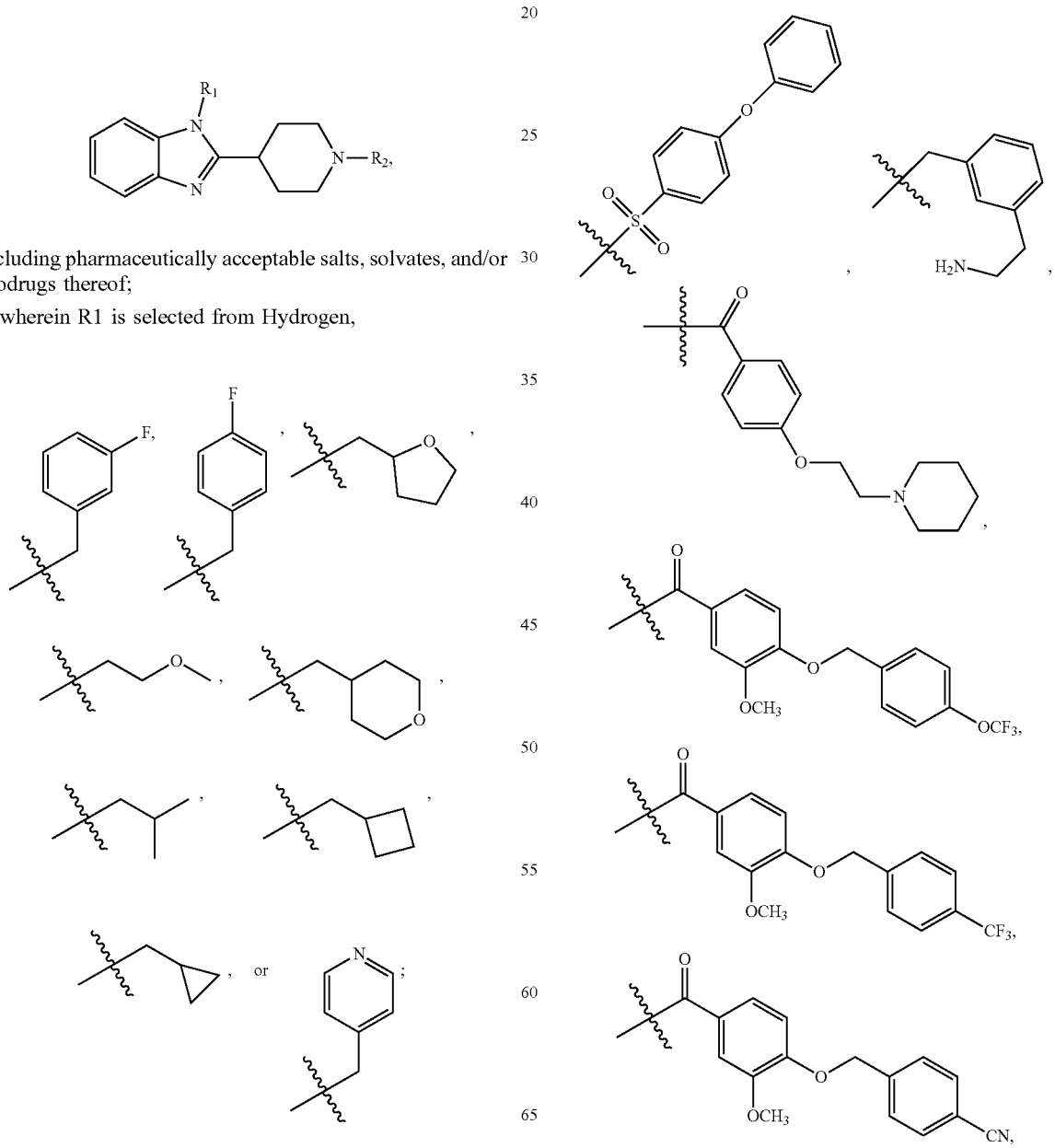

including pharmaceutically acceptable salts, solvates, and/or prodrugs thereof;

wherein R1 is selected from Hydrogen, wherein R2 is

123
-continued
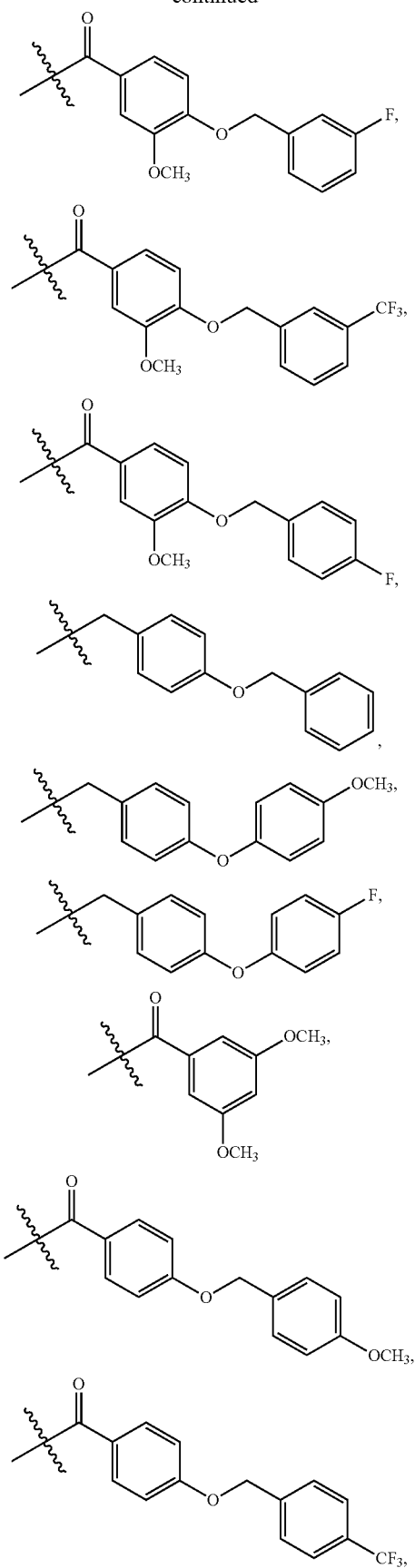
124
-continued
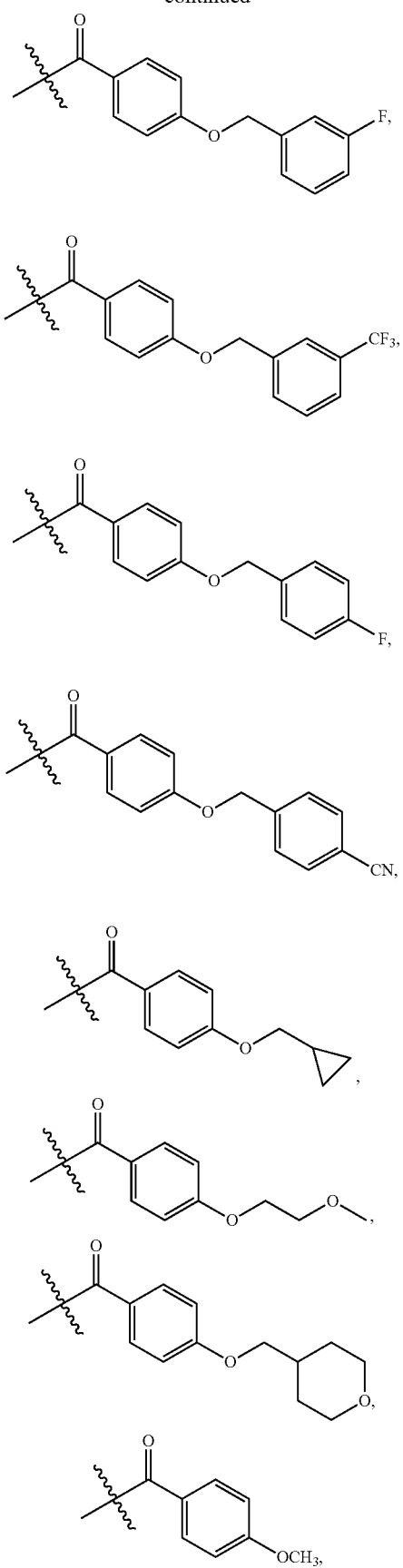

125
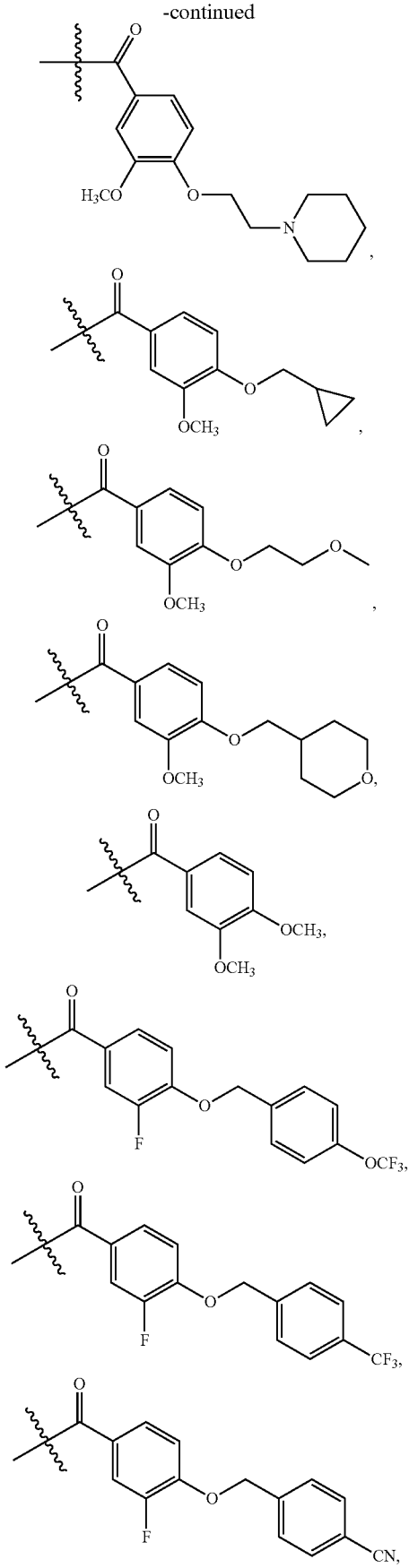
126
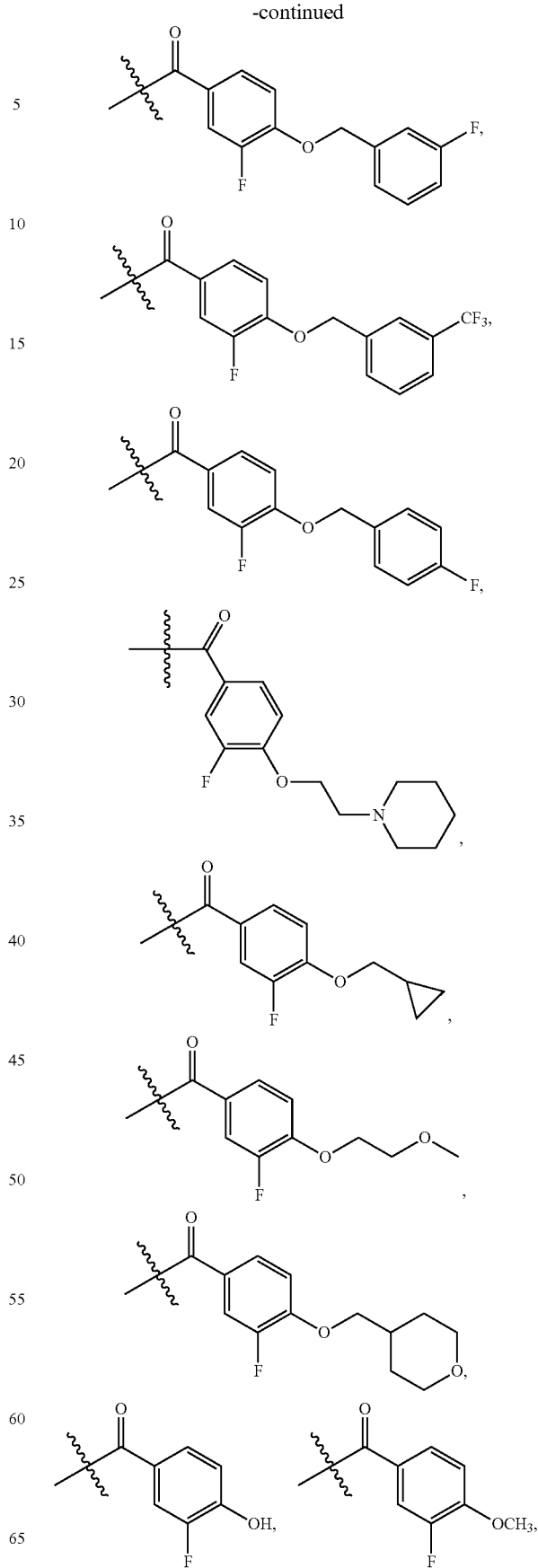

127

-continued

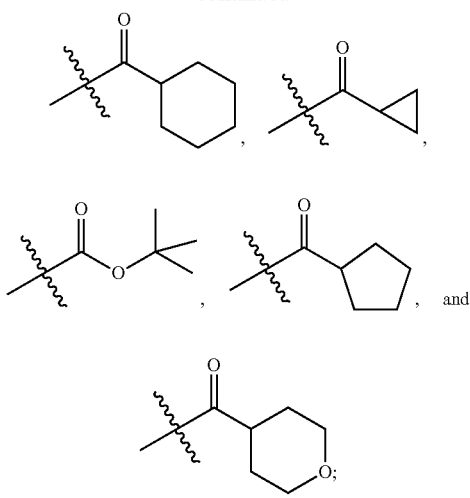

wherein if R1 is Hydrogen, then R2 cannot be

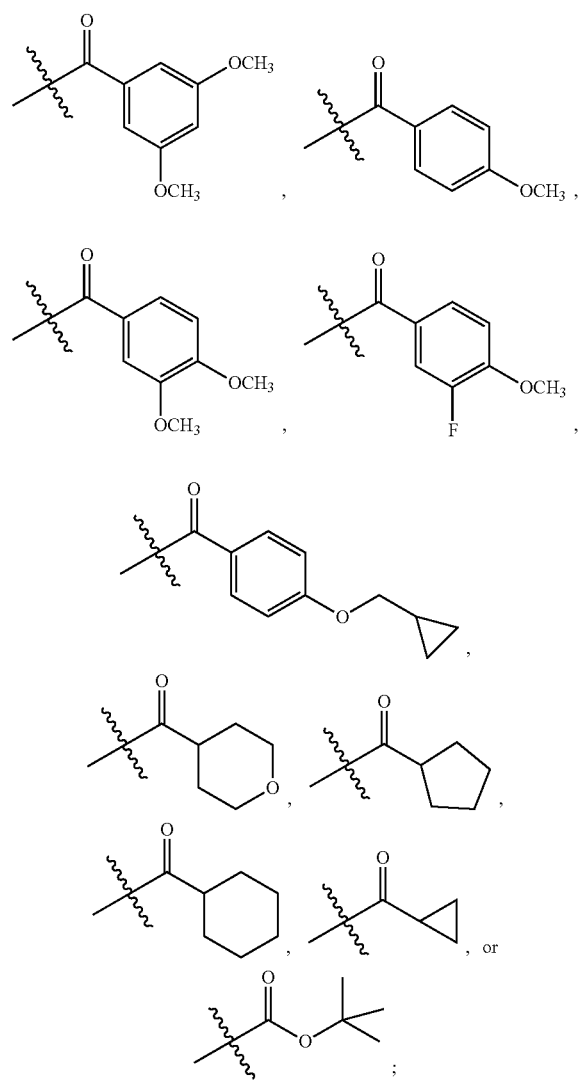

128 wherein if R1

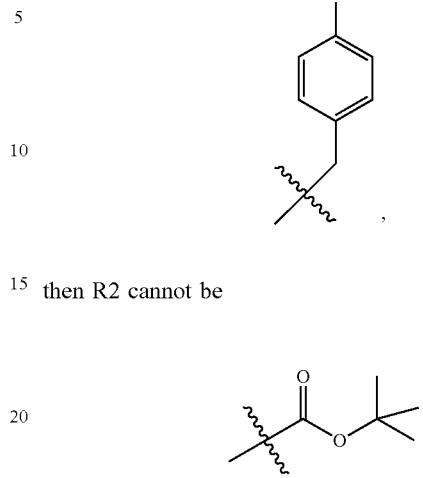

then R2 cannot be

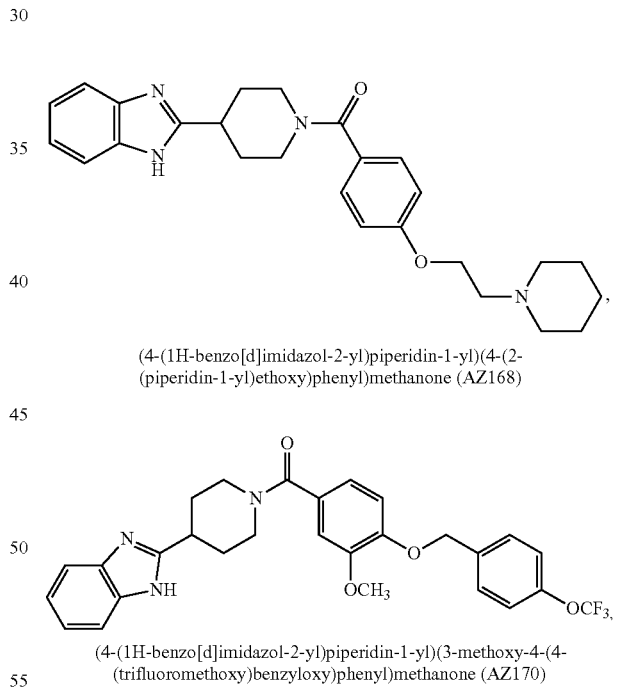

2. The compound of claim 1, wherein the resulting compound is able to inhibit Nav1.7 activity.

3. The compound of claim 1, wherein the compound is selected from the group consisting of:

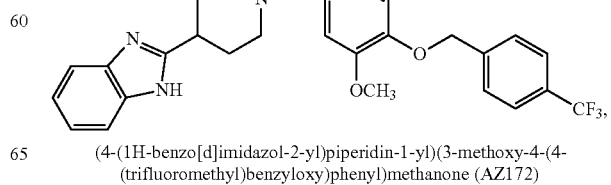

(4-(1H-benzo[d]imidazol-2-yl)piperidin-1-yl)(4-(2-(piperidin-1-yl)ethoxy)phenyl)methanone (AZ168)

(4-(1H-benzo[d]imidazol-2-yl)piperidin-1-yl)(3-methoxy-4-(4-(trifluoromethoxy)benzyloxy)phenyl)methanone (AZ170)

(4-(1H-benzo[d]imidazol-2-yl)piperidin-1-yl)(3-methoxy-4-(4-(trifluoromethyl)benzyloxy)phenyl)methanone (AZ172)

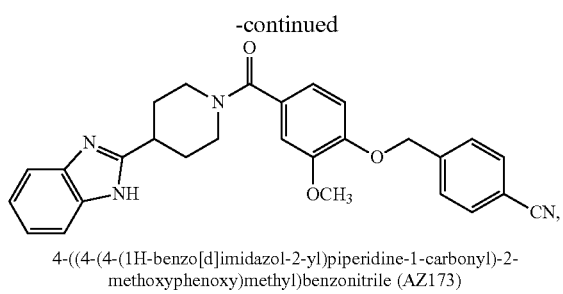

4-((4-(4-(1H-benzo[d]imidazol-2-yl)piperidine-1-carbonyl)-2-methoxyphenoxy)methyl)benzonitrile (AZ173)

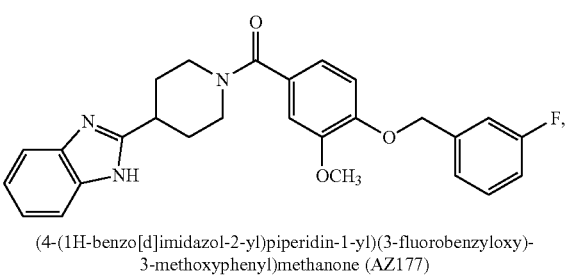

(4-(1H-benzo[d]imidazol-2-yl)piperidin-1-yl)(3-fluorobenzyloxy)-3-methoxyphenyl)methanone (AZ177)

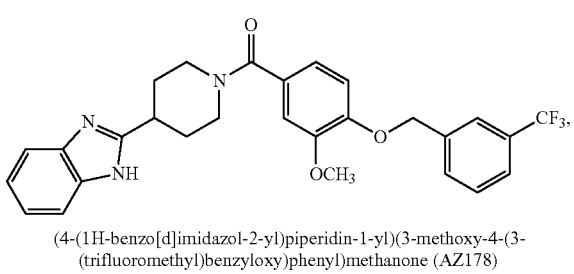

(4-(1H-benzo[d]imidazol-2-yl)piperidin-1-yl)(3-methoxy-4-(3-(trifluoromethyl)benzyloxy)phenyl)methanone (AZ178)

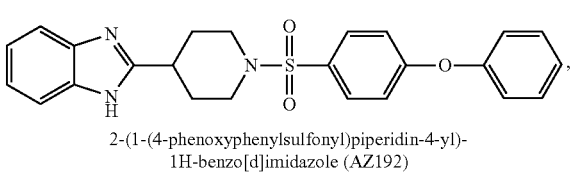

2-(1-(4-phenoxyphenylsulfonyl)piperidin-4-yl)-1H-benzo[d]imidazole (AZ192)

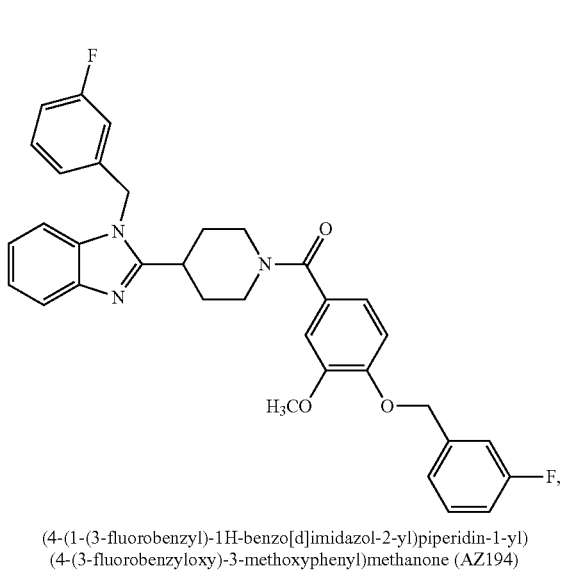

(4-(1-(3-fluorobenzyl)-1H-benzo[d]imidazol-2-yl)piperidin-1-yl)(4-(3-fluorobenzyloxy)-3-methoxyphenyl)methanone (AZ194)

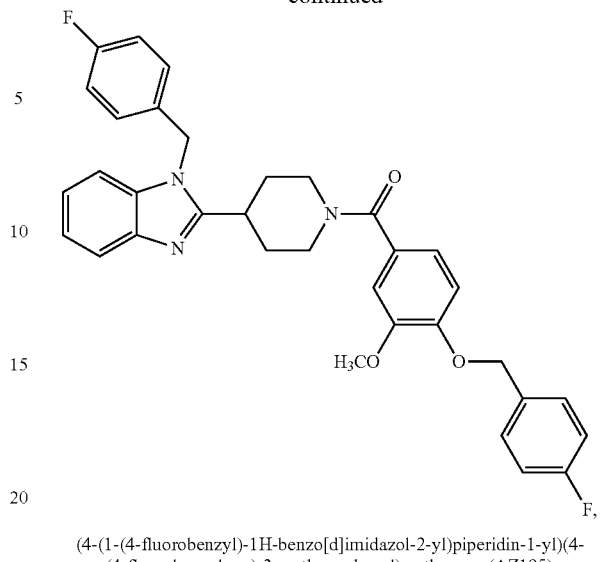

(4-(1-(4-fluorobenzyl)-1H-benzo[d]imidazol-2-yl)piperidin-1-yl)(4-(4-fluorobenzyloxy)-3-methoxyphenyl)methanone (AZ195)

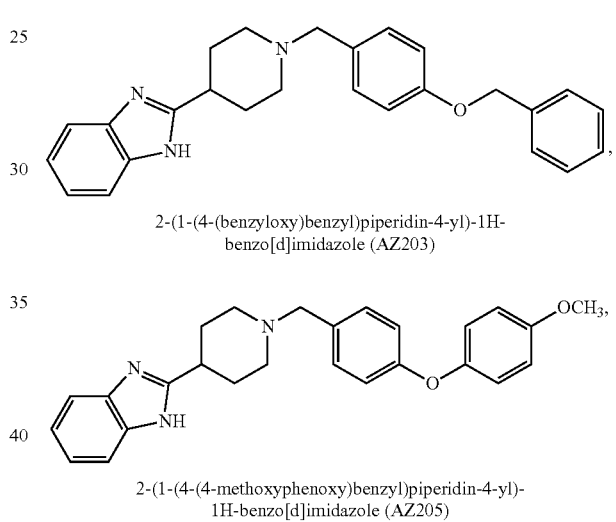

2-(1-(4-(benzyloxy)benzyl)piperidin-4-yl)-1H-benzo[d]imidazole (AZ203)

2-(1-(4-(4-methoxyphenoxy)benzyl)piperidin-4-yl)-1H-benzo[d]imidazole (AZ205)

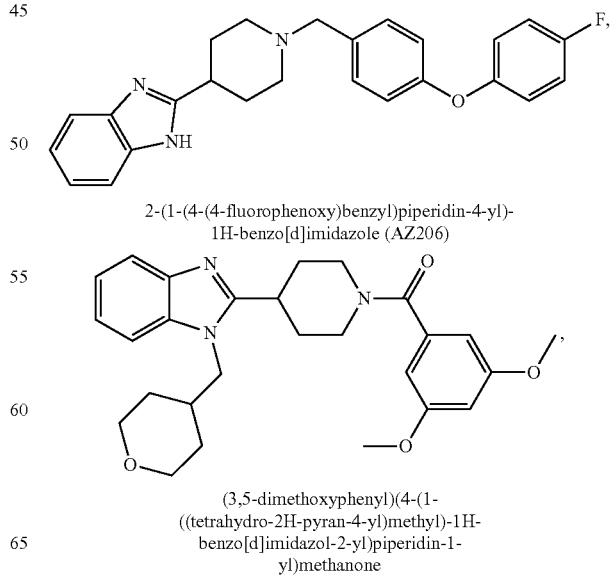

2-(1-(4-(4-fluorophenoxy)benzyl)piperidin-4-yl)-1H-benzo[d]imidazole (AZ206)

(3,5-dimethoxyphenyl)(4-(1-((tetrahydro-2H-pyran-4-yl)methyl)-1H-benzo[d]imidazol-2-yl)piperidin-1-yl)methanone

131

-continued

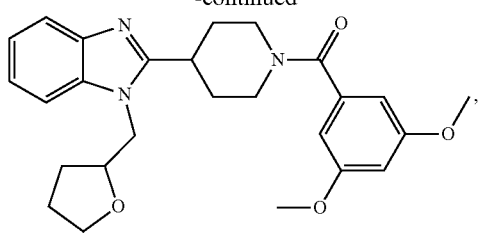

(3,5-dimethoxyphenyl)(4-(1-
((tetrahydrofuran-2-yl)methyl)-1H-
benzo[d]imidazol-2-yl)piperidin-1-
yl)methanone

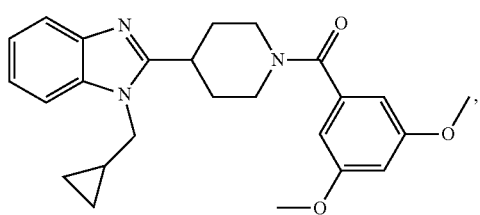

(4-(1-(cyclopropylmethyl)-1H-
benzo[d]imidazol-2-yl)piperidin-1-
yl)(3,5-dimethoxyphenyl)methanone

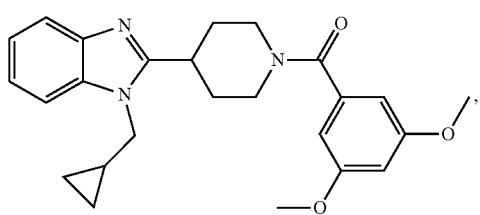

(4-(1-(cyclopropylmethyl)-1H-
benzo[d]imidazol-2-yl)piperidin-1-
yl)(3,5-dimethoxyphenyl)methanone

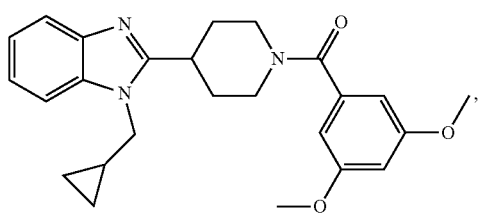

(4-(1-(cyclopropylmethyl)-1H-
benzo[d]imidazol-2-yl)piperidin-1-
yl)(3,5-dimethoxyphenyl)methanone

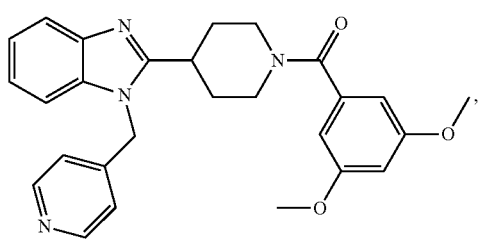

(3,5-dimethoxyphenyl)(4-(1-(pyridin-4-
ylmethyl)-1H-benzo[d]imidazol-2-
yl)piperidin-1-yl)methanone

132

-continued

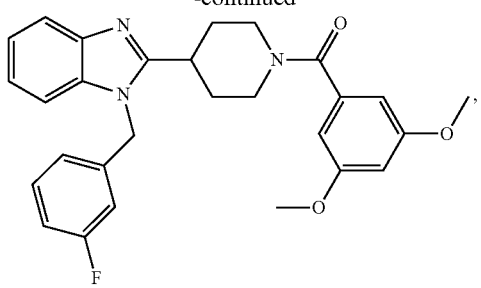

(3,5-dimethoxyphenyl)(4-(1-(3-
fluorobenzyl)-1H-benzo[d]imidazol-2-
yl)piperidin-1-yl)methanone

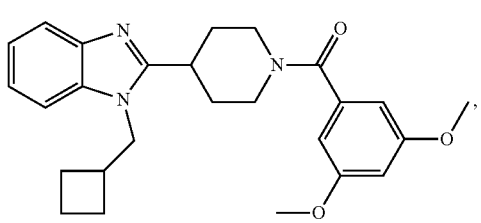

(4-(1-(cyclobutylmethyl)-1H-
benzo[d]imidazol-2-yl)piperidin-1-
yl)(3,5-dimethoxyphenyl)methanone

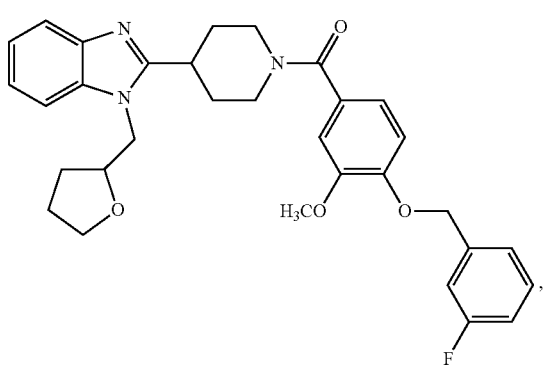

(4-((3-fluorobenzyl)oxy)-3-methoxyphenyl)(4-(1-
((tetrahydrofuran-2-yl)methyl)-1H-benzo[d]imidazol-2-
yl)piperidin-1-yl)methanone

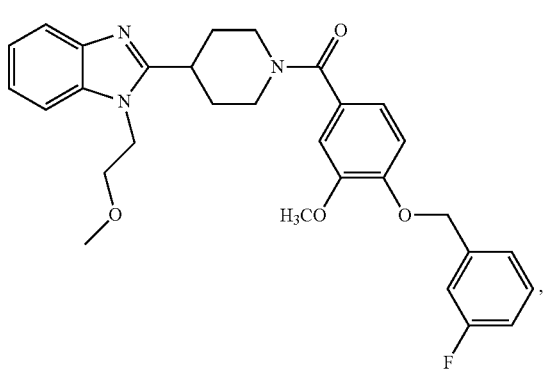

(4-((3-fluorobenzyl)oxy)-3-methoxyphenyl)(4-(1-(2-
methoxyethyl)-1H-benzo[d]imidazol-2-yl)piperidin-1-
yl)methanone -continued

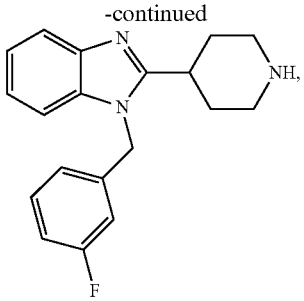

1-(3-fluorobenzyl)-2-(piperidin-4-yl)-1H-benzo[d]imidazole

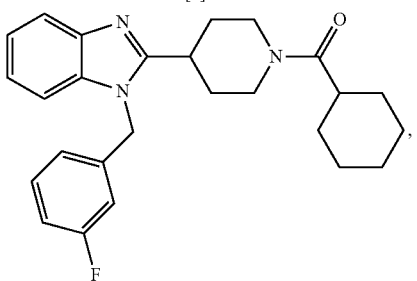

cyclohexyl(4-(1-(3-fluorobenzyl)-1H-benzo[d]imidazol-2-yl)piperidin-1-yl)methanone

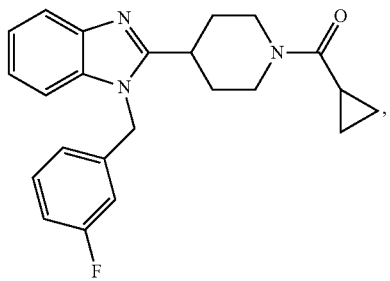

cyclopropyl(4-(1-(3-fluorobenzyl)-1H-benzo[d]imidazol-2-yl)piperidin-1-yl)methanone

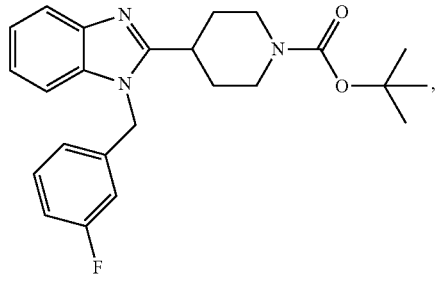

tert-buty 4-(1-(3-fluorobenzyl)-1H-benzo[d]imidazol-2-yl)piperidine-1-carboxylate

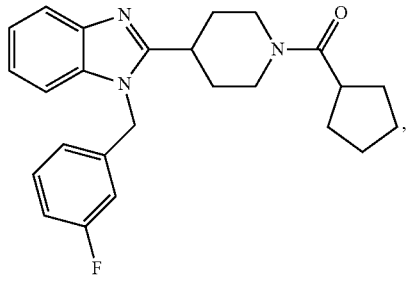

cyclopentyl(4-(1-(3-fluorobenzyl)-1H-benzo[d]imidazol-2-yl)piperidin-1-yl)methanone -continued

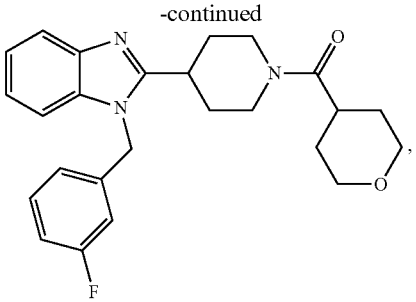

(4-(1-(3-fluorobenzyl)-1H-benzo[d]imidazol-2-yl)piperidin-1-yl)(tetrahydro-2H-pyran-4-yl)methanone

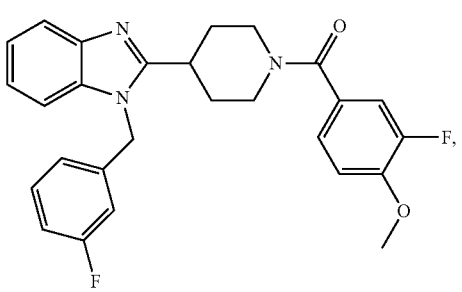

(3-fluoro-4-methoxyphenyl)(4-(1-(3-fluorobenzyl)-1H-benzo[d]imidazol-2-yl)piperidin-1-yl)methanone

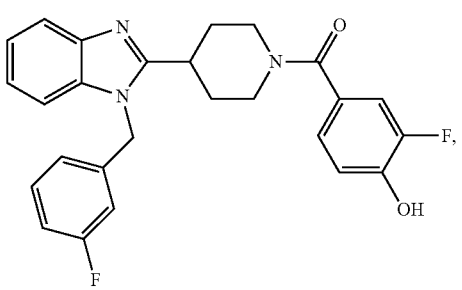

(3-fluoro-4-hydroxyphenyl)(4-(1-(3-fluorobenzyl)-1H-benzo[d]imidazol-2-yl)piperidin-1-yl)methanone

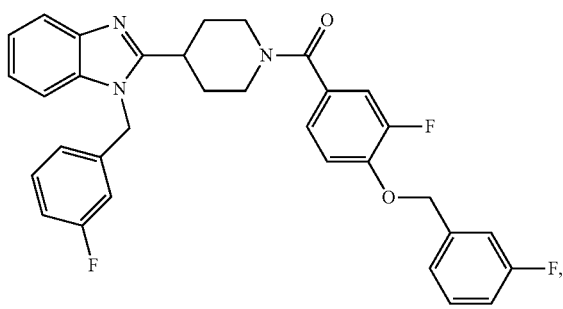

(3-fluoro-4-((3-fluorobenzyl)oxy)phenyl)(4-(1-(3-fluorobenzyl)-1H-benzo[d]imidazol-2-yl)piperidin-1-yl)methanone -continued

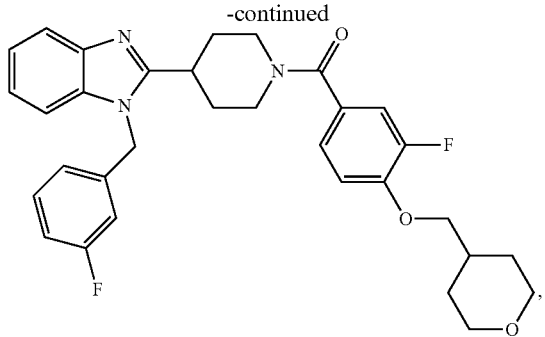

(3-fluoro-4-((tetrahydro-2H-pyran-4-yl)methoxy)phenyl)
(4-(1-(3-fluorobenzyl)-1H-benzol[d]imidazol-2-yl)
piperidin-1-yl)methanone

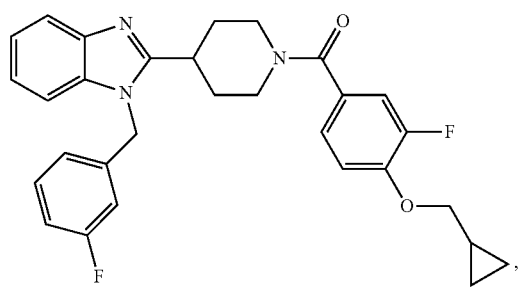

(4-(cyclopropylmethoxy)-3-fluorophenyl)(4-(1-3-
fluorobenzyl)-1H-benzo[d]imidazol-2-yl)piperidin-
1-yl)methanone

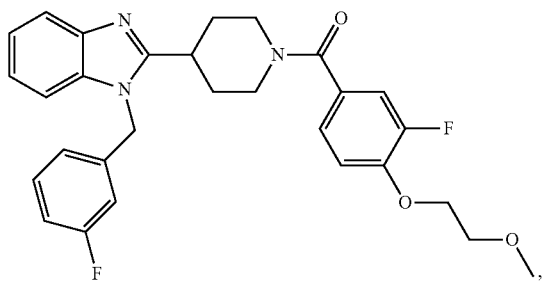

(3-fluoro-4-(2-methoxyethoxy)phenyl)(4-(1-(3-
fluorobenzyl)-1H-benzo[d]imidazol-2-yl)
piperidin-1-yl)methanone

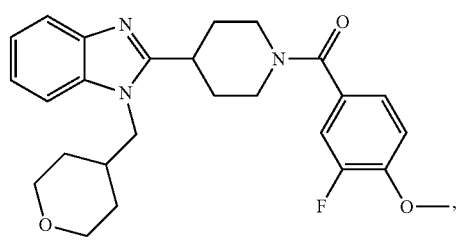

(3-fluoro-4-methoxyphenyl)(4-(1-
((tetrahydro-2H-pyran-4-yl)methyl)-1H-
benzo[d]imidazol-2-yl)piperidin-1-
yl)methanone

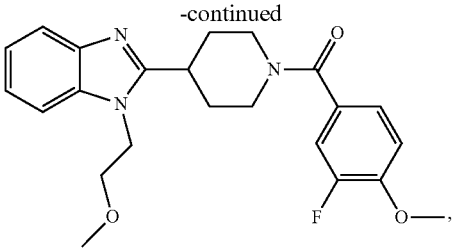

(3-fluoro-4-methoxyphenyl)(4-(1-(2-
methoxyethyl)-1H-benzo[d]imidazol-2-
yl)piperidin-1-yl)methanone

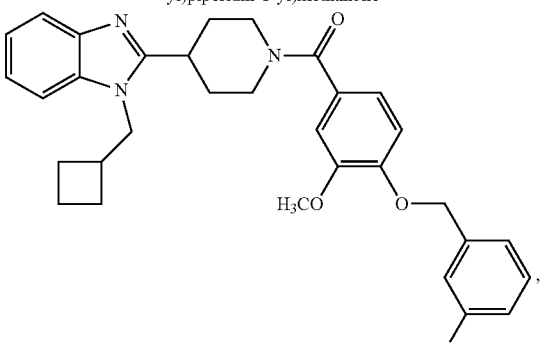

(4-(1-(cyclobutylmethyl)-1H-benzo[d]imidazol-2-yl)
piperidin-1-yl)(4-((3-fluorobenzyl)oxy)-3-
methoxyphenyl)methanone

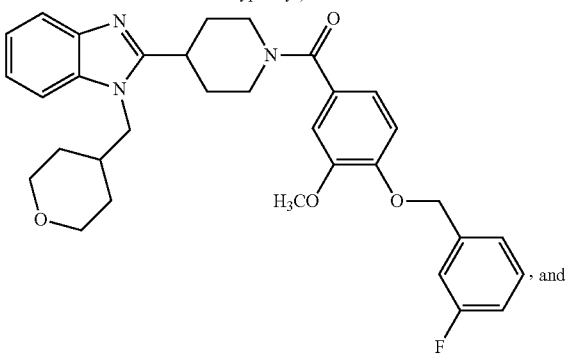

(4-((3-fluorobenzyl)oxy)-3-methoxyphenyl)(4-(1-
((tetrahydro-2H-pyran-4-yl)methyl)-1H-benzo[d]
imidazol-2-yl)piperidin-1-yl)methanone, and

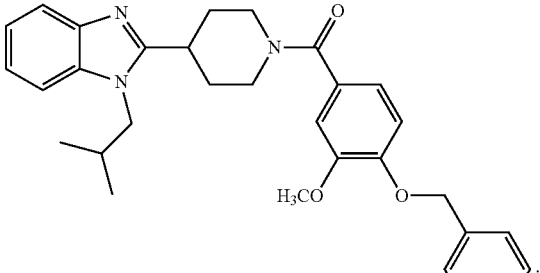

(4-((3-fluorobenzyl)oxy)-3-methoxyphenyl)(4-
(1-isobutyl-1H-benzo[d]imidazol-2-yl)
piperidin-1-yl)methanone.

4. A pharmaceutical composition comprising a compound of claim 1.

5. A method of treating, ameliorating, or preventing itch, anosmia, a migraine event, or pain related to Nav1.7 activity in a patient comprising administering to said patient a therapeutically effective amount of a piperidinyl-benzoimidazole structure
encompassed within Formula I:
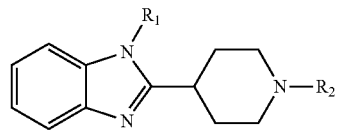
or Formula II:
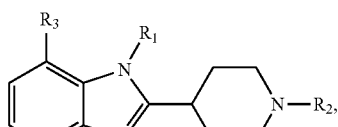
including pharmaceutically acceptable salts, solvates, and/or prodrugs thereof,
wherein R1 is selected from Hydrogen,
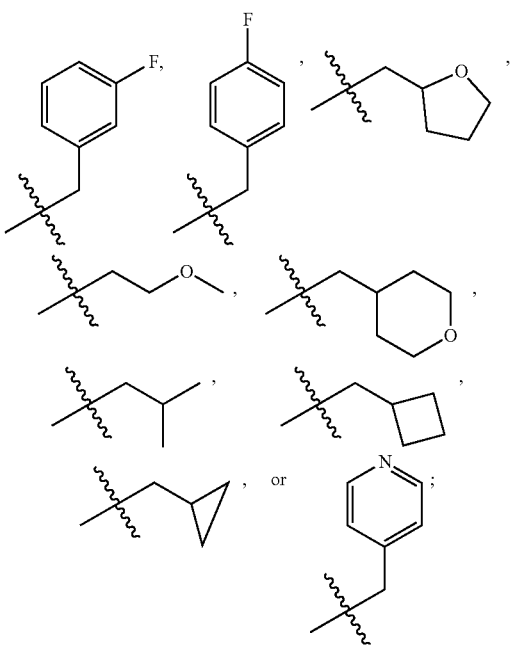
wherein R2 is selected from Hydrogen,
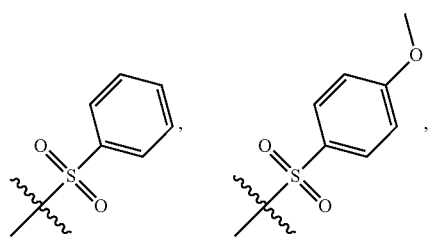
-continued
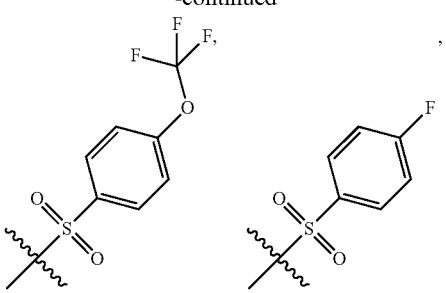
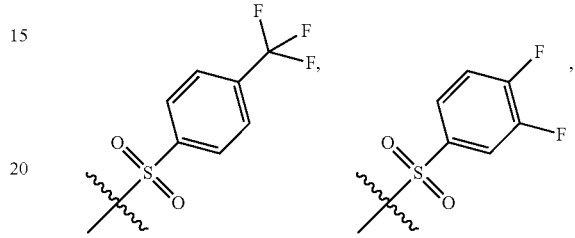
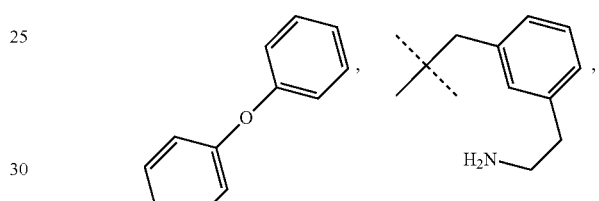
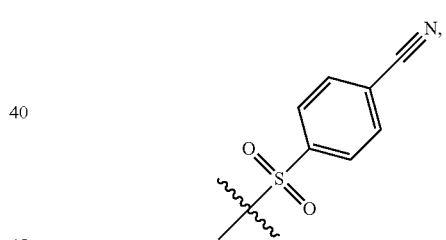
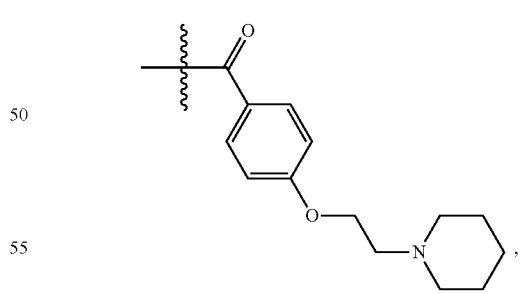
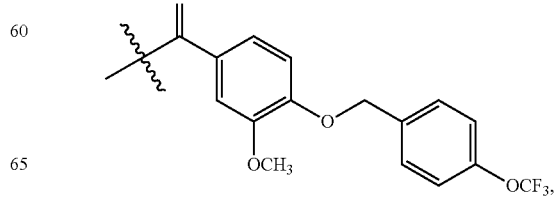

-continued
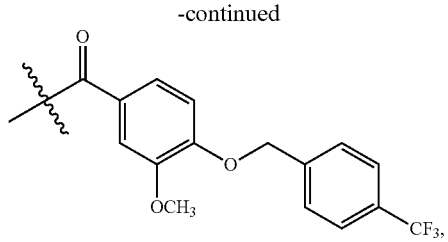
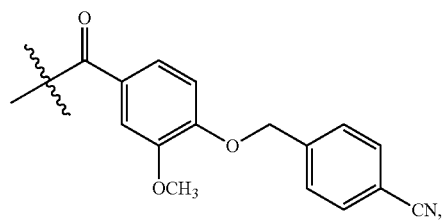
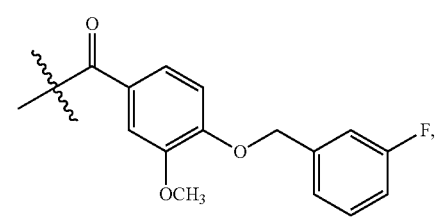
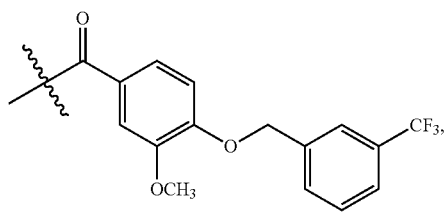
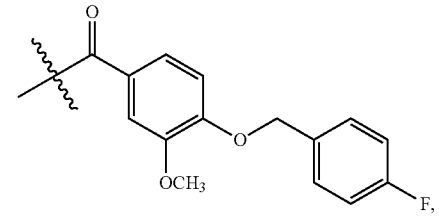
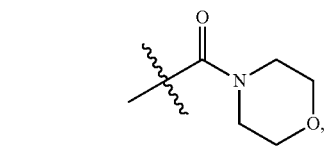
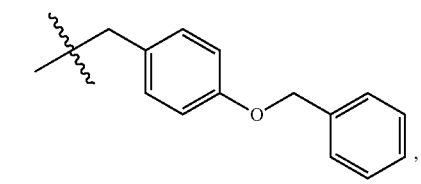
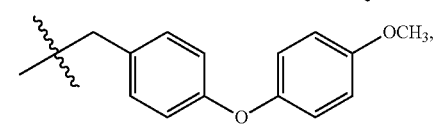
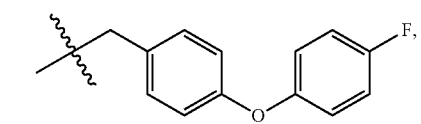
-continued
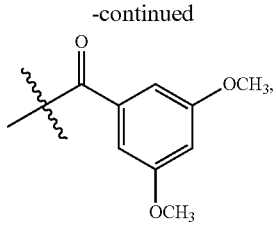
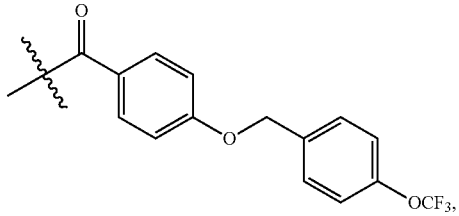
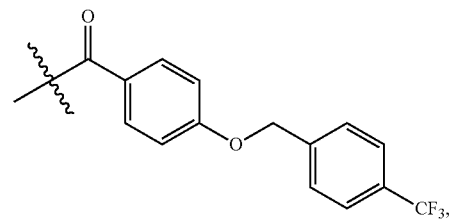
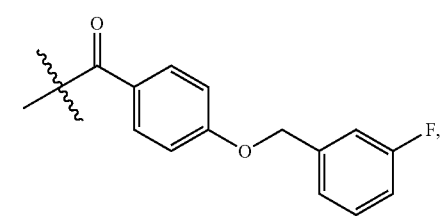
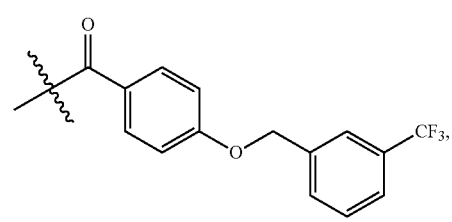
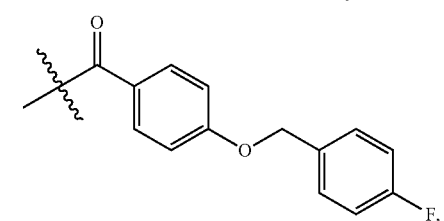
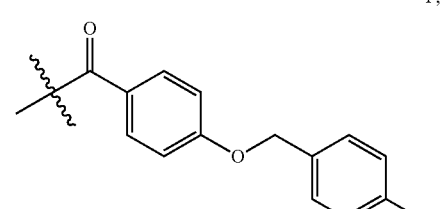
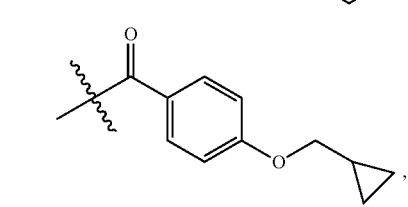

141
-continued
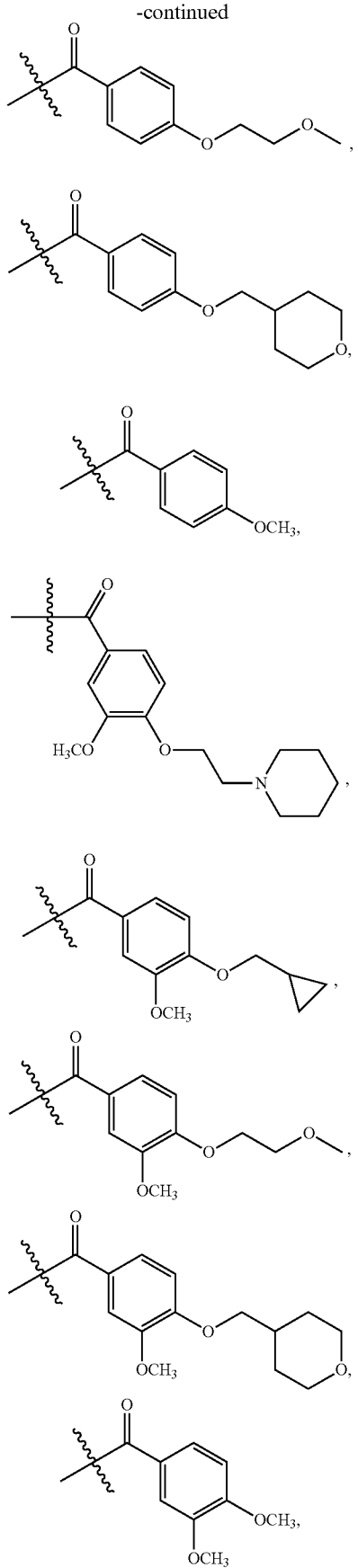
142
-continued
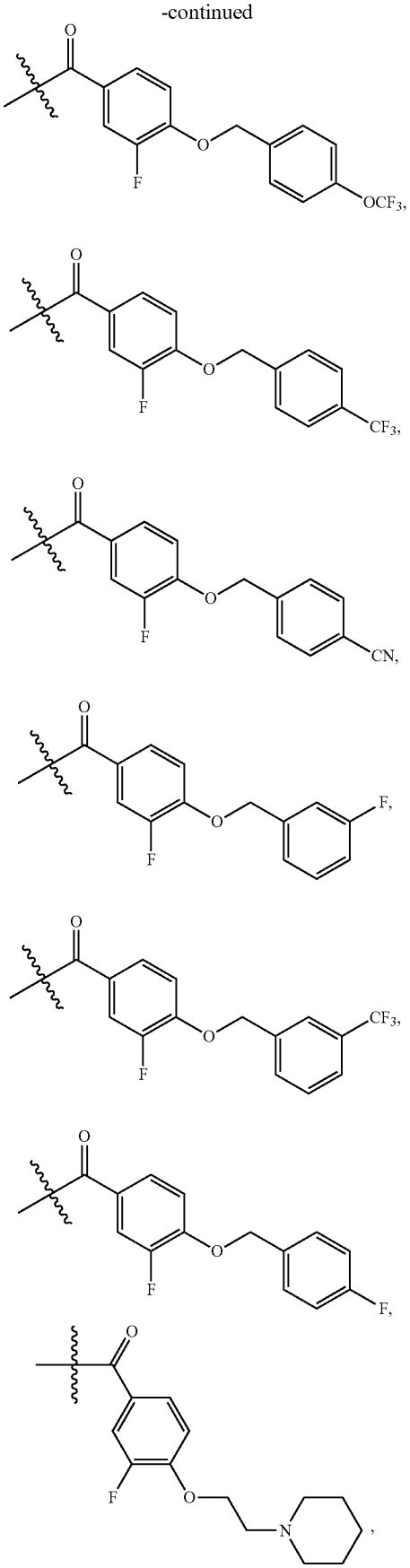

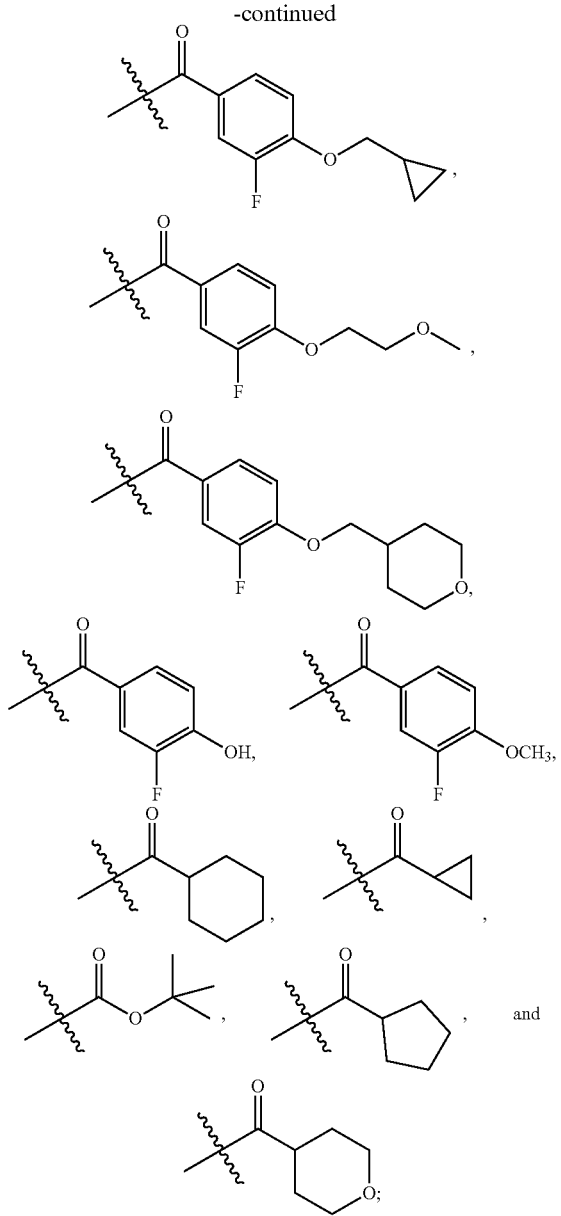

wherein R3 is selected from Hydrogen or CH3.

6. The method of claim 5, wherein the compound is capable of binding within a CRMP2 binding pocket characterized by one or more of the following CRMP2 amino acid residues: Lys23, Val25, Ser30, Tyr32, Met64, Ser319, Ser322, Trp366, Val370, Val371, Gly373, Lys374, Met375, Asp376, Glu377, Glu377, Gln379, Pro414, Asp415, Ser416, Val417, and Arg440.

7. The method of claim 5, wherein the compound is capable of inhibiting binding of Ubc9 within a CRMP2 binding pocket characterized by one or more of the following CRMP2 amino acid residues: Lys23, Val25, Ser30, Tyr32, Met64, Ser319, Ser322, Trp366, Val370, Val371, Gly373, Lys374, Met375, Asp376, Glu377, Glu377, Gln379, Pro414, Asp415, Ser416, Val417, and Arg440.

8. The method of claim 5, wherein the pain related to Nav1.7 activity is acute, inflammatory and/or neuropathic pain or itch.

9. The method of claim 5, wherein the compound is selected from

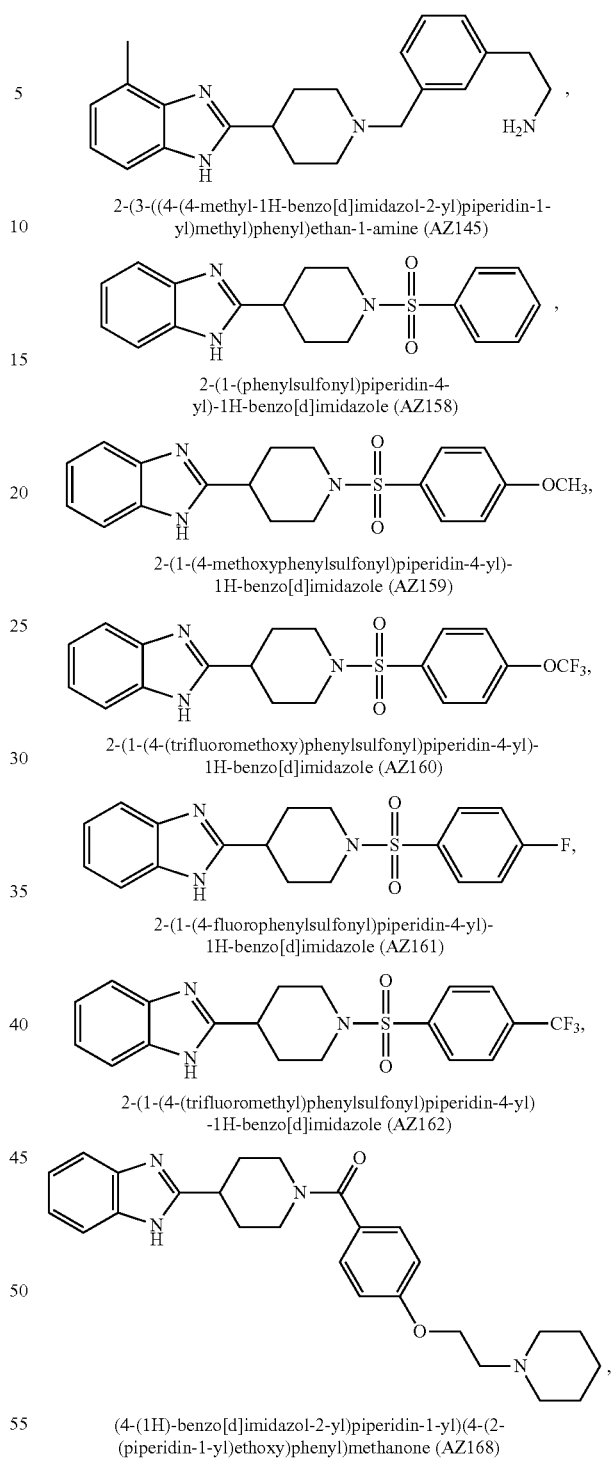

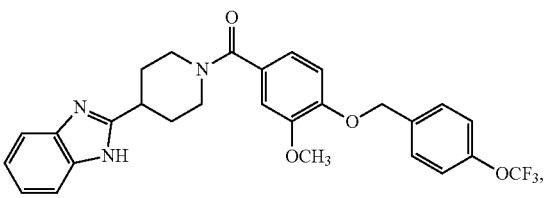

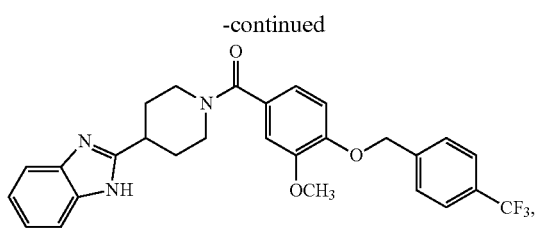

(4-(1H-benzo[d]imidazol-2-yl)piperidin-1-yl)(3-methoxy-4-(4-
(trifluoromethyl)benzyloxy)phenyl)methanone (AZ172)

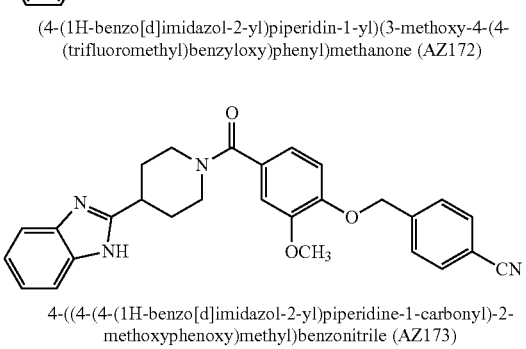

4-((4-(4-(1H-benzo[d]imidazol-2-yl)piperidine-1-carbonyl)-2-
methoxyphenoxy)methyl)benzonitrile (AZ173)

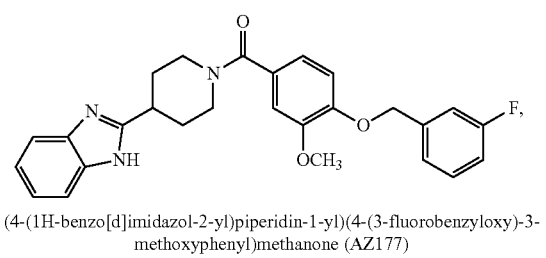

(4-(1H-benzo[d]imidazol-2-yl)piperidin-1-yl)(4-(3-fluorobenzyloxy)-3-
methoxyphenyl)methanone (AZ177)

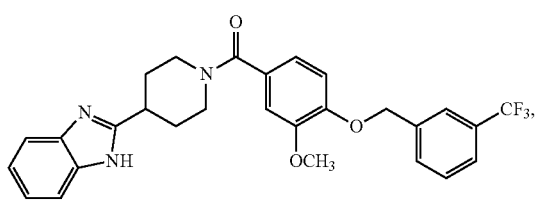

(4-(1H-benzo[d]imidazol-2-yl)piperidin-1-yl)(3-methoxy-4-(3-
(trifluoromethyl)benzyloxy)phenyl)methanone (AZ178)

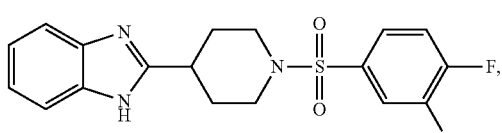

2-(1-(3,4-difluorophenylsulfonyl)piperidin-4-yl)-
1H-benzo[d]imidazole (AZ190)

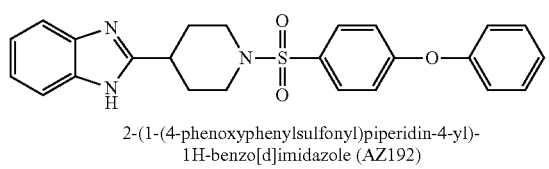

2-(1-(4-phenoxyphenylsulfonyl)piperidin-4-yl)-
1H-benzo[d]imidazole (AZ192)

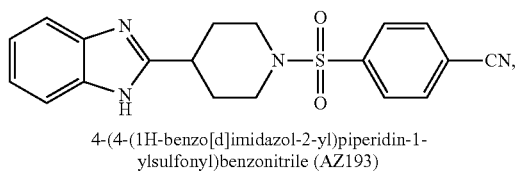

4-(4-(1H-benzo[d]imidazol-2-yl)piperidin-1-
ylsulfonyl)benzonitrile (AZ193)

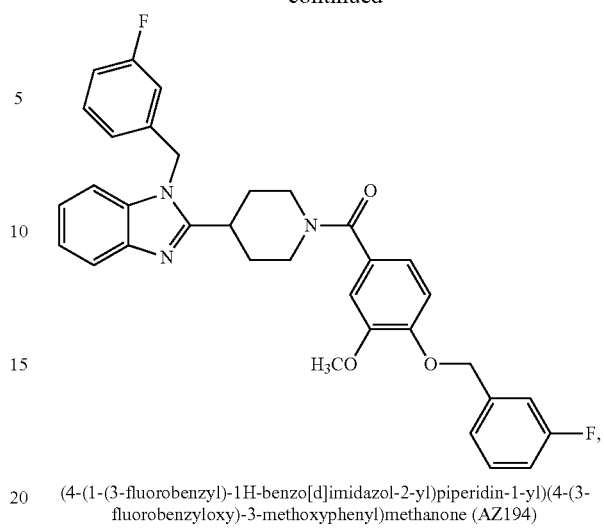

(4-(1-(3-fluorobenzyl)-1H-benzo[d]imidazol-2-yl)piperidin-1-yl)(4-(3-
fluorobenzyloxy)-3-methoxyphenyl)methanone (AZ194)

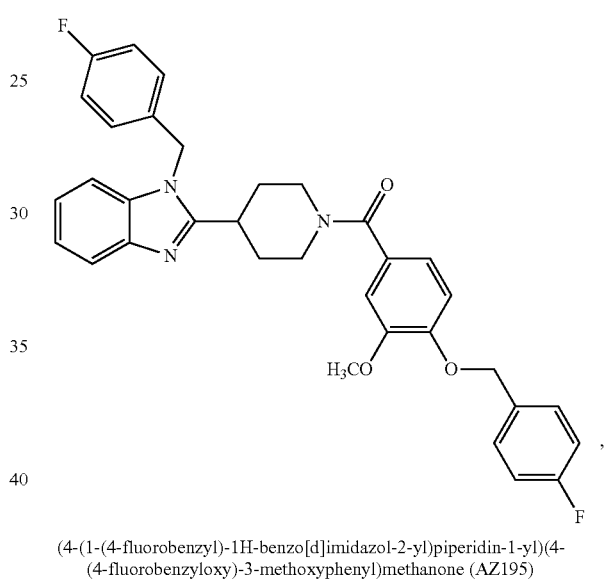

(4-(1-(4-fluorobenzyl)-1H-benzo[d]imidazol-2-yl)piperidin-1-yl)(4-
(4-fluorobenzyloxy)-3-methoxyphenyl)methanone (AZ195)

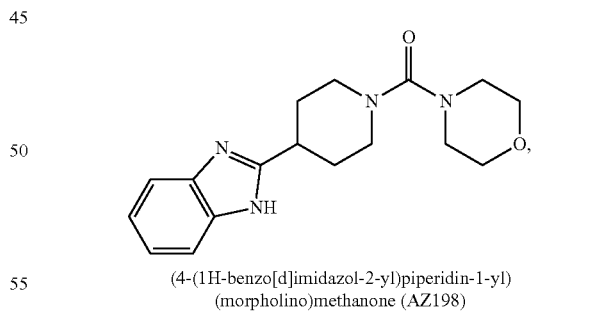

(4-(1H-benzo[d]imidazol-2-yl)piperidin-1-yl)
(morpholino)methanone (AZ198)

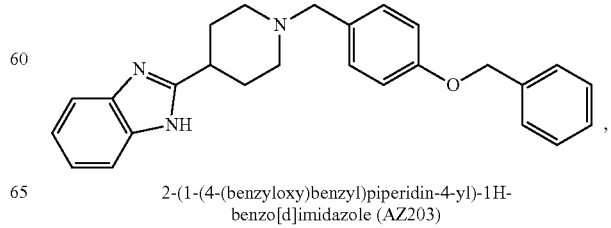

2-(1-(4-(benzyloxy)benzyl)piperidin-4-yl)-1H-
benzo[d]imidazole (AZ203)

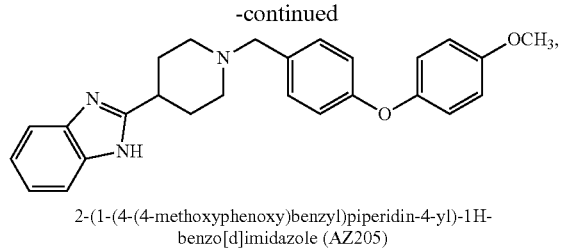

2-(1-(4-(4-methoxyphenoxy)benzyl)piperidin-4-yl)-1H-benzo[d]imidazole (AZ205)

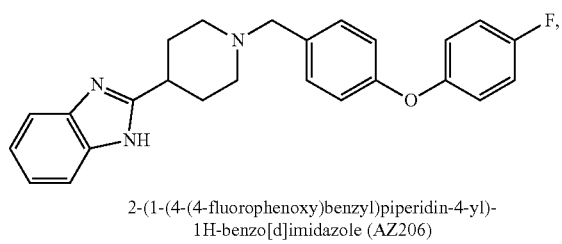

2-(1-(4-(4-fluorophenoxy)benzyl)piperidin-4-yl)-1H-benzo[d]imidazole (AZ206)

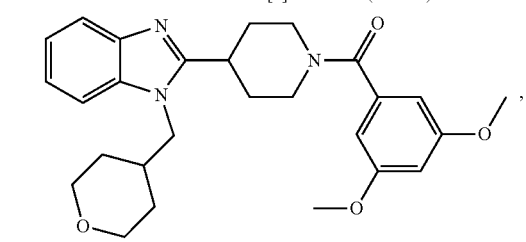

(3,5-dimethoxyphenyl)(4-(1-((tetrahydro-2H-pyran-4-yl)methyl)-1H-benzo[d]imidazol-2-yl)piperidin-1-yl)methanone

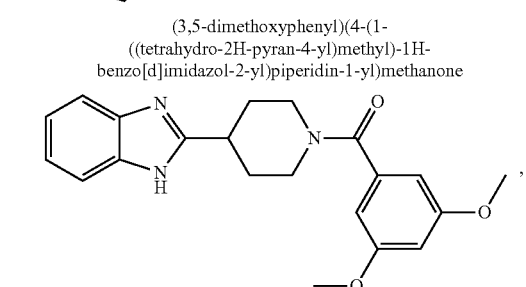

(4-(1H-benzo[d]imidazol-2-yl)piperidin-1-yl)(3,5-dimethoxyphenyl)methanone

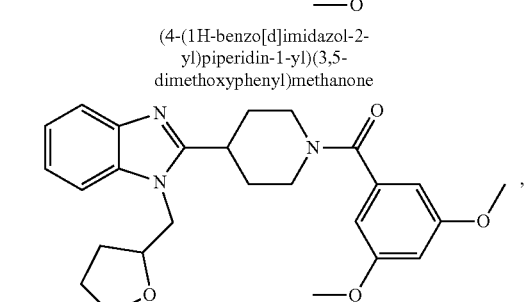

(3,5-dimethoxyphenyl)(4-(1-((tetrahydrofuran-2-yl)methyl)-1H-benzo[d]imidazol-2-yl)piperidin-1-yl)methanone

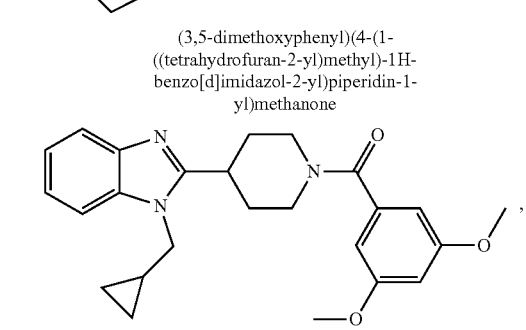

(4-(1-(cyclopropylmethyl)-1H-benzo[d]imidazol-2-yl)piperidin-1-yl)(3,5-dimethoxyphenyl)methanone

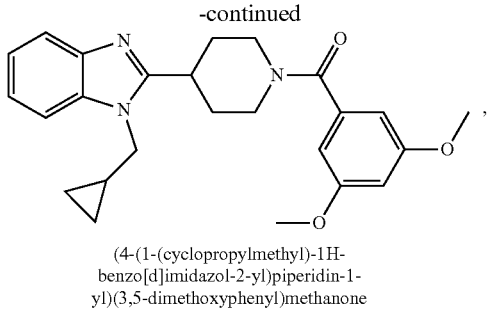

(4-(1-(cyclopropylmethyl)-1H-benzo[d]imidazol-2-yl)piperidin-1-yl)(3,5-dimethoxyphenyl)methanone

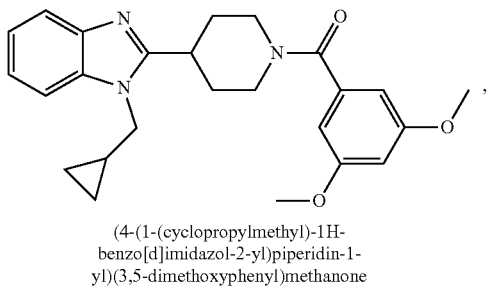

(4-(1-(cyclopropylmethyl)-1H-benzo[d]imidazol-2-yl)piperidin-1-yl)(3,5-dimethoxyphenyl)methanone

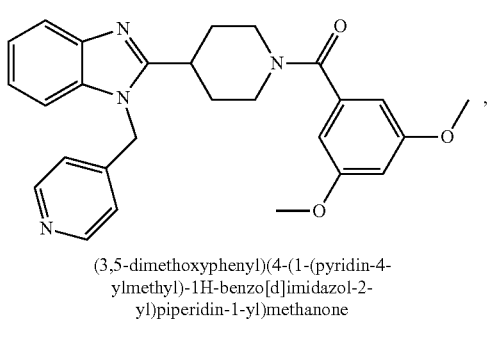

(3,5-dimethoxyphenyl)(4-(1-(pyridin-4-ylmethyl)-1H-benzo[d]imidazol-2-yl)piperidin-1-yl)methanone

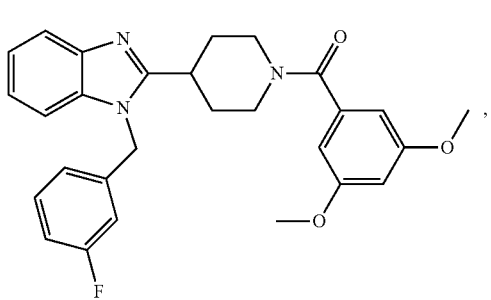

(3,5-dimethoxyphenyl)(4-(1-(3-fluorobenzyl)-1H-benzo[d]imidazol-2-yl)piperidin-1-yl)methanone

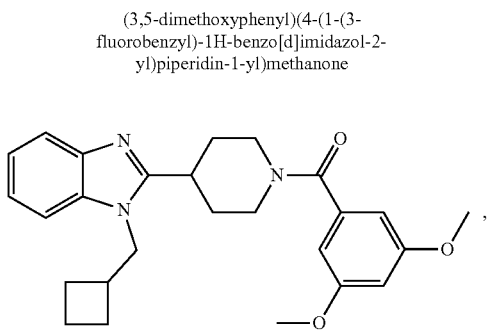

(4-(1-(cyclobutylmethyl)-1H-benzo[d]imidazol-2-yl)piperidin-1-yl)(3,5-dimethoxyphenyl)methanone -continued

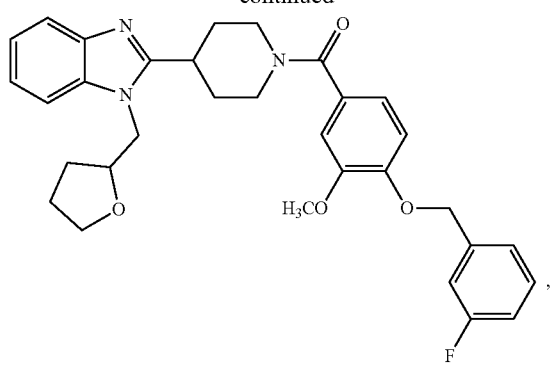

(4-((3-fluorobenzyl)oxy)-3-methoxyphenyl)(4-(1-((tetrahydrofuran-2-yl)methyl)-1H-benzo[d]imidazol-2-yl)piperidin-1-yl)methanone

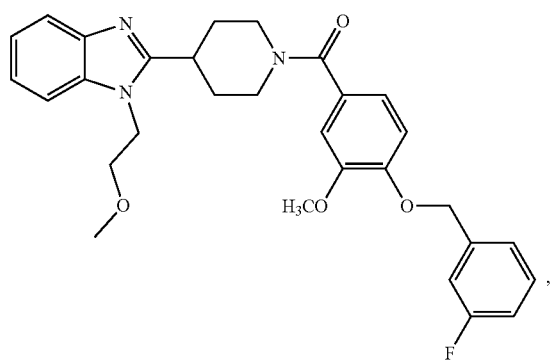

(4-((3-fluorobenzyl)oxy)-3-methoxyphenyl)(4-(1-(2-methoxyethyl)-1H-benzo[d]imidazol-2-yl)piperidin-1-yl)methanone

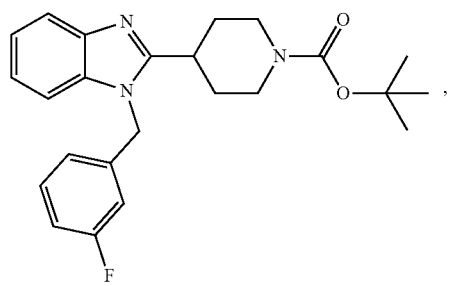

tert-butyl 4-(1-(3-fluorobenzyl)-1H-benzo[d]imidazol-2-yl)piperidine-1-carboxylate

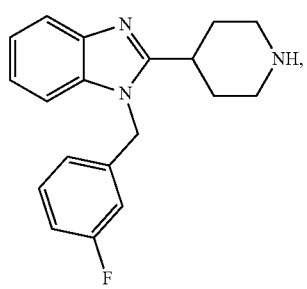

1-(3-fluorobenzyl)-2-(piperidin-4-yl)-1H-benzo[d]imidazole

-continued

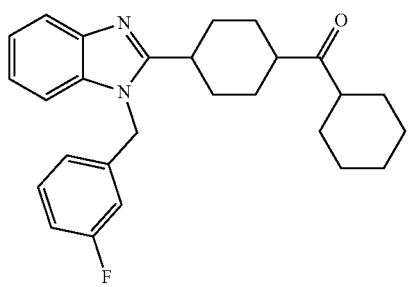

cyclohexyl(4-(1-(3-fluorobenzyl)-1H-benzo[d]imidazol-2-yl)piperidin-1-yl)methanone

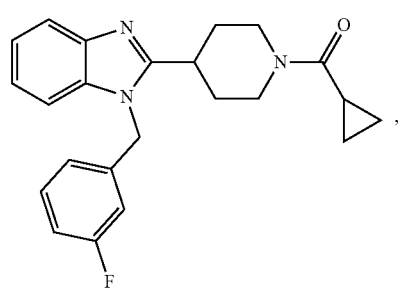

cyclopropyl(4-(1-(3-fluorobenzyl)-1H-benzo[d]imidazol-2-yl)piperidin-1-yl)methanone

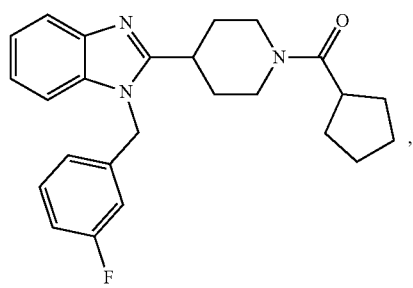

cyclopentyl(4-(1-(3-fluorobenzyl)-1H-benzo[d]imidazol-2-yl)piperidin-1-yl)methanone

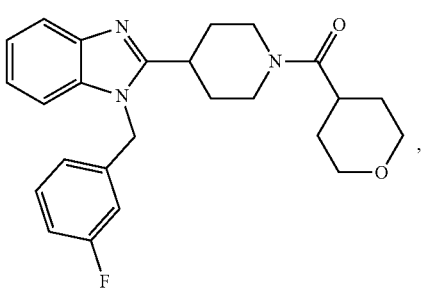

(4-(1-(3-fluorobenzyl)-1H-benzo[d]imidazol-2-yl)(piperidin-1-yl)(tetrahydro-2H-pyran-4-yl)methanone

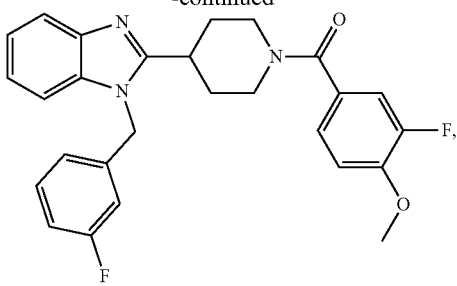

(3-fluoro-4-methoxyphenyl)(4-(1-(3-fluorobenzyl)-1H-benzo[d]imidazol-2-yl)piperidin-1-yl)methanone

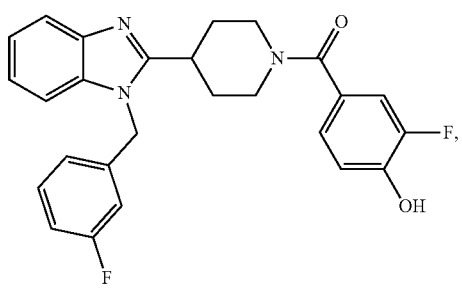

(3-fluoro-4-hydroxyphenyl)(4-(1-(3-fluorobenzyl)-1H-benzo[d]imidazol-2-yl)piperidin-1-yl)methanone

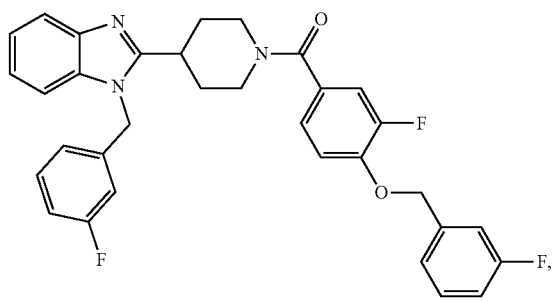

(3-fluoro-4-((3-fluorobenzyl)oxy)phenyl)(4-(1-(3-fluorobenzyl)-1H-benzo[d]imidazol-2-yl)piperidin-1-yl)methanone

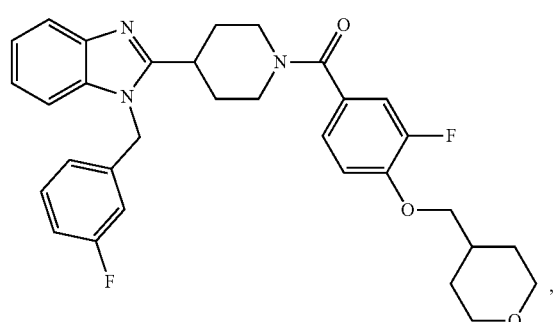

(3-fluoro-4-((tetrahydro-2H-pyran-4-yl)methoxy)phenyl)(4-(1-(3-fluorobenzyl)-1H-benzo[d]imidazol-2-yl)piperidin-1-yl)methanone

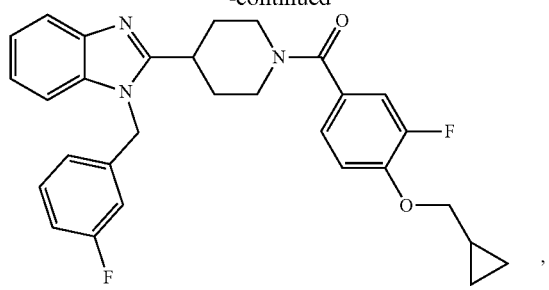

(4-(cyclopropylmethoxy)-3-fluorophenyl)(4-(1-(3-fluorobenzyl)-1H-benzo[d]imidazol-2-yl)piperidin-1-yl)methanone

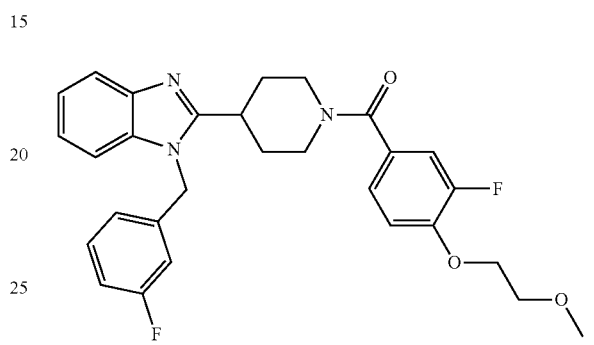

(3-fluoro-4-(2-methoxyethoxy)phenyl)(4-(1-(3-fluorobenzyl)-1H-benzo[d]imidazol-2-yl)piperidin-1-yl)methanone

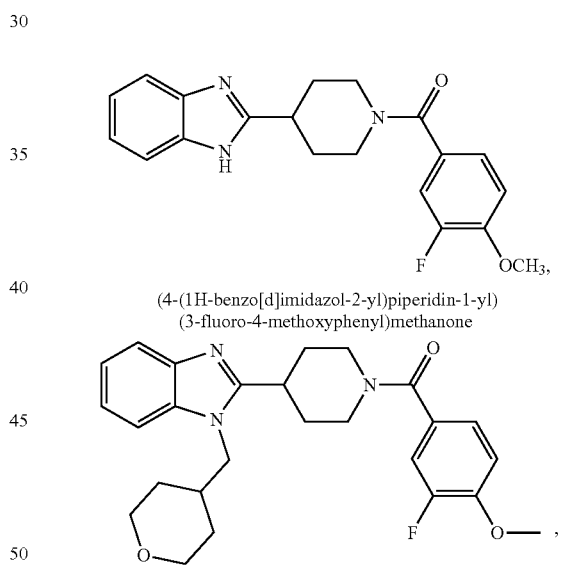

(4-(1H-benzo[d]imidazol-2-yl)piperidin-1-yl)(3-fluoro-4-methoxyphenyl)methanone (3-fluoro-4-methoxyphenyl)(4-(1-((tetrahydro-2H-pyran-4-yl)methyl)-1H-benzo[d]imidazol-2-yl)piperidin-1-yl)methanone

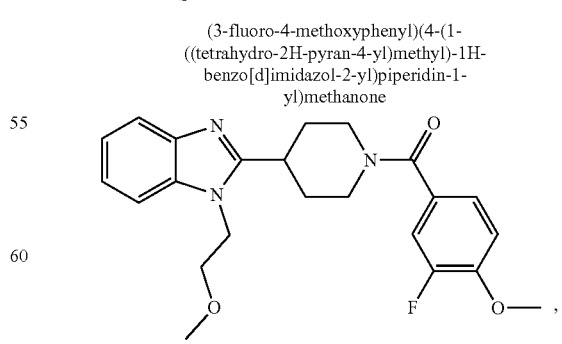

(3-fluoro-4-methoxyphenyl)(4-(1-(2-methoxyethyl)-1*H*-benzo[*d*]imidazol-2-yl)piperidin-1-yl)methanone -continued

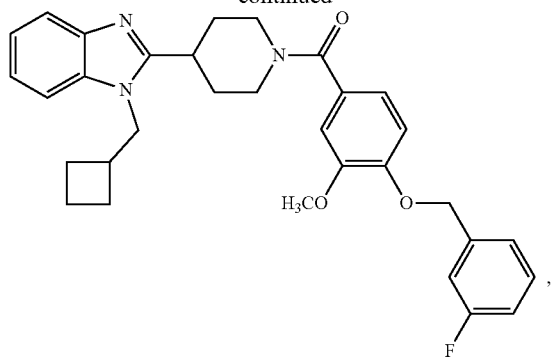

(4-(1-(cyclobutylmethyl)-1H-benzo[d]imidazol-2-yl)
piperidin-1-yl)(4-((3-fluorobenzyl)oxy)-3-methoxyphenyl)
methanone

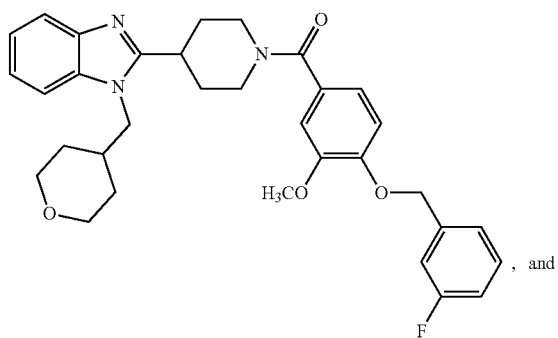

, and (4-((3-fluorobenzyl)oxy)-3-methoxyphenyl)(4-(1-((tetrahydro-
2H-pyran-4-yl)-1H-benzo[d]imidazol-2-yl)piperidin-1-
yl)methanone

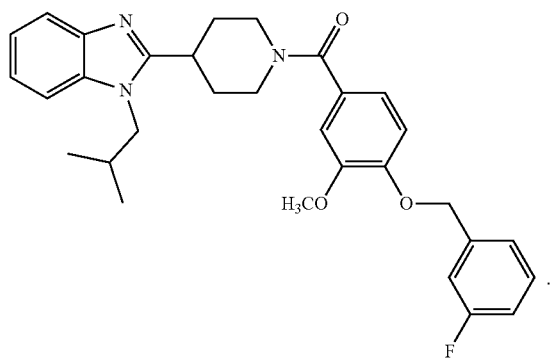

(4-((3-fluorobenzyl)oxy)-3-methoxyphenyl)(4-(1-isobutyl-1H-
benzo[d]imidazol-2-yl)piperidin-1-yl)methanone

10. A method of inhibiting SUMOylation of CRMP2 in a subject comprising administering to said subject therapeutically effective amount of a therapeutically effective amount of a piperidinyl-benzoimidazole structure encompassed within Formula I:

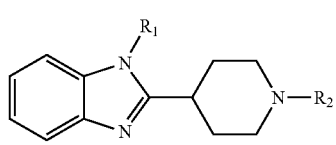

or Formula II:

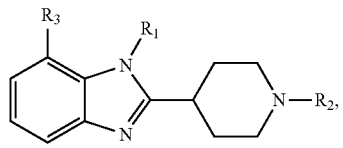

including pharmaceutically acceptable salts, solvates, and/or prodrugs thereof, wherein R1 is selected from Hydrogen,

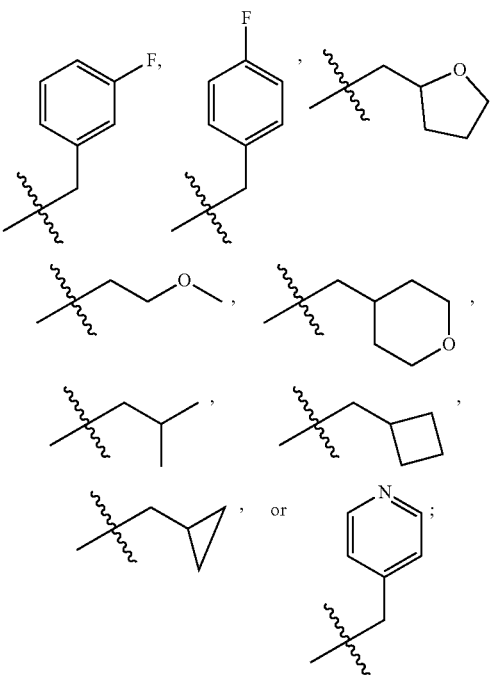

wherein R2 is selected from Hydrogen,

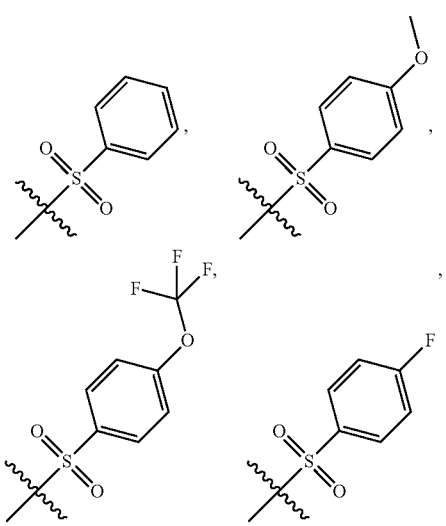

155
-continued
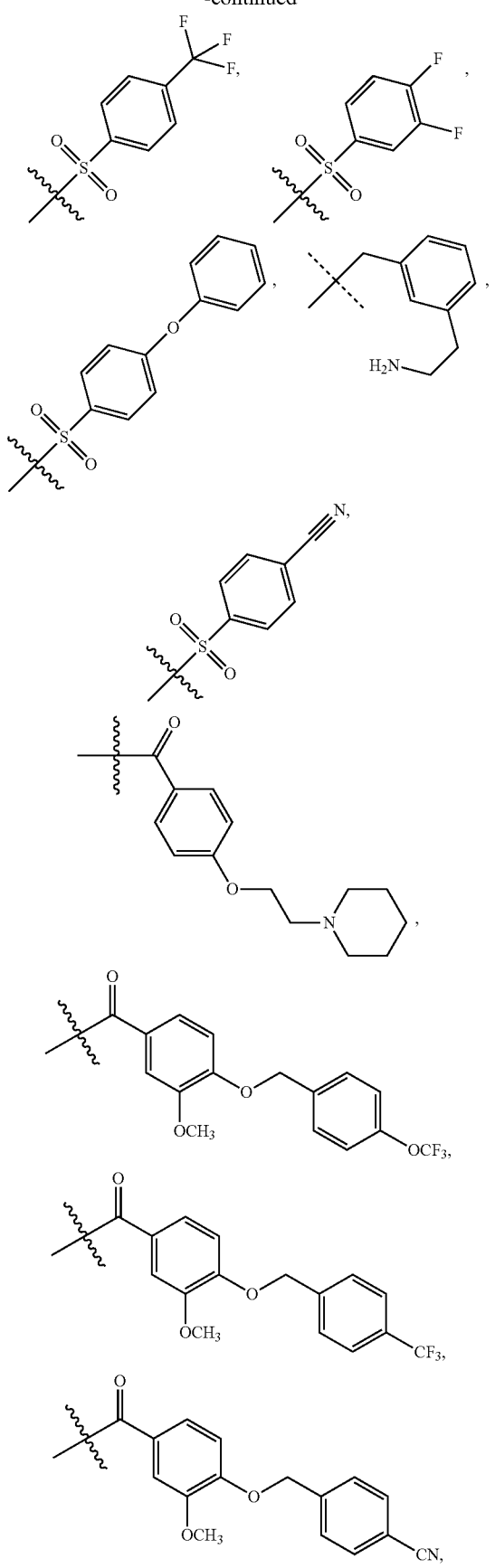
156
-continued
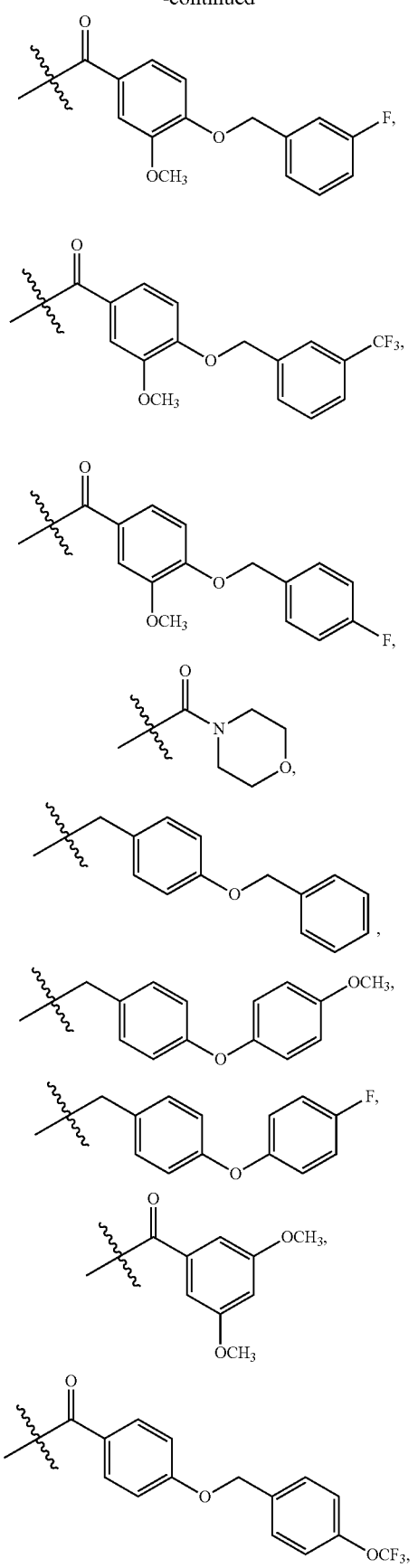

157
-continued
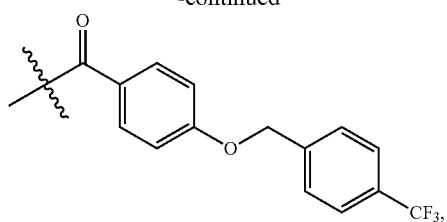
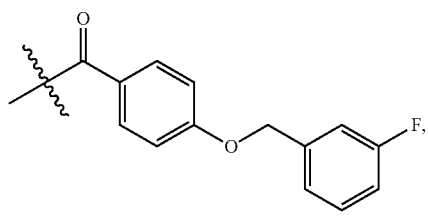
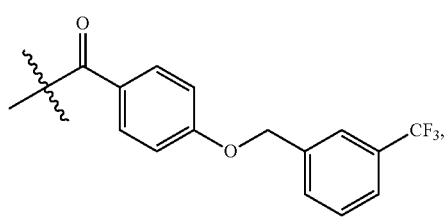
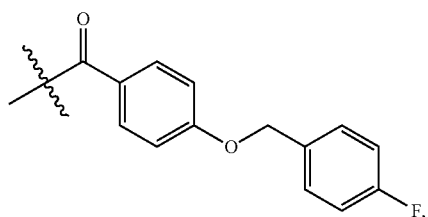
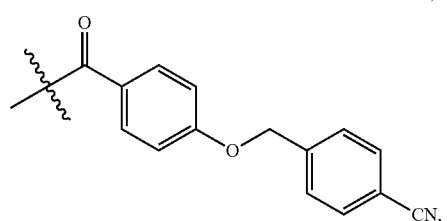
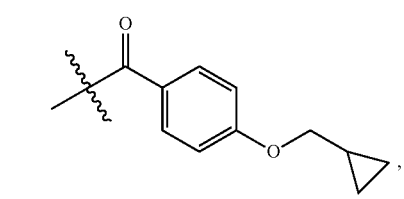
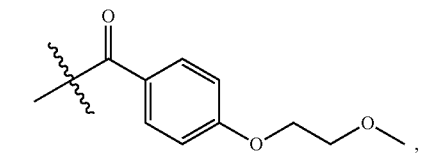
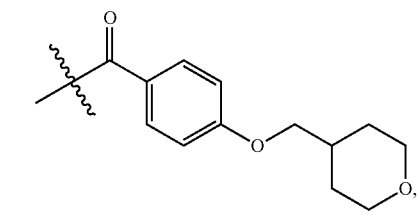
158
-continued
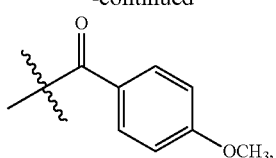
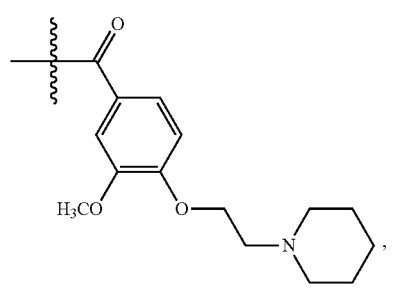
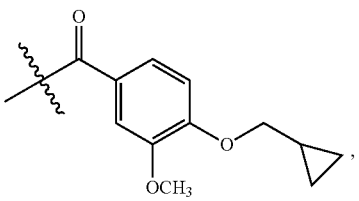
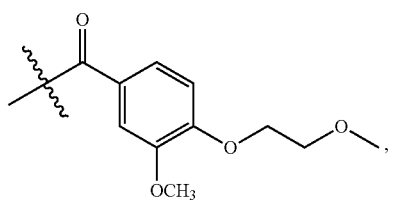
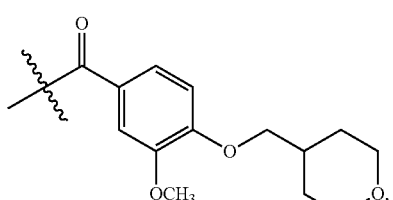
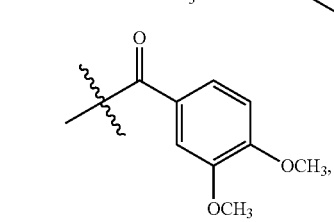
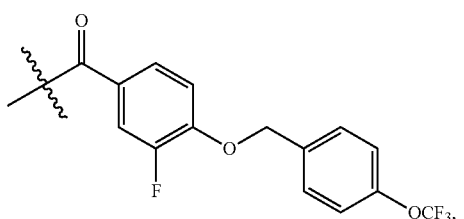
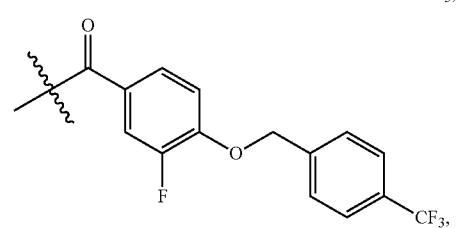

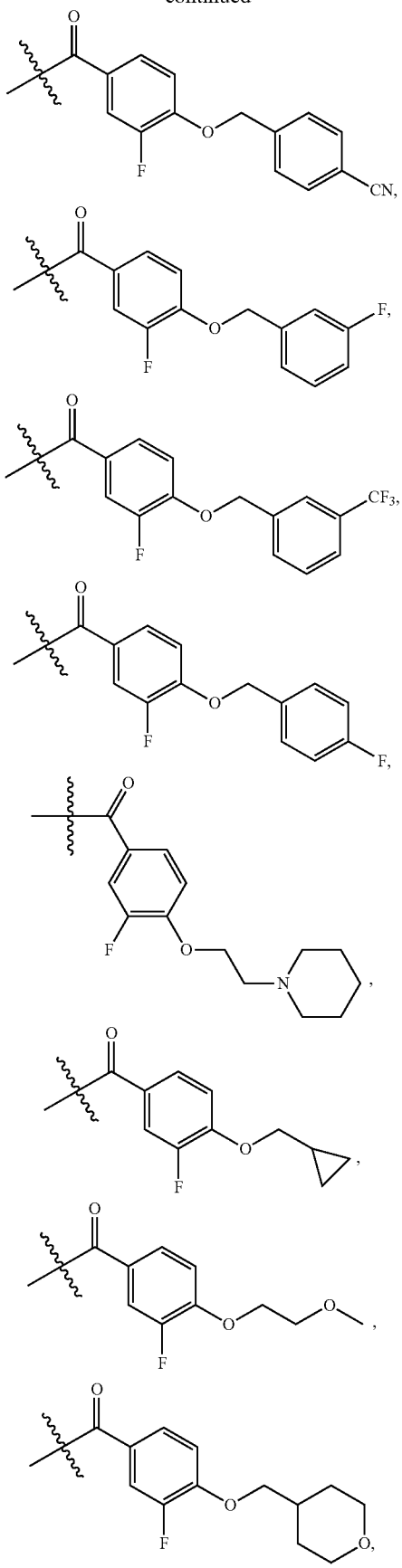

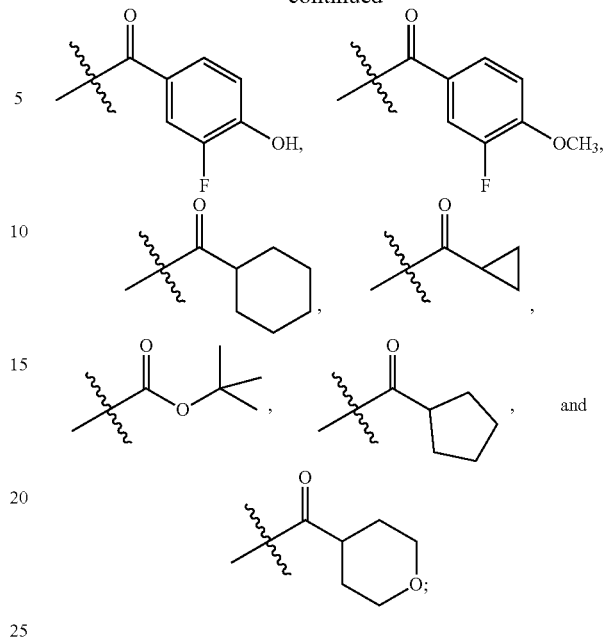

wherein R3 is selected from Hydrogen or CH3.

11. The method of claim 10, wherein the compound is capable of binding within a CRMP2 binding pocket characterized by one or more of the following CRMP2 amino acid residues: Lys23, Val125, Ser30, Tyr32, Met64, Ser319, Ser322, Trp366, Val370, Val1371, Gly373, Lys374, Met375, Asp376, Glu377, Glu377, Gln379, Pro414, Asp415, Ser416, Val1417, and Arg440.

12. The method of claim 10, wherein the compound is capable of inhibiting binding of Ubc9 within a CRMP2 binding pocket characterized by one or more of the following CRMP2 amino acid residues: Lys23, Val25, Ser30, Tyr32, Met64, Ser319, Ser322, Trp366, Val370, Val371, Gly373, Lys374, Met375, Asp376, Glu377, Glu377, Gln379, Pro414, Asp415, Ser416, Val417, and Arg440.

13. The method of claim 10, wherein the compound is selected from

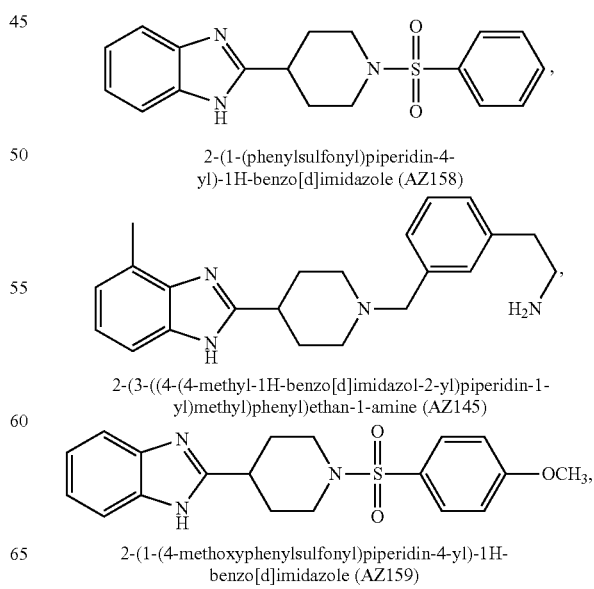

-continued

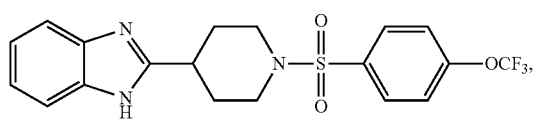

2-(1-(4-trifluoromerthoxy)phenylsulfonyl)piperidin-4-yl)-
1H-benzo[d]imidazole (AZ160)

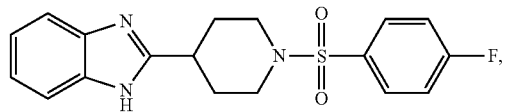

2-(1-(4-fluorophenylsulfonyl)piperidin-4-yl)-
1H-benzo[d]imidazole (AZ161)

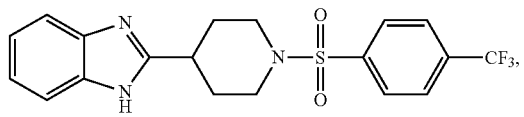

2-(1-(4-trifluoromerthyl)phenylsulfonyl)piperidin-4-yl)-
1H-benzo[d]imidazole (AZ162)

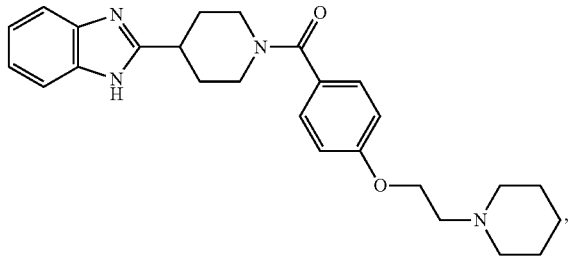

(4-(1H-benzo[d]imidazol-2-yl)piperidin-1-yl)(4-(2-
(piperidin-1-yl)ethoxy)phenyl)methaneone (AZ168)

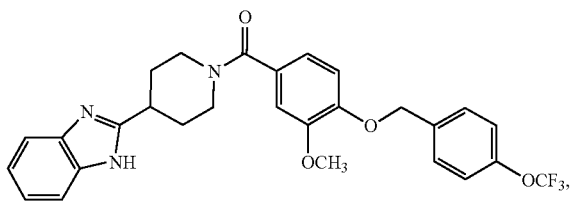

(4-(1H-benzo[d]imidazol-2-yl)piperidin-1-yl)(3-methoxy-4-(4-
(trifluoromethoxy)benzyloxy)phenyl)methanone (AZ170)

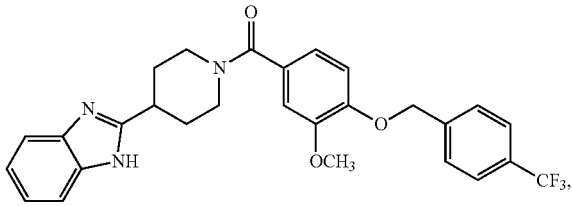

(4-(1H-benzo[d]imidazol-2-yl)piperidin-1-yl)(3-methoxy-4-(4-
(trifluoromethoxy)benzyloxy)phenyl)methanone (AZ172)

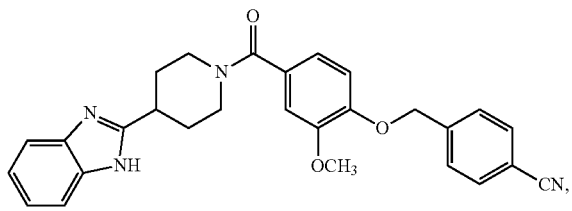

4-((4-(4-(1H-benzo[d]imidazol-2-yl)piperidine-1-carbonyl)-2-
methoxyphenoxy)methyl)benzonitrile (AZ173)

-continued

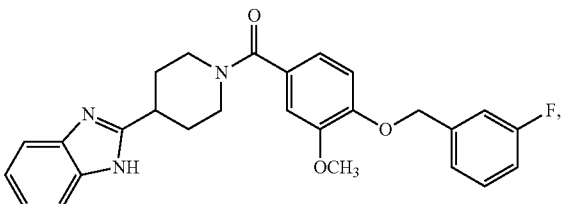

(4-(1H-benzo[d]imidazol-2-yl)piperidin-1-yl)(4-(3-fluorobenzyloxy)-3-
methoxyphenyl)methanone (AZ177)

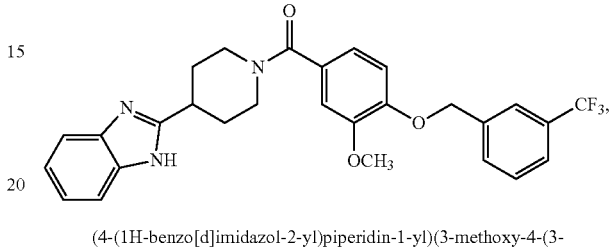

(4-(1H-benzo[d]imidazol-2-yl)piperidin-1-yl)(3-methoxy-4-(3-
(trifluoromethoxy)benzyloxy)phenyl)methanone (AZ178)

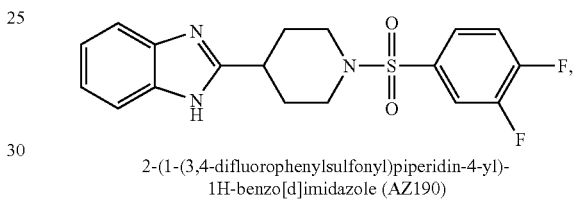

2-(1-(3,4-difluorophenylsulfonyl)piperidin-4-yl)-
1H-benzo[d]imidazole (AZ190)

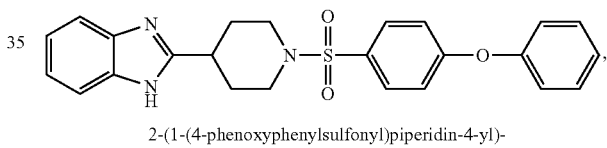

2-(1-(4-phenoxyphenylsulfonyl)piperidin-4-yl)-
1H-benzo[d]imidazole (AZ192)

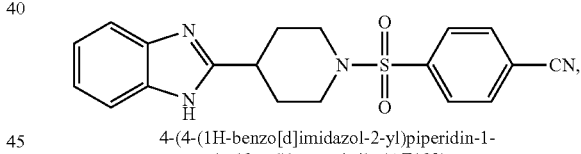

4-(4-(1H-benzo[d]imidazol-2-yl)piperidin-1-
ylsulfonyl)benzonitrile (AZ193)

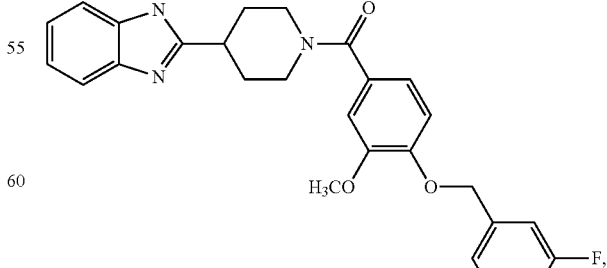

(4-(1-(3-fluorobenzyl)-1H-benzo[d]imidazol-2-yl)piperidin-1-yl)(4-(3-
fluorobenzyloxy)-3-methoxyphenyl)methanone (AZ194)

-continued

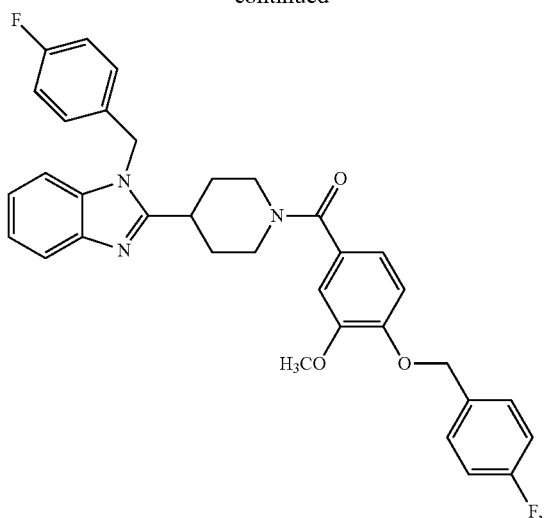

(4-(1-(4-fluorobenzyl)-1H-benzo[d]imidazol-2-yl)piperidin-1-yl)(4-(4-fluorobenzyloxy)-3-methoxyphenyl)methanone (AZ195)

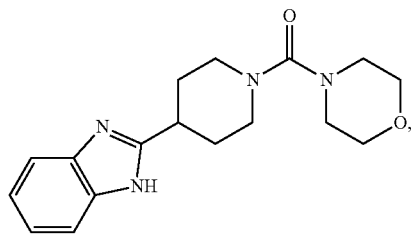

(4-(1H-benzo[d]imidazol-2-yl)piperidin-1-yl)(morpholino)methanone (AZ198)

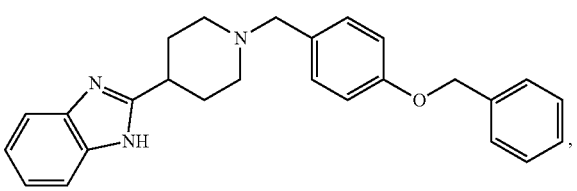

2-(1-(4-(benzyloxy)benzyl)piperidin-4-yl)-1H-benzo[d]imidazole (AZ203)

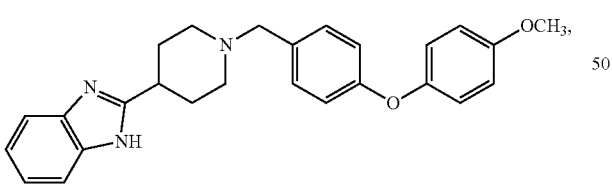

2-(1-(4-(4-methoxyphenoxy)benzyl)piperidin-4-yl)-1H-benzo[d]imidazole (AZ205)

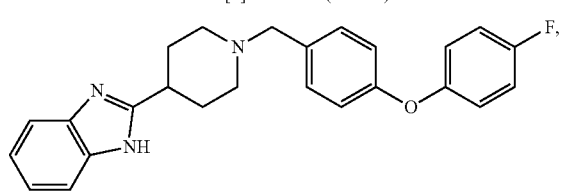

2-(1-(4-(4-fluorophenoxy)benzyl)piperidin-4-yl)-1H-benzo[d]imidazole (AZ206)

-continued

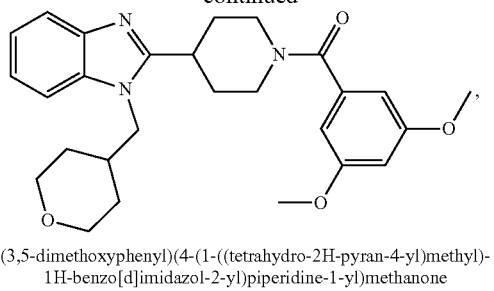

(3,5-dimethoxyphenyl)(4-(1-((tetrahydro-2H-pyran-4-yl)methyl)-1H-benzo[d]imidazol-2-yl)piperidine-1-yl)methanone

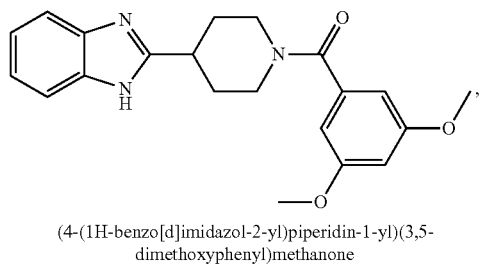

(4-(1H-benzo[d]imidazol-2-yl)piperidin-1-yl)(3,5-dimethoxyphenyl)methanone

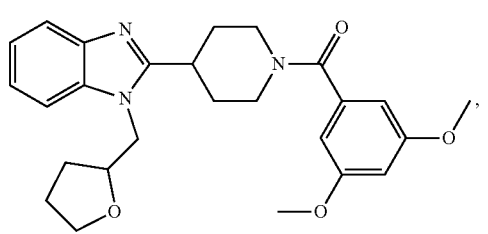

(3,5-dimethoxyphenyl)(4-(1-((tetrahydrofuran-2-yl)methyl)-1H-benzo[d]imidazol-2-yl)piperidine-1-yl)methanone

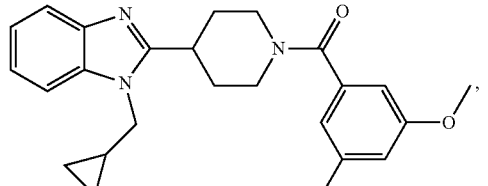

(4-(1-(cyclopropylmethyl)-1H-benzo[d]imidazol-2-yl)piperidin-1-yl)(3,5-dimethoxyphenyl)methanone

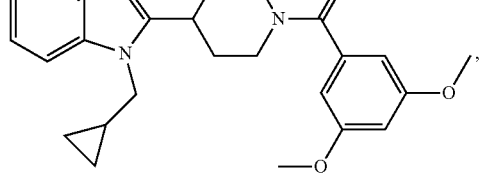

(4-(1-(cyclopropylmethyl)-1H-benzo[d]imidazol-2-yl)piperidin-1-yl)(3,5-dimethoxyphenyl)methanone

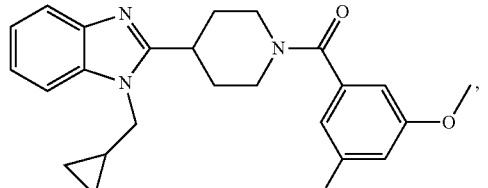

(4-(1-(cyclopropylmethyl)-1H-benzo[d]imidazol-2-yl)piperidin-1-yl)(3,5-dimethoxyphenyl)methanone

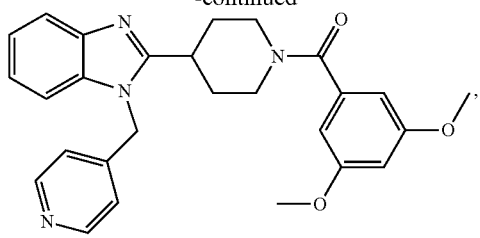

(3,5-dimethoxyphenyl)(4-(1-(pyridin-4-ylmethyl)-1H-benzo[d]imidazol-2-yl)piperidin-1-yl)methanone

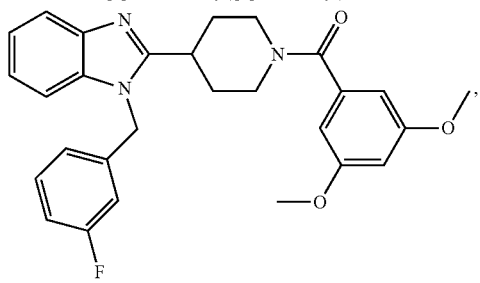

(3,5-dimethoxyphenyl)(4-(1-(3-fluorobenzyl)-1H-benzo[d]imidazol-2-yl)piperidin-1-yl)methanone

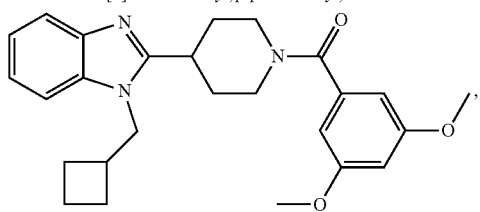

(4-(1-(cyclobutylmethyl)-1H-benzo[d]imidazol-2-yl)piperidin-1-yl)(3,5-dimethoxyphenyl)methanone

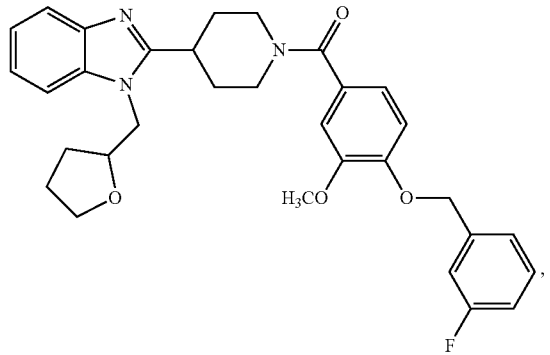

(4-((3-fluorobenzyl)oxy)-3-methoxyphenyl)(4-(1-((tertrahydrofuran-2-yl)methyl)-1H-benzo[d]imidazol-2-yl)piperidin-1-yl)methanone

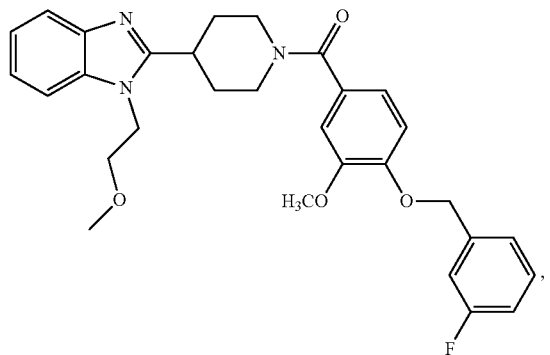

(4-((3-fluorobenzyl)oxy)-3-methoxyphenyl)(4-(1-(2-methoxyethyl)-1H-benzo[d]imidazol-2-yl)piperidin-1-yl)methanone

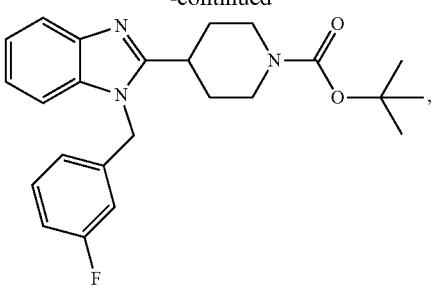

tert-butyl 4-(1-(3-fluorobenzyl)-1H-benzo[d]imidazol-2-yl)piperidine-1-carboxylate

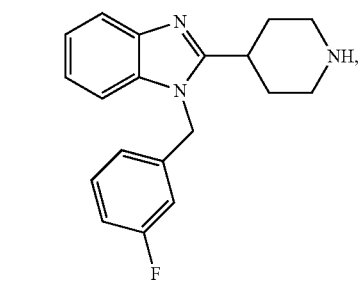

1-(3-fluorobenzyl)-2-(piperidin-4-yl)-1H-benzo[d]imidazole

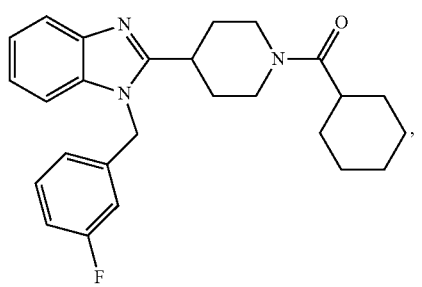

cyclohexyl(4-(1-(3-fluorobenzyl)-1H-benzo[d]imidazol-2-yl)piperidin-1-yl)methanone

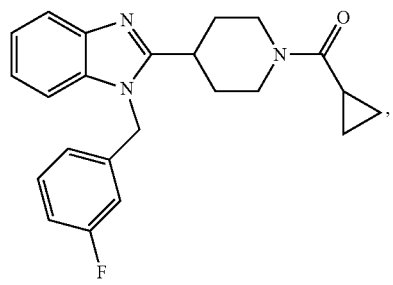

cyclopropyl(4-(1-(3-fluorobenzyl)-1H-benzo[d]imidazol-2-yl)piperidin-1-yl)methanone

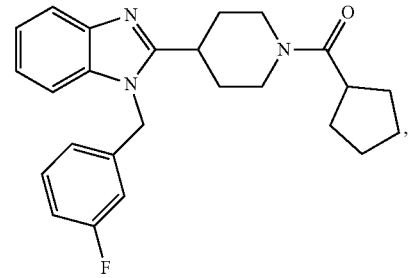

cyclopentyl(4-(1-(3-fluorobenzyl)-1H-benzo[d]imidazol-2-yl)piperidin-1-yl)methanone -continued

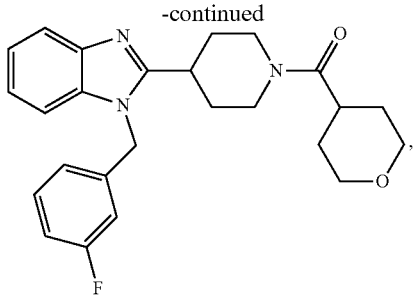

(4-(1-(3-fluorobenzyl)-1H-benzo[d]imidazol-2-yl)piperidin-1-yl)(tetrahydro-2H-pyran-4-yl)methanone

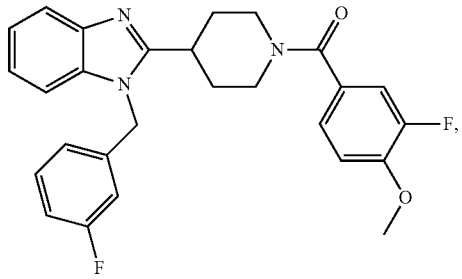

(3-fluoro-4-methoxyphenyl)(4-(1-(3-fluorobenzyl)-1H-benzo[d]imidazol-2-yl)piperidin-1-yl)methanone

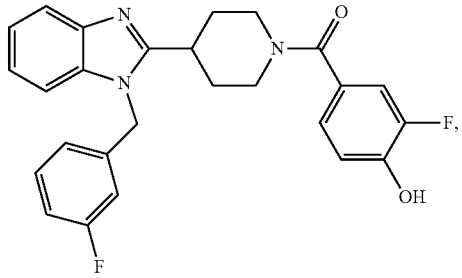

(3-fluoro-4-hydrophenyl)(4-(1-(3-fluorobenzyl)-1H-benzo[d]imidazol-2-yl)piperidin-1-yl)methanone

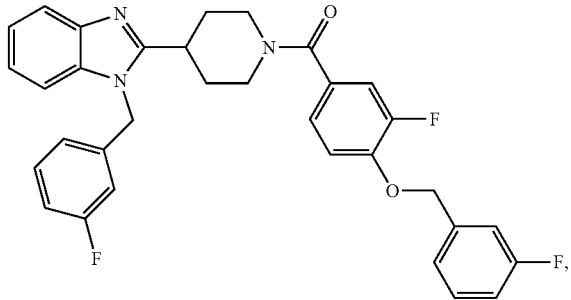

(3-fluoro-4-((3-fluorobenzyl)oxy)phenyl)(4-(1-(3-fluorobenzyl)-1H-benzo[d]imidazol-2-yl)piperidin-1-yl)methanone

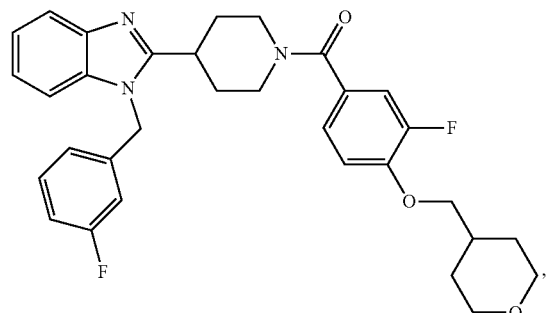

(3-fluoro-4-((tetrahydro-2H-pyran-4-yl)methoxy)phenyl)(4-(1-(3-fluorobenzyl)-1H-benzo[d]imidazol-2-yl)piperidin-1-yl)methanone -continued

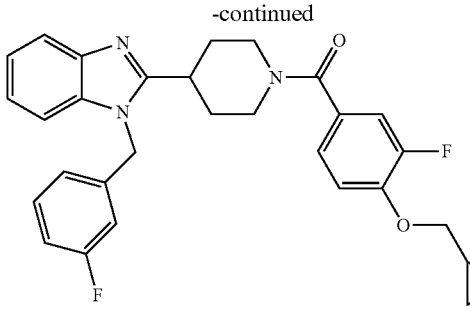

(4-(cyclopropylmethoxy)-3-fluorophenyl)(4-(1-(3-fluorobenzyl)-1H-benzo[d]imidazol-2-yl)piperidin-1-yl)methanone

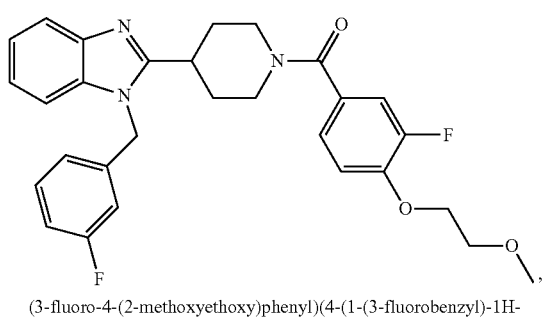

(3-fluoro-4-(2-methoxyethoxy)phenyl)(4-(1-(3-fluorobenzyl)-1H-benzo[d]imidazol-2-yl)piperidin-1-yl)methanone

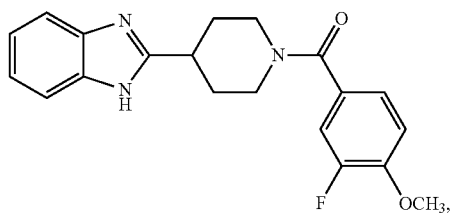

(4-(1H-benzo[d]imidazol-2-yl)piperidin-1-yl)(3-fluoro-4-methoxyphenyl)methanone

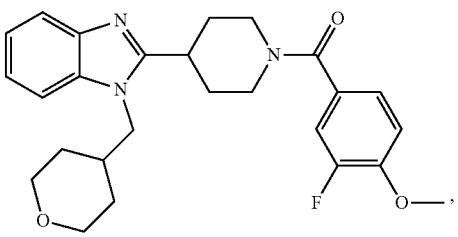

(3-fluoro-4-methoxyphenyl)(4-(1-((tetrahydro-2H-pyran-4-yl)methyl)-1H-benzo[d]imidazol-2-yl)piperidin-1-yl)methanone

169

-continued

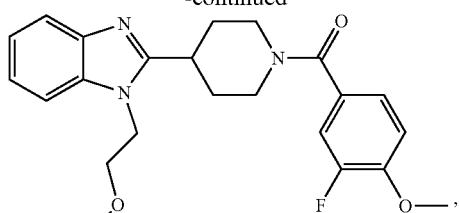

(3-fluoro-4-methoxyphenyl)(4-(1-(2-methoxyethyl)-1H-benzo[d]imidazol-2-yl)piperidin-1-yl)methanone

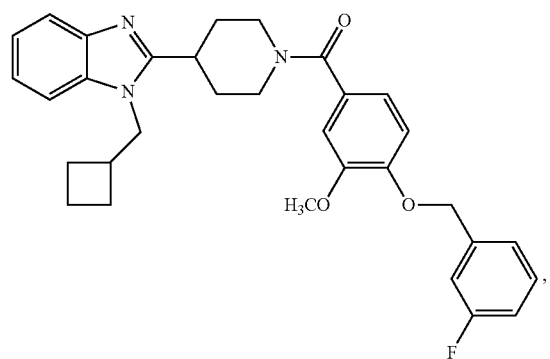

(4-(1-(cyclobutylmethyl)-1H-benzo[d]imidazol-2-yl)piperidin-1-yl)(4-((3-fluorobenzyl)oxy)-3-methoxyphenyl)methanone,

170

-continued

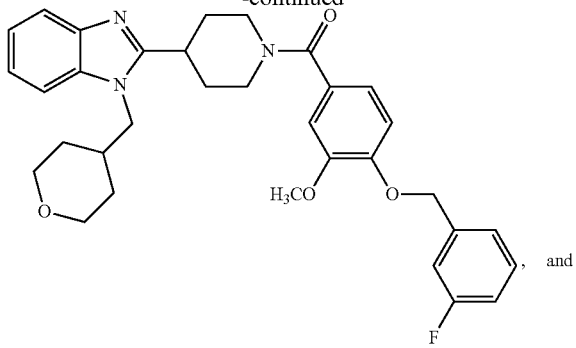

, and (4-((3-fluorobenzyl)oxy)-3-methoxyphenyl)(4-(1-((tetrahydro-2H-pyran-4-yl)methyl)-1H-benzo[d]imidazol-2-yl)piperidin-1-yl)methanone

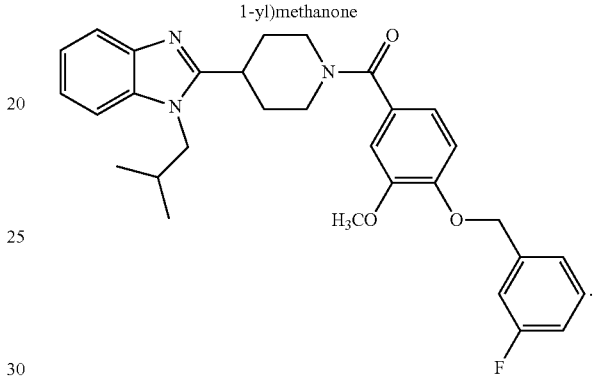

(4-((3-fluorobenzyl)oxy)-1-methoxyphenyl)(4-(1-isobutyl-1H-benzo[d]imidazol-2-yl)piperidin-1-yl)methanone

\* \* \* \* \*